(12) United States Patent
Reppas et al.

(10) Patent No.: US 7,919,303 B2
(45) Date of Patent: *Apr. 5, 2011

(54) METHODS AND COMPOSITIONS FOR THE RECOMBINANT BIOSYNTHESIS OF N-ALKANES

(75) Inventors: Nikos Basil Reppas, Brookline, MA (US); Christian Perry Ridley, Acton, MA (US)

(73) Assignee: Joule Unlimited, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/879,862

(22) Filed: Sep. 10, 2010

(65) Prior Publication Data

US 2011/0009674 A1    Jan. 13, 2011

Related U.S. Application Data

(63) Continuation of application No. 12/759,657, filed on Apr. 13, 2010, now Pat. No. 7,794,969.

(60) Provisional application No. 61/224,463, filed on Jul. 9, 2009, provisional application No. 61/228,937, filed on Jul. 27, 2009.

(51) Int. Cl.
*C12N 1/12* (2006.01)
*C12N 1/20* (2006.01)

(52) U.S. Cl. ............... 435/252.1; 435/252.3; 435/257.1; 435/257.2

(58) Field of Classification Search ........................ None
See application file for complete search history.

(56) References Cited

U.S. PATENT DOCUMENTS

| 7,794,969 B1 * | 9/2010 | Reppas et al. ............ 435/41 |
| 2004/0048343 A1 | 3/2004 | Hermann et al. |
| 2006/0225145 A1 | 10/2006 | Ozawa |
| 2009/0004715 A1 | 1/2009 | Trimbur et al. |
| 2009/0011480 A1 | 1/2009 | Trimbur et al. |
| 2009/0061493 A1 | 3/2009 | Trimbur et al. |
| 2009/0155873 A1 | 6/2009 | Kashiyama |
| 2009/0203070 A1 | 8/2009 | Devroe et al. |
| 2010/0136595 A1 | 6/2010 | Tittiger et al. |
| 2010/0151539 A1 | 6/2010 | Franklin et al. |
| 2010/0154293 A1 | 6/2010 | Hom et al. |
| 2010/0170826 A1 | 7/2010 | Friedman et al. |
| 2010/0249470 A1 | 9/2010 | Schirmer et al. |

FOREIGN PATENT DOCUMENTS

| EP | 711351 B1 | 3/2006 |
| WO | WO 92/14816 A1 | 9/1992 |
| WO | WO 2007/136762 | 11/2007 |
| WO | WO 2008/119082 | 10/2008 |
| WO | WO 2008/147781 A2 | 12/2008 |
| WO | WO 2009/006430 | 1/2009 |
| WO | WO 2009/036095 A1 | 3/2009 |
| WO | WO 2009/062190 | 5/2009 |
| WO | WO 2009/111513 | 9/2009 |
| WO | WO 2009/140695 | 11/2009 |
| WO | WO 2009/140696 | 11/2009 |
| WO | WO 2010/068288 | 6/2010 |

OTHER PUBLICATIONS

Beer, L.L. et al., "Engineering Algae for Biohydrogen and Biofuel Production," *Current Opinion in Biotechnology*, 2009, vol. 20, No. 3, pp. 264-271.

Fehler, S.W.G. et al., "Biosynthesis of Hydrocarbons in Anabaena Variabilis. Incorporation of [methyl-$^{14}$C]- and [methyl-$^{2}$H$_3$] Methionine into 7- and 8-Methylheptadecanes," *Biochemistry*, 1970, vol. 8, No. 2, pp. 418-422.

Heipieper, H., "Adaptation of *Escherichia coli* to Ethanol on the Level of Membrane Fatty Acid Composition," *Applied Environmental Microbiology*, 2005, vol. 71, p. 3388.

Jetter, R., et al., "Plant surface lipid biosynthetic pathways and their utility for metabolic engineering of waxes and hydrocarbon biofuels." *The Plant Journal*, 2008, pp. 670-683, vol. 54.

Ladygina, N., et al., "A review on microbial synthesis of hydrocarbons." *Process Biochemistry*, 2006, pp. 1001-1014, vol. 41, No. 5.

Maeda, S-I. et al., "cis-Acting Sequences Required for NtcB-Dependent, Nitrite-Responsive Positive Regulation of the Nitrate Assimilation Operon in the Cyanobacterium *Synechococcus* sp. Strain PCC 7942," *Journal of Bacteriology*, 1998, vol. 180, No. 16, pp. 4080-4088.

Mpuru, S. et al., "Mechanism of Hydrocarbon Biosynthesis from Aldehyde in Selected Insect Species: Requirement for O$_2$ and NADPH and Carbonyl Group Released as CO$_2$," *Insect Biochemistry Molecular Biology*, 1996, vol. 26, No. 2, pp. 203-208.

Murata, N. et al., "Modes of Fatty-Acid Desaturation in Cyanobacteria," *Plant Cell Physiology*, 1992, vol. 33, pp. 933-941.

PCT Invitation to Pay Additional Fees, etc., PCT Application No. PCT/US2010/041691, Sep. 30, 2010, two pages.

Phung, L.T., "Genes for Fatty Acid Biosynthesis in the Cyanobacterium *Synechococcus*," Abstracts of the 95$^{th}$ General Meeting of the American Society for Microbiology, Jan. 1, 1995, p. 524.

Reed, J.R. et al., "Unusual Mechanism of Hydrocarbon Formation in the Housefly: Cytochrome P450 Converts Aldehyde to the Sex Pheromone Component (Z)-9-tricosene and CO$_2$ ," *Proceedings of the National Academy of Science USA*, Oct. 1994, vol. 91, pp. 1000-10004.

Reed, J.R. et al., Proposed Mechanism for the Cytochrome P450-Catalyzed Conversion of Aldehydes to Hydrocarbons in the House Fly, *Musca domestica, Biochemistry*, 1995, vol. 34, pp. 16221-16227.

(Continued)

*Primary Examiner* — Mark Navarro
(74) *Attorney, Agent, or Firm* — Chang B. Hong; Fenwick & West LLP

(57) ABSTRACT

The present disclosure identifies methods and compositions for modifying photoautotrophic organisms as hosts, such that the organisms efficiently convert carbon dioxide and light into n-alkanes, and in particular the use of such organisms for the commercial production of n-alkanes and related molecules.

8 Claims, 37 Drawing Sheets

OTHER PUBLICATIONS

Rude, M.A. et al., "New Microbial Fuels: A Biotech Perspective," *Current Opinion in Microbiology*, 2009, vol. 12, No. 3, pp. 274-281.

Wentzel, A. et al., "Bacterial Metabolism of Long-chain *n*-Alkanes," *Applied Microbiology and Biotechnology*, 2007, vol. 76, pp. 1209-1221.

Winters, K. et al., "Hydrocarbons of Blue-Green Algae: Geochemical Significance," *Science*, 1969, vol. 163, No. 3866, pp. 467-468.

Copeland, A. et al. UniProt Direct Submission ID Q31C01, Jan. 24, 2006, 1 page. [Online] [Retrieved Dec. 7, 2010] Retrieved from the Internet: <URL:http//www.uniprot.org/uniprot/Q31C01.txt?version=1.>.

Copeland, A. et al. UniProt Direct Submission ID Q31C02, Jan. 24, 2006, 1 page. [Online] [Retrieved Dec. 7, 2010] Retrieved from the Internet: <URL:http//www.uniprot.org/uniprot/Q31C02.txt?version=1.>.

Luque, I. et al., "*Synechococcus* sp. Nir Gene for Nitrite Reductase," GenBank Direct Submission Accession X67680, May 27, 1993, two pages. [Online] [Retrieved Dec. 7, 2010] Retrieved from the Internet: <URL:http://www.ncbi.nlm.nih.gov/nuccore/288053.>.

Murata, N. et al., "Acyl-lipid Desaturases and their Importance in the Tolerance and Acclimatization to Cold Cyanobacteria," *Biochem J.*, 1995, vol. 308, pp. 1-8.

PCT International Search Report and Written Opinion, PCT Application No. PCT/US2010/041619, Jan. 10, 2011, twenty pages.

Phung, L.T. et al. UniProt Direct Submission ID Q54764, Nov. 1, 1996, one page. [Online] [Retrieved Dec. 7, 2010] Retrieved from the Internet: <URL:http://www.uniprot.org/uniprot/Q54764.txt?version=1.>.

Phung, L.T. et al. UniProt Direct Submission ID Q54765, Nov. 1, 1996, one page. [Online] [Retrieved Dec. 7, 2010] Retrieved from the Internet: <URL:http://www.uniprot.org/uniprot/Q54765.txt?version=1.>.

Qi, Q. et al., "Application of the *Synechococcus nir*A Promoter to Establish an Inducible Expression System for Engineering the *Synechocystis* Tocopherol Pathway," *Applied and Environmental Microbiology*, Oct. 2005, pp. 5678-5684, vol. 71, No. 10.

Welsh, E.A. et al. UniProt Direct Submission B1WR71, May 20, 2008, one page. [Online] [Retrieved on Dec. 7, 2010] Retrieved from the Internet: <URL:http://www.uniprot.org/uniprot/B1WR71.txt?version=1.>.

Welsh, E.A. et al. UniProt Direct Submission B1WWQ6, May 20, 2008, one page. [Online] [Retrieved on Dec. 7, 2010] Retrieved from the Internet: <URL:http://www.uniprot.org/uniprot/B1WWQ6.txt?version=1.>.

* cited by examiner

SEQUENCE LISTING

<160> NUMBER OF SEQ ID NOS: 128

<210> SEQ ID NO 1
<211> LENGTH: 1029
<212> TYPE: DNA
<213> ORGANISM: Thermosynechococcus elongatus

<400> SEQUENCE: 1
atgtttggat taattggtca tctgacgagt ctggagcacg cccaagccgt tgcccatcag      60
ttgggttacc ccgaatatgc cgatcaaggc ttggaatttt ggtgtatggc accgccgcag     120
atcgtcgatg agattacggt gacgagcgta acgggcaaaa ctatctatgg caaatacgtt     180
gagtcctgct ttttaccaga gatgctggcc aaccagcggg tgaaggcagc gactcgcaaa     240

```
gttattaacg ccatggccca tgcccaaaag cacaacattg acattacggc cttgggggc      300 ttctcctcga tcatctttga aactttgat ctggagaaaa tgtcccacat cgcaacatt      360 gaactggact ttcgccgctt tacaacgggg aatacccata ccgcctatat catctgccaa      420
caaattgagc aggcggcgcc ccaagtgggg attgatttgc ggcaggcaac cgtggctgtt      480 tgtgggcta cggggatat tggtagtgcc gtctgccgtt ggttgaatac ctgtttagat      540
gtgcaagatc tcttactcgt agcacggaat cgcgatcgcc tgctggagct acaggcggaa      600
ttgggacggg ggaaaatcct cgacttgatg gaggcgctgc ccttgccga tattgtggtt      660 tgggtggcca gtatgcccaa gggagttgag ctgagcattg agcagttaaa acgcccctcc      720
ctgatgattg atggtggtta tcccaaaaat atggccacca aaattcagca ccccagatt      780 catgttctca atggtggcat tgtcgagcat gccctcgaca ttgactggaa aattatggaa      840
attgtgaata tggatgtgcc ctcgcggcag atgtttgcct gttttgcaga ggctatgctt      900
ttagagttcg agggctggca caccaatttc tcttggggac gcaatcaaat cactgtggaa      960
aagatgcagc aaattggtga ggtctcccgt aaacatggat ttcagccact actgttgaat     1020
cctcagtaa                                                             1029

<210> SEQ ID NO 2
<211> LENGTH: 342
<212> TYPE: PRT
<213> ORGANISM: Thermosynechococcus elongatus

<400> SEQUENCE: 2

Met Phe Gly Leu Ile Gly His Leu Thr Ser Leu Glu His Ala Gln Ala
1               5                   10                  15

Val Ala His Gln Leu Gly Tyr Pro Glu Tyr Ala Asp Gln Gly Leu Glu
            20                  25                  30

Phe Trp Cys Met Ala Pro Pro Gln Ile Val Asp Glu Ile Thr Val Thr
        35                  40                  45

Ser Val Thr Gly Lys Thr Ile Tyr Gly Lys Tyr Val Glu Ser Cys Phe
    50                  55                  60

Leu Pro Glu Met Leu Ala Asn Gln Arg Val Lys Ala Ala Thr Arg Lys
65                  70                  75                  80

Val Ile Asn Ala Met Ala His Ala Gln Lys His Asn Ile Asp Ile Thr
                85                  90                  95

Ala Leu Gly Gly Phe Ser Ser Ile Ile Phe Glu Asn Phe Asp Leu Glu
            100                 105                 110

Lys Met Ser His Ile Arg Asn Ile Glu Leu Asp Phe Arg Arg Phe Thr
        115                 120                 125

Thr Gly Asn Thr His Thr Ala Tyr Ile Ile Cys Gln Gln Ile Glu Gln
    130                 135                 140

Ala Ala Pro Gln Val Gly Ile Asp Leu Arg Gln Ala Thr Val Ala Val
145                 150                 155                 160

Cys Gly Ala Thr Gly Asp Ile Gly Ser Ala Val Cys Arg Trp Leu Asn
                165                 170                 175

Thr Cys Leu Asp Val Gln Asp Leu Leu Val Ala Arg Asn Arg Asp
            180                 185                 190

Arg Leu Leu Glu Leu Gln Ala Glu Leu Gly Arg Gly Lys Ile Leu Asp
        195                 200                 205

Leu Met Glu Ala Leu Pro Leu Ala Asp Ile Val Val Trp Val Ala Ser
    210                 215                 220

Met Pro Lys Gly Val Glu Leu Ser Ile Glu Gln Leu Lys Arg Pro Ser
```

```
                225                 230                 235                 240
Leu Met Ile Asp Gly Gly Tyr Pro Lys Asn Met Ala Thr Lys Ile Gln
                    245                 250                 255

His Pro Gln Ile His Val Leu Asn Gly Gly Ile Val Glu His Ala Leu
                260                 265                 270

Asp Ile Asp Trp Lys Ile Met Glu Ile Val Asn Met Asp Val Pro Ser
            275                 280                 285

Arg Gln Met Phe Ala Cys Phe Ala Glu Ala Met Leu Leu Glu Phe Glu
        290                 295                 300

Gly Trp His Thr Asn Phe Ser Trp Gly Arg Asn Gln Ile Thr Val Glu
305                 310                 315                 320

Lys Met Gln Gln Ile Gly Glu Val Ser Arg Lys His Gly Phe Gln Pro
                325                 330                 335

Leu Leu Leu Asn Pro Gln
            340

<210> SEQ ID NO 3
<211> LENGTH: 696
<212> TYPE: DNA
<213> ORGANISM: Thermosynechococcus elongatus

<400> SEQUENCE: 3
atgacaacgg ctaccgctac acctgttttg gactaccata gcgatcgcta caaggatgcc      60
tacagccgca ttaacgccat tgtcattgaa ggtgaacagg aagctcacga taactatatc     120
gatttagcca agctgctgcc acaacaccaa gaggaactca cccgccttgc caagatggaa     180
gctcgccaca aaaaggggtt tgaggcctgt ggtcgcaacc tgagcgtaac gccagatatg     240
gaatttgcca agcccttctt tgaaaaactg cgcgctaact ttcagagggc tctggcggag     300
ggaaaaactg cgacttgtct tctgattcaa gctttgatca tcgaatcctt tgcgatcgcg     360
gcctacaaca tctacatccc aatggcggat cctttcgccc gtaaaattac tgagagtgtt     420
gttaaggacg aatacagcca cctcaacttt ggcgaaatct ggctcaagga cactttgaa      480 agcgtcaaag gagagctcga agaagccaat cgcgccaatt tacccttggt ctggaaaatg     540
ctcaaccaag tggaagcaga tgccaaagtg ctcggcatgg aaaaagatgc ccttgtggaa     600
gacttcatga ttcagtacag tggtgcccta gaaaatatcg ctttaccac ccgcgaaatt      660 atgaagatgt cagtttatgg cctcactggg gcataa                               696

<210> SEQ ID NO 4
<211> LENGTH: 231
<212> TYPE: PRT
<213> ORGANISM: Thermosynechococcus elongatus

<400> SEQUENCE: 4

Met Thr Thr Ala Thr Ala Thr Pro Val Leu Asp Tyr His Ser Asp Arg
1               5                   10                  15

Tyr Lys Asp Ala Tyr Ser Arg Ile Asn Ala Ile Val Ile Glu Gly Glu
            20                  25                  30

Gln Glu Ala His Asp Asn Tyr Ile Asp Leu Ala Lys Leu Leu Pro Gln
        35                  40                  45

His Gln Glu Glu Leu Thr Arg Leu Ala Lys Met Glu Ala Arg His Lys
    50                  55                  60

Lys Gly Phe Glu Ala Cys Gly Arg Asn Leu Ser Val Thr Pro Asp Met
65                  70                  75                  80

Glu Phe Ala Lys Ala Phe Phe Glu Lys Leu Arg Ala Asn Phe Gln Arg
                85                  90                  95
```

Ala Leu Ala Glu Gly Lys Thr Ala Thr Cys Leu Leu Ile Gln Ala Leu
            100                 105                 110

Ile Ile Glu Ser Phe Ala Ile Ala Ala Tyr Asn Ile Tyr Ile Pro Met
        115                 120                 125

Ala Asp Pro Phe Ala Arg Lys Ile Thr Glu Ser Val Val Lys Asp Glu
    130                 135                 140

Tyr Ser His Leu Asn Phe Gly Glu Ile Trp Leu Lys Glu His Phe Glu
145                 150                 155                 160

Ser Val Lys Gly Glu Leu Glu Glu Ala Asn Arg Ala Asn Leu Pro Leu
                165                 170                 175

Val Trp Lys Met Leu Asn Gln Val Glu Ala Asp Ala Lys Val Leu Gly
            180                 185                 190

Met Glu Lys Asp Ala Leu Val Glu Asp Phe Met Ile Gln Tyr Ser Gly
        195                 200                 205

Ala Leu Glu Asn Ile Gly Phe Thr Thr Arg Glu Ile Met Lys Met Ser
    210                 215                 220

Val Tyr Gly Leu Thr Gly Ala
225                 230

<210> SEQ ID NO 5
<211> LENGTH: 1026
<212> TYPE: DNA
<213> ORGANISM: Synechococcus elongatus

<400> SEQUENCE: 5
atgttcggtc ttatcggtca tctcaccagt ttggagcagg cccgcgacgt ttctcgcagg      60
atgggctacg acgaatacgc cgatcaagga ttggagtttt ggagtagcgc tcctcctcaa     120
atcgttgatg aaatcacagt caccagtgcc acaggcaagg tgattcacgg tcgctacatc     180
gaatcgtgtt tcttgccgga atgctggcg gcgcgccgct tcaaaacagc acgcgcaaa      240 gttctcaatg ccatgtccca tgcccaaaaa cacggcatcg acatctcggc cttgggggc     300 tttacctcga ttattttcga gaatttcgat ttggccagtt tgcggcaagt gcgcgacact    360
accttggagt ttgaacggtt caccaccggc aatactcaca cggcctacgt aatctgtaga    420
caggtggaag ccgctgctaa aacgctgggc atcgacatta cccaagcgac agtagcggtt    480
gtcggcgcga ctggcgatat cggtagcgct gtctgccgct ggctcgacct caaactgggt    540
gtcggtgatt tgatcctgac ggcgcgcaat caggagcgtt tggataacct gcaggctgaa    600
ctcggccggg gcaagattct gcccttggaa gccgctctgc cggaagctga ctttatcgtg    660
tgggtcgcca gtatgcctca gggcgtagtg atcgacccag caaccctgaa gcaaccctgc    720
gtcctaatcg acggggcta ccccaaaaac ttgggcagca agtccaagg tgagggcatc      780 tatgtcctca atggcggggt agttgaacat tgcttcgaca tcgactggca gatcatgtcc    840
gctgcagaga tggcgcggcc cgagcgccag atgtttgcct gctttgccga ggcgatgctc    900
ttggaatttg aaggctggca tactaacttc tcctgggcc gcaaccaaat cacgatcgag     960
aagatggaag cgatcggtga ggcatcggtg cgccacggct ccaacccctt ggcattggca   1020
atttga                                                               1026

<210> SEQ ID NO 6
<211> LENGTH: 341
<212> TYPE: PRT
<213> ORGANISM: Synechococcus elongatus

<400> SEQUENCE: 6

```
Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
                35                  40                  45

Ser Ala Thr Gly Lys Val Ile His Gly Arg Tyr Ile Glu Ser Cys Phe
50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
                100                 105                 110

Ser Leu Arg Gln Val Arg Asp Thr Thr Leu Glu Phe Glu Arg Phe Thr
            115                 120                 125

Thr Gly Asn Thr His Thr Ala Tyr Val Ile Cys Arg Gln Val Glu Ala
        130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340

<210> SEQ ID NO 7
<211> LENGTH: 696
<212> TYPE: DNA
<213> ORGANISM: Synechococcus elongatus

<400> SEQUENCE: 7
atgccgcagc ttgaagccag ccttgaactg gactttcaaa gcgagtccta caaagacgct       60
tacagccgca tcaacgcgat cgtgattgaa ggcgaacaag aggcgttcga caactacaat      120
cgccttgctg agatgctgcc cgaccagcgg gatgagcttc acaagctagc caagatggaa      180
```

```
cagcgccaca tgaaaggctt tatggcctgt ggcaaaaatc tctccgtcac tcctgacatg    240
ggttttgccc agaaattttt cgagcgcttg cacgagaact tcaaagcggc ggctgcggaa    300
ggcaaggtcg tcacctgcct actgattcaa tcgctaatca tcgagtgctt tgcgatcgcg    360
gcttacaaca tctacatccc agtggcggat gcttttgccc gcaaaatcac ggaggggtc     420 gtgcgcgacg aatacctgca ccgcaacttc ggtgaagagt ggctgaaggc gaattttgat    480
gcttccaaag ccgaactgga agaagccaat cgtcagaacc tgcccttggt ttggctaatg    540
ctcaacgaag tggccgatga tgctcgcgaa ctcgggatgg agcgtgagtc gctcgtcgag    600
gactttatga ttgcctacgg tgaagctctg gaaaacatcg gcttcacaac gcgcgaaatc    660
atgcgtatgt ccgcctatgg ccttgcggcc gtttga                             696
```

<210> SEQ ID NO 8
<211> LENGTH: 231
<212> TYPE: PRT
<213> ORGANISM: Synechococcus elongatus

<400> SEQUENCE: 8

```
Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30

Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80

Gly Phe Ala Gln Lys Phe Phe Glu Arg Leu His Glu Asn Phe Lys Ala
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190

Met Glu Arg Glu Ser Leu Val Glu Asp Phe Met Ile Ala Tyr Gly Glu
        195                 200                 205

Ala Leu Glu Asn Ile Gly Phe Thr Thr Arg Glu Ile Met Arg Met Ser
    210                 215                 220

Ala Tyr Gly Leu Ala Ala Val
225                 230
```

<210> SEQ ID NO 9
<211> LENGTH: 1041
<212> TYPE: DNA
<213> ORGANISM: Prochlorococcus marinus

<400> SEQUENCE: 9

```
atgtttggtc tgattggtca tagcaccagc tttgaggacg caaagcgcaa ggcgagcctg     60
```

-continued

```
ctgggtttcg accacatcgc ggatggcgat ctggatgtgt ggtgtaccgc accgccgcaa    120
ctggttgaaa acgtggaagt caaaagcgcg acgggtatca gcattgaagg tagctatatc    180
gatagctgct tcgtgccgga gatgctgagc cgcttcaaga ccgcgcgtcg taaagttctg    240
aatgcaatgg agctggcgca gaaaaagggt atcaatatca ctgccctggg tggctttacc    300
tccattatct ttgagaactt caacctgttg cagcacaagc aaatccgtaa taccagcctg    360
gagtgggagc gtttcaccac gggtaacacg cacacggcat gggtgatttg tcgtcagctg    420
gagatcaacg caccgcgcat tggcatcgac ctgaaaactg caacggtcgc tgttatcggc    480
gcgaccggcg atattggtag cgcggtgtgt cgctggctgg tcaataagac cggcattagc    540
gaactgctga tggtcgctcg ccaacaacag ccactgaccc tgctgcaaaa agaactggac    600
ggtggcacca tcaagagcct ggatgaagcc ctgccgcagg cggatattgt cgtgtgggtt    660
gcttcgatgc ctaagacgat cgaaattgag attgaaaacc tgaaaaagcc gtgcctgatg    720
atcgacggtg gctacccgaa gaatctggac gagaaattca aggcaaaaa cattcacgtg    780
ttgaagggtg gtatcgtcga gttttcaac gacattggct ggaacatgat ggagttggcg    840
gagatgcaaa acccgcagcg tgagatgttt gcgtgcttcg ccgaagctat gattctggag    900
tttgagaaat gccataccaa ctttagctgg ggccgtaaca atatcagctt ggagaagatg    960
gagttcatcg gtgctgcatc tctgaagcac ggtttcagcg cgatcggtct ggataaacag   1020
ccgaaagtct tgaccgtttg a                                             1041

<210> SEQ ID NO 10
<211> LENGTH: 345
<212> TYPE: PRT
<213> ORGANISM: Prochlorococcus marinus

<400> SEQUENCE: 10

Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
                20                  25                  30

Val Trp Cys Thr Ala Pro Pro Gln Leu Val Glu Asn Val Glu Val Lys
            35                  40                  45

Ser Ala Thr Gly Ile Ser Ile Glu Gly Ser Tyr Ile Asp Ser Cys Phe
        50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Arg Ile Gly Ile Asp Leu Lys Thr Ala Thr Val Ala Val Ile Gly
145                 150                 155                 160

Ala Thr Gly Asp Ile Gly Ser Ala Val Cys Arg Trp Leu Val Asn Lys
                165                 170                 175

Thr Gly Ile Ser Glu Leu Leu Met Val Ala Arg Gln Gln Gln Pro Leu
            180                 185                 190

Thr Leu Leu Gln Lys Glu Leu Asp Gly Gly Thr Ile Lys Ser Leu Asp
```

```
                195                  200                       205
Glu Ala Leu Pro Gln Ala Asp Ile Val Val Trp Val Ala Ser Met Pro
    210                 215                 220
Lys Thr Ile Glu Ile Glu Ile Glu Asn Leu Lys Lys Pro Cys Leu Met
225                 230                 235                 240
Ile Asp Gly Gly Tyr Pro Lys Asn Leu Asp Glu Lys Phe Lys Gly Lys
                245                 250                 255
Asn Ile His Val Leu Lys Gly Ile Val Glu Phe Phe Asn Asp Ile
            260                 265                 270
Gly Trp Asn Met Met Glu Leu Ala Glu Met Gln Asn Pro Gln Arg Glu
            275                 280                 285
Met Phe Ala Cys Phe Ala Glu Ala Met Ile Leu Glu Glu Lys Cys His
            290                 295                 300
Thr Asn Phe Ser Trp Gly Arg Asn Asn Ile Ser Leu Glu Lys Met Glu
305                 310                 315                 320
Phe Ile Gly Ala Ala Ser Leu Lys His Gly Phe Ser Ala Ile Gly Leu
                325                 330                 335
Asp Lys Gln Pro Lys Val Leu Thr Val
                340                 345

<210> SEQ ID NO 11
<211> LENGTH: 756
<212> TYPE: DNA
<213> ORGANISM: Prochlorococcus marinus

<400> SEQUENCE: 11
atgcacaatg aattgaaaat cacggatatg caaacgctgg aaaccaacac caagacgacc      60
gaagagtcta ttgacaccaa tagcctgaac ctgccggact ttactaccga cagctacaag     120
gatgcctatt ctcgcattaa cgccatcgtt attgagggcg aacaggaagc tcatgacaat     180
tacatctcca tcgcaacgct gatcccgaat gagctggaag agctgacgaa gctggcacgt     240
atggagctga acacaagaa aggttttact gcgtgcggtc gtaatctggg tgtggacgca      300
gacatggttt tcgcgaaaaa gttcttcagc aaactgcacg gcaatttcca aatcgcgctg     360
gaaaaaggta acctgaccac ctgcttgctg atccaagcga ttctgatcga agcatttgcg     420
atttccgcgt acaatgttta catccgtgtg gccgacccat tgccaaaaa gattaccgag      480
ggtgttgtca agacgagta tctgcatctg aactatggtc aggagtggct gaaaaagaat      540
ctgtccacgt gtaaagaaga gctgatggag gccaacaagg tcaatctgcc gctgattaag     600
aaaatgctgg acgaagtggc agaagatgcg agcgttttgg cgatggatcg tgaagagttg     660
atggaagagt tcatgattgc gtaccaggat accctgttgg agattggcct ggataatcgc     720
gaaattgccc gtatggcgat ggcggccatt gtttag                               756

<210> SEQ ID NO 12
<211> LENGTH: 251
<212> TYPE: PRT
<213> ORGANISM: Prochlorococcus marinus

<400> SEQUENCE: 12

Met His Asn Glu Leu Lys Ile Thr Asp Met Gln Thr Leu Glu Thr Asn
1               5                   10                  15
Thr Lys Thr Thr Glu Glu Ser Ile Asp Thr Asn Ser Leu Asn Leu Pro
                20                  25                  30
Asp Phe Thr Thr Asp Ser Tyr Lys Asp Ala Tyr Ser Arg Ile Asn Ala
            35                  40                  45
```

Ile Val Ile Glu Gly Glu Gln Glu Ala His Asp Asn Tyr Ile Ser Ile
 50                  55                  60

Ala Thr Leu Ile Pro Asn Glu Leu Glu Leu Thr Lys Leu Ala Arg
 65                  70                  75                  80

Met Glu Leu Lys His Lys Lys Gly Phe Thr Ala Cys Gly Arg Asn Leu
                 85                  90                  95

Gly Val Asp Ala Asp Met Val Phe Ala Lys Lys Phe Ser Lys Leu
                100                 105                 110

His Gly Asn Phe Gln Ile Ala Leu Glu Lys Gly Asn Leu Thr Thr Cys
                115                 120                 125

Leu Leu Ile Gln Ala Ile Leu Ile Glu Ala Phe Ala Ile Ser Ala Tyr
                130                 135                 140

Asn Val Tyr Ile Arg Val Ala Asp Pro Phe Ala Lys Lys Ile Thr Glu
145                 150                 155                 160

Gly Val Val Lys Asp Glu Tyr Leu His Leu Asn Tyr Gly Gln Glu Trp
                165                 170                 175

Leu Lys Lys Asn Leu Ser Thr Cys Lys Glu Leu Met Glu Ala Asn
                180                 185                 190

Lys Val Asn Leu Pro Leu Ile Lys Lys Met Leu Asp Glu Val Ala Glu
                195                 200                 205

Asp Ala Ser Val Leu Ala Met Asp Arg Glu Glu Leu Met Glu Phe
210                 215                 220

Met Ile Ala Tyr Gln Asp Thr Leu Leu Glu Ile Gly Leu Asp Asn Arg
225                 230                 235                 240

Glu Ile Ala Arg Met Ala Met Ala Ala Ile Val
                245                 250

<210> SEQ ID NO 13
<211> LENGTH: 1041
<212> TYPE: DNA
<213> ORGANISM: Prochlorococcus marinus

<400> SEQUENCE: 13

```
atgtttgggt taataggcca ctcaactagt tttgaagatg caaaagaaa agcttcatta      60
ctaggctttg atcatattgc tgatggtgat ctagatgttt ggtgtacagc ccctcctcaa    120
ttggttgaaa atgtagaagt taagagtgct actggaatat ctattgaagg ttcttatata    180
gattcttgct tgttcctga atgctttct aggtttaaaa ccgcaagaag aaaagtatta     240
aatgctatgg aattagctca gaaaaaaggg attaacatta cggctttagg aggatttact    300
tctattattt tcgaaaattt taatcttctt caacataaac aaattagaaa tacttcatta    360
gagtgggaaa ggtttactac aggtaataca cacactgcct gggttatttg taggcaacta    420
gaaataaatg ctcctcgcat agggatagat cttaaaactg caactgttgc tgttattggt    480
gctacaggtg atataggaag tgctgtttgt aggtggcttg tcaataaaac tggtatttca    540
gaacttctta tggtggctag acaacaacaa ccattaactc tattacagaa agaattagat    600
ggtggcacta aaaagttt agatgaagca ttgcctcaag cggatattgt tgtatgggtt    660
gcaagtatgc ctaaaacgat tgaaattgaa attgaaaact aaaaaaacc atgtttaatg    720
attgatggtg atacccctaa aaatcttgat gagaaatta aaggtaaaa tattcatgtt    780
ttaaaaggag gtatagtaga ttttttcaat gatattggct ggaatatgat ggaacttgca    840
gaaatgcaga accctcagag agagatgttt gcttgctttg cagaagctat gattttagaa    900
tttgaaaagt gtcataccaa ctttagttgg ggaaggaata cattctctct gaaaaaatg    960
gaatttattg gagcagcttc tttgaaacat ggtttttctg cgattggact tgataaacag   1020
```

```
cctaaagtat tgactgtttg a                                                1041

<210> SEQ ID NO 14
<211> LENGTH: 756
<212> TYPE: DNA
<213> ORGANISM: Prochlorococcus marinus

<400> SEQUENCE: 14
atgcataatg agctaaagat tactgacatg caaactctag aaacaaatac aaaaactact         60
gaagaatcca tagacacgaa ttctttgaat cttcccgact ttacaacaga ttcctataag        120
gatgcatata gcagaataaa tgcaattgtt atagagggag agcaagaggc tcatgataat        180
tacatttcaa tagcaacgtt aataccaaat gagttagaag aattaactaa gttggcgaga        240
atggaactca agcataaaaa aggatttact gcttgtggaa gaaatttagg agtagatgct        300
gatatggtat tcgcaaaaaa attcttttct aaattgcatg gtaattttca aattgcttta        360
gaaaaaggaa atttaacaac ttgtcttctg atacaagcta ttttaattga agcttttgct        420
atatctgctt ataacgttta cataagagtt gctgatcctt ttgcaaaaaa ataacagag         480 ggagtggtta aagatgaata tctccatcta aattcggcc aagagtggct taaaaagaat        540
ttatctactt gtaaagaaga attaatggaa gccataagg ttaaccttcc cttaattaaa        600
aagatgttag atgaagtagc agaagatgca tcagttttgg ctatggatag agaagagtta        660
atggaagaat ttatgattgc ttaccaagac actcttctag aaataggtct tgataataga        720
gaaattgcaa gaatggctat ggcagcgatt gtttaa                                  756

<210> SEQ ID NO 15
<211> LENGTH: 7026
<212> TYPE: DNA
<213> ORGANISM: Artificial Sequence
<220> FEATURE:
<223> OTHER INFORMATION: Description of Artificial Sequence: Synthetic
      plasmid JB823

<400> SEQUENCE: 15
gtcagcaagc tctggaattt cccgattctc tgatgggaga tccaaaaatt ctcgcagtcc         60
ctcaatcacg atatcggtct tggatcgccc tgtagcttcc gacaactgct caatttttc         120 gagcatctct accgggcatc ggaatgaaat taacggtgtt ttagccatgt gttatacagt        180
gtttacaact tgactaacaa atacctgcta gtgtatacat attgtattgc aatgtatacg        240
ctattttcac tgctgtcttt aatggggatt atcgcaagca agtaaaaaag cctgaaaacc        300
ccaataggta agggattccg agcttactcg ataattatca cctttgagcg cccctaggag        360
gaggcgaaaa gctatgtctg acaaggggtt tgacccctga gtcgttgcg cgagcattaa        420 ggtctgcgga tagcccataa catactttg ttgaacttgt gcgcttttat caaccccta         480 agggcttggg agcgttttat gcggccgcgg ggggggggg gaaagccacg ttgtgtctca        540
aaatctctga tgttacattg cacaagataa aaatatatca tcatgaacaa taaaactgtc        600
tgcttacata aacagtaata caaggggtca tatgccgcag cttgaagcca gccttgaact        660
ggactttcaa agcgagtcct acaaagacgc ttacagccgc atcaacgcga tcgtgattga        720
aggcgaacaa gaggcgttcg acaactacaa tcgccttgct gagatgctgc ccgaccagcg        780
ggatgagctt cacaagctag ccaagatgga acagcgccac atgaaaggct ttatggcctg        840
tggcaaaaat ctctccgtca ctcctgacat gggttttgcc cagaaatttt tcgagcgctt        900
gcacgagaac ttcaaagcgg cggctgcgga aggcaaggtc gtcacctgcc tactgattca        960
```

```
atcgctaatc atcgagtgct tgcgatcgc ggcttacaac atctacatcc cagtggcgga   1020
tgcttttgcc cgcaaaatca cggaggggggt cgtgcgcgac gaatacctgc accgcaactt   1080
cggtgaagag tggctgaagg cgaattttga tgcttccaaa gccgaactgg aagaagccaa   1140
tcgtcagaac ctgcccttgg tttggctaat gctcaacgaa gtggccgatg atgctcgcga   1200
actcgggatg gagcgtgagt cgctcgtcga ggactttatg attgcctacg gtgaagctct   1260
ggaaaacatc ggcttcacaa cgcgcgaaat catgcgtatg tccgcctatg gccttgcggc   1320
cgtttgatcc aggaaatctg aatgttcggt cttatcggtc atctcaccag tttggagcag   1380
gcccgcgacg tttctcgcag gatgggctac gacgaatacg ccgatcaagg attggagttt   1440
tggagtagcg ctcctcctca aatcgttgat gaaatcacag tcaccagtgc cacaggcaag   1500
gtgattcacg tcgctacat cgaatcgtgt ttcttgccgg aaatgctggc ggcgcgccgc   1560
ttcaaaacag ccacgcgcaa agttctcaat gccatgtccc atgcccaaaa acacggcatc   1620
gacatctcgg cctggggggg ctttacctcg attattttcg agaatttcga tttggccagt   1680
ttgcggcaag tgcgcgacac taccttggag tttgaacggt tcaccaccgg caatactcac   1740
acggcctacg taatctgtag acaggtggaa gccgctgcta aaacgctggg catcgacatt   1800
acccaagcga cagtagcggt tgtcggcgcg actggcgata tcggtagcgc tgtctgccgc   1860
tggctcgacc tcaaactggg tgtcggtgat ttgatcctga cggcgcgcaa tcaggagcgt   1920
ttggataacc tgcaggctga actcggccgg ggcaagattc tgcccttgga agccgctctg   1980
ccggaagctg actttatcgt gtgggtcgcc agtatgcctc agggcgtagt gatcgaccca   2040
gcaaccctga agcaaccctg cgtcctaatc gacgggggct acccaaaaa cttgggcagc   2100 aaagtccaag gtgagggcat ctatgtcctc aatggcgggg tagttgaaca ttgcttcgac   2160
atcgactggc agatcatgtc cgctgcagag atggcgcggc ccgagcgcca gatgtttgcc   2220
tgctttgccg aggcgatgct cttggaattt gaaggctggc atactaactt ctcctgggc   2280 cgcaaccaaa tcacgatcga gaagatggaa gcgatcggtg aggcatcggt gcgccacggc   2340
ttccaaccct tggcattggc aatttgaggt ctgtgaattc ggttttccgt cctgtcttga   2400
ttttcaagca aacaatgcct ccgatttcta atcggaggca tttgttttg tttattgcaa   2460 aaacaaaaaa tattgttaca aattttaca ggctattaag cctaccgtca taaataattt   2520
gccatttact agttttaat taaccagaac cttgaccgaa cgcagcggtg gtaacgcgc   2580 agtggcggtt ttcatggctt gttatgactg ttttttttggg gtacagtcta tgcctcgggc   2640
atccaagcag caagcgcgtt acgccgtggg tcgatgtttg atgttatgga gcagcaacga   2700
tgttacgcag cagggcagtc gccctaaaac aaagttaaac atcatgaggg aagcggtgat   2760
cgccgaagta tcgactcaac tatcagaggt agttggcgtc atcgagcgcc atctcgaacc   2820
gacgttgctg gccgtacatt tgtacggctc cgcagtggat ggcggcctga agccacacag   2880
tgatattgat ttgctggtta cggtgaccgt aaggcttgat gaaacaacgc ggcgagcttt   2940
gatcaacgac ctttttggaaa cttcggcttc ccctggagag agcgagattc tccgcgctgt   3000
agaagtcacc attgttgtgc acgacgacat cattccgtgg cgttatccag ctaagcgcga   3060
actgcaattt ggagaatggc agcgcaatga cattcttgca ggtatcttcg agccagccac   3120
gatcgacatt gatctggcta tcttgctgac aaaagcaaga gaacatagcg ttgccttggt   3180
aggtccagcg gcggaggaac tctttgatcc ggttcctgaa caggatctat ttgaggcgct   3240
aaatgaaacc ttaacgctat ggaactcgcc gcccgactgg gctggcgatg agcgaaatgt   3300
agtgcttacg ttgtcccgca tttggtacag cgcagtaacc ggcaaaatcg cgccgaagga   3360
```

-continued

```
tgtcgctgcc gactgggcaa tggagcgcct gccggcccag tatcagcccg tcatacttga    3420
agctagacag gcttatcttg gacaagaaga agatcgcttg gcctcgcgcg cagatcagtt    3480
ggaagaattt gtccactacg tgaaaggcga gatcaccaag gtagtcggca aataatgtct    3540
aacaattcgt tcaagccgac gccgcttcgc ggcgcggctt aactcaagcg ttagatgcac    3600
taagcacata attgctcaca gccaaactat caggtcaagt ctgcttttat tatttttaag    3660
cgtgcataat aagccctaca caaattggga gatatatcat gaggcgcgcc acgagtgcgg    3720
ggaaatttcg ggggcgatcg cccctatatc gcaaaaagga gttaccccat cagagctata    3780
gtcgagaaga aaaccatcat tcactcaaca aggctatgtc agaagagaaa ctagaccgga    3840
tcgaagcagc cctagagcaa ttggataagg atgtgcaaac gctccaaaca gagcttcagc    3900
aatcccaaaa atggcaggac aggacatggg atgttgtgaa gtgggtaggc ggaatctcag    3960
cgggcctagc ggtgagcgct tccattgccc tgttcgggtt ggtctttaga ttttctgttt    4020
ccctgccata aaagcacatt cttataagtc atacttgttt acatcaagga acaaaaacgg    4080
cattgtgcct tgcaaggcac aatgtctttc tcttatgcac agatggggac tggaaaccac    4140
acgcacaatt cccttaaaaa gcaaccgcaa aaataacca tcaaaataaa actgacaaaa    4200
ttctcatgtg ggccggccaa aatgaagtga agttcctata ctttctagag aataggaact    4260
tctatagtga gtcgaataag ggcgacacaa aatttattct aaatgcataa taaatactga    4320
taacatctta tagtttgtat tatattttgt attatcgttg acatgtataa ttttgatatc    4380
aaaaactgat tttcccttta ttattttcga gatttatttt cttaattctc tttaacaaac    4440
tagaaatatt gtatatacaa aaaatcataa ataatagatg aatagtttaa ttataggtgt    4500
tcatcaatcg aaaaagcaac gtatcttatt taaagtgcgt tgcttttttc tcatttataa    4560
ggttaaataa ttctcatata tcaagcaaag tgacaggcgc ccttaaatat tctgacaaat    4620
gctctttccc taaactcccc ccataaaaaa acccgccgaa gcgggttttt acgttatttg    4680
cggattaacg attactcgtt atcagaaccg cccaggggc ccgagcttaa gactggccgt    4740
cgttttacaa cacagaaaga gtttgtagaa acgcaaaaag gccatccgtc aggggccttc    4800
tgcttagttt gatgcctggc agttccctac tctcgccttc cgcttcctcg ctcactgact    4860
cgctgcgctc ggtcgttcgg ctgcggcgag cggtatcagc tcactcaaag gcggtaatac    4920
ggttatccac agaatcaggg gataacgcag gaaagaacat gtgagcaaaa ggccagcaaa    4980
aggccaggaa ccgtaaaaag gccgcgttgc tggcgttttt ccataggctc cgcccccctg    5040
acgagcatca caaaaatcga cgctcaagtc agaggtggcg aaacccgaca ggactataaa    5100
gataccaggc gtttccccct ggaagctccc tcgtgcgctc tcctgttccg accctgccgc    5160
ttaccggata cctgtccgcc tttctccctt cgggaagcgt ggcgctttct catagctcac    5220
gctgtaggta tctcagttcg gtgtaggtcg ttcgctccaa gctgggctgt gtgcacgaac    5280
cccccgttca gcccgaccgc tgcgccttat ccggtaacta tcgtcttgag tccaacccgg    5340
taagacacga cttatcgcca ctggcagcag ccactggtaa caggattagc agagcgaggt    5400
atgtaggcgg tgctacagag ttcttgaagt ggtgggctaa ctacggctac actagaagaa    5460
cagtatttgg tatctgcgct ctgctgaagc cagttacctt cggaaaaaga gttggtagct    5520
cttgatccgg caaacaaacc accgctggta gcggtggttt ttttgtttgc aagcagcaga    5580
ttacgcgcag aaaaaaagga tctcaagaag atcctttgat cttttctacg ggtctgacg    5640 ctcagtggaa cgacgcgcgc gtaactcacg ttaagggatt ttggtcatga gcttcgcccg    5700
tcccgtcaag tcagcgtaat gctctgcttt taccaatgct taatcagtga ggcacctatc    5760
```

-continued

```
tcagcgatct gtctatttcg ttcatccata gttgcctgac tccccgtcgt gtagataact    5820
acgatacggg agggcttacc atctggcccc agcgctgcga tgataccgcg agaaccacgc    5880
tcaccggctc cggatttatc agcaataaac cagccagccg aagggccga gcgcagaagt    5940
ggtcctgcaa ctttatccgc ctccatccag tctattaatt gttgccggga agctagagta    6000
agtagttcgc cagttaatag tttgcgcaac gttgttgcca tcgctacagg catcgtggtg    6060
tcacgctcgt cgtttggtat ggcttcattc agctccggtt cccaacgatc aaggcgagtt    6120
acatgatccc ccatgttgtg caaaaaagcg gttagctcct tcggtcctcc gatcgttgtc    6180
agaagtaagt tggccgcagt gttatcactc atggttatgg cagcactgca taattctctt    6240
actgtcatgc catccgtaag atgcttttct gtgactggtg agtactcaac caagtcattc    6300
tgagaatagt gtatgcggcg accgagttgc tcttgcccgg cgtcaatacg ggataatacc    6360
gcgccacata gcagaacttt aaaagtgctc atcattggaa aacgttcttc ggggcgaaaa    6420
ctctcaagga tcttaccgct gttgagatcc agttcgatgt aacccactcg tgcacccaac    6480
tgatcttcag catcttttac tttcaccagc gtttctgggt gagcaaaaac aggaaggcaa    6540
aatgccgcaa aaaagggaat aagggcgaca cggaaatgtt gaatactcat attcttcctt    6600
tttcaatatt attgaagcat ttatcagggt tattgtctca tgagcggata catatttgaa    6660
tgtatttaga aaataaaca atagggggtc agtgttacaa ccaattaacc aattctgaac    6720
attatcgcga gcccatttat acctgaatat ggctcataac accccttgtt tgcctggcgg    6780
cagtagcgcg gtggtcccac ctgacccccat gccgaactca gaagtgaaac gccgtagcgc    6840
cgatggtagt gtggggactc cccatgcgag agtagggaac tgccaggcat caaataaaac    6900
gaaaggctca gtcgaaagac tgggcctttc gcccgggcta attatggggt gtcgccctta    6960
ttcgactcta tagtgaagtt cctattctct agaaagtata ggaacttctg aagtgggggcc    7020
tgcagg                                                                7026
```

<210> SEQ ID NO 16
<211> LENGTH: 5513
<212> TYPE: DNA
<213> ORGANISM: Artificial Sequence
<220> FEATURE:
<223> OTHER INFORMATION: Description of Artificial Sequence: Synthetic plasmid pJB855

<400> SEQUENCE: 16

```
ggggaattgt gagcggataa caattcccct gtagaaataa ttttgtttaa ctttaataag      60
gagatatacc atgggcagca gccatcacca tcatcaccac agccaggatc cgaattcgag     120
ctcggcgcgc ctgcaggtcg acaagcttgc ggccgcataa tgcttaagtc gaacagaaag     180
taatcgtatt gtacacggcc gcataatcga aattaatacg actcactata ggggaattgt     240
gagcggataa caattcccca tcttagtata ttagttaagt ataagaagga gatatacata     300
tgccgcagct tgaagccagc cttgaactgg actttcaaag cgagtcctac aaagacgctt     360
acagccgcat caacgcgatc gtgattgaag gcgaacaaga ggcgttcgac aactacaatc     420
gccttgctga gatgctgccc gaccagcggg atgagcttca caagctagcc aagatggaac     480
agcgccacat gaaaggcttt atggcctgtg caaaaatct ctccgtcact cctgacatgg     540
gttttgccca gaatttttc gagcgcttgc acgaaactt caaagcggcg gctgcggaag     600
gcaaggtcgt cacctgccta ctgattcaat cgctaatcat cgagtgcttt gcgatcgcgg     660
cttacaacat ctacatccca gtggcggatg cttttgcccg caaaatcacg gagggggtcg     720
tgcgcgacga atacctgcac cgcaacttcg gtgaagagtg gctgaaggcg aatttgatg     780
```

```
cttccaaagc cgaactggaa gaagccaatc gtcagaacct gcccttggtt tggctaatgc      840
tcaacgaagt ggccgatgat gctcgcgaac tcgggatgga gcgtgagtcg ctcgtcgagg      900
actttatgat tgcctacggt gaagctctgg aaaacatcgg cttcacaacg cgcgaaatca      960
tgcgtatgtc cgcctatggc cttgcggccg tttgatccag gaaatctgaa tgttcggtct     1020
tatcggtcat ctcaccagtt tggagcaggc ccgcgacgtt tctcgcagga tgggctacga     1080
cgaatacgcc gatcaaggat tggagttttg gagtagcgct cctcctcaaa tcgttgatga     1140
aatcacagtc accagtgcca caggcaaggt gattcacggt cgctacatcg aatcgtgttt     1200
cttgccggaa atgctggcgg cgcgccgctt caaaacagcc acgcgcaaag ttctcaatgc     1260
catgtcccat gcccaaaaac acggcatcga catctcggcc ttgggggggct ttacctcgat     1320 tattttcgag aatttcgatt tggccagttt gcggcaagtg cgcgacacta ccttggagtt     1380
tgaacggttc accaccggca atactcacac ggcctacgta atctgtagac aggtggaagc     1440
cgctgctaaa acgctgggca tcgacattac ccaagcgaca gtagcggttg tcggcgcgac     1500
tggcgatatc ggtagcgctg tctgccgctg gctcgacctc aaactgggtg tcggtgattt     1560
gatcctgacg gcgcgcaatc aggagcgttt ggataacctg caggctgaac tcggccgggg     1620
caagattctg cccttggaag ccgctctgcc ggaagctgac tttatcgtgt gggtcgccag     1680
tatgcctcag ggcgtagtga tcgacccagc aaccctgaag caaccctgcg tcctaatcga     1740
cgggggctac cccaaaaact gggcagcaa agtccaaggt gagggcatct atgtcctcaa      1800
tggcggggta gttgaacatt gcttcgacat cgactggcag atcatgtccg ctgcagagat     1860
ggcgcggccc gagcgccaga tgtttgcctg ctttgccgag gcgatgctct ggaatttga     1920 aggctggcat actaacttct cctggggccg caaccaaatc acgatcgaga agatggaagc     1980
gatcggtgag gcatcggtgc gccacggctt ccaacccttg gcattggcaa tttgaggtct     2040
gtgaattgga tatcggccgg ccacgcgatc gctgacgtcg gtaccctcga gtctggtaaa     2100
gaaaccgctg ctgcgaaatt tgaacgccag cacatggact cgtctactag cgcagcttaa     2160
ttaacctagg ctgctgccac cgctgagcaa taactagcat aacccttgg ggcctctaaa      2220 cgggtcttga ggggtttttt gctgaaacct caggcatttg agaagcacac ggtcacactg     2280
cttccggtag tcaataaacc ggtaaaccag caatagacat aagcggctat ttaacgaccc     2340
tgccctgaac cgacgaccgg gtcatcgtgg ccggatcttg cggcccctcg gcttgaacga     2400
attgttagac attatttgcc gactaccttg gtgatctcgc ctttcacgta gtggacaaat     2460
tcttccaact gatctgcgcg cgaggccaag cgatcttctt cttgtccaag ataagcctgt     2520
ctagcttcaa gtatgacggg ctgatactgg gccggcaggc gctccattgc ccagtcggca     2580
gcgacatcct tcggcgcgat tttgccggtt actgcgctgt accaaatgcg ggacaacgta     2640
agcactacat ttcgctcatc gccagcccag tcggcggcg agttccatag cgttaaggtt      2700
tcatttagcg ccctcaaatag atcctgttca ggaaccggat caaagagttc ctccgccgct     2760
ggacctacca aggcaacgct atgttctctt gcttttgtca gcaagatagc cagatcaatg     2820
tcgatcgtgg ctggctcgaa gatacctgca agaatgtcat tgcgctgcca ttctccaaat     2880
tgcagttcgc gcttagctgg ataacgccac ggaatgatgt cgtcgtgcac aacaatggtg     2940
acttctacag cgcggagaat ctcgctctct ccagggggaag ccgaagtttc caaaggtcg     3000 ttgatcaaag ctcgccgcgt tgtttcatca agccttacgg tcaccgtaac cagcaaatca     3060
atatcactgt gtggcttcag gccgccatcc actgcgagc cgtacaaatg tacggccagc      3120
aacgtcggtt cgagatggcg ctcgatgacg ccaactacct ctgatagttg agtcgatact     3180
```

```
tcggcgatca ccgcttccct catactcttc cttttttcaat attattgaag catttatcag    3240
ggttattgtc tcatgagcgg atacatattt gaatgtattt agaaaaataa acaaatagct    3300
agctcactcg gtcgctacgc tccgggcgtg agactgcggc gggcgctgcg gacacataca    3360
aagttaccca cagattccgt ggataagcag gggactaaca tgtgaggcaa aacagcaggg    3420
ccgcgccggt ggcgtttttc cataggctcc gccctcctgc cagagttcac ataaacagac    3480
gcttttccgg tgcatctgtg ggagccgtga ggctcaacca tgaatctgac agtacgggcg    3540
aaacccgaca ggacttaaag atccccaccg tttccggcgg gtcgctccct cttgcgctct    3600
cctgttccga ccctgccgtt taccggatac ctgttccgcc tttctccctt acgggaagtg    3660
tggcgctttc tcatagctca cacactggta tctcggctcg gtgtaggtcg ttcgctccaa    3720
gctgggctgt aagcaagaac tccccgttca gcccgactgc tgcgccttat ccggtaactg    3780
ttcacttgag tccaacccgg aaaagcacgg taaaacgcca ctggcagcag ccattggtaa    3840
ctgggagttc gcagaggatt tgtttagcta aacacgcggt tgctcttgaa gtgtgcgcca    3900
aagtccggct acactggaag gacagatttg gttgctgtgc tctgcgaaag ccagttacca    3960
cggttaagca gttccccaac tgacttaacc ttcgatcaaa ccacctcccc aggtggtttt    4020
ttcgtttaca gggcaaaaga ttacgcgcag aaaaaaagga tctcaagaag atcctttgat    4080
cttttctact gaaccgctct agatttcagt gcaatttatc tcttcaaatg tagcacctga    4140
agtcagcccc atacgatata agttgtaatt ctcatgttag tcatgccccg cgcccaccgg    4200
aaggagctga ctgggttgaa ggctctcaag ggcatcggtc gagatcccgg tgcctaatga    4260
gtgagctaac ttacattaat tgcgttgcgc tcactgcccg ctttccagtc gggaaacctg    4320
tcgtgccagc tgcattaatg aatcggccaa cgcgcgggga gaggcggttt gcgtattggg    4380
cgccagggtg ttttttcttt tcaccagtga gacgggcaac agctgattgc ccttcaccgc    4440
ctggccctga gagagttgca gcaagcggtc cacgctggtt tgcccagca ggcgaaaatc    4500
ctgtttgatg gtggttaacg gcgggatata acatgagctg tcttcggtat cgtcgtatcc    4560
cactaccgag atgtccgcac caacgcgcag cccggactcg gtaatggcgc gcattgcgcc    4620
cagcgccatc tgatcgttgg caaccagcat cgcagtggga acgatgccct cattcagcat    4680
ttgcatggtt tgttgaaaac cggacatggc actccagtcg ccttcccgtt ccgctatcgg    4740
ctgaatttga ttgcgagtga gatatttatg ccagccagcc agacgcagac gcgccgagac    4800
agaacttaat gggcccgcta acagcgcgat ttgctggtga cccaatgcga ccagatgctc    4860
cacgcccagt cgcgtaccgt cttcatggga gaaaataata ctgttgatgg gtgtctggtc    4920
agagacatca agaaataacg ccggaacatt agtgcaggca gcttccacag caatggcatc    4980
ctggtcatcc agcggatagt taatgatcag cccactgacg cgttgcgcga agagattgtg    5040
caccgccgct ttacaggctt cgacgccgct tcgttctacc atcgacacca ccacgctggc    5100
acccagttga tcggcgcgag atttaatcgc cgcgacaatt tgcgacggcg cgtgcagggc    5160
cagactggag gtggcaacgc caatcagcaa cgactgtttg cccgccagtt gttgtgccac    5220
gcggttggga atgtaattca gctccgccat cgccgcttcc acttttttccc gcgttttcgc    5280
agaaacgtgg ctggcctggt tcaccacgcg ggaaacggtc tgataagaga ccggcata    5340
ctctgcgaca tcgtataacg ttactggttt cacattcacc accctgaatt gactctcttc    5400
cgggcgctat catgccatac cgcgaaaggt tttgcgccat tcgatggtgt ccgggatctc    5460
gacgctctcc cttatgcgac tcctgcatta ggaaattaat acgactcact ata         5513
```

<210> SEQ ID NO 17
<211> LENGTH: 7118
<212> TYPE: DNA
<213> ORGANISM: Artificial Sequence
<220> FEATURE:
<223> OTHER INFORMATION: Description of Artificial Sequence: Synthetic plasmid pJB947

<400> SEQUENCE: 17

| | | | | | |
|---|---|---|---|---|---|
| gtcagcaagc | tctggaattt | cccgattctc | tgatgggaga | tccaaaaatt | ctcgcagtcc | 60 |
| ctcaatcacg | atatcggtct | tggatcgccc | tgtagcttcc | gacaactgct | caatttttc | 120 |
| gagcatctct | accgggcatc | ggaatgaaat | taacggtgtt | ttagccatgt | gttatacagt | 180 |
| gtttacaact | tgactaacaa | atacctgcta | gtgtatacat | attgtattgc | aatgtatacg | 240 |
| ctattttcac | tgctgtcttt | aatggggatt | atcgcaagca | agtaaaaaag | cctgaaaacc | 300 |
| ccaataggta | agggattccg | agcttactcg | ataattatca | cctttgagcg | ccctaggag | 360 |
| gaggcgaaaa | gctatgtctg | acaagggggtt | tgaccctga | agtcgttgcg | cgagcattaa | 420 |
| ggtctgcgga | tagcccataa | catacttttg | ttgaacttgt | gcgcttttat | caacccctta | 480 |
| agggcttggg | agcgttttat | gcggccgcgg | gggggggggg | gaaagccacg | ttgtgtctca | 540 |
| aaatctctga | tgttacattg | cacaagataa | aaatatatca | tcatgaacaa | taaaactgtc | 600 |
| tgcttacata | aacagtaata | caaggggtca | tatgcacaat | gaattgaaaa | tcacggatat | 660 |
| gcaaacgctg | gaaaccaaca | ccaagacgac | cgaagagtct | attgacacca | atagcctgaa | 720 |
| cctgccggac | tttactaccg | acagctacaa | ggatgcctat | tctcgcatta | cgccatcgt | 780 |
| tattgagggc | gaacaggaag | ctcatgacaa | ttacatctcc | atcgcaacgc | tgatcccgaa | 840 |
| tgagctggaa | gagctgacga | agctggcacg | tatggagctg | aaacacaaga | aaggttttac | 900 |
| tgcgtgcggt | cgtaatctgg | gtgtggacgc | agacatggtt | ttcgcgaaaa | agttcttcag | 960 |
| caaactgcac | ggcaatttcc | aaatcgcgct | ggaaaaaggt | aacctgacca | cctgcttgct | 1020 |
| gatccaagcg | attctgatcg | aagcatttgc | gatttccgcg | tacaatgttt | acatccgtgt | 1080 |
| ggccgaccca | tttgccaaaa | agattaccga | gggtgttgtc | aaagacgagt | atctgcatct | 1140 |
| gaactatggt | caggagtggc | tgaaaaagaa | tctgtccacg | tgtaaagaag | agctgatgga | 1200 |
| ggccaacaag | gtcaatctgc | cgctgattaa | gaaaatgctg | gacgaagtgg | cagaagatgc | 1260 |
| gagcgttttg | gcgatggatc | gtgaagagtt | gatggaagag | ttcatgattg | cgtaccagga | 1320 |
| taccctgttg | gagattggcc | tggataatcg | cgaaattgcc | cgtatggcga | tggcggccat | 1380 |
| tgtttagtaa | tatttctaat | taactaataa | aggaagtctg | aatgtttggt | ctgattggtc | 1440 |
| atagcaccag | ctttgaggac | gcaaagcgca | aggcgagcct | gctgggtttc | gaccacatcg | 1500 |
| cggatggcga | tctggatgtg | tggtgtaccg | caccgccgca | actggttgaa | aacgtggaag | 1560 |
| tcaaaagcgc | gacgggtatc | agcattgaag | gtagctatat | cgatagctgc | ttcgtgccgg | 1620 |
| agatgctgag | ccgcttcaag | accgcgcgtc | gtaaagttct | gaatgcaatg | gagctggcgc | 1680 |
| agaaaaaggg | tatcaatatc | actgccctgg | gtggctttac | ctccattatc | tttgagaact | 1740 |
| tcaacctgtt | gcagcacaag | caaatccgta | ataccagcct | ggagtgggag | cgtttcacca | 1800 |
| cgggtaacac | gcacacggca | tgggtgattt | gtcgtcagct | ggagatcaac | gcaccgcgca | 1860 |
| ttggcatcga | cctgaaaact | gcaacggtcg | ctgttatcgg | cgcgaccggc | gatattggta | 1920 |
| gcgcggtgtg | tcgctggctg | gtcaataaga | ccggcattag | cgaactgctg | atggtcgctc | 1980 |
| gccaacaaca | gccactgacc | ctgctgcaaa | aagaactgga | cggtggcacc | atcaagagcc | 2040 |
| tggatgaagc | cctgccgcag | gcggatattg | tcgtgtgggt | tgcttcgatg | cctaagacga | 2100 |

```
tcgaaattga gattgaaaac ctgaaaaagc cgtgcctgat gatcgacggt ggctacccga   2160
agaatctgga cgagaaattc aaaggcaaaa acattcacgt gttgaagggt ggtatcgtcg   2220 agttttttcaa cgacattggc tggaacatga tggagttggc ggagatgcaa aacccgcagc   2280
gtgagatgtt tgcgtgcttc gccgaagcta tgattctgga gtttgagaaa tgccatacca   2340
actttagctg gggccgtaac aatatcagct ggagaagat ggagttcatc ggtgctgcat    2400
ctctgaagca cggtttcagc gcgatcggtc tggataaaca gccgaaagtc ttgaccgttt   2460
gaaattgaat tcggttttcc gtcctgtctt gattttcaag caaacaatgc ctccgatttc   2520
taatcggagg catttgtttt tgtttattgc aaaaacaaaa aatattgtta caaatttta    2580 caggctatta agcctaccgt cataaataat ttgccattta ctagttttta attaaccaga   2640
accttgaccg aacgcagcgg tggtaacggc gcagtggcgg ttttcatggc ttgttatgac   2700 tgttttttg gggtacagtc tatgcctcgg gcatccaagc agcaagcgcg ttacgccgtg    2760
ggtcgatgtt tgatgttatg gagcagcaac gatgttacgc agcagggcag tcgccctaaa   2820
acaaagttaa acatcatgag ggaagcggtg atcgccgaag tatcgactca actatcagag   2880
gtagttggcg tcatcgagcg ccatctcgaa ccgacgttgc tggccgtaca tttgtacggc   2940
tccgcagtgg atggcggcct gaagccacac agtgatattg atttgctggt tacggtgacc   3000
gtaaggcttg atgaaacaac gcggcgagct ttgatcaacg acctttttgga aacttcggct   3060 tccctggag agagcgagat tctccgcgct gtagaagtca ccattgttgt gcacgacgac    3120
atcattccgt ggcgttatcc agctaagcgc gaactgcaat ttggagaatg gcagcgcaat   3180
gacattcttg caggtatctt cgagccagcc acgatcgaca ttgatctggc tatcttgctg   3240
acaaaagcaa gagaacatag cgttgccttg gtaggtccag cggcggagga actctttgat   3300
ccggttcctg aacaggatct atttgaggcg ctaaatgaaa ccttaacgct atggaactcg   3360
ccgcccgact gggctggcga tgagcgaaat gtagtgctta cgttgtcccg catttggtac   3420
agcgcagtaa ccggcaaaat cgcgccgaag gatgtcgctg ccgactgggc aatggagcgc   3480
ctgccggccc agtatcagcc cgtcatactt gaagctagac aggcttatct tggacaagaa   3540
gaagatcgct tggcctcgcg cgcagatcag ttggaagaat ttgtccacta cgtgaaaggc   3600
gagatcacca aggtagtcgg caaataatgt ctaacaattc gttcaagccg acgccgcttc   3660
gcggcgcggc ttaactcaag cgttagatgc actaagcaca taattgctca cagccaaact   3720
atcaggtcaa gtctgctttt attattttta agcgtgcata ataagcccta cacaaattgg   3780
gagatatatc atgaggcgcg ccacgagtgc ggggaaattt cggggggcgat cgcccctata   3840 tcgcaaaaag gagttacccc atcagagcta tagtcgagaa gaaaaccatc attcactcaa   3900
caaggctatg tcagaagaga aactagaccg gatcgaagca gccctagagc aattggataa   3960
ggatgtgcaa acgctccaaa cagagcttca gcaatcccaa aaatggcagg acaggacatg   4020
ggatgttgtg aagtgggtag gcggaatctc agcgggccta gcgtgagcg cttccattgc     4080 cctgttcggg ttggtcttta gattttctgt ttccctgcca taaaagcaca ttcttataag   4140
tcatacttgt ttacatcaag gaacaaaaac ggcattgtgc cttgcaaggc acaatgtctt   4200
tctcttatgc acagatgggg actggaaacc acacgcacaa ttcccttaaa aagcaaccgc   4260
aaaaaataac catcaaaata aaactggaca aattctcatg tgggccggcc aaaatgaagt   4320
gaagttccta tactttctag agaataggaa cttctatagt gagtcgaata agggcgacac   4380
aaaatttatt ctaaatgcat aataaatact gataacatct tatagtttgt attatatttt   4440
gtattatcgt tgacatgtat aattttgata tcaaaaactg attttcctt tattattttc    4500
```

```
gagatttatt ttcttaattc tctttaacaa actagaaata ttgtatatac aaaaaatcat   4560
aaataataga tgaatagttt aattataggt gttcatcaat cgaaaaagca acgtatctta   4620
tttaaagtgc gttgctttt tctcatttat aaggttaaat aattctcata tatcaagcaa   4680
agtgacaggc gcccttaaat attctgacaa atgctctttc cctaaactcc ccccataaaa   4740
aaacccgccg aagcgggttt ttacgttatt tgcggattaa cgattactcg ttatcagaac   4800
cgcccagggg gcccgagctt aagactggcc gtcgttttac aacacagaaa gagtttgtag   4860
aaacgcaaaa aggccatccg tcaggggcct tctgcttagt ttgatgcctg cagttccct    4920
actctcgcct tccgcttcct cgctcactga ctcgctgcgc tcggtcgttc ggctgcggcg   4980
agcggtatca gctcactcaa aggcggtaat acggttatcc acagaatcag gggataacgc   5040
aggaaagaac atgtgagcaa aaggccagca aaaggccagg aaccgtaaaa aggccgcgtt   5100
gctggcgttt ttccataggc tccgccccc tgacgagcat cacaaaaatc gacgctcaag   5160
tcagaggtgg cgaaacccga caggactata aagataccag gcgtttcccc ctggaagctc   5220
cctcgtgcgc tctcctgttc cgaccctgcc gcttaccgga tacctgtccg cctttctccc   5280
ttcgggaagc gtggcgcttt ctcatagctc acgctgtagg tatctcagtt cggtgtaggt   5340
cgttcgctcc aagctgggct gtgtgcacga accccccgtt cagcccgacc gctgcgcctt   5400
atccggtaac tatcgtcttg agtccaaccc ggtaagacac gacttatcgc cactggcagc   5460
agccactggt aacaggatta gcagagcgag gtatgtaggc ggtgctacag agttcttgaa   5520
gtggtgggct aactacggct acactagaag aacagtattt ggtatctgcg ctctgctgaa   5580
gccagttacc ttcggaaaaa gagttggtag ctcttgatcc ggcaaacaaa ccaccgctgg   5640
tagcggtggt ttttttgttt gcaagcagca gattacgcgc agaaaaaaag gatctcaaga   5700
agatcctttg atcttttcta cggggtctga cgctcagtgg aacgacgcgc gcgtaactca   5760
cgttaaggga ttttggtcat gagcttgcgc cgtcccgtca agtcagcgta atgctctgct   5820
tttaccaatg cttaatcagt gaggcaccta tctcagcgat ctgtctattt cgttcatcca   5880
tagttgcctg actccccgtc gtgtagataa ctacgatacg ggagggctta ccatctggcc   5940
ccagcgctgc gatgataccg cgagaaccac gctcaccggc tccggattta tcagcaataa   6000
accagccagc cggaagggcc gagcgcagaa gtggtcctgc aactttatcc gcctccatcc   6060
agtctattaa ttgttgccgg gaagctagag taagtagttc gccagttaat agtttgcgca   6120
acgttgttgc catcgctaca ggcatcgtgg tgtcacgctc gtcgtttggt atggcttcat   6180
tcagctccgg ttcccaacga tcaaggcgag ttacatgatc cccatgttg tgcaaaaaag   6240
cggttagctc cttcggtcct ccgatcgttg tcagaagtaa gttggccgca gtgttatcac   6300
tcatggttat ggcagcactg cataattctc ttactgtcat gccatccgta agatgctttt   6360
ctgtgactgg tgagtactca accaagtcat tctgagaata gtgtatgcgg cgaccgagtt   6420
gctcttgccc ggcgtcaata cgggataata ccgcgccaca tagcagaact ttaaaagtgc   6480
tcatcattgg aaaacgttct tcggggcgaa aactctcaag gatcttaccg ctgttgagat   6540
ccagttcgat gtaacccact cgtgcaccca actgatcttc agcatctttt actttcacca   6600
gcgtttctgg gtgagcaaaa acaggaaggc aaaatgccgc aaaaaaggga ataagggcga   6660
cacgaaaatg ttgaatactc atattcttcc tttttcaata ttattgaagc atttatcagg   6720
gttattgtct catgagcgga tacatatttg aatgtattta gaaaaataaa caaatagggg   6780
tcagtgttac aaccaattaa ccaattctga acattatcgc gagcccattt atacctgaat   6840
atggctcata cacccccttg tttgcctggc ggcagtagcg cggtggtccc acctgacccc   6900
```

```
atgccgaact cagaagtgaa acgccgtagc gccgatggta gtgtgggac tccccatgcg    6960 agagtaggga actgccaggc atcaaataaa acgaaaggct cagtcgaaag actgggcctt   7020
tcgcccgggc taattatggg gtgtcgccct tattcgactc tatagtgaag ttcctattct   7080
ctagaaagta taggaacttc tgaagtgggg cctgcagg                           7118
```

<210> SEQ ID NO 18
<211> LENGTH: 13852
<212> TYPE: DNA
<213> ORGANISM: Artificial Sequence
<220> FEATURE:
<223> OTHER INFORMATION: Description of Artificial Sequence: Synthetic plasmid pJB825t

<400> SEQUENCE: 18

```
tgggagtcaa taaacccgat gtgcgttgga tttgccacta ccagccgccc ctgcaactca     60
gtgaatatct ccaagaggtg ggacgcgctg ggcgagatgg cgaagcggca caggccctgg    120
ttttggtgag cgatcgctgg ggcttggatc gcgaagatca acagcgttgg tcttttttc    180 agcaccaaag tcaagacacc tacaatcgcg ccatggcact tcagacgcag ctgcccctcc    240
agggtaatct gcagcaactg cggcaacact ttcctgaagt ggaattgacc ctggcattac    300
tgcatcaaca gggggccctc cgctggcaag atccctttca ctattgccgt caacccttgg    360
cacaggtgcc accccaccc aaagaccctc aagaacagtt gatgcaaaag ttcctctatc    420
accggggctg ccgctggcag tttctcctcc aagcctttgg ttttgccact gaggcaaggg    480
gattccactg tggccattgc gatcgctgtc ggccgccgca ccgctcccgc aaaataccgt    540
aaattgccag cgctgtatca ctggaatatt gggtacactg gcacatagaa cggtcgcttt    600
accattggta ggcaaaagtt tctcagcagt cattctgttg ccgcaaggta ggggttgcag    660
gcatggggct actacaagtt gaggaaattc gcgaagcact tcaagatgtg ctttcagaac    720
acgcccttgt tgtgcaagtt aatcagtttc gcaaccaatt aaacattatt ttgaacaagc    780
cccccggcac cgttgcccat tattctgccc tagcggattt tctcaagtcg cgcttgggac    840
agtttcatct caatgatatt gaccgcatta aaataattgg ccgcatacag ggttcgccta    900
aacccgattg ggaagaggtc attgatctac gtcccccaa cccagcccta gctgcccctg    960
tgtatgcttc ttctgccccg tgggtggtgg cgatcgctgc tggctttgtc agtttactgg   1020
tgatctttag ctatcacctt ggtcagtagc agcaacagca acggctgtag ccgttgatcg   1080
aaggttcctt tggtcaaaag ggcgtcgtga tgacggactt taagtggcac attgaggtg    1140 gtacagggtt tattgtcggg gttcttaaaa actacagtaa agggtatttt cgcttagttc   1200
aggcggactt tgaactcttt gaccaaggcg gtcagcaagt tgggacagtg gcggtacagg   1260
tttatggtct tggccctgag gaaacatggc aattccgtga actgatagcc aatcatcagg   1320
cagtgcgagc acggctggta aaattacagt cattcaatta aggttttct aatgtttagg    1380 tttccccagc agggagcgac accgcttgct atggcacacc ttaaagccct gatctttgat   1440
gtcgatggca ccttagcaga tacgagcgg gatggccatc gtatcgcctt caacaaggcc   1500
tttgccgccg ctggtctaga ttgggaatgg gacattcccc tctatggtca actcctggcg   1560
gtggctgggg caaggagcg gatcggtat taccttgagt gctttcgtcc cgattggcca    1620
cgtccccaaa atttggatgc tctgattgcc gatttacaca aggccaagac ccgctattat   1680
accgagctat tggcggcagg ggctattccc ctgcggccgg gggtgaaacg gctcctcact   1740
gaagcccggg aagcaggatt acgtttggcg atcgccacca cgaccacccc tgccaatgtc   1800
accgcactcc ttgaaaatgc cctcgctcct gatggcgtca gttggtttga gataattgct   1860
```

```
gccggggatg tagttccagc caagaaaccc gcgcccgaca tttacttcta cacgcttgaa    1920
aagatgcgcc tctcacccca agagtgcctt gcctttgagg attccgccaa tgggattcag    1980
gcggccactg ccagtcacct agcgaccatt atcacgatta ccgactacac caaggatcat    2040
gattttcgtg atgcagcgct ggtcttggat tgcttagggg aaccggacta ccccttttcag    2100 gttctgcgcg gtgaggtggg ttggacaacc tatgtggatg tccccctatt gcgatcgctg    2160
caccagcagt ggacaagcac gttgagtcag ggataatttt ctggccgcag cgttttacat    2220
tgaatatgac ccccttagtc tgaggatcaa ggaacataat gtacgcgatt gatttaattc    2280
tgcgtcatgt ccccatgccc gtcagcattg aacgcaagga aagtgcagca gcgatggcag    2340
tctatcagca aattcagcag gccatggcca gtggtactcc aactttcctc gaactgacgt    2400
gcgatcgcca agtgggcaag aagttaacgg tgctcacctc agaaattgtc gccgtgcaaa    2460
tggcggataa ggatgccccc tccagtacta tcagtcgtgg gggattcttt gctcaattag    2520
tgcagcaaac cagcaactga gggaaaatgc ctcaataaag ttgagttttt cttggcaatg    2580
ctgattcttt gccgttagga tactaagcag accgatccgt aggggaacgt gaagcaaatc    2640
ctccccgtct gaaagtcagg tatctctggt gtgtcgtaat agggttgtct atggtgcagc    2700
gtttcctgcc ggttctgatt ttgttggggt gtagttttgg tcttgcgacc cctgcccttg    2760
tgcgtgccca agccaatcag ggctttacgt ttacttgggg tgaggggccg agtggccgac    2820
agcagttgca ataccactta gataacggca ccccggtttt tatgggcgat cgctattggc    2880
tgcggctggg tcagcagaaa gtggccatca atcgcattaa cattacctat cccgactact    2940
acaacggtat tattgatccc aaaggcattg aggtgcgcat cggtggcgat cgcggcaatc    3000
gcttcttcca atttcgccgt gaccccggca ccaaaattca attggcggaa gtctccgttg    3060
atcgcgataa ccgcgtgatt gatattgtgc cggctgaggt gattcccgcc ggaacaccgg    3120
tgcaagttat tctcaataat gtgcgcaacc ctaacaatgg cggcatgtac tatttcaatg    3180
cccgcattgg ctcccctgga gatattcccc tcatgcgcta cgttggcacc tggattctca    3240
gcattgccaa taactaaaac ccgtcaaact cgagcattgg tgagcgggtt agccatttct    3300
aactattgcg gggcgatcgc cctagactag ttttttgtct attattgccg gttcactctt    3360
tacaccagat gccagattcc gttaggtctt cattcccctc catttctcct ctgctcacgc    3420
ctctgatgta ccgcctcgtg ggggacgttg tcctgcggcg ctattttcgt acccttgagg    3480
tgcaagggca ggagcgggtg ccccaaaggg gtccagtgat cttggccccc acccaccgtt    3540
cccgctggga tgcgctgatt attccctatg tcactgggcg gcgggtgagt gggcgcgacc    3600
tctactacat ggtgtcccac gatgagatgt tgggactaca gggctgggtg attgctcagt    3660
gtggcggttt tcccgtcaat acccaagcgc cttcggtgag tgcgttgcgt acgggtgtgg    3720
aactgctccg gcaggggcaa gccttggtgg tgttccctga ggggaatatc tttcgcgatc    3780
gccagattca tcccctcaag ccgggggttgg ctcgcttagc ccttcaggcg gcccagcgct    3840
gtgaacaagc aatccagatt ctgccaattt tactcgatta tgcccagccc tacccacagt    3900
ggggaagtgc ggtcaaggta atcattgggg ctcccttgag taccgacaat tacgatgcca    3960
gccggccaaa aagtgctgcc caacaactga ccagtgatct ctttagaaga cttcagcagc    4020 tccaggggg gcgatcgccc ctgtgttttg cttagacctc aaacttccat ccccgcggcc    4080
gctcttgata acccaagagg gcatttttta ggcgcgcctc gagtaacacc gtgcgtgttg    4140 actatttac ctctggcggt gataatggtt gcaggatcct tttgctggag gaagaattca    4200
tgacaacggc taccgctaca cctgtttttgg actaccatag cgatcgctac aaggatgcct    4260
```

```
acagccgcat taacgccatt gtcattgaag gtgaacagga agctcacgat aactatatcg    4320
atttagccaa gctgctgcca caacaccaag aggaactcac ccgccttgcc aagatggaag    4380
ctcgccacaa aaagggcttt gaggcctgtg gtcgcaaccct gagcgtaacg ccagatatgg    4440
aatttgccaa agccttcttt gaaaaactgc gcgctaactt tcagagggct ctggcggagg    4500
gaaaaactgc gacttgtctt ctgattcaag cttttgatcat cgaatccttt gcgatcgcgg    4560
cctacaacat ctacatccca atggcggatc ctttcgcccg taaaattact gagagtgttg    4620
ttaaggacga atacagccac ctcaactttg gcgaaatctg gctcaaggaa cactttgaaa    4680
gcgtcaaagg agagctcgaa gaagccaatc gcgccaattt acccttggtc tggaaaatgc    4740
tcaaccaagt ggaagcagat gccaaagtgc tcggcatgga aaagatgcc cttgtggaag    4800 acttcatgat tcagtacagt ggtgccctag aaaatatcgg ctttaccacc cgcgaaatta    4860
tgaagatgtc agtttatggc ctcactgggg cataatggtg gcttaacgta tcgttacatt    4920
tcagtcacca cacgcttgta tgtttggatt aattggtcat ctgacgagtc tggagcacgc    4980
ccaagccgtt gcccatcagt tgggttaccc cgaatatgcc gatcaaggct tggaattttg    5040
gtgtatggca ccgccgcaga tcgtcgatga gattacggtg acgagcgtaa cgggcaaaac    5100
tatctatggc aaatacgttg agtcctgctt tttaccagag atgctggcca accagcgggt    5160
gaaggcagca actcgcaaag ttattaacgc catggcccat gcccaaaagc acaacattga    5220
cattacggcc ttgggggct tctcctcgat catctttgag aactttgatc tggagaaaat    5280
gtcccacatt cgcaacattg aactggactt tcgccgcttt acaacgggga atacccatac    5340
cgcctatatc atctgccaac aaattgagca ggcggcgccc caagtgggga ttgatttgcg    5400
gcaggcaacc gtggctgttt gtggggctac ggggatatt ggtagtgccg tctgccgttg    5460
gttgaatacc tgtttagatg tgcaagatct cttactcgta gcacggaatc gcgatcgcct    5520
gctggagcta caggcggaat tgggacgggg gaaaatcctc gacttgatgg aggcgctgcc    5580
ccttgccgat attgtggttt gggtggccag tatgcccaag ggagttgagc tgagcattga    5640
gcagttaaaa cgcccctccc tgatgattga tggtggttat cccaaaaata tggccaccaa    5700
aattcagcac ccccagattc atgttctcaa tggtggcatt gtcgagcatg ccctcgacat    5760
tgactgaaaa attatggaaa ttgtgaatat ggatgtgccc tcgcggcaga tgtttgcctg    5820
ttttgcagag gctatgcttt tagagttcga gggctggcac accaatttct cttggggacg    5880
caatcaaatc actgtggaaa agatgcagca aattggtgag gtctcccgta acatggatt    5940 tcagccacta ctgttgaatc ctcagtaagc ggccgcaaaa aaaacgggcc ggcgtattat    6000
cgccggcccg agtaacaccg tgcgtgttga ctatttacc tctggcggtg ataatggttg    6060
caggatcctt ttgctggagg aaaaccatat gaaaggacca ataataatga ctagagaaga    6120
aagaatgaag attgttcatg aaattaagga acgaatattg gataaatatg gggatgatgt    6180
taaggcaatt ggtgtttatg gctctcttgg tcgtcagact gatgggccct attcggatat    6240
tgagatgatg tgtgttctgt caacagaggg agtagagttc agctatgaat ggacaaccgg    6300
tgagtggaag gcggaagtga atttttatag cgaagagatt ctactagatt atgcatctcg    6360
ggtggaaccg gattggccgc ttacacatgg tcgattttc tctatttgc cgatttatga    6420 tccaggtgga tactttgaga aagtgtacca aactgctaaa tcggtagaag cccaaaagtt    6480
ccacgatgcg atctgtgccc ttatcgtaga agagctgttt gaatatgcag gcaaatggcg    6540
taatattcgt gtgcaaggac cgacaacatt tctaccatcc ttgactgtac aggtggcaat    6600
ggcaggtgcc atgttgattg gtctgcatca tcgcatctgt tatacgacga gcgcttcggt    6660
```

```
cttaactgaa gcagttaagc aaccagatct tcctccaggt tatgtccaac tgtgccagct   6720
cgtaatgtct ggtcaacttt ccgaccctga gaaacttctg gaatcgctag agaatttctg   6780
gaatggggtt caggagtggg cggaacgaca cggatatata gtggatgtgt caaaacgcat   6840
accattttga tgtctaaccc ccttccttgc ccacagcttc gtcgatggcg cgaaatttcg   6900
ggtaaatata atgaccctct tgataaccca agagggcatt ttttaggcgc gccctaagcg   6960
tccgtaggca caattaaggc ttcaaattgt tggcgaagct gctcagtcac ttccttgacg   7020
gcttgccgtg cccccttggcg atcgcgccgg tacagaggcc aatagctctc taaattgaga   7080
gggtcgccga cactgaggcg cacctgccgc aaacccacca acgattgag attcgagctt    7140 tttccctcta gccaatcaaa tgtgcgcag agaatcagcg cgacatctgc aaagcgatga    7200
atcgtgaatt tctcacggat atagctaccc gtaattgagg taaatcgctc cgcaagacgc   7260
atatgacgca atcgcacatt ggcttcctcg gccaaccaat cggctaggca gcgctctacg   7320
gccgaaagtt gtgccaaatc actgcgaaac atccgttccc aagcagcctg ttcaatgcgt    7380
cggcagcgac tcacaaaatc ggcactgggc ttcagaccaa agtaggactc tgccaccaca   7440
agggcgctgt tgaggaggcg ctgaattcgc gctgccaatt tagcattggc agagtcaaag   7500
gggggcagtt cgggaaaatc ttgaccatag gaggtggcat aaaaagcctc caggcgatcc   7560
aagaggtgga tcgctaaatt cagcaggcgg cggtagaggt cgtctggctg ggtactgtga   7620
gaatctgtag ggcacccaag gcggttctcc agttgtgcca tcagccttgc catgcgctcc   7680
caagagggct gactgaggct gtactgaatg ccaatgggaa gaatgaccac ggggagcgat   7740
cgccccgcct tggctaaatc ttctagacac caaaatccca gttgggccac ccccggctcc   7800
aaaggtgcga ccagttcgtt gtgctcattc gttgctccct ccggcgctgc cgctagggga   7860
aatcgtcctc cgagaagtag ctcccgcgct gagcgcaggg cttggctatc gagcttaccg    7920
cgcatgatga aaatccccccc caaccgtgaa aagagccaac caatctgcgc ccctgcccag   7980
aggggaatcc cgcgatcgta gagaaaatag ccatttgtcg gcggacgcaa gggaatgccc   8040
agccgccgtg ctgtttgcgg cagtaaatgc cacatcaaat agcccatcac caacggatca    8100
tccgtacagg gatggcgaaa ggcaatgagg agccggacct gtccctgctg aaactgctgg   8160
taataacggg caagggtctc cacattcacc ccttcaaccc gctgtagccc aagaccatag    8220
cgaatgtaga ggggcaggag tcttgctact gtccaccaga cggggtagct aaaccgctgg   8280
gggagaaaat gcaacggcgg ttgggcagtt gtcactacac tggacattag gcaagctcct    8340
cagggcaatg gctaaactga ggcagtggcc aactccgcaa ttaactgctc taacatcggt   8400
tgatcggccc aatagacagc attacaaaac tgacaggtgg cttctgcctt tgcctctgtg   8460
gctaggatat ctcttaattc tgcctcccct aggagcttga gtgccgctaa catccgttca   8520
tgggaacagc cacagtggaa gcgcaccatt tgccgttggg gcaagatttg taaatccata   8580 tccccctaaga gttcctgaaa gatatctggc agtgtccgcc ctgcctgtag cagtggtgta   8640
aagcccttaa gattggccac ccgttgttca agggtcgcga tcaggtgttc atcattggcc    8700
gctttgggta gcacctgtaa catcaaccca ccggcggcag tcaccccgga ctcttcgaca   8760
aaaacaccca acatcagggc ggagggggtt tgctctgagg tggcgaggta gtaggtgatg   8820
tcttctgcaa tttcgccgga gactagctcc accgtgctgg aataggggta gccgtagcca   8880
agatcgtgga tgacgtagag atatccctga tggcccaccg ctgccccac atcgagtttg    8940 cccttggcat tgggggggcag ttcaacactg gggtactgca catagccgcg aactgtgcca   9000
tcggcaccag catcggcaaa aatggttcct aggggaccgt tgccctgaat gcgcacattc   9060
```

```
acccgtgctt ggggctgttt gaaactggag gcaaggatta agcctgcggc catggttcgt    9120
cccaaggccg ctgtggccac gtaggacagt tggtgacgtt tgcgggcttc atcagtgagt    9180
tgagtggtaa tcacacctac ggcccggatg ccttcggcag cggcagttgc tcgcaacaga    9240
aaatcggcca tgttcaacct acgaaatgtt ttgttacatt tagtgtgaca tactcccacc    9300
gctgaccagg gcacaatggg gcaaaaaacc atcaatcctg cctttggtga ccgatccagt    9360
acagccagcc agggcttaag actgggaaga cccctagcac tggggctaga aaattggcga    9420
tgataggcaa gcaatagtca ttcagcgtcc agtcattccg cctatggcca tgcccctcac    9480
tgtcttgcct gccacaactg ttttgacaga agcgactcaa ttgccccagg gcggcttgat    9540
tacggagatt ccgacgctgg cgatcgccca ccgtttggcc cagcagttgc gccgccattg    9600
gcccctagag acccccttaa cgctgattga tgcgcaatac cagagtatcc ccctgaccct    9660
tggggaattg gccgagctca ccgatgccaa ctgtcctttta cagctctatg tgccgccccc    9720
cttgccagag gccttgacgc aatttcaacg cctgatggat gtggttcgag agctgcgcca    9780
tccggagcgt ggctgtcctt gggatttgca gcaaacccca accagtctca ttccctatgt    9840
ccttgaggaa gcctatgaag tggtacatgc cctgcaggag ggagatgcgg gggcgatcgc    9900
cgaagaattg ggagacctgt tgcttcaagt tgttctccag agccaacttg cccaagaagc    9960
cggccaattt acccttgctc aagtcattca aaggattacc gataaactca tccgccgcca   10020 tcccccacgtc tttggtgaag tggcactcac cactgctcaa gaggtgcgcg accaatggga   10080
gcaaatcaaa gcggctgaaa aaggcaccga actcccctg agtcaaacgc tgcaacgtta    10140
cgcacgcacc ctcccacccc tgatggccgg catgaaaatt ggtgagcgag ccagtcgcgc   10200
tggcctcgat tggccgacga ttagtggtgc atgggagaaa ttttacgagg aactggcgga   10260
gtttcaggag gcccttctgc aagggaatgc tgagcaacag gcagcggaat taggagacct   10320
gctcttcagt gtgattaacc ttgcccgctg gtgccaactg gatcctgtta atgccctgca   10380
acaaacctac caacgcttta ttcaacgctt ggcctgtatt gaggcagtca tcgatcgccc   10440
ccttgagacg tacaccctag aagaactaga agccctctgg caacaggcca aagtacagtt   10500
agccaccgac agcgaggcaa cccctatgga gactgaggaa gaggcctagt ccgctgcggc   10560
ccttgccacc ttcagttcat cgagattcca caggggcccc cccagcgccg tgggcttggc   10620
gccaatgaca tgattgcgaa aagctgtaag ggagagggga ttcacgaggt aaataaaggg   10680
gagatattcc tgagctagtc gttgggcttc cgcataaatt tgctgccgtc gttccagatt   10740
gagctcctgg gcaccttgga catacaggtc actgatgcgc tgctcccagt cagcgacgac   10800
tcgacccgta atgggtggtt gattcggtga cggttgctga ttgaatgtat gcaaaaggcc   10860
atccacacgc cagatattgg caccgctatt gggttcattg cccccccccag taaagccgag   10920 gatatgggct tcccactcta gggaattgga gagacgatcc acgagggtac caaaggccaa   10980
aaattgcaga tccacctgca tgccgatcgc ccctaggtcc tgctgaactt gcgtcgggcc   11040
ggccaaaatg aagtgaagtt cctatacttt ctagagaata ggaacttcta tagtgagtcg   11100
aataagggcg acacaaaatt tattctaaat gcataataaa tactgataac atcttatagt   11160
ttgtattata ttttgtatta tcgttgacat gtataatttt gatatcaaaa actgattttc   11220
cctttattat tttcgagatt tattttctta attctcttta acaaactaga aatattgtat   11280
atacaaaaaa tcataaataa tagatgaata gtttaattat aggtgttcat caatcgaaaa   11340
agcaacgtat cttatttaaa gtgcgttgct ttttctcat ttataaggtt aaataattct    11400
catatatcaa gcaaagtgac aggcgccctt aaatattctg acaaatgctc tttccctaaa   11460
```

```
ctcccccat aaaaaaaccc gccgaagcgg gtttttacgt tatttgcgga ttaacgatta    11520
ctcgttatca gaaccgccca gggggcccga gcttaagact ggccgtcgtt ttacaacaca    11580
gaaagagttt gtagaaacgc aaaaaggcca tccgtcaggg gccttctgct tagtttgatg    11640
cctggcagtt ccctactctc gccttccgct tcctcgctca ctgactcgct gcgctcggtc    11700
gttcggctgc ggcgagcggt atcagctcac tcaaaggcgg taatacggtt atccacagaa    11760
tcaggggata acgcaggaaa gaacatgtga gcaaaaggcc agcaaaaggc caggaaccgt    11820
aaaaaggccg cgttgctggc gtttttccat aggctccgcc ccctgacga gcatcacaaa    11880 aatcgacgct caagtcagag gtggcgaaac ccgacaggac tataaagata ccaggcgttt    11940
ccccctggaa gctccctcgt gcgctctcct gttccgaccc tgccgcttac cggatacctg    12000
tccgcctttc tcccttcggg aagcgtggcg ctttctcata gctcacgctg taggtatctc    12060
agttcggtgt aggtcgttcg ctccaagctg ggctgtgtgc acgaaccccc cgttcagccc    12120
gaccgctgcg ccttatccgg taactatcgt cttgagtcca acccggtaag acacgactta    12180
tcgccactgg cagcagccac tggtaacagg attagcagag cgaggtatgt aggcggtgct    12240
acagagttct tgaagtggtg gcctaactac ggctacacta agaacagt atttggtatc    12300 tgcgctctgc tgaagccagt taccttcgga aaagagttg gtagctcttg atccggcaaa    12360
caaaccaccg ctggtagcgg tggttttttt gtttgcaagc agcagattac gcgcagaaaa    12420
aaaggatctc aagaagatcc tttgatcttt tctacggggt ctgacgctca gtggaacgac    12480
gcgcgcgtaa ctcacgttaa gggattttgg tcatgagctt gcgccgtccc gtcaagtcag    12540
cgtaatgctc tgcttttacc aatgcttaat cagtgaggca cctatctcag cgatctgtct    12600
atttcgttca tccatagttg cctgactccc cgtcgtgtag ataactacga tacgggaggg    12660
cttaccatct ggccccagcg ctgcgatgat accgcgagaa ccacgctcac cggctccgga    12720
tttatcagca ataaaccagc cagccggaag ggccgagcgc agaagtggtc ctgcaacttt    12780
atccgcctcc atccagtcta ttaattgttg ccgggaagct agagtaagta gttcgccagt    12840
taatagtttg cgcaacgttg ttgccatcgc tacaggcatc gtggtgtcac gctcgtcgtt    12900
tggtatggct tcattcagct ccggttccca acgatcaagg cgagttacat gatccccat    12960 gttgtgcaaa aaagcggtta gctccttcgg tcctccgatc gttgtcagaa gtaagttggc    13020
cgcagtgtta tcactcatgg ttatggcagc actgcataat tctcttactg tcatgccatc    13080
cgtaagatgc ttttctgtga ctggtgagta ctcaaccaag tcattctgag aatagtgtat    13140
gcggcgaccg agttgctctt gcccggcgtc aatacgggat aataccgcgc cacatagcag    13200
aactttaaaa gtgctcatca ttggaaaacg ttcttcgggg cgaaaactct caaggatctt    13260
accgctgttg agatccagtt cgatgtaacc cactcgtgca cccaactgat cttcagcatc    13320
ttttactttc accagcgttt ctgggtgagc aaaaacagga aggcaaaatg ccgcaaaaaa    13380
gggaataagg gcgacacgga aatgttgaat actcatattc ttccttttc aatattattg    13440 aagcatttat cagggttatt gtctcatgag cggatacata tttgaatgta tttagaaaaa    13500
taaacaaata ggggtcagtg ttacaaccaa ttaaccaatt ctgaacatta tcgcgagccc    13560
atttatacct gaatatggct cataacaccc cttgtttgcc tggcggcagt agcgcggtgg    13620
tcccacctga ccccatgccg aactcagaag tgaaacgccg tagcgccgat ggtagtgtgg    13680
ggactcccca tgcgagagta gggaactgcc aggcatcaaa taaaacgaaa ggctcagtcg    13740
aaagactggg cctttcgccc gggctaatta tggggtgtcg cccttattcg actctatagt    13800
gaagttccta ttctctagaa agtataggaa cttctgaagt ggggcctgca gg           13852
```

<210> SEQ ID NO 19
<211> LENGTH: 92
<212> TYPE: DNA
<213> ORGANISM: Artificial Sequence
<220> FEATURE:
<223> OTHER INFORMATION: Description of Artificial Sequence: Synthetic
      PcI promoter

<400> SEQUENCE: 19
gcggccgctc gagtaacacc gtgcgtgttg actattttac ctctggcggt gataatggtt     60
gcaggatcct tttgctggag gaaaaccata tg                                   92

<210> SEQ ID NO 20
<211> LENGTH: 605
<212> TYPE: DNA
<213> ORGANISM: Artificial Sequence
<220> FEATURE:
<223> OTHER INFORMATION: Description of Artificial Sequence: Synthetic
      PcpcB promoter

<400> SEQUENCE: 20
gcggccgctt cgttataaaa taaacttaac aaatctatac ccacctgtag agaagagtcc     60
ctgaatatca aaatggtggg ataaaaagct caaaaaggaa agtaggctgt ggttccctag    120
gcaacagtct tccctacccc actggaaact aaaaaaacga gaaagttcg caccgaacat     180 caattgcata attttagccc taaaacataa gctgaacgaa actggttgtc ttcccttccc    240
aatccaggac aatctgagaa tcccctgcaa cattacttaa caaaaagca ggaataaaat     300 taacaagatg taacagacat aagtcccatc accgttgtat aaagttaact gtgggattgc    360
aaaagcattc aagcctaggc gctgagctgt ttgagcatcc cggtggccct tgtcgctgcc    420
tccgtgtttc tccctggatt tatttaggta atatctctca taaatccccg ggtagttaac    480
gaaagttaat ggagatcagt aacaataact ctagggtcat tactttggac tccctcagtt    540
tatccggggg aattgtgttt aagaaaatcc caactcataa agtcaagtag gagattaatc    600
atatg                                                                605

<210> SEQ ID NO 21
<211> LENGTH: 1510
<212> TYPE: DNA
<213> ORGANISM: Artificial Sequence
<220> FEATURE:
<223> OTHER INFORMATION: Description of Artificial Sequence: Synthetic
      PlacI-trc promoter

<400> SEQUENCE: 21
gcggccgcga aggcgaagcg gcatgcattt acgttgacac catcgaatgg tgcaaaacct     60
ttcgcggtat ggcatgatag cgcccggaag agagtcaatt cagggtggtg aatatgaaac    120
cagtaacgtt atacgatgtc gcagagtatg ccggtgtctc ttatcagacc gtttcccgcg    180
tggtgaacca ggccagccac gtttctgcga aaacgcggga aaaagtggaa gcggcgatgg    240
cggagctgaa ttacattccc aaccgcgtgg cacaacaact ggcgggcaaa cagtcgttgc    300
tgattggcgt tgccacctcc agtctggccc tgcacgcgcc gtcgcaaatt gtcgcggcga    360
ttaaatctcg cgccgatcaa ctgggtgcca gcgtggtggt gtcgatggta gaacgaagcg    420
gcgtcgaagc ctgtaaagcg gcggtgcaca atcttctcgc gcaacgcgtc agtgggctga    480
tcattaacta tccgctggat gaccaggatg ccattgctgt ggaagctgcc tgcactaatg    540
ttccggcgtt atttcttgat gtctctgacc agacacccat caacagtatt attttctccc    600

-continued

| | |
|---|---|
| atgaagacgg tacgcgactg ggcgtggagc atctggtcgc attgggtcac cagcaaatcg | 660 |
| cgctgttagc gggcccatta agttctgtct cggcgcgtct gcgtctggct ggctggcata | 720 |
| aatatctcac tcgcaatcaa attcagccga tagcggaacg ggaaggcgac tggagtgcca | 780 |
| tgtccggttt tcaacaaacc atgcaaatgc tgaatgaggg catcgttccc actgcgatgc | 840 |
| tggttgccaa cgatcagatg gcgctgggcg caatgcgcgc cattaccgag tccgggctgc | 900 |
| gcgttggtgc ggatatctcg gtagtgggat acgacgatac cgaagacagc tcatgttata | 960 |
| tcccgccgtc aaccaccatc aaacaggatt ttcgcctgct ggggcaaacc agcgtggacc | 1020 |
| gcttgctgca actctctcag ggccaggcgg tgaagggcaa tcagctgttg cccgtctcac | 1080 |
| tggtgaaaag aaaaaccacc ctggcgccca atacgcaaac cgcctctccc cgcgcgttgg | 1140 |
| ccgattcatt aatgcagctg gcacgacagg tttcccgact ggaaagcggg cagtgagcgc | 1200 |
| aacgcaatta atgtgagtta gcgcgaattg atctggtttg acagcttatc atcgagctcg | 1260 |
| actgcacggt gcaccaatgc ttctggcgtc aggcagccat cggaagctgt ggtatggctg | 1320 |
| tgcaggtcgt aaatcactgc ataattcgtg tcgctcaagg cgcactcccg ttctggataa | 1380 |
| tgttttttgc gccgacatca taacggttct ggcaaatatt ctgaaatgag ctgttgacaa | 1440 |
| ttaatcatcc ggctcgtata atgtgtggaa ttgtgagcgg ataacaattt cacacaggaa | 1500 |
| acagcatatg | 1510 |

```
<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: Synthetic
      EM7 promoter

<400> SEQUENCE: 22
```

| | |
|---|---|
| gcggccgctg ttgacaatta atcatcggca tagtatatcg gcatagtata atacgacaag | 60 |
| gtgaggaact aacatatg | 78 |

```
<210> SEQ ID NO 23
<211> LENGTH: 341
<212> TYPE: PRT
<213> ORGANISM: Synechococcus elongatus

<400> SEQUENCE: 23
```

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
                20                  25                  30

Phe Trp Ser Ser Ala Pro Pro Gln Ile Val Asp Glu Ile Thr Val Thr
            35                  40                  45

Ser Ala Thr Gly Lys Val Ile His Gly Arg Tyr Ile Glu Ser Cys Phe
        50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala

```
            130                 135                 140
Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
                180                 185                 190

Arg Leu Asp Asn Leu Gln Ala Glu Leu Gly Arg Gly Lys Ile Leu Pro
                195                 200                 205

Leu Glu Ala Ala Leu Pro Glu Ala Asp Phe Ile Val Trp Val Ala Ser
210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
                260                 265                 270

Asp Ile Asp Trp Gln Ile Met Ser Ala Ala Glu Met Ala Arg Pro Glu
                275                 280                 285

Arg Gln Met Phe Ala Cys Phe Ala Glu Ala Met Leu Leu Glu Phe Glu
                290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
                340

<210> SEQ ID NO 24
<211> LENGTH: 341
<212> TYPE: PRT
<213> ORGANISM: Synechococcus elongatus

<400> SEQUENCE: 24

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
                20                  25                  30

Phe Trp Ser Ser Ala Pro Pro Gln Ile Val Asp Glu Ile Thr Val Thr
            35                  40                  45

Ser Ala Thr Gly Lys Val Ile His Gly Arg Tyr Ile Glu Ser Cys Phe
50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
                100                 105                 110

Ser Leu Arg Gln Val Arg Asp Thr Thr Leu Glu Phe Glu Arg Phe Thr
            115                 120                 125

Thr Gly Asn Thr His Thr Ala Tyr Val Ile Cys Arg Gln Val Glu Ala
            130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
```

```
                     165                 170                 175
Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
            195                 200                 205

Leu Glu Ala Ala Leu Pro Glu Ala Asp Phe Ile Val Trp Val Ala Ser
            210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
            275                 280                 285

Arg Gln Met Phe Ala Cys Phe Ala Glu Ala Met Leu Leu Glu Phe Glu
            290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340

<210> SEQ ID NO 25
<211> LENGTH: 339
<212> TYPE: PRT
<213> ORGANISM: Anabaena variabilis

<400> SEQUENCE: 25

Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Lys Val Thr
        35                  40                  45

Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190

Arg Leu Gln Glu Leu Gln Ser Glu Leu Gly Arg Gly Lys Ile Met Ser
```

-continued

```
                195                 200                 205
Leu Asp Glu Ala Leu Pro Gln Ala Asp Ile Val Val Trp Val Ala Ser
210                 215                 220

Met Pro Lys Gly Val Glu Ile Asn Pro Gln Val Leu Lys Gln Pro Cys
225                 230                 235                 240

Leu Leu Ile Asp Gly Tyr Pro Lys Asn Leu Gly Thr Lys Val Gln
                245                 250                 255

Tyr Pro Gly Val Tyr Val Leu Asn Gly Gly Ile Val Glu His Ser Leu
                260                 265                 270

Asp Ile Asp Trp Lys Ile Met Lys Ile Val Asn Met Asp Val Pro Ala
                275                 280                 285

Arg Gln Leu Phe Ala Cys Phe Ala Glu Ser Met Leu Leu Glu Phe Glu
                290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val

<210> SEQ ID NO 26
<211> LENGTH: 339
<212> TYPE: PRT
<213> ORGANISM: Nostoc sp.

<400> SEQUENCE: 26

Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
                20                  25                  30

Phe Trp Cys Ser Ala Pro Pro Gln Ile Val Asp His Ile Lys Val Thr
            35                  40                  45

Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys Asn Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190

Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
225                 230                 235                 240
```

Leu Leu Ile Asp Gly Gly Tyr Pro Lys Asn Leu Gly Thr Lys Val Gln
                245                 250                 255

Tyr Pro Gly Val Tyr Val Leu Asn Gly Gly Ile Val Glu His Ser Leu
            260                 265                 270

Asp Ile Asp Trp Lys Ile Met Lys Ile Val Asn Met Asp Val Pro Ala
            275                 280                 285

Arg Gln Leu Phe Ala Cys Phe Ala Glu Ser Met Leu Leu Glu Phe Glu
        290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val

<210> SEQ ID NO 27
<211> LENGTH: 339
<212> TYPE: PRT
<213> ORGANISM: Nostoc azollae

<400> SEQUENCE: 27

Met Phe Gly Leu Ile Gly His Leu Thr Ser Leu Glu His Ala Gln Ser
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Thr Val Thr
        35                  40                  45

Ser Ile Thr Gly Gln Lys Ile Glu Gly Arg Tyr Val Glu Ser Cys Phe
    50                  55                  60

Leu Pro Glu Met Leu Ala Asn Arg Arg Ile Lys Ala Ala Thr Arg Lys
65                  70                  75                  80

Ile Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Asn Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Glu
    130                 135                 140

Ala Ser Lys Gln Leu Gly Ile Glu Leu Ser Lys Ala Thr Val Ala Val
145                 150                 155                 160

Cys Gly Ala Thr Gly Asp Ile Gly Ser Ala Val Thr Arg Trp Leu Asp
                165                 170                 175

Lys Lys Thr Asp Val Gln Glu Leu Leu Leu Ile Ala Arg Asn Gln Glu
            180                 185                 190

Arg Leu Gln Glu Leu Gln Ala Glu Leu Gly Arg Gly Lys Ile Thr Asp
        195                 200                 205

Leu His Glu Ala Leu Pro Gln Ser Asp Ile Val Val Trp Val Ala Ser
    210                 215                 220

Met Pro Lys Gly Val Glu Ile Asp Pro Ile Val Leu Lys Gln Pro Cys
225                 230                 235                 240

Leu Leu Ile Asp Gly Gly Tyr Pro Lys Asn Leu Gly Thr Lys Ile Gln
                245                 250                 255

His Pro Gly Val Tyr Val Leu Asn Gly Gly Ile Val Glu His Ser Leu
            260                 265                 270

```
Asp Ile Asp Trp Lys Ile Met Lys Ile Val Ser Met Glu Val Pro Gly
        275                 280                 285

Arg Gln Leu Phe Ala Cys Phe Ala Glu Ser Met Leu Leu Glu Phe Glu
        290                 295                 300

Lys Leu Tyr Thr Asn Phe Ser Trp Gly Arg Asn Gln Ile Thr Val Asp
305                 310                 315                 320

Lys Met Asp His Ile Gly Gln Val Ser Val Lys His Gly Phe Lys Pro
                325                 330                 335

Leu Leu Val

<210> SEQ ID NO 28
<211> LENGTH: 340
<212> TYPE: PRT
<213> ORGANISM: Cyanothece sp.

<400> SEQUENCE: 28

Met Phe Gly Leu Ile Gly His Leu Thr Ser Leu Glu His Ala Gln Ser
1               5                   10                  15

Val Ala Glu Ala Leu Gly Tyr Pro Glu Tyr Ala Asn Gln Gly Leu Glu
            20                  25                  30

Phe Trp Cys Met Ala Pro Pro Gln Ile Val Asp Ser Ile Thr Val Thr
        35                  40                  45

Ser Ile Thr Gly Gln Lys Ile Tyr Gly Lys Tyr Val Glu Ser Cys Phe
    50                  55                  60

Leu Pro Glu Met Leu Ala Thr Gln Arg Ile Lys Ala Ala Thr Arg Lys
65                  70                  75                  80

Ile Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Asn Leu His
            100                 105                 110

Thr Ile Thr Gln Ile His Asn Ile Lys Leu Glu Leu Gln Arg Phe Thr
        115                 120                 125

Thr Gly Asn Thr His Thr Ala Tyr Ile Ile Cys Arg Gln Val Glu Gln
    130                 135                 140

Ala Ser Ala Gln Ile Gly Ile Asp Leu Ser Lys Ala Thr Val Ala Val
145                 150                 155                 160

Cys Gly Ala Thr Gly Asp Ile Gly Ser Ala Val Cys Arg Trp Leu Asn
                165                 170                 175

Ser Arg Leu Asp Val Ala Glu Leu Leu Leu Val Ala Arg Asn Gln Glu
            180                 185                 190

Arg Leu Gln Glu Leu Gln Glu Leu Gly Arg Gly Lys Ile Leu Ser
        195                 200                 205

Leu Glu Ala Ala Leu Pro Leu Ala Asp Ile Val Val Trp Val Ala Ser
    210                 215                 220

Met Pro Arg Gly Val Glu Ile Asp Pro Thr Ser Leu Arg Thr Pro Cys
225                 230                 235                 240

Leu Met Ile Asp Gly Gly Tyr Pro Lys Asn Leu Ala Thr Gln Ile Gln
                245                 250                 255

His Pro Gly Val His Val Leu Asn Gly Gly Ile Val Glu His Ser Leu
            260                 265                 270

Asp Ile Asp Trp Arg Ile Met Glu Ile Val Asn Met Ser Ile Pro Ser
        275                 280                 285

Arg Gln Leu Phe Ala Cys Phe Ala Glu Ser Met Leu Leu Glu Phe Glu
    290                 295                 300

Gln Trp Tyr Thr Asn Phe Ser Trp Gly Arg Asn Gln Ile Ser Val Glu
```

```
                305                 310                 315                 320
Lys Met Glu Lys Ile Gly Gln Ile Ser Val Lys His Gly Phe Gln Pro
                    325                 330                 335
Leu Leu Phe Gln
            340

<210> SEQ ID NO 29
<211> LENGTH: 346
<212> TYPE: PRT
<213> ORGANISM: Nodularia spumigena

<400> SEQUENCE: 29

Met Phe Gly Leu Ile Gly His Leu Thr Ser Leu Glu His Ala Gln Ser
1               5                   10                  15

Val Ala Lys Glu Leu Gly Tyr Pro Glu Tyr Ala Asp Gln Gly Leu Asp
            20                  25                  30

Phe Trp Cys Ser Ala Pro Pro Gln Ile Val Asp Glu Ile Thr Val Thr
        35                  40                  45

Ser Val Thr Gly Gln Thr Ile Glu Gly Arg Tyr Val Glu Ser Cys Phe
    50                  55                  60

Leu Pro Glu Met Leu Ala Asn Arg Arg Ile Lys Ala Ala Thr Arg Lys
65                  70                  75                  80

Ile Leu Asn Ala Met Ala His Ala Gln Lys His Gly Ile Asn Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Ile Lys Leu Glu Phe Glu Arg Phe Thr
        115                 120                 125

Thr Gly Asn Thr His Thr Ala Tyr Ile Ile Cys Arg Gly Val Glu Gln
    130                 135                 140

Ala Ser Lys Gln Ile Gly Ile Asp Leu Ser Lys Ala Thr Val Ala Ile
145                 150                 155                 160

Cys Gly Ala Thr Gly Asp Ile Gly Ser Ala Val Thr Arg Trp Leu Asp
                165                 170                 175

Ala Arg Thr Asp Val Lys Glu Leu Leu Leu Ile Ala Arg Asn His Glu
            180                 185                 190

Arg Leu Lys Asp Leu Gln Asp Glu Leu Gly Arg Gly Lys Ile Met Ala
        195                 200                 205

Leu Asn Glu Ala Leu Pro Glu Ala Asp Ile Val Val Trp Val Ala Ser
    210                 215                 220

Met Pro Lys Ser Met Glu Ile Asp Phe Gln Val Leu Lys Arg Pro Cys
225                 230                 235                 240

Leu Leu Ile Asp Gly Gly Tyr Pro Lys Asn Leu Ala Thr Lys Ile Gln
                245                 250                 255

Tyr Pro Gly Val His Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
    290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Ile Lys His Gly Phe Arg Pro
                325                 330                 335

Leu Leu Val Glu Ser Leu Val Val Asn Ser
```

<210> SEQ ID NO 30
<211> LENGTH: 341
<212> TYPE: PRT
<213> ORGANISM: Lyngbya sp.

<400> SEQUENCE: 30

Met Phe Gly Leu Ile Gly His Leu Thr Ser Leu Glu His Ala Gln Leu
1               5                   10                  15

Val Ala Lys Asp Leu Gly Tyr Pro Glu Tyr Ala Asp Gln Gly Leu Asp
            20                  25                  30

Phe Trp Cys Ser Ala Pro Pro Gln Ile Val Asp Glu Ile Lys Val Thr
        35                  40                  45

Ser Val Thr Gly Gln Val Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Ile Ile Asn Ala Met Ala His Ala Gln Lys His Gly Ile Asn Ile Thr
                85                  90                  95

Ala Leu Gly Gly Phe Ser Ser Ile Ile Phe Glu Asn Phe Asn Leu Glu
            100                 105                 110

Lys Ile Lys Gln Val Arg Asn Ile Lys Leu Glu Phe Glu Arg Phe Thr
        115                 120                 125

Thr Gly Asn Thr His Thr Ala Tyr Ile Ile Cys Ser Gln Val Glu Gln
    130                 135                 140

Met Ala Pro Lys Leu Gly Ile Asp Leu Ser Asn Ala Thr Val Ala Val
145                 150                 155                 160

Cys Gly Ala Thr Gly Asp Ile Gly Ser Ala Val Cys Arg Trp Leu Asn
                165                 170                 175

Gln Arg Thr Gln Val Gly Glu Leu Leu Leu Ile Ala Arg Asp Arg Glu
            180                 185                 190

Arg Leu Gln Asn Leu Gln Gly Glu Leu Gly Arg Gly Lys Ile Leu Gly
        195                 200                 205

Leu Glu Glu Ala Leu Pro Gln Ala Asn Val Val Trp Val Ala Ser
    210                 215                 220

Met Ala Lys Gly Val Asp Ile Asp Pro Ser Arg Leu Gln Gln Pro Cys
225                 230                 235                 240

Leu Leu Ile Asp Gly Gly Tyr Pro Lys Asn Met Ala Thr Lys Leu Gln
                245                 250                 255

His Pro Gly Val His Ile Leu Glu Gly Gly Ile Val Glu His Ser Leu
            260                 265                 270

Asp Ile Asp Trp Lys Ile Met Lys Ile Val Asn Met Gln Phe Pro Ala
        275                 280                 285

Arg Gln Leu Phe Ala Cys Phe Ala Glu Ala Met Leu Leu Glu Phe Glu
    290                 295                 300

Lys Ile Tyr Thr Asn Phe Ser Trp Gly Arg Asn Gln Ile Thr Val Asp
305                 310                 315                 320

Lys Met Asp Met Ile Gly Arg Val Ser Ile Lys His Gly Phe Lys Pro
                325                 330                 335

Leu Leu Leu Ser Leu
            340

<210> SEQ ID NO 31
<211> LENGTH: 339
<212> TYPE: PRT

<213> ORGANISM: Nostoc punctiforme

<400> SEQUENCE: 31

```
Met Phe Gly Leu Ile Gly His Leu Thr Ser Leu Glu His Ala Gln Ala
1               5                   10                  15
Val Ala Gln Glu Leu Gly Tyr Pro Glu Tyr Ala Asp Gln Gly Leu Asp
            20                  25                  30
Phe Trp Cys Ser Ala Pro Pro Gln Ile Val Asp Ser Ile Ile Val Thr
        35                  40                  45
Ser Val Thr Gly Gln Gln Ile Glu Gly Arg Tyr Val Glu Ser Cys Phe
    50                  55                  60
Leu Pro Glu Met Leu Ala Ser Arg Arg Ile Lys Ala Ala Thr Arg Lys
65                  70                  75                  80
Ile Leu Asn Ala Met Ala His Ala Gln Lys His Gly Ile Asn Ile Thr
                85                  90                  95
Ala Leu Gly Gly Phe Ser Ser Ile Ile Phe Glu Asn Phe Lys Leu Glu
            100                 105                 110
Gln Phe Ser Gln Val Arg Asn Ile Lys Leu Glu Phe Glu Arg Phe Thr
        115                 120                 125
Thr Gly Asn Thr His Thr Ala Tyr Ile Ile Cys Lys Gln Val Glu Glu
    130                 135                 140
Ala Ser Lys Gln Leu Gly Ile Asn Leu Ser Asn Ala Thr Val Ala Val
145                 150                 155                 160
Cys Gly Ala Thr Gly Asp Ile Gly Ser Ala Val Thr Arg Trp Leu Asp
                165                 170                 175
Ala Arg Thr Asp Val Gln Glu Leu Leu Leu Ile Ala Arg Asp Gln Glu
            180                 185                 190
Arg Leu Lys Glu Leu Gln Gly Glu Leu Gly Arg Gly Lys Ile Met Gly
        195                 200                 205
Leu Thr Glu Ala Leu Pro Gln Ala Asp Val Val Trp Val Ala Ser
    210                 215                 220
Met Pro Arg Gly Val Glu Ile Asp Pro Thr Thr Leu Lys Gln Pro Cys
225                 230                 235                 240
Leu Leu Ile Asp Gly Gly Tyr Pro Lys Asn Leu Ala Thr Lys Ile Gln
                245                 250                 255
Tyr Pro Gly Val His Val Leu Asn Gly Gly Ile Val Glu His Ser Leu
            260                 265                 270
Asp Ile Asp Trp Lys Ile Met Lys Ile Val Asn Met Asp Val Pro Ala
        275                 280                 285
Arg Gln Leu Phe Ala Cys Phe Ala Glu Ser Met Leu Leu Glu Phe Glu
    290                 295                 300
Lys Leu Tyr Thr Asn Phe Ser Trp Gly Arg Asn Gln Ile Thr Val Asp
305                 310                 315                 320
Lys Met Glu Gln Ile Gly Arg Val Ser Val Lys His Gly Phe Arg Pro
                325                 330                 335
Leu Leu Val
```

<210> SEQ ID NO 32
<211> LENGTH: 339
<212> TYPE: PRT
<213> ORGANISM: Trichodesmium erythraeum

<400> SEQUENCE: 32

```
Met Phe Gly Leu Ile Gly His Leu Thr Asn Leu Glu His Ala Gln Ser
1               5                   10                  15
```

-continued

Val Ala Arg Asp Leu Gly Tyr Pro Glu Tyr Ala Asp Gln Gly Leu Asp
            20                  25                  30

Phe Trp Cys Ser Ala Pro Pro Gln Ile Val Asp Thr Ile Lys Val Thr
            35                  40                  45

Ser Ile Thr Gly Gln Lys Ile Glu Gly Lys Tyr Val Glu Ser Cys Phe
 50                  55                  60

Leu Pro Glu Met Leu Ala Ser Ser Arg Ile Lys Ala Ala Thr Arg Lys
 65                  70                  75                  80

Ile Met Asn Ala Met Ala His Ala Gln Lys His Gly Ile Asp Ile Thr
                 85                  90                  95

Ala Leu Gly Gly Phe Ser Ser Ile Val Phe Glu Asn Phe Asn Leu Gln
            100                 105                 110

Lys Phe Lys Gln Ile Arg Asn Ile Thr Leu Glu Phe Lys Arg Phe Thr
            115                 120                 125

Thr Gly Asn Thr His Thr Ala Tyr Ile Val Cys Gln Gln Val Glu Gln
            130                 135                 140

Gly Ala Gln Lys Leu Gly Ile Asp Leu Ser Lys Ala Thr Val Ala Val
145                 150                 155                 160

Cys Gly Ala Thr Gly Asp Ile Gly Ser Ala Val Cys Arg Trp Leu Asn
                165                 170                 175

Thr Lys Thr Glu Val Glu Glu Leu Leu Leu Ile Ala Arg Lys Gln Glu
            180                 185                 190

Arg Leu Asn Ala Leu Gln Lys Glu Leu Lys Arg Gly Lys Ile Leu Glu
            195                 200                 205

Leu Asn Ser Ala Leu Pro Met Ala Asp Ile Ile Val Trp Val Ala Ser
            210                 215                 220

Ile Pro Glu Ala Leu Glu Ile Asn Pro Asn Val Leu Lys Lys Pro Cys
225                 230                 235                 240

Leu Leu Ile Asp Gly Gly Tyr Pro Lys Asn Met Ala Thr Lys Val Gln
                245                 250                 255

Gln Glu Gly Ile Tyr Val Leu Asn Gly Gly Ile Val Glu His Ser Leu
            260                 265                 270

Asp Ile Asp Trp Lys Ile Met Lys Ile Val Asn Met Glu Val Pro Gly
            275                 280                 285

Arg Gln Leu Phe Ala Cys Phe Ala Glu Ser Met Leu Leu Glu Phe Glu
            290                 295                 300

Lys Leu Tyr Thr Asn Phe Ser Trp Gly Arg Asn Leu Ile Thr Val Glu
305                 310                 315                 320

Lys Met Glu Leu Ile Gly Lys Leu Ser Val Lys His Gly Phe Lys Pro
                325                 330                 335

Leu Met Leu

<210> SEQ ID NO 33
<211> LENGTH: 341
<212> TYPE: PRT
<213> ORGANISM: Acaryochloris marina

<400> SEQUENCE: 33

Met Phe Gly Leu Ile Gly His Leu Thr Ser Leu Gln His Ala Gln Ser
1               5                   10                  15

Val Ala Arg Glu Leu Gly Tyr Pro Glu Tyr Ala Asp Gln Gly Leu Asp
            20                  25                  30

Phe Trp Cys Met Ala Pro Pro Gln Ile Val Asp Asp Ile Thr Val Thr
            35                  40                  45

Ser Ile Thr Gly Gln Thr Ile Tyr Gly Lys Tyr Val Glu Ser Cys Phe

```
                50                  55                  60
Leu Pro Glu Met Leu Ala Ser Gln Arg Ile Lys Ala Ala Thr Arg Lys
 65                  70                  75                  80

Ile Val Asn Ala Met Ala His Ala Gln Lys Asn Gly Ile Asn Ile Thr
                 85                  90                  95

Ala Leu Gly Gly Phe Ser Ser Ile Ile Phe Glu Asn Phe Asn Leu Gln
                100                 105                 110

Arg Ile Thr Arg Ile Arg Asn Ile Gln Leu Asp Leu Gln Arg Phe Thr
                115                 120                 125

Thr Gly Asn Thr His Thr Ala Tyr Ile Ile Cys Arg Gln Val Glu Gln
130                 135                 140

Gly Ala Gln Lys Leu Gly Ile Asp Leu Asn Lys Ala Thr Val Ala Val
145                 150                 155                 160

Cys Gly Ala Thr Gly Asp Ile Gly Ser Ala Val Cys Arg Trp Leu Asp
                165                 170                 175

Ala Arg Thr Asp Thr Ala Glu Leu Leu Val Ala Arg His Gln Gly
                180                 185                 190

Arg Leu Glu Thr Leu Gln Ser Glu Leu Gly Arg Gly Lys Ile Met Ser
                195                 200                 205

Ile Glu Glu Ala Leu Pro Gln Ala Asp Ile Val Val Trp Val Ala Ser
210                 215                 220

Met Pro Lys Gly Ile Glu Ile Asp Ala Glu Asn Leu Lys His Pro Cys
225                 230                 235                 240

Leu Met Ile Asp Gly Gly Tyr Pro Lys Asn Leu Gly Thr Lys Ile Gln
                245                 250                 255

His Pro Asp Val His Ile Leu Asn Gly Gly Ile Val Glu His Ser Leu
                260                 265                 270

Asp Ile Asp Trp Lys Ile Met His Ile Val Asn Met Asn Ile Pro Asn
                275                 280                 285

Arg Gln Leu Phe Ala Cys Phe Ala Glu Ser Met Leu Leu Glu Phe Glu
                290                 295                 300

Gln Leu His Thr Asn Phe Ser Trp Gly Arg Asn Glu Ile Thr Val Ala
305                 310                 315                 320

Lys Met Glu Lys Ile Gly Glu Ile Ser Leu Lys His Gly Phe Lys Pro
                325                 330                 335

Leu Ala Leu Ala Val
                340

<210> SEQ ID NO 34
<211> LENGTH: 340
<212> TYPE: PRT
<213> ORGANISM: Cyanothece sp.

<400> SEQUENCE: 34

Met Phe Gly Leu Ile Gly His Leu Thr Ser Leu Glu His Ala Gln Gln
 1               5                  10                  15

Val Ala Glu Ala Leu Gly Tyr Pro Glu Tyr Ala Asn Gln Gly Leu Asp
                 20                  25                  30

Phe Trp Cys Ala Ala Pro Pro Gln Ile Val Asp His Phe His Val Thr
                 35                  40                  45

Ser Val Thr Gly Gln Ile Ile Glu Gly Lys Tyr Val Glu Ser Cys Phe
                 50                  55                  60

Leu Pro Glu Met Leu Val Asn Arg Arg Ile Lys Ala Ala Ile Arg Lys
 65                  70                  75                  80

Ile Leu Asn Ala Met Ala Leu Ala Gln Lys Ala Asp Leu Asn Ile Thr
```

```
                    85                  90                  95
Ala Leu Gly Gly Phe Ser Ser Ile Ile Phe Glu Glu Phe Asn Leu Lys
            100                 105                 110

Glu Asn Lys Gln Val Arg Asn Val Glu Leu Glu Phe Glu Arg Phe Thr
            115                 120                 125

Thr Gly Asn Thr His Thr Ala Tyr Ile Ile Cys Arg Gln Leu Glu Gln
            130                 135                 140

Val Ser Ala Gln Leu Gly Leu Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Gln Lys Thr Asp Val Ala Glu Leu Leu Leu Ile Ala Arg Asn Gln Glu
            180                 185                 190

Arg Leu Gln Gly Leu Gln Ala Glu Leu Gly Arg Gly Lys Ile Met Glu
            195                 200                 205

Leu Glu Glu Ala Leu Pro Gln Ala Asp Ile Ile Val Trp Val Ala Ser
            210                 215                 220

Met Pro Lys Gly Val Glu Ile Asn Pro Glu Thr Leu Lys Lys Pro Cys
225                 230                 235                 240

Leu Ile Ile Asp Gly Gly Tyr Pro Lys Asn Leu Gly Thr Gln Val Gln
                245                 250                 255

His Pro Asp Val Tyr Val Leu Lys Gly Gly Ile Val Glu His Ser Leu
            260                 265                 270

Asp Ile Asp Trp Lys Ile Met Glu Ile Val Ser Met Asp Ile Pro Ser
            275                 280                 285

Arg Gln Met Phe Ala Cys Phe Ala Glu Gly Ile Leu Leu Glu Phe Glu
            290                 295                 300

Gly Trp His Thr Asn Phe Ser Trp Gly Arg Asn Gln Ile Ser Val Pro
305                 310                 315                 320

Lys Met Glu Gln Ile Gly Glu Ala Ser Leu Lys His Gly Phe Arg Pro
                325                 330                 335

Leu Leu Ser Trp
            340

<210> SEQ ID NO 35
<211> LENGTH: 340
<212> TYPE: PRT
<213> ORGANISM: Cyanothece sp.

<400> SEQUENCE: 35

Met Phe Gly Leu Ile Gly His Leu Thr Ser Leu Glu His Ala Gln Gln
1               5                   10                  15

Val Ala Glu Ala Leu Gly Tyr Pro Glu Tyr Ala Asn Gln Gly Leu Asp
            20                  25                  30

Phe Trp Cys Ala Ala Pro Pro Gln Ile Val Asp His Phe His Val Thr
            35                  40                  45

Ser Val Thr Gly Gln Ile Ile Glu Gly Lys Tyr Val Glu Ser Cys Phe
            50                  55                  60

Leu Pro Glu Met Leu Val Asn Arg Arg Ile Lys Ala Ala Ile Arg Lys
65                  70                  75                  80

Ile Leu Asn Ala Met Ala Leu Ala Gln Lys Ala Asp Leu Asn Ile Thr
                85                  90                  95

Ala Leu Gly Gly Phe Ser Ser Ile Ile Phe Glu Glu Phe Asn Leu Lys
            100                 105                 110

Glu Asn Lys Gln Val Arg Asn Val Glu Leu Glu Phe Glu Arg Phe Thr
```

```
                    115                 120                 125
Thr Gly Asn Thr His Thr Ala Tyr Ile Ile Cys Arg Gln Leu Glu Gln
            130                 135                 140
Val Ser Ala Gln Leu Gly Leu Asp Leu Ser Gln Ala Thr Val Ala Val
145                 150                 155                 160
Cys Gly Ala Thr Gly Asp Ile Gly Ser Ala Val Cys Arg Trp Leu Asp
                165                 170                 175
Gln Lys Thr Asp Val Ala Glu Leu Leu Ile Ala Arg Asn Gln Glu
            180                 185                 190
Arg Leu Gln Gly Leu Gln Ala Glu Leu Gly Arg Gly Lys Ile Met Glu
            195                 200                 205
Leu Glu Glu Ala Leu Pro Gln Ala Asp Ile Ile Val Trp Val Ala Ser
            210                 215                 220
Met Pro Lys Gly Val Glu Ile Asn Pro Glu Thr Leu Lys Lys Pro Cys
225                 230                 235                 240
Leu Ile Ile Asp Gly Gly Tyr Pro Lys Asn Leu Gly Thr Gln Val Gln
                245                 250                 255
His Pro Asp Val Tyr Val Leu Lys Gly Gly Ile Val Glu His Ser Leu
                260                 265                 270
Asp Ile Asp Trp Lys Ile Met Glu Ile Val Ser Met Asp Ile Pro Ser
            275                 280                 285
Arg Gln Met Phe Ala Cys Phe Ala Glu Gly Ile Leu Leu Glu Phe Glu
            290                 295                 300
Gly Trp His Thr Asn Phe Ser Trp Gly Arg Asn Gln Ile Ser Val Pro
305                 310                 315                 320
Lys Met Glu Gln Ile Gly Glu Ala Ser Leu Lys His Gly Phe Arg Pro
                325                 330                 335
Leu Leu Ser Trp
            340

<210> SEQ ID NO 36
<211> LENGTH: 340
<212> TYPE: PRT
<213> ORGANISM: Microcoleus chthonoplastes

<400> SEQUENCE: 36

Met Phe Gly Leu Ile Gly His Leu Thr Ser Leu Gln His Ala Gln Ala
1               5                   10                  15
Val Ala Arg Asp Leu Gly Tyr Pro Glu Tyr Ala Asp Gln Gly Leu Asp
                20                  25                  30
Phe Trp Cys Ser Ala Pro Pro Gln Ile Val Asp Thr Ile Lys Val Thr
            35                  40                  45
Ser Leu Thr Gly Glu Thr Ile Glu Gly Arg Tyr Val Glu Ser Cys Phe
        50                  55                  60
Leu Pro Glu Met Leu Ala Thr Arg Arg Ile Lys Ala Ala Ile Arg Lys
65                  70                  75                  80
Val Leu Asn Ala Met Ala His Ala Gln Lys Asn Gly Ile Glu Ile Thr
                85                  90                  95
Ala Leu Gly Gly Phe Ser Ser Ile Ile Phe Glu Glu Phe His Leu Tyr
                100                 105                 110
Glu Lys Ser Gln Val Arg Asn Ile Lys Leu Glu Phe Glu Arg Phe Thr
            115                 120                 125
Thr Gly Asn Thr His Thr Ala Tyr Ile Ile Ser Ala Gln Val Glu Gln
            130                 135                 140
Gly Ala Gln Lys Leu Gly Ile Asp Leu Ser Lys Ala Thr Val Ala Val
```

```
                145                 150                 155                 160
Cys Gly Ala Thr Gly Asp Ile Gly Ser Ala Val Cys Arg Trp Leu Asn
                    165                 170                 175

Thr Arg Thr Asp Val Ala Glu Ile Leu Leu Thr Ala Arg Asn Gln Glu
                180                 185                 190

Arg Leu Gln Ala Leu Gln Asp Gln Leu Gly Arg Gly Lys Ile Met Gly
            195                 200                 205

Leu Glu Glu Ala Leu Pro Gln Ala Asp Ile Ile Val Trp Val Ala Ser
        210                 215                 220

Met Ser Lys Gly Ile Asp Ile Asp Ala Ser Leu Leu Lys Lys Pro Cys
225                 230                 235                 240

Leu Leu Ile Asp Gly Gly Tyr Pro Lys Asn Leu Ala Thr Lys Leu Gln
                245                 250                 255

His Pro Asp Ile Tyr Val Leu Asn Gly Gly Ile Val Glu His Ser Leu
                260                 265                 270

Asp Ile Asp Trp Lys Ile Met Gln Ile Val Glu Met Lys Asp Pro Gly
            275                 280                 285

Arg Gln Leu Phe Ala Cys Phe Ala Glu Ser Met Leu Leu Glu Phe Glu
        290                 295                 300

Lys Trp Tyr Thr Asn Phe Ser Trp Gly Arg Asn Gln Ile Thr Val Glu
305                 310                 315                 320

Lys Met Asp Lys Ile Gly Gln Val Ser Ile Lys His Gly Phe Arg Pro
                325                 330                 335

Leu Leu Asn Val
            340

<210> SEQ ID NO 37
<211> LENGTH: 339
<212> TYPE: PRT
<213> ORGANISM: Arthrospira maxima

<400> SEQUENCE: 37

Met Phe Gly Leu Ile Gly His Leu Thr Ser Leu Glu His Ala Gln Val
1               5                   10                  15

Val Ala Arg Asp Leu Gly Tyr Ala Glu Tyr Ala Asp Gln Gly Leu Asp
                20                  25                  30

Phe Trp Cys Ser Ala Pro Pro Val Ile Val Glu Asp Leu Lys Val Thr
            35                  40                  45

Ser Ile Thr Gly Gln Val Ile Glu Gly Arg Tyr Val Glu Ser Cys Phe
        50                  55                  60

Leu Pro Glu Met Leu Ala Thr Asn Arg Met Lys Ala Ala Thr Arg Lys
65                  70                  75                  80

Ile Ile Asn Ala Met Ala His Ala Gln Lys Asn Gly Ile Asn Ile Thr
                85                  90                  95

Ala Leu Gly Gly Phe Ser Ser Ile Ile Leu Glu Arg Phe Asn Leu Asp
            100                 105                 110

Gln Leu Gly Arg Ile Arg Asn Ile Lys Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ala Pro Lys Leu Gly Ile Asp Leu Ser Lys Ala Thr Val Ala Val
145                 150                 155                 160

Cys Gly Ala Thr Gly Asp Ile Gly Ser Ala Val Cys Arg Trp Leu Asn
                165                 170                 175

Gly Arg Leu Asp Val Ala Glu Ile Leu Leu Ile Ala Arg Asp Arg Gln
```

```
                      180                 185                 190
Arg Leu Gln Asn Leu Gln Ala Glu Leu Gly Arg Gly Lys Ile Met Ala
                  195                 200                 205

Leu Asp Glu Ala Leu Pro Gln Ala Asp Ile Val Val Trp Val Ala Ser
210                 215                 220

Met Pro Gln Gly Val Glu Ile Asp Pro Glu Val Leu Lys Lys Pro Cys
225                 230                 235                 240

Leu Leu Ile Asp Gly Gly Tyr Pro Lys Asn Met Ala Thr Lys Phe Gln
                245                 250                 255

Ser Pro Gly Val His Val Leu Ser Gly Gly Ile Val Glu His Ala Leu
              260                 265                 270

Asp Ile Asp Trp Lys Ile Met Lys Ile Val Asn Met Asn Val Pro Gly
            275                 280                 285

Arg Gln Leu Phe Ala Cys Phe Ala Glu Ser Met Leu Leu Glu Phe Glu
          290                 295                 300

Ser Ile Tyr Thr Asn Phe Ser Trp Gly Arg Asn Gln Ile Thr Leu Asp
305                 310                 315                 320

Lys Met Asp Met Ile Gly Arg Met Ser Ile Lys His Gly Phe Lys Pro
                325                 330                 335

Leu Met Leu

<210> SEQ ID NO 38
<211> LENGTH: 340
<212> TYPE: PRT
<213> ORGANISM: Synechocystis sp.

<400> SEQUENCE: 38

Met Phe Gly Leu Ile Gly His Leu Thr Ser Leu Glu His Ala Gln Ala
1               5                   10                  15

Val Ala Glu Asp Leu Gly Tyr Pro Glu Tyr Ala Asn Gln Gly Leu Asp
                20                  25                  30

Phe Trp Cys Ser Ala Pro Pro Gln Val Val Asp Asn Phe Gln Val Lys
            35                  40                  45

Ser Val Thr Gly Gln Val Ile Glu Gly Lys Tyr Val Glu Ser Cys Phe
        50                  55                  60

Leu Pro Glu Met Leu Thr Gln Arg Arg Ile Lys Ala Ala Ile Arg Lys
65                  70                  75                  80

Ile Leu Asn Ala Met Ala Leu Ala Gln Lys Val Gly Leu Asp Ile Thr
                85                  90                  95

Ala Leu Gly Gly Phe Ser Ser Ile Val Phe Glu Glu Phe Asn Leu Lys
            100                 105                 110

Gln Asn Asn Gln Val Arg Asn Val Glu Leu Asp Phe Gln Arg Phe Thr
        115                 120                 125

Thr Gly Asn Thr His Thr Ala Tyr Val Ile Cys Arg Gln Val Glu Ser
130                 135                 140

Gly Ala Lys Gln Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Ser Lys His Gln Val Lys Glu Leu Leu Leu Ile Ala Arg Asn Arg Gln
            180                 185                 190

Arg Leu Glu Asn Leu Gln Glu Glu Leu Gly Arg Gly Lys Ile Met Asp
        195                 200                 205

Leu Glu Thr Ala Leu Pro Gln Ala Asp Ile Ile Val Trp Val Ala Ser
210                 215                 220
```

```
Met Pro Lys Gly Val Glu Ile Ala Gly Glu Met Leu Lys Pro Cys
225                 230                 235                 240

Leu Ile Val Asp Gly Gly Tyr Pro Lys Asn Leu Asp Thr Arg Val Lys
        245                 250                 255

Ala Asp Gly Val His Ile Leu Lys Gly Gly Ile Val Glu His Ser Leu
            260                 265                 270

Asp Ile Thr Trp Glu Ile Met Lys Ile Val Glu Met Asp Ile Pro Ser
        275                 280                 285

Arg Gln Met Phe Ala Cys Phe Ala Glu Ala Ile Leu Leu Glu Phe Glu
        290                 295                 300

Gly Trp Arg Thr Asn Phe Ser Trp Gly Arg Asn Gln Ile Ser Val Asn
305                 310                 315                 320

Lys Met Glu Ala Ile Gly Glu Ala Ser Val Lys His Gly Phe Cys Pro
                325                 330                 335

Leu Val Ala Leu
            340

<210> SEQ ID NO 39
<211> LENGTH: 340
<212> TYPE: PRT
<213> ORGANISM: Cyanothece sp.

<400> SEQUENCE: 39

Met Phe Gly Leu Ile Gly His Leu Thr Ser Leu Glu His Ala Gln Ser
1               5                   10                  15

Val Ala Asp Ala Leu Gly Tyr Pro Glu Tyr Ala Asn Gln Gly Leu Asp
            20                  25                  30

Phe Trp Cys Ser Ala Pro Pro Gln Ile Val Asp His Phe His Val Thr
        35                  40                  45

Ser Val Thr Gly Gln Thr Ile Glu Gly Lys Tyr Val Glu Ser Cys Phe
    50                  55                  60

Leu Pro Glu Met Leu Met Asn Arg Arg Ile Lys Ala Ala Ile Arg Lys
65                  70                  75                  80

Ile Leu Asn Ala Met Ala Leu Ala Gln Lys Asn Ser Ile Asn Ile Thr
                85                  90                  95

Ala Leu Gly Gly Phe Ser Ser Ile Ile Phe Glu Glu Phe Asn Leu Lys
            100                 105                 110

Asp Asn Lys Gln Val Arg Asn Val Ser Leu Glu Phe Asp Arg Phe Thr
        115                 120                 125

Thr Gly Asn Thr His Thr Ala Tyr Val Ile Cys Arg Gln Val Glu Gln
    130                 135                 140

Gly Ser Ala Lys Leu Gly Ile Asp Leu Ser Lys Ala Thr Ile Ala Val
145                 150                 155                 160

Cys Gly Ala Thr Gly Asp Ile Gly Ser Gly Val Cys Arg Trp Leu Asp
                165                 170                 175

Arg Asn Thr Asn Thr Gln Glu Leu Leu Leu Ile Ala Arg Asn Gln Glu
            180                 185                 190

Arg Leu Lys Arg Leu Gln Asp Glu Leu Gly Arg Gly Lys Ile Met Gly
        195                 200                 205

Leu Glu Glu Ala Leu Pro Glu Ala Asp Val Ile Val Trp Val Ala Ser
    210                 215                 220

Met Pro Lys Gly Val Glu Ile Asn Pro Glu Thr Leu Lys Lys Pro Cys
225                 230                 235                 240

Leu Ile Ile Asp Gly Gly Tyr Pro Lys Asn Leu Asp Thr Lys Ile Lys
        245                 250                 255
```

His Ser Asp Val His Ile Leu Lys Gly Gly Ile Val Glu His Ser Leu
            260                 265                 270

Asp Ile Asp Trp Lys Ile Met Glu Ile Val Ser Met Asp Ile Pro Ser
            275                 280                 285

Arg Gln Met Phe Ala Cys Phe Ala Glu Ala Ile Leu Leu Glu Phe Glu
            290                 295                 300

Gln Trp His Thr Asn Phe Ser Trp Gly Arg Asn Gln Ile Thr Val Thr
305                 310                 315                 320

Lys Met Glu Gln Ile Gly Thr Ala Ser Val Lys His Gly Phe Gln Pro
                325                 330                 335

Leu Leu Asn Trp
            340

<210> SEQ ID NO 40
<211> LENGTH: 339
<212> TYPE: PRT
<213> ORGANISM: Synechococcus sp.

<400> SEQUENCE: 40

Met Phe Gly Leu Ile Gly His Leu Thr Ser Leu Glu His Ala Lys Ser
1               5                   10                  15

Val Ala His Lys Leu Gly Tyr Pro Glu Tyr Ala Glu Gln Gly Leu Asp
            20                  25                  30

Phe Trp Cys Ser Ala Pro Pro Gln Val Val Asp His Phe Lys Val Val
            35                  40                  45

Ser Ala Thr Gly Gln Thr Ile Glu Gly Lys Tyr Val Glu Ser Cys Phe
        50                  55                  60

Leu Pro Glu Met Leu Ala Asn Arg Arg Ile Lys Ala Ala Thr Arg Lys
65                  70                  75                  80

Ile Leu Asn Ala Met Ala His Ala Gln Lys Glu Gly Ile Asn Ile Thr
                85                  90                  95

Ala Leu Gly Gly Phe Ser Ser Ile Ile Phe Glu Asn Phe Lys Leu Glu
            100                 105                 110

Gln Ile Lys Arg Val Arg Asn Leu Asp Leu Asp Phe Ser Lys Phe Thr
            115                 120                 125

Thr Gly Asn Thr His Thr Ala Tyr Val Ile Cys Lys Gln Val Glu Glu
        130                 135                 140

Ala Ala Pro Ser Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Thr
                165                 170                 175

Ala Arg Thr Gly Val Lys Asn Leu Leu Leu Val Ala Arg Asn Gln Glu
            180                 185                 190

Arg Leu Glu Asn Leu Gln Ala Asp Leu Lys Phe Gly Gln Val Gln Thr
            195                 200                 205

Leu Asp Glu Ala Leu Pro Gln Ala Asp Val Val Trp Val Ala Ser
        210                 215                 220

Met Pro Lys Gly Val Glu Val Asp Leu Glu Thr Leu Lys Gln Pro Cys
225                 230                 235                 240

Leu Met Val Asp Gly Gly Tyr Pro Lys Asn Met Asp Val Thr Phe Ser
                245                 250                 255

His Pro Gly Ile Thr Val Leu Lys Gly Gly Ile Val Glu His Met Leu
            260                 265                 270

Asp Ile Asp Trp His Ile Met Asn Ile Val Asn Met Asp Val Pro Gly
            275                 280                 285

```
Arg Gln Leu Phe Ala Cys Phe Ala Glu Ser Met Leu Leu Glu Phe Glu
    290                 295                 300

Lys Leu His Thr Asn Phe Ser Trp Gly Arg Asn Gln Ile Thr Leu Glu
305                 310                 315                 320

Lys Met Asp Leu Ile Gly Glu Ala Ser Arg Arg His Gly Phe Lys Pro
                325                 330                 335

Leu Leu Thr

<210> SEQ ID NO 41
<211> LENGTH: 340
<212> TYPE: PRT
<213> ORGANISM: Cyanothece sp.

<400> SEQUENCE: 41

Met Phe Gly Leu Ile Gly His Leu Thr Ser Leu Glu His Ala His Ser
1               5                  10                  15

Val Ala Asp Ala Phe Gly Tyr Gly Pro Tyr Ala Thr Gln Gly Leu Asp
            20                  25                  30

Leu Trp Cys Ser Ala Pro Pro Gln Phe Val Glu His Phe His Val Thr
        35                  40                  45

Ser Ile Thr Gly Gln Thr Ile Glu Gly Lys Tyr Ile Glu Ser Ala Phe
    50                  55                  60

Leu Pro Glu Met Leu Ile Lys Arg Arg Ile Lys Ala Ala Ile Arg Lys
65                  70                  75                  80

Ile Leu Asn Ala Met Ala Phe Ala Gln Lys Asn Asn Leu Asn Ile Thr
                85                  90                  95

Ala Leu Gly Gly Phe Ser Ser Ile Ile Phe Glu Glu Phe Asn Leu Lys
            100                 105                 110

Glu Asn Arg Gln Val Arg Asn Val Ser Leu Glu Phe Asp Arg Phe Thr
        115                 120                 125

Thr Gly Asn Thr His Thr Ala Tyr Ile Ile Cys Arg Gln Val Glu Gln
    130                 135                 140

Ala Ser Ala Lys Leu Gly Ile Asp Leu Ser Gln Ala Thr Val Ala Ile
145                 150                 155                 160

Cys Gly Ala Thr Gly Asp Ile Gly Ser Ala Val Cys Arg Trp Leu Asp
                165                 170                 175

Arg Lys Thr Asp Thr Gln Glu Leu Phe Leu Ile Ala Arg Asn Lys Glu
            180                 185                 190

Arg Leu Gln Arg Leu Gln Asp Glu Leu Gly Arg Gly Lys Ile Met Gly
        195                 200                 205

Leu Glu Glu Ala Leu Pro Glu Ala Asp Ile Ile Val Trp Val Ala Ser
    210                 215                 220

Met Pro Lys Gly Val Glu Ile Asn Ala Glu Thr Leu Lys Lys Pro Cys
225                 230                 235                 240

Leu Ile Ile Asp Gly Gly Tyr Pro Lys Asn Leu Asp Thr Lys Ile Lys
                245                 250                 255

His Pro Asp Val His Ile Leu Lys Gly Gly Ile Val Glu His Ser Leu
            260                 265                 270

Asp Ile Asp Trp Lys Ile Met Glu Thr Val Asn Met Asp Val Pro Ser
        275                 280                 285

Arg Gln Met Phe Ala Cys Phe Ala Glu Ala Ile Leu Leu Glu Phe Glu
    290                 295                 300

Gln Trp His Thr Asn Phe Ser Trp Gly Arg Asn Gln Ile Thr Val Thr
305                 310                 315                 320
```

```
Lys Met Glu Gln Ile Gly Glu Ala Ser Val Lys His Gly Leu Gln Pro
            325                 330                 335

Leu Leu Ser Trp
            340

<210> SEQ ID NO 42
<211> LENGTH: 350
<212> TYPE: PRT
<213> ORGANISM: Gloeobacter violaceus

<400> SEQUENCE: 42

Met Phe Gly Leu Ile Gly His Leu Thr Asn Leu Ser His Ala Gln Arg
1               5                   10                  15

Val Ala Arg Asp Leu Gly Tyr Asp Glu Tyr Ala Ser His Asp Leu Glu
            20                  25                  30

Phe Trp Cys Met Ala Pro Pro Gln Ala Val Asp Glu Ile Thr Ile Thr
        35                  40                  45

Ser Val Thr Gly Gln Val Ile His Gly Gln Tyr Val Glu Ser Cys Phe
    50                  55                  60

Leu Pro Glu Met Leu Ala Gln Gly Arg Phe Lys Thr Ala Met Arg Lys
65                  70                  75                  80

Ile Leu Asn Ala Met Ala Leu Val Gln Lys Arg Gly Ile Asp Ile Thr
                85                  90                  95

Ala Leu Gly Gly Phe Ser Ser Ile Ile Phe Glu Asn Phe Ser Leu Asp
            100                 105                 110

Lys Leu Leu Asn Val Arg Asp Ile Thr Leu Asp Ile Gln Arg Phe Thr
        115                 120                 125

Thr Gly Asn Thr His Thr Ala Tyr Ile Leu Cys Gln Gln Val Glu Gln
    130                 135                 140

Gly Ala Val Arg Tyr Gly Ile Asp Pro Ala Lys Ala Thr Val Ala Val
145                 150                 155                 160

Val Gly Ala Thr Gly Asp Ile Gly Ser Ala Val Cys Arg Trp Leu Thr
                165                 170                 175

Asp Arg Ala Gly Ile His Glu Leu Leu Leu Val Ala Arg Asp Ala Glu
            180                 185                 190

Arg Leu Asp Arg Leu Gln Gln Glu Leu Gly Thr Gly Arg Ile Leu Pro
        195                 200                 205

Val Glu Glu Ala Leu Pro Lys Ala Asp Ile Val Val Trp Val Ala Ser
    210                 215                 220

Met Asn Gln Gly Met Ala Ile Asp Pro Ala Gly Leu Arg Thr Pro Cys
225                 230                 235                 240

Leu Leu Ile Asp Gly Gly Tyr Pro Lys Asn Met Ala Gly Thr Leu Gln
                245                 250                 255

Arg Pro Gly Ile His Ile Leu Asp Gly Gly Met Val Glu His Ser Leu
            260                 265                 270

Asp Ile Asp Trp Gln Ile Met Ser Phe Leu Asn Val Pro Asn Pro Ala
        275                 280                 285

Arg Gln Phe Phe Ala Cys Phe Ala Glu Ser Met Leu Leu Glu Phe Glu
    290                 295                 300

Gly Leu His Phe Asn Phe Ser Trp Gly Arg Asn His Ile Thr Val Glu
305                 310                 315                 320

Lys Met Ala Gln Ile Gly Ser Leu Ser Lys Lys His Gly Phe Arg Pro
                325                 330                 335

Leu Leu Glu Pro Ser Gln Arg Ser Gly Glu Leu Val His Gly
            340                 345                 350
```

<210> SEQ ID NO 43
<211> LENGTH: 339
<212> TYPE: PRT
<213> ORGANISM: Microcystis aeruginosa

<400> SEQUENCE: 43

```
Met Phe Gly Leu Ile Gly His Leu Thr Ser Leu Glu His Ala Gln Ser
1               5                   10                  15

Val Ala Asp Asp Leu Gly Tyr Pro Glu Tyr Ala Asn Gln Gly Leu Asp
            20                  25                  30

Phe Trp Cys Ala Ala Pro Pro Gln Ile Val Asp Asp Phe His Val Thr
        35                  40                  45

Ser Ile Thr Gly Gln Thr Ile Arg Gly Lys Tyr Ile Glu Ser Cys Phe
    50                  55                  60

Leu Pro Glu Met Leu Ser Asn Arg Trp Val Lys Ser Ala Ile Arg Lys
65                  70                  75                  80

Val Leu Asn Ala Met Ala Leu Ala Gln Lys Ser Asp Ile Asn Ile Thr
                85                  90                  95

Ala Leu Gly Gly Phe Ser Ser Ile Ile Phe Glu Glu Phe Asn Leu Lys
            100                 105                 110

Asp Asn Arg Gln Val Arg Asn Ile Glu Leu Asp Phe Gly Arg Phe Thr
        115                 120                 125

Thr Gly Asn Thr His Thr Ala Tyr Val Ile Cys Thr Gln Val Glu Thr
    130                 135                 140

Leu Ala Glu Lys Met Gly Ile Asp Leu Ala Gln Ser Thr Val Val Val
145                 150                 155                 160

Cys Gly Ala Thr Gly Asp Ile Gly Ser Ala Val Cys Arg Trp Leu Asn
                165                 170                 175

Glu Lys Thr Asp Thr Lys Glu Leu Ile Cys Val Ala Arg Asn Gln Glu
            180                 185                 190

Arg Leu Gln Ser Leu Gln Glu Glu Leu Gly Arg Gly Lys Ile Leu Pro
        195                 200                 205

Leu Glu Glu Ala Leu Pro Leu Ala Asp Ile Ile Val Trp Val Ala Ser
    210                 215                 220

Leu Pro Lys Gly Val Glu Ile Asp Pro Asp Lys Leu Lys Arg Pro Cys
225                 230                 235                 240

Ile Ile Ile Asp Gly Gly Tyr Pro Lys Asn Leu Gly Thr Val Leu Asn
                245                 250                 255

Ala Pro Asp Ile Ser Val Ile Lys Gly Gly Ile Val Glu His Ser Leu
            260                 265                 270

Asp Ile Asp Trp Lys Ile Met Lys Ile Val Asn Met Asp Ile Pro Ser
        275                 280                 285

Arg Gln Met Phe Ala Cys Phe Ala Glu Ala Ile Leu Leu Glu Leu Glu
    290                 295                 300

Gly Trp Gln Thr Asn Phe Ser Trp Gly Arg Asn Gln Ile Thr Val Pro
305                 310                 315                 320

Lys Met Glu Gln Ile Gly Ala Ala Ser Arg Lys His Gly Phe Gln Pro
                325                 330                 335

Leu Leu Phe
```

<210> SEQ ID NO 44
<211> LENGTH: 340
<212> TYPE: PRT
<213> ORGANISM: Crocosphaera watsonii

<400> SEQUENCE: 44

Met Phe Gly Leu Ile Gly His Leu Thr Ser Leu Glu His Ala His Ser
1               5                   10                  15

Val Ala Asp Ala Phe Gly Tyr Gly Pro Tyr Ala Thr Gln Gly Leu Asp
                20                  25                  30

Leu Trp Cys Ser Ala Pro Pro Gln Phe Val Glu Gln Phe His Val Thr
            35                  40                  45

Ser Ile Thr Gly Gln Thr Ile Glu Gly Lys Tyr Ile Glu Ser Ala Phe
50                  55                  60

Leu Pro Glu Met Leu Met Lys Arg Arg Ile Lys Ala Ala Ile Arg Lys
65                  70                  75                  80

Ile Leu Asn Ala Met Ala Phe Ala Gln Lys Asn Asp Leu Asn Ile Thr
                85                  90                  95

Ala Leu Gly Gly Phe Ser Ser Ile Ile Phe Glu Glu Phe Asn Leu Lys
                100                 105                 110

Gly Asn Arg Gln Val Arg Asn Val Ser Leu Glu Phe Asp Arg Phe Thr
            115                 120                 125

Thr Gly Asn Thr His Thr Ala Tyr Ile Ile Ala Arg Gln Val Glu Gln
130                 135                 140

Ala Ser Ala Lys Leu Gly Ile Asp Leu Ser Arg Ala Thr Val Ala Val
145                 150                 155                 160

Cys Gly Ala Thr Gly Asp Ile Gly Ser Ala Val Cys Arg Trp Leu Asp
                165                 170                 175

Arg Lys Thr Asp Thr Gln Glu Leu Leu Leu Ile Ala Arg Asn Gln Glu
            180                 185                 190

Arg Leu Gln Arg Leu Gln Asp Glu Leu Gly Arg Gly Lys Ile Met Gly
            195                 200                 205

Leu Glu Glu Ala Leu Pro Glu Ala Asp Val Ile Val Trp Val Ala Ser
        210                 215                 220

Met Pro Lys Gly Val Glu Ile Asn Pro Glu Thr Leu Lys Lys Pro Cys
225                 230                 235                 240

Leu Ile Val Asp Gly Gly Tyr Pro Lys Asn Leu Asp Thr Lys Ile Lys
                245                 250                 255

His Pro Asp Val His Ile Leu Lys Gly Gly Val Val Glu His Ser Leu
            260                 265                 270

Asp Ile Asp Trp Lys Ile Met Glu Thr Val Asn Met Asp Val Pro Ser
            275                 280                 285

Arg Gln Met Phe Ala Cys Phe Ala Glu Ala Ile Leu Leu Glu Phe Glu
        290                 295                 300

Gln Trp His Thr Asn Phe Ser Trp Gly Arg Asn Gln Ile Thr Val Thr
305                 310                 315                 320

Lys Met Glu Gln Ile Gly Ala Ser Val Lys His Gly Leu Gln Pro
                325                 330                 335

Leu Leu Ser Trp
            340

<210> SEQ ID NO 45
<211> LENGTH: 339
<212> TYPE: PRT
<213> ORGANISM: Microcystis aeruginosa

<400> SEQUENCE: 45

Met Phe Gly Leu Ile Gly His Leu Thr Ser Leu Glu His Ala Gln Ser
1               5                   10                  15

Val Ala Asp Asp Leu Gly Tyr Pro Glu Tyr Ala Asn Gln Gly Leu Asp
                20                  25                  30

```
Phe Trp Cys Ala Ala Pro Pro Gln Ile Val Asp Asp Phe His Val Thr
            35                  40                  45

Ser Ile Thr Gly Gln Thr Ile Thr Gly Lys Tyr Ile Glu Ser Cys Phe
 50                      55                  60

Leu Pro Glu Met Leu Ser Asn Arg Trp Val Lys Ser Ala Ile Arg Lys
 65                  70                  75                  80

Val Leu Asn Ala Met Ala Leu Ala Gln Lys Ser Asp Ile Asn Ile Thr
                 85                  90                  95

Ala Leu Gly Gly Phe Ser Ser Ile Ile Phe Glu Glu Phe Asn Leu Lys
                100                 105                 110

Asp Asn Arg Gln Val Arg Asn Ile Glu Leu Asp Phe Gly Arg Phe Thr
            115                 120                 125

Thr Gly Asn Thr His Thr Ala Tyr Val Ile Cys Thr Gln Val Gln Thr
            130                 135                 140

Leu Ala Asp Lys Met Gly Ile Asp Leu Ala Gln Ser Thr Val Val Val
145                 150                 155                 160

Cys Gly Ala Thr Gly Asp Ile Gly Ser Ala Val Cys Arg Trp Leu Asn
                165                 170                 175

Glu Lys Thr Asp Thr Lys Glu Leu Ile Cys Val Ala Arg Asn Gln Glu
            180                 185                 190

Arg Leu Gln Ser Leu Gln Glu Glu Leu Gly Arg Gly Lys Ile Leu Pro
            195                 200                 205

Leu Glu Glu Ala Leu Pro Leu Ala Asp Ile Ile Val Trp Val Ala Ser
210                 215                 220

Met Pro Lys Gly Val Glu Ile Asp Pro Asp Lys Leu Lys Arg Pro Cys
225                 230                 235                 240

Leu Ile Ile Asp Gly Gly Tyr Pro Lys Asn Leu Gly Thr Val Leu Asn
                245                 250                 255

Ala Pro Asp Val Ser Val Ile Lys Gly Gly Ile Val Glu His Ser Leu
            260                 265                 270

Asp Ile Asp Trp Lys Ile Met Lys Ile Val Asn Met Asp Ile Pro Ser
            275                 280                 285

Arg Gln Met Phe Ala Cys Phe Ala Glu Ala Ile Leu Leu Glu Leu Glu
            290                 295                 300

Gly Trp Gln Thr Asn Phe Ser Trp Gly Arg Asn Gln Ile Ser Val Ser
305                 310                 315                 320

Lys Met Glu Gln Ile Gly Ala Ala Ser Arg Lys His Gly Phe Gln Pro
                325                 330                 335

Leu Leu Phe

<210> SEQ ID NO 46
<211> LENGTH: 348
<212> TYPE: PRT
<213> ORGANISM: Synechococcus sp.

<400> SEQUENCE: 46

Met Phe Gly Leu Ile Gly His Ser Thr Ser Leu Glu Gln Ala Arg Ser
 1               5                  10                  15

Lys Ala Leu Glu Leu Gly Phe Pro Glu Tyr Ala Asp Gly Asp Leu Asp
                 20                  25                  30

Leu Trp Cys Val Ala Pro Pro Gln Leu Val Glu Asn Val Ser Ile Thr
            35                  40                  45

Ser Pro Thr Gly Lys Thr Ile Glu Gly Ala Tyr Ile Asp Ser Val Phe
 50                  55                  60
```

```
Val Pro Glu Met Leu Ser Arg Phe Lys Thr Ala Arg Arg Lys Val Leu
 65                  70                  75                  80

Asn Ala Met Glu Leu Ala Gln Lys Ser Gly Ile Asp Ile Thr Ala Leu
                 85                  90                  95

Gly Gly Phe Thr Ser Ile Ile Phe Glu Asn Phe Asn Leu Leu Lys Asn
            100                 105                 110

Gln Gln Ile Arg Ser Thr Ala Leu Glu Trp Glu Arg Phe Thr Thr Gly
        115                 120                 125

Asn Thr His Thr Ala Trp Val Ile Ala Gln Gln Val Glu Thr Asn Ala
130                 135                 140

Pro Ala Leu Gly Ile Asp Leu Ser Arg Ala Lys Val Ala Val Val Gly
145                 150                 155                 160

Ala Thr Gly Asp Ile Gly Ser Ala Val Cys Arg Trp Leu Ser Gln Asn
                165                 170                 175

Thr Gly Val Gly Glu Leu Leu Leu Val Ala Arg Gln Pro Gln Pro Leu
            180                 185                 190

Leu Asp Leu Gln Ala Glu Leu Gly Ser Gly Arg Ile Leu Ser Leu Glu
        195                 200                 205

Glu Ala Leu Pro Glu Ala Asp Val Val Val Trp Val Ala Ser Leu Pro
210                 215                 220

Gln Gly Leu Ser Ile Asp Pro Ala Ser Leu Lys Ser Pro Cys Leu Met
225                 230                 235                 240

Ile Asp Gly Gly Tyr Pro Lys Asn Leu Asp Ser Lys Val Thr Gly Ala
                245                 250                 255

Gly Val His Val Ile Lys Gly Gly Ile Val Glu Phe Trp Gln Asp Ile
            260                 265                 270

Gly Trp Gln Met Met Gln Val Ala Glu Met Glu Asn Pro Arg Arg Gln
        275                 280                 285

Leu Phe Ala Cys Phe Ala Glu Ala Met Leu Leu Glu Phe Glu Gly Leu
290                 295                 300

His Thr Asn Phe Ser Trp Gly Arg Asn Asn Ile Thr Leu Ala Asn Met
305                 310                 315                 320

Glu Leu Ile Gly Ala Ala Ser Leu Arg His Gly Phe Arg Ser Ile Gly
                325                 330                 335

Leu Asn Gln Val Pro Arg Pro Gln Leu Ala Ala Val
            340                 345

<210> SEQ ID NO 47
<211> LENGTH: 349
<212> TYPE: PRT
<213> ORGANISM: Synechococcus sp.

<400> SEQUENCE: 47

Met Phe Gly Leu Ile Gly His Ser Ser Ser Phe Arg Asp Ala Arg Asn
1               5                   10                  15

Thr Ala Arg Asp Leu Gly Phe Glu Asp Leu Ala Asp Gly Glu Leu Asp
                20                  25                  30

Leu Trp Cys Ser Ala Pro Pro Gln Leu Val Glu Ser Phe Glu Val Thr
            35                  40                  45

Ser Ser Thr Gly Lys Thr Ile Glu Gly Thr Tyr Ile Asp Ser Cys Phe
        50                  55                  60

Val Pro Glu Met Leu Ser Arg Phe Lys Thr Ala Thr Arg Lys Val Gln
 65                  70                  75                  80

Asn Ala Met Glu Leu Ala Gln Lys Arg Gly Ile Asn Ile Thr Ala Leu
                 85                  90                  95
```

-continued

```
Gly Gly Phe Thr Ser Ile Ile Phe Glu Asn Phe Asn Leu Ala Lys Phe
            100                 105                 110

Gln Gln Ile Arg Ser Thr Leu Leu Gln Trp Asp Arg Phe Thr Thr Gly
        115                 120                 125

Asn Thr His Thr Ala Trp Val Ile Cys Arg Gln Val Glu Gln Asn Ala
    130                 135                 140

Pro Arg Leu Gly Ile Asp Leu Lys Ala Ala Lys Val Ala Val Val Gly
145                 150                 155                 160

Ala Thr Gly Asp Ile Gly Ser Ala Val Cys Arg Trp Met Ala Asn Lys
                165                 170                 175

Thr Gly Val Ala Glu Leu Leu Val Ala Arg Gln Gln Gln Arg Leu
            180                 185                 190

Glu Asp Leu Arg Glu Glu Leu Gly Gly Arg Ile Leu Thr Leu Glu
        195                 200                 205

Gln Ala Leu Pro Glu Ala Asp Val Val Trp Val Ala Ser Leu Pro
    210                 215                 220

Gln Thr Leu Glu Ile Asp Ser Asn Ser Leu Arg Lys Pro Cys Leu Met
225                 230                 235                 240

Ile Asp Gly Gly Tyr Pro Lys Asn Leu Asp Ser Lys Val Met Ser Glu
                245                 250                 255

His Val Thr Val Leu Lys Gly Gly Ile Val Glu Phe Ala Arg Asp Ile
            260                 265                 270

Gly Trp Gln Met Met Thr Val Ala Asp Met Ala Asn Pro Arg Arg Gln
        275                 280                 285

Leu Phe Ala Cys Phe Ala Glu Ala Met Leu Glu Phe Glu Gly Ile
    290                 295                 300

His Thr Asn Phe Ser Trp Gly Arg Asn Asn Ile Thr Leu Glu Ala Met
305                 310                 315                 320

Glu Gln Ile Gly Met Ala Ser Ile Arg His Gly Phe Ser Ala Leu Gly
                325                 330                 335

Ile Asp Pro Asn Thr Leu Asn Pro Gln Pro Leu Ala Ala
            340                 345

<210> SEQ ID NO 48
<211> LENGTH: 346
<212> TYPE: PRT
<213> ORGANISM: Synechococcus sp.

<400> SEQUENCE: 48

Met Phe Gly Leu Ile Gly His Ser Thr Ser Phe Asp Ala Ala Arg Arg
1               5                   10                  15

Lys Ala Met Glu Leu Gly Phe Asp His Ile Ala Asp Gly Asp Leu Asp
            20                  25                  30

Val Trp Cys Ser Ala Pro Pro Gln Leu Val Glu His Val Glu Ile Ser
        35                  40                  45

Ser Pro Thr Gly Thr Thr Ile Lys Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Leu Glu Trp Gln Arg Phe Thr Thr Gly
        115                 120                 125
```

```
Asn Thr His Thr Ala Trp Val Ile Cys Arg Gln Val Glu Asn Asn Ala
            130                 135                 140

Pro Thr Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Val Ala Arg Gln Gln Pro Leu
            180                 185                 190

Val Asp Leu Gln Ala Gln Ile Gly Gly Arg Ile Leu Thr Leu Asp
        195                 200                 205

Glu Ala Leu Pro Glu Ala Asp Val Val Trp Val Ala Ser Met Pro
210                 215                 220

Arg Thr Leu Glu Ile Asp Gln Ala Ser Leu Arg Lys Pro Cys Leu Met
225                 230                 235                 240

Ile Asp Gly Gly Tyr Pro Lys Asn Leu Asp Thr Lys Val Ala Gly Gly
                245                 250                 255

Gly Ile His Val Leu Lys Gly Gly Ile Val Glu Phe Cys Lys Asp Ile
            260                 265                 270

Gly Trp Thr Met Met Gln Ile Ala Glu Met Lys Pro Gln Arg Gln
            275                 280                 285

Met Phe Ala Cys Phe Ala Glu Ala Met Leu Leu Glu Phe Glu Arg Cys
290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Asn Pro Ser Ala Gln Ala Ala Ala
            340                 345

<210> SEQ ID NO 49
<211> LENGTH: 346
<212> TYPE: PRT
<213> ORGANISM: Synechococcus sp.

<400> SEQUENCE: 49

Met Phe Gly Leu Ile Gly His Ser Thr Ser Phe Asp Ala Ala Arg Arg
1               5                   10                  15

Lys Ala Met Glu Leu Gly Phe Asp His Ile Ala Asp Gly Asp Leu Asp
            20                  25                  30

Val Trp Cys Ser Ala Pro Pro Gln Leu Val Glu His Val Glu Ile Ser
        35                  40                  45

Ser Pro Thr Gly Thr Thr Ile Lys Gly Ala Tyr Ile Asp Ser Cys Phe
50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
            130                 135                 140

Pro Thr Leu Gly Ile Asp Leu Lys Thr Ala Lys Val Ala Val Val Gly
145                 150                 155                 160
```

```
Ala Thr Gly Asp Ile Gly Ser Ala Val Cys Arg Trp Leu Ser Ala Arg
                165                 170                 175

Thr Gly Val Gly Glu Leu Leu Val Ala Arg Gln Gln Gln Pro Leu
        180                 185                 190

Leu Asp Leu Gln Ala Gln Ile Gly Gly Arg Ile Leu Thr Leu Asp
            195                 200                 205

Glu Ala Leu Pro Glu Ala Asp Val Val Trp Val Ala Ser Met Pro
210                 215                 220

Arg Thr Leu Glu Ile Asp Gln Ala Ser Leu Arg Lys Pro Cys Leu Met
225                 230                 235                 240

Ile Asp Gly Gly Tyr Pro Lys Asn Leu Asp Thr Lys Val Ala Gly Gly
                245                 250                 255

Gly Ile His Val Leu Lys Gly Gly Ile Val Glu Phe Cys Lys Asp Ile
            260                 265                 270

Gly Trp Thr Met Met Gln Ile Ala Glu Met Glu Lys Pro Gln Arg Gln
            275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Asn Pro Ser Ala Gln Ala Ala Ala Ala
                340                 345

<210> SEQ ID NO 50
<211> LENGTH: 346
<212> TYPE: PRT
<213> ORGANISM: Synechococcus sp.

<400> SEQUENCE: 50

Met Phe Gly Leu Ile Gly His Ser Thr Ser Phe Glu Ala Ala Arg Arg
1               5                   10                  15

Lys Ala Ser Glu Leu Gly Phe Asp His Ile Ala Glu Gly Asp Leu Asp
            20                  25                  30

Val Trp Cys Ser Ala Pro Pro Gln Leu Val Glu His Val Glu Val Thr
        35                  40                  45

Ser Ala Thr Gly Arg Thr Ile Gln Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asp Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Ala Trp Glu Arg Phe Thr Thr Gly
        115                 120                 125

Asn Thr His Thr Ala Trp Val Ile Cys Arg Gln Val Glu Asn Asn Ala
    130                 135                 140

Pro Ala Leu Gly Ile Asp Leu Lys Lys Ala Ser Val Ala Val Val Gly
145                 150                 155                 160

Ala Thr Gly Asp Ile Gly Ser Ala Val Cys Arg Trp Leu Ser Ser Arg
                165                 170                 175

Thr Gly Val Ala Glu Leu Leu Val Ala Arg Gln Gln Lys Pro Leu
        180                 185                 190
```

```
Glu Glu Leu Arg Glu Leu Gly Gly Gly Arg Ile Leu Ser Leu Glu
        195                 200                 205

Asp Ala Leu Pro Glu Ala Asp Val Val Trp Val Ala Ser Met Pro
210                 215                 220

Arg Thr Leu Glu Ile Asp Thr Ser Arg Leu Lys Thr Pro Cys Leu Met
225                 230                 235                 240

Ile Asp Gly Gly Tyr Pro Lys Asn Leu Asp Ala Arg Val Ala Ala Lys
                245                 250                 255

Gly Ile His Val Leu Lys Gly Ile Val Glu Phe Phe Thr Asp Ile
                260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Glu Phe Glu Ser His
        290                 295                 300

His Thr Asn Phe Ser Trp Gly Arg Asn Asn Ile Thr Leu Glu Lys Met
305                 310                 315                 320

Asp Phe Ile Gly Gly Ala Ser Val Arg His Gly Phe Thr Thr Leu Asn
                325                 330                 335

Leu Gln Gly Leu Pro Gln Ala Ala Val Ala
            340                 345

<210> SEQ ID NO 51
<211> LENGTH: 346
<212> TYPE: PRT
<213> ORGANISM: Synechococcus sp.

<400> SEQUENCE: 51

Met Phe Gly Leu Ile Gly His Ser Thr Ser Phe Asp Ala Ala Arg Arg
1               5                   10                  15

Lys Ala Met Glu Leu Gly Phe Asp His Ile Ala Asp Gly Asp Leu Asp
                20                  25                  30

Val Trp Cys Ser Ala Pro Pro Gln Leu Val Glu His Val Glu Ile Ser
            35                  40                  45

Ser Pro Thr Gly Thr Thr Ile Lys Gly Ala Tyr Ile Asp Ser Cys Phe
        50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
130                 135                 140

Pro Ser Leu Gly Ile Asp Leu Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Leu Asp Leu Gln Ala Gln Ile Gly Gly Arg Ile Leu Thr Leu Asp
        195                 200                 205

Glu Ala Leu Pro Glu Ala Asp Val Val Val Trp Val Ala Ser Met Pro
210                 215                 220
```

```
Arg Thr Leu Glu Ile Asp Gln Ser Ser Leu Pro Lys Pro Cys Leu Met
225                 230                 235                 240

Ile Asp Gly Gly Tyr Pro Lys Asn Leu Asp Ser Lys Val Ala Gly Gly
            245                 250                 255

Gly Ile His Val Leu Lys Gly Gly Ile Val Glu Phe Cys Lys Asp Ile
        260                 265                 270

Gly Trp Thr Met Met Gln Ile Ala Glu Met Asp Asn Pro Gln Arg Gln
    275                 280                 285

Met Phe Ala Cys Phe Ala Glu Ala Met Leu Leu Glu Phe Glu Arg Cys
        290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
            325                 330                 335

Leu Asn Pro Ser Val Gln Ala Ala Ala Ala
            340                 345

<210> SEQ ID NO 52
<211> LENGTH: 346
<212> TYPE: PRT
<213> ORGANISM: Synechococcus sp.

<400> SEQUENCE: 52

Met Phe Gly Leu Ile Gly His Ser Thr Ser Phe Glu Ala Ala Arg Arg
1               5                   10                  15

Lys Ala Ser Asp Leu Gly Phe Asp His Ile Ala Glu Gly Asp Leu Asp
            20                  25                  30

Val Trp Cys Ser Ala Pro Pro Gln Leu Val Glu His Val Glu Val Thr
        35                  40                  45

Ser Pro Thr Gly Lys Ser Ile Gln Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asp Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Ala Trp Glu Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Lys Lys Ala Ser Val Ala Val Val Gly
145                 150                 155                 160

Ala Thr Gly Asp Ile Gly Ser Ala Val Cys Arg Trp Leu Ser Ser Arg
                165                 170                 175

Thr Gly Val Ala Glu Leu Leu Leu Val Ala Arg Gln Gln Lys Pro Leu
            180                 185                 190

Glu Asp Leu Arg Asp Glu Leu Gly Gly Arg Ile Leu Ser Leu Glu
        195                 200                 205

Asp Ala Leu Pro Glu Ala Asp Val Val Trp Val Ala Ser Met Pro
    210                 215                 220

Arg Thr Leu Glu Ile Asp Ala Ser Arg Leu Lys Thr Pro Cys Leu Met
225                 230                 235                 240

Ile Asp Gly Gly Tyr Pro Lys Asn Leu Asp Ala Arg Val Ala Ala Lys
            245                 250                 255
```

```
Gly Ile His Val Leu Lys Gly Ile Val Glu Phe Phe Thr Asp Ile
            260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Glu Phe Glu Ser His
        290                 295                 300

His Thr Asn Phe Ser Trp Gly Arg Asn Asn Ile Thr Leu Glu Lys Met
305                 310                 315                 320

Asp Phe Ile Gly Gly Ala Ser Val Arg His Gly Phe Ser Thr Leu Asn
                325                 330                 335

Leu Gln Gly Leu Pro Gln Ala Ala Ala
            340                 345

<210> SEQ ID NO 53
<211> LENGTH: 346
<212> TYPE: PRT
<213> ORGANISM: Synechococcus sp.

<400> SEQUENCE: 53

Met Phe Gly Leu Ile Gly His Ser Thr Ser Phe Asp Ala Ala Arg Arg
1               5                   10                  15

Lys Ala Leu Glu Leu Gly Phe Asp His Ile Ala Asp Gly Asp Leu Asp
            20                  25                  30

Val Trp Cys Ser Ala Pro Pro Gln Leu Val Glu His Val Glu Ile Thr
        35                  40                  45

Ser Pro Val Gly Thr Thr Ile Lys Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Ile Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
130                 135                 140

Pro Ala Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Thr Ala Arg
                165                 170                 175

Thr Gly Val Gly Glu Leu Leu Leu Val Ala Arg Gln Gln Gln Pro Leu
            180                 185                 190

Leu Asp Leu Gln Gly Glu Leu Gly Gly Arg Ile Leu Ser Leu Asp
        195                 200                 205

Glu Ala Met Pro Glu Ala Asp Val Val Val Trp Val Ala Ser Met Pro
210                 215                 220

Arg Thr Leu Gln Ile Asp Gln Glu Ser Leu Arg Lys Pro Cys Leu Met
225                 230                 235                 240

Ile Asp Gly Gly Tyr Pro Lys Asn Leu Asp Ala Lys Val Ala Gly Gly
                245                 250                 255

Gly Ile His Val Leu Lys Gly Ile Val Glu Phe Cys Lys Asp Ile
            260                 265                 270

Gly Trp Thr Met Met Gln Ile Ala Glu Met Glu Lys Pro Gln Arg Gln
        275                 280                 285
```

```
Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Gln Ala Ser Val Arg His Gly Phe Ser Thr Leu Asn
                325                 330                 335

Leu Asn Pro Ser Leu Gln Val Ala Ala Ala
                340                 345

<210> SEQ ID NO 54
<211> LENGTH: 346
<212> TYPE: PRT
<213> ORGANISM: Synechococcus sp.

<400> SEQUENCE: 54

Met Phe Gly Leu Ile Gly His Ser Thr Ser Phe Glu Ala Ala Arg Gln
1               5                   10                  15

Lys Ala Phe Glu Leu Gly Phe Asp His Ile Ala Asp Gly Asp Leu Asp
                20                  25                  30

Val Trp Cys Ser Ala Pro Pro Gln Leu Val Glu Thr Phe Asp Val Thr
                35                  40                  45

Ser Pro Thr Gly Arg Thr Ile Thr Gly Ala Tyr Ile Asp Ser Cys Phe
50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
                100                 105                 110

Gln His Val Arg Ser Thr Thr Leu Glu Trp Glu Arg Phe Thr Thr Gly
                115                 120                 125

Asn Thr His Thr Ala Trp Val Ile Ser Arg Gln Val Glu Ile Asn Ala
                130                 135                 140

Pro Arg Leu Gly Ile Asp Leu Ser Lys Ala Arg Val Ala Val Val Gly
145                 150                 155                 160

Ala Thr Gly Asp Ile Gly Ser Ala Val Cys Arg Trp Leu Ser Gln Arg
                165                 170                 175

Thr Gly Val Ala Glu Leu Leu Leu Val Ala Arg Gln Gln Gln Pro Leu
                180                 185                 190

Leu Asp Leu Gln Lys Glu Leu Gly Gly Gly Arg Ile Leu Ser Leu Asp
                195                 200                 205

Glu Ala Val Pro Glu Ala Asp Val Val Trp Val Ala Ser Met Pro
210                 215                 220

Arg Thr Leu Glu Ile Asp Ala Ala Ser Leu Arg Gln Pro Cys Leu Met
225                 230                 235                 240

Ile Asp Gly Gly Tyr Pro Lys Asn Leu Asn Ala Arg Ile Ala Gly Ser
                245                 250                 255

Gly Val His Val Leu Lys Gly Gly Ile Val Glu Phe Gly Ser Asp Ile
                260                 265                 270

Gly Trp Asn Met Met Glu Leu Ala Glu Met Glu Lys Pro Gln Arg Gln
                275                 280                 285

Met Phe Ala Cys Phe Ala Glu Ala Met Leu Leu Glu Phe Glu Ser Cys
                290                 295                 300

His Thr Asn Phe Ser Trp Gly Arg Asn Asn Ile Thr Leu Glu Lys Met
305                 310                 315                 320
```

```
Asp Phe Ile Gly Glu Ala Ser Arg Arg His Gly Phe Ser Thr Leu Asn
            325                 330                 335

Leu Ser Ala Pro Val Gln Val Ala Ala
        340                 345

<210> SEQ ID NO 55
<211> LENGTH: 346
<212> TYPE: PRT
<213> ORGANISM: Synechococcus sp.

<400> SEQUENCE: 55

Met Phe Gly Leu Ile Gly His Ser Thr Ser Phe Glu Ala Ala Arg Arg
1               5                   10                  15

Lys Ala Leu Glu Leu Gly Phe Asp His Ile Ala Asp Gly Asp Leu Asp
            20                  25                  30

Val Trp Cys Ser Ala Pro Pro Gln Leu Val Glu His Val Glu Val Thr
        35                  40                  45

Ser Pro Ala Gly Ile Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Asp Trp Gln Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Thr Ala Arg
                165                 170                 175

Thr Asn Val Gly Glu Leu Leu Leu Val Ala Arg Gln Pro Gln Pro Leu
            180                 185                 190

Ala Asp Leu Gln Ala Glu Leu Gly Gly Gly Arg Ile Leu Ala Leu Ser
        195                 200                 205

Asp Ala Leu Ser Glu Ala Asp Val Val Val Trp Val Ala Ser Met Pro
    210                 215                 220

Arg Thr Leu Glu Ile Asp Asn Asn Ser Leu Lys Lys Pro Cys Leu Met
225                 230                 235                 240

Ile Asp Gly Gly Tyr Pro Lys Asn Leu Asp Ser Lys Val Ala Gly Gly
                245                 250                 255

Gly Ile His Val Leu Lys Gly Gly Ile Val Glu Phe Cys Arg Asp Ile
            260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Lys Thr Asn Leu Gln Ala Val Ala
            340                 345
```

```
<210> SEQ ID NO 56
<211> LENGTH: 347
<212> TYPE: PRT
<213> ORGANISM: Prochlorococcus marinus

<400> SEQUENCE: 56

Met Phe Gly Leu Ile Gly His Ser Thr Ser Phe Lys Asp Ala Arg Gln
1               5                   10                  15

Lys Ala Met Asp Leu Gly Tyr Asp His Ile Ala Glu Gly Asp Leu Asp
            20                  25                  30

Val Trp Cys Ser Ala Pro Pro Gln Leu Val Glu His Val Lys Val Val
        35                  40                  45

Ser Ala Ile Gly Lys Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Glu Asn
            100                 105                 110

Lys Gln Val Arg Asn Thr Thr Leu Asp Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Leu Leu Gly Ile Asp Leu Gln Lys Ala Arg Val Ala Val Val Gly
145                 150                 155                 160

Ala Thr Gly Asp Ile Gly Ser Ala Val Cys Arg Trp Leu Ser Gln Arg
                165                 170                 175

Thr Gly Val Ser Glu Leu Leu Leu Val Ala Arg Gln Gln Pro Leu
            180                 185                 190

Lys Asp Leu Gln Lys Asp Leu Gly Gly Arg Val Leu Arg Leu Glu
        195                 200                 205

Glu Ala Leu Pro Glu Ala Asp Ala Val Ile Trp Val Ala Ser Leu Pro
    210                 215                 220

Lys Asn Leu Gln Ile Asp Lys Ser Lys Leu Arg Lys Pro Cys Leu Met
225                 230                 235                 240

Ile Asp Gly Gly Tyr Pro Lys Asn Leu Asp Glu Lys Phe Ser Gly Ser
                245                 250                 255

Gly Ile His Val Leu Lys Gly Ile Val Glu Phe Phe Glu Asp Ile
        260                 265                 270

Gly Trp Asn Met Met Glu Ile Ala Glu Met Asp Val Pro Gln Arg Gln
    275                 280                 285

Met Phe Ala Cys Phe Ala Glu Ala Met Leu Leu Glu Phe Glu Asn Cys
290                 295                 300

His Thr Asn Phe Ser Trp Gly Arg Asn Asn Ile Thr Leu Glu Lys Met
                305                 310                 315                 320

Asp Phe Ile Gly Glu Ala Ser Leu Arg His Gly Phe Ser Val Leu Arg
            325                 330                 335

Leu Gln Pro Asn Asn Leu Gln Ala Ala Phe Ala
        340                 345

<210> SEQ ID NO 57
<211> LENGTH: 345
<212> TYPE: PRT
<213> ORGANISM: Prochlorococcus marinus
```

<400> SEQUENCE: 57

```
Met Phe Gly Leu Ile Gly His Ser Thr Ser Phe Glu Asp Ala Arg Lys
1               5                   10                  15

Thr Ala Leu Gln Ile Gly Tyr Asp His Leu Asp Gly Asp Leu Asp Val
            20                  25                  30

Trp Cys Ser Ala Pro Pro Gln Phe Leu Glu Gln Ile Glu Val Glu Ser
        35                  40                  45

Leu Thr Gly Lys Lys Ile Glu Gly Ala Tyr Ile Asp Ser Cys Phe Val
    50                  55                  60

Pro Glu Met Leu Ser Arg Phe Lys Thr Ala Arg Arg Lys Val Leu Asn
65                  70                  75                  80

Ala Met Glu Met Ala Gln Lys Arg Gly Ile Gln Ile Ser Ala Leu Gly
                85                  90                  95

Gly Phe Thr Ser Ile Ile Phe Glu Asn Phe Asn Leu Leu Lys His Gln
            100                 105                 110

His Val Arg Asn Thr Thr Leu Glu Trp Glu Arg Phe Thr Thr Gly Asn
        115                 120                 125

Thr His Thr Ala Trp Val Ile Cys Arg Gln Leu Glu Asn Asn Ala Pro
    130                 135                 140

Leu Leu Gly Ile Asp Leu Ser Lys Ala Arg Val Ala Val Val Gly Ala
145                 150                 155                 160

Thr Gly Asp Ile Gly Ser Ala Val Cys Arg Trp Leu Ser Ala Arg Thr
                165                 170                 175

Gly Val Ala Glu Leu Leu Leu Val Ala Arg Gln Gln Pro Leu Ile
            180                 185                 190

Asp Leu Gln Thr Glu Leu Ala Gly Gly Arg Ile Leu Ser Leu Glu Glu
        195                 200                 205

Ala Leu Pro Glu Ala Asp Val Val Trp Val Ala Ser Met Pro Arg
210                 215                 220

Thr Leu Glu Ile Asp Met Glu Ser Leu Arg Lys Pro Cys Leu Met Ile
225                 230                 235                 240

Asp Gly Gly Tyr Pro Lys Asn Leu Asp Ala Lys Phe Ala Gly Ser Gly
                245                 250                 255

Val His Val Leu Lys Gly Gly Ile Val Glu Phe Cys Asn Asp Ile Ser
            260                 265                 270

Trp Asp Val Gly Trp Ile Ala Glu Met Asp Lys Pro Ala Arg Gln Met
        275                 280                 285

Phe Ala Cys Phe Ala Glu Ala Met Leu Leu Phe Glu Asn Cys His
    290                 295                 300

Thr Asn Phe Ser Trp Gly Arg Asn Gln Ile Thr Leu Glu Lys Met Asp
305                 310                 315                 320

Phe Ile Gly Met Ala Ser Leu Arg His Gly Phe Ser Ser Leu Asn Leu
                325                 330                 335

Asn His Gln Leu Gln Ala Ala Ala
            340                 345
```

<210> SEQ ID NO 58
<211> LENGTH: 346
<212> TYPE: PRT
<213> ORGANISM: Synechococcus sp.

<400> SEQUENCE: 58

```
Met Phe Gly Leu Ile Gly His Ser Thr Ser Phe Asp Ala Ala Arg Arg
1               5                   10                  15

Lys Ala Met Glu Leu Gly Phe Asp His Ile Ala Glu Gly Asp Leu Asp
```

```
                20                  25                  30
Val Trp Cys Ser Ala Pro Pro Gln Leu Val Glu His Val Gln Val Thr
            35                  40                  45

Ser Pro Val Gly Thr Thr Ile Glu Gly Ala Tyr Ile Asp Ser Cys Phe
 50                  55                  60

Val Pro Glu Met Leu Ser Arg Phe Lys Thr Ala Arg Arg Lys Val Leu
 65                  70                  75                  80

Asn Ala Met Glu Leu Ala Gln Lys Lys Asp Ile Ala Ile Thr Ala Leu
                85                  90                  95

Gly Gly Phe Thr Ser Ile Ile Phe Glu Asn Phe Asn Leu Leu Gln Asn
            100                 105                 110

Gln Thr Val Arg Ser Thr Thr Leu Asp Trp Arg Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Ser Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Pro Leu
            180                 185                 190

Met Asp Leu Gln Lys Glu Leu Gly Gly Arg Ile Leu Thr Leu Glu
        195                 200                 205

Glu Ala Leu Pro Glu Ala Asp Val Val Trp Val Ala Ser Met Pro
    210                 215                 220

Arg Thr Leu Gln Ile Asp Gln Asp Ser Leu Arg Ser Pro Cys Leu Met
225                 230                 235                 240

Ile Asp Gly Gly Tyr Pro Lys Asn Leu Asp Ala Lys Val Ala Gly Gly
                245                 250                 255

Gly Ile His Val Leu Lys Gly Gly Ile Val Glu Phe Cys Arg Asp Ile
            260                 265                 270

Gly Trp Thr Met Met Glu Ile Ala Glu Met Glu Lys Pro Gln Arg Gln
        275                 280                 285

Met Phe Ala Cys Phe Ala Glu Ala Met Leu Leu Glu Phe Glu Arg Cys
290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Gln Ser Arg Leu Gln Ala Ala Ala
            340                 345

<210> SEQ ID NO 59
<211> LENGTH: 346
<212> TYPE: PRT
<213> ORGANISM: Synechococcus sp.

<400> SEQUENCE: 59

Met Phe Gly Leu Ile Gly His Ser Thr Ser Phe Asp Ala Ala Arg Arg
1               5                   10                  15

Lys Ala Met Glu Leu Gly Phe Asp His Ile Ala Glu Gly Asp Leu Asp
                20                  25                  30

Val Trp Cys Ser Ala Pro Pro Gln Leu Val Glu His Val Gln Val Thr
            35                  40                  45

Ser Pro Val Gly Thr Thr Ile Glu Gly Ala Tyr Ile Asp Ser Cys Phe
```

```
                    50                  55                  60
Val Pro Glu Met Leu Ser Arg Phe Lys Thr Ala Arg Arg Lys Val Leu
 65                  70                  75                  80

Asn Ala Met Glu Leu Ala Gln Lys Lys Asp Ile Ala Ile Thr Ala Leu
                 85                  90                  95

Gly Gly Phe Thr Ser Ile Ile Phe Glu Asn Phe Asn Leu Leu Gln Asn
            100                 105                 110

Gln Thr Val Arg Ser Thr Thr Leu Asp Trp Arg Arg Phe Thr Thr Gly
            115                 120                 125

Asn Thr His Thr Ala Trp Val Ile Cys Arg Gln Val Glu Asn Asn Ala
            130                 135                 140

Pro Ser Leu Gly Ile Asp Leu Ser Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Met Asp Leu Gln Lys Glu Leu Gly Gly Arg Ile Leu Thr Leu Glu
            195                 200                 205

Glu Ala Leu Pro Glu Ala Asp Val Val Trp Val Ala Ser Met Pro
210                 215                 220

Arg Thr Leu Gln Ile Asp Gln Asp Ser Leu Arg Ser Pro Cys Leu Met
225                 230                 235                 240

Ile Asp Gly Gly Tyr Pro Lys Asn Leu Asp Ala Lys Val Ala Gly Gly
                245                 250                 255

Gly Ile His Val Leu Lys Gly Gly Ile Val Glu Phe Cys Arg Asp Ile
            260                 265                 270

Gly Trp Thr Met Met Glu Ile Ala Glu Met Glu Lys Pro Gln Arg Gln
            275                 280                 285

Met Phe Ala Cys Phe Ala Glu Ala Met Leu Leu Glu Phe Glu Arg Cys
            290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Gln Ser Arg Leu Gln Ala Ala Ala
            340                 345

<210> SEQ ID NO 60
<211> LENGTH: 346
<212> TYPE: PRT
<213> ORGANISM: Synechococcus sp.

<400> SEQUENCE: 60

Met Phe Gly Leu Ile Gly His Ser Thr Ser Phe Glu Ala Ala Arg Arg
  1               5                  10                  15

Lys Ala Leu Glu Leu Gly Phe Asp His Ile Ala Asp Gly Asp Leu Asp
                 20                  25                  30

Val Trp Cys Ser Ala Pro Pro Gln Leu Val Glu His Val Glu Val Thr
             35                  40                  45

Ser Pro Ala Gly Ile Thr Ile Glu Gly Ala Tyr Ile Asp Ser Cys Phe
            50                  55                  60

Val Pro Glu Met Leu Ser Arg Phe Lys Thr Ala Arg Arg Lys Val Leu
 65                  70                  75                  80

Asn Ala Met Glu Leu Ala Gln Lys Lys Gly Ile Asn Ile Thr Ala Leu
```

-continued

```
                85                  90                  95
Gly Gly Phe Thr Ser Ile Ile Phe Glu Asn Phe Asn Leu Leu Gln His
            100                 105                 110
Gln Thr Ile Arg Ser Thr Thr Leu Asp Trp Gln Arg Phe Thr Thr Gly
            115                 120                 125
Asn Thr His Thr Ala Trp Val Ile Cys Arg Gln Val Glu Asn Asn Ala
            130                 135                 140
Pro Ser Leu Gly Ile Asp Leu Lys Thr Ala Lys Val Ala Val Val Gly
145                 150                 155                 160
Ala Thr Gly Asp Ile Gly Ser Ala Val Cys Arg Trp Leu Ser Ala Arg
                165                 170                 175
Thr Asn Val Gly Glu Leu Leu Val Ala Arg Gln Pro Gln Pro Leu
                180                 185                 190
Ala Asp Leu Gln Ser Glu Leu Gly Gly Arg Ile Leu Ala Leu Ser
            195                 200                 205
Asp Ala Leu Ser Glu Ala Asp Val Val Trp Val Ala Ser Met Pro
210                 215                 220
Arg Thr Leu Glu Ile Asp Asn Asn Ser Leu Lys Lys Pro Cys Leu Met
225                 230                 235                 240
Ile Asp Gly Gly Tyr Pro Lys Asn Leu Asp Ser Lys Val Ala Gly Gly
                245                 250                 255
Gly Ile His Val Leu Lys Gly Gly Ile Val Glu Phe Cys Arg Asp Ile
                260                 265                 270
Gly Trp Ser Met Met Glu Ile Ala Glu Met Glu Asn Pro Gln Arg Gln
                275                 280                 285
Met Phe Ala Cys Phe Ala Glu Ala Met Leu Leu Glu Phe Glu Arg Cys
            290                 295                 300
His Thr Asn Phe Ser Trp Gly Arg Asn Asn Ile Thr Leu Glu Lys Met
305                 310                 315                 320
Asp Phe Ile Gly Ala Ala Ser Val Arg His Gly Phe Ser Thr Leu Asn
                325                 330                 335
Leu Lys Thr Asn Leu Gln Ala Ala Ala Ala
            340                 345

<210> SEQ ID NO 61
<211> LENGTH: 349
<212> TYPE: PRT
<213> ORGANISM: Cyanobium sp.

<400> SEQUENCE: 61

Met Phe Gly Leu Ile Gly His Ser Thr Ser Phe Glu Glu Ala Arg Ala
1               5                   10                  15
Lys Ala Arg Ser Leu Gly Phe Asp Glu Tyr Ala Asp Gly Asp Leu Asp
                20                  25                  30
Met Trp Cys Ala Ala Pro Pro Gln Leu Val Glu Lys Val Thr Val Thr
            35                  40                  45
Ser Arg Thr Gly Lys Thr Ile Glu Gly Ala Tyr Ile Asp Ser Val Phe
        50                  55                  60
Val Pro Glu Met Leu Arg Arg Phe Lys Thr Ala Lys Arg Lys Val Leu
65                  70                  75                  80
Lys Ala Met Glu Leu Ala Gln Arg Ser Gly Ile Asp Ile Thr Ala Leu
                85                  90                  95
Gly Gly Phe Thr Ser Ile Ile Phe Glu Asp Met Asn Leu Leu Arg Glu
            100                 105                 110
Glu Arg Val Ser Ala Val Gln Leu Asn Trp Glu Arg Phe Thr Thr Gly
```

```
            115                 120                 125
Asn Thr His Thr Ala Trp Val Ile Cys Gln Gln Val Glu Arg Asn Ala
130                 135                 140
Ser Ser Leu Gly Ile Asp Leu Ala Ser Ala Lys Val Ala Val Val Gly
145                 150                 155                 160
Ala Ser Gly Asp Ile Gly Ser Ala Val Cys Arg Trp Leu Gln Arg Arg
                165                 170                 175
Gly Val Gly Glu Leu Leu Leu Val Ala Arg Arg Pro Gln Pro Leu Val
            180                 185                 190
Asp Leu Gln Glu Ser Leu Gly Glu Gly Arg Ile Leu Asp Leu Glu Ala
        195                 200                 205
Ala Leu Pro Glu Ala Asp Val Val Trp Val Ala Ser Leu Pro Gln
    210                 215                 220
Ser Leu Gln Ile Asp Thr Ala Ser Leu Lys Arg Pro Cys Leu Met Ile
225                 230                 235                 240
Asp Gly Gly Tyr Pro Lys Asn Leu Asp Ala Lys Ala Ala Ala Glu Gly
                245                 250                 255
Val His Val Leu Lys Gly Gly Ile Val Glu Phe Trp Gln Asp Ile Gly
            260                 265                 270
Trp Gln Met Met Glu Val Ala Glu Met Ala Val Pro Gln Arg Gln Met
        275                 280                 285
Phe Ala Cys Phe Ala Glu Ala Met Leu Leu Asp Phe Glu Asp Leu His
    290                 295                 300
Thr Asn Phe Ser Trp Gly Arg Asn Asn Ile Thr Leu Ala Ala Met Asp
305                 310                 315                 320
Arg Ile Gly Glu Ala Ser Leu Arg His Gly Phe Glu Ala Leu Gly Leu
                325                 330                 335
Gln His Ala Gly Ala Val Ser Pro Ala Leu Ala Ala Ala
            340                 345

<210> SEQ ID NO 62
<211> LENGTH: 346
<212> TYPE: PRT
<213> ORGANISM: Prochlorococcus marinus

<400> SEQUENCE: 62

Met Phe Gly Leu Ile Gly His Ser Thr Ser Phe Glu Asp Ala Lys Arg
1               5                   10                  15
Lys Ala Leu Gly Leu Gly Tyr Asp His Ile Ala Glu Gly Asp Leu Asp
            20                  25                  30
Val Trp Cys Thr Ala Pro Pro Gln Leu Val Glu Asn Val Lys Val Val
        35                  40                  45
Ser Ala Ile Gly Lys Thr Ile Glu Gly Ala Tyr Ile Asp Ser Cys Phe
    50                  55                  60
Val Pro Glu Met Leu Ser Arg Phe Lys Thr Ala Arg Arg Lys Val Leu
65                  70                  75                  80
Asn Ala Met Glu Leu Ala Gln Lys Lys Gly Ile Ser Ile Thr Ala Leu
                85                  90                  95
Gly Gly Phe Thr Ser Ile Ile Phe Glu Asn Phe Asn Leu Leu Gln Asn
            100                 105                 110
Gln Gln Val Arg Asn Thr Thr Leu Asp Trp Arg Phe Thr Thr Gly
        115                 120                 125
Asn Thr His Thr Ala Trp Val Ile Cys Arg Gln Leu Glu Gln Asn Ala
130                 135                 140
Pro Arg Ile Gly Ile Asp Leu Ser Lys Ser Lys Val Ala Val Val Gly
```

```
            145                 150                 155                 160
Ala Thr Gly Asp Ile Gly Ser Ala Val Cys Arg Trp Leu Ser Asn Arg
                165                 170                 175

Thr Gly Val Ser Glu Leu Leu Val Ala Arg Gln Gln Lys Pro Leu
            180                 185                 190

Leu Glu Leu Gln Ser Gln Leu Gly Gly Arg Ile Leu Ser Leu Asp
        195                 200                 205

Asp Ala Leu Pro Glu Ala Asp Ile Val Ile Trp Val Ala Ser Met Pro
210                 215                 220

Lys Thr Leu Glu Ile Asp Pro Ser Lys Ile Lys Arg Pro Cys Leu Met
225                 230                 235                 240

Ile Asp Gly Gly Tyr Pro Lys Asn Leu Gly Glu Lys Phe Ser Gly Pro
                245                 250                 255

Gly Ile His Val Leu Lys Gly Gly Ile Val Gln Phe Phe Lys Asp Ile
                260                 265                 270

Gly Trp Ser Met Met Glu Leu Ala Glu Met Glu Asn Pro Lys Arg Glu
            275                 280                 285

Met Phe Ala Cys Phe Ala Glu Ala Met Leu Leu Glu Phe Glu Asn Cys
        290                 295                 300

His Thr Asn Phe Ser Trp Gly Arg Asn Asn Ile Thr Leu Glu Lys Met
305                 310                 315                 320

Asp Phe Ile Gly Lys Ala Ser Glu Arg His Gly Phe Ser Ala Val Gly
                325                 330                 335

Leu Lys Ser Asn Ile Gln Thr Leu Thr Val
                340                 345

<210> SEQ ID NO 63
<211> LENGTH: 346
<212> TYPE: PRT
<213> ORGANISM: Prochlorococcus marinus

<400> SEQUENCE: 63

Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
                20                  25                  30

Val Trp Cys Thr Ala Pro Pro Gln Leu Val Glu Asn Val Glu Val Lys
            35                  40                  45

Ser Ala Thr Gly Ile Ser Ile Glu Gly Ser Tyr Ile Asp Ser Cys Phe
        50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
130                 135                 140

Pro Lys Val Gly Ile Glu Leu Lys Lys Ala Thr Val Ala Val Val Gly
145                 150                 155                 160

Ala Thr Gly Asp Ile Gly Ser Ala Val Cys Arg Trp Leu Ile Asn Lys
                165                 170                 175

Thr Gly Ile Gly Glu Leu Leu Leu Val Ala Arg Gln Lys Glu Pro Leu
```

```
                        180                 185                 190
Asp Asn Leu Gln Lys Glu Leu Asp Gly Gly Thr Ile Lys Ser Leu Asp
                195                 200                 205

Glu Ala Leu Pro Glu Ala Asp Ile Val Val Trp Val Ala Ser Met Pro
            210                 215                 220

Lys Thr Met Glu Ile Asn Thr Asn Asn Leu Lys Gln Pro Cys Leu Met
225                 230                 235                 240

Ile Asp Gly Gly Tyr Pro Lys Asn Leu Asp Glu Lys Phe Gln Gly Asn
                245                 250                 255

Asn Ile His Val Val Lys Gly Gly Ile Val Lys Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
        290                 295                 300

His Thr Asn Phe Ser Trp Gly Arg Asn Asn Ile Ser Leu Glu Lys Met
305                 310                 315                 320

Glu Phe Ile Gly Ala Ala Ser Val Lys His Gly Phe Ser Ala Ile Gly
                325                 330                 335

Leu Asp Lys His Pro Lys Val Leu Ala Val
                340                 345

<210> SEQ ID NO 64
<211> LENGTH: 346
<212> TYPE: PRT
<213> ORGANISM: Synechococcus sp.

<400> SEQUENCE: 64

Met Phe Gly Leu Ile Gly His Ser Thr Ser Phe Glu Ala Ala Arg Arg
1               5                   10                  15

Lys Ala Met Glu Leu Gly Phe Asp His Ile Ala Asp Gly Asp Leu Asp
                20                  25                  30

Val Trp Cys Ser Ala Pro Pro Gln Leu Val Glu His Val Glu Val Thr
            35                  40                  45

Ser Pro Val Gly Thr Thr Ile Glu Gly Ala Tyr Ile Asp Ser Cys Phe
        50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Asp Trp Gln Arg Phe Thr Thr Gly
        115                 120                 125

Asn Thr His Thr Ala Trp Val Ile Cys Arg Gln Val Glu Asn Asn Ala
130                 135                 140

Pro Thr Leu Gly Ile Asp Leu Ser Lys Ala Lys Val Ala Val Val Gly
145                 150                 155                 160

Ala Thr Gly Asp Ile Gly Ser Ala Val Cys Arg Trp Leu Gln Ala Arg
                165                 170                 175

Thr Arg Val Gly Glu Leu Leu Val Ala Arg Gln Gln Pro Leu
            180                 185                 190

Leu Asp Leu Gln Gln Glu Leu Gly Gly Gly Arg Ile Leu Ser Leu Asp
        195                 200                 205

Glu Ala Leu Pro Glu Ala Asp Val Val Val Trp Val Ala Ser Met Pro
```

```
            210                 215                 220
Arg Thr Leu Glu Ile Asp Gln Asp Ser Leu Lys Lys Pro Cys Leu Met
225                 230                 235                 240

Ile Asp Gly Gly Tyr Pro Lys Asn Leu Asp Thr Lys Val Ala Gly Gly
                245                 250                 255

Gly Ile His Val Leu Lys Gly Gly Ile Val Glu Phe Cys Arg Asp Ile
                260                 265                 270

Gly Trp Ser Met Met Ala Ile Ala Glu Met Glu Arg Pro Gln Arg Gln
            275                 280                 285

Met Phe Ala Cys Phe Ala Glu Ala Met Leu Leu Glu Phe Glu Arg Cys
290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu His Pro Asn Leu Gln Ala Thr Ala Ala
                340                 345

<210> SEQ ID NO 65
<211> LENGTH: 346
<212> TYPE: PRT
<213> ORGANISM: Prochlorococcus marinus

<400> SEQUENCE: 65

Met Phe Gly Leu Ile Gly His Ser Thr Ser Phe Asp Asp Ala Lys Lys
1               5                   10                  15

Lys Ala Met Asp Leu Gly Tyr Asp His Ile Ala Gln Gly Asp Leu Asp
                20                  25                  30

Val Trp Cys Ser Ala Pro Pro Gln Leu Val Glu His Val Asn Ile Val
            35                  40                  45

Ser Ala Ile Gly Lys Asn Ile Glu Gly Ala Tyr Ile Asp Ser Cys Phe
        50                  55                  60

Val Pro Glu Met Leu Gly Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln Asn
            100                 105                 110

Lys Gln Val Arg Asn Thr Thr Leu Glu Trp Glu Arg Phe Thr Thr Gly
        115                 120                 125

Asn Thr His Thr Ala Trp Val Ile Cys Arg Gln Leu Glu Leu Asn Ala
130                 135                 140

Pro Leu Leu Gly Ile Asp Leu Lys Lys Ala Arg Val Ala Val Val Gly
145                 150                 155                 160

Ala Thr Gly Asp Ile Gly Ser Ala Val Cys Arg Trp Leu Ser Glu Arg
                165                 170                 175

Thr Gly Val Gln Glu Leu Leu Leu Val Ala Arg Gln Gln Pro Leu
            180                 185                 190

Ile Glu Leu Gln Lys Ser Leu Gly Gly Lys Ile Leu Gly Leu Glu
        195                 200                 205

Asp Ala Leu Pro Glu Ala Asp Val Val Ile Trp Val Ala Ser Leu Pro
    210                 215                 220

Lys Thr Leu Glu Ile Asp Lys Ala Lys Leu Arg Lys Pro Cys Leu Met
225                 230                 235                 240

Ile Asp Gly Gly Tyr Pro Lys Asn Leu Asp Glu Lys Phe Asn Gly Ser
```

```
                            245                 250                 255
Gly Val His Val Leu Lys Gly Gly Ile Val Glu Phe Phe Thr Asp Ile
                260                 265                 270

Gly Trp Ser Met Met Glu Leu Ala Ala Met Glu Lys Pro Arg Arg Glu
            275                 280                 285

Met Phe Ala Cys Phe Ala Glu Ala Met Leu Leu Glu Phe Glu Gly Cys
        290                 295                 300

His Thr Asn Phe Ser Trp Gly Arg Asn Asn Ile Thr Leu Glu Lys Met
305                 310                 315                 320

Asp Phe Ile Gly Gln Ala Ser Glu Lys His Gly Phe Ser Val Ile Gly
                325                 330                 335

Leu Asn Pro Lys Leu Gln Ala Ala Ile Ala
                340                 345

<210> SEQ ID NO 66
<211> LENGTH: 346
<212> TYPE: PRT
<213> ORGANISM: Prochlorococcus marinus

<400> SEQUENCE: 66

Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
                20                  25                  30

Val Trp Cys Thr Ala Pro Pro Gln Leu Val Glu Asn Val Glu Val Lys
            35                  40                  45

Ser Ala Ile Gly Ile Ser Ile Glu Gly Ser Tyr Ile Asp Ser Cys Phe
        50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Met Asn Ala
130                 135                 140

Pro Lys Ile Gly Ile Asp Leu Lys Ser Ala Thr Val Ala Val Val Gly
145                 150                 155                 160

Ala Thr Gly Asp Ile Gly Ser Ala Val Cys Arg Trp Leu Ile Asn Lys
                165                 170                 175

Thr Gly Ile Gly Glu Leu Leu Leu Val Ala Arg Gln Lys Glu Pro Leu
            180                 185                 190

Asp Ser Leu Gln Lys Glu Leu Asp Gly Gly Thr Ile Lys Asn Leu Asp
        195                 200                 205

Glu Ala Leu Pro Glu Ala Asp Ile Val Val Trp Val Ala Ser Met Pro
210                 215                 220

Lys Thr Met Glu Ile Asp Ala Asn Asn Leu Lys Gln Pro Cys Leu Met
225                 230                 235                 240

Ile Asp Gly Gly Tyr Pro Lys Asn Leu Asp Glu Lys Phe Gln Gly Asn
                245                 250                 255

Asn Ile His Val Val Lys Gly Gly Ile Val Arg Phe Phe Asn Asp Ile
            260                 265                 270

Gly Trp Asn Met Met Glu Leu Ala Glu Met Gln Asn Pro Gln Arg Glu
```

```
                    275                 280                 285
Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Val Lys His Gly Phe Ser Ala Ile Gly
                325                 330                 335

Leu Asp Lys His Pro Lys Val Leu Ala Val
            340                 345

<210> SEQ ID NO 67
<211> LENGTH: 346
<212> TYPE: PRT
<213> ORGANISM: Prochlorococcus marinus

<400> SEQUENCE: 67

Met Phe Gly Leu Ile Gly His Ser Thr Ser Phe Glu Asp Ala Lys Arg
1               5                   10                  15

Lys Ala Ser Met Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Lys Gln Leu Glu Ile Asn Ala
    130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Ile Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Ser Leu Asp
        195                 200                 205

Glu Ala Leu Pro Gln Ala Asp Ile Val Val Trp Val Ala Ser Met Pro
    210                 215                 220

Lys Thr Ile Glu Ile Asp Thr Asp Asn Leu Lys Lys Pro Cys Leu Met
225                 230                 235                 240

Ile Asp Gly Gly Tyr Pro Lys Asn Leu Asp Glu Lys Phe Gln Gly Glu
                245                 250                 255

Asn Ile Tyr Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
```

```
                305                 310                 315                 320
Glu Phe Ile Gly Ala Ala Ser Leu Lys His Gly Phe Ser Ala Ile Gly
                    325                 330                 335
Leu Asp Lys Gln Pro Lys Val Leu Thr Val
                340                 345

<210> SEQ ID NO 68
<211> LENGTH: 346
<212> TYPE: PRT
<213> ORGANISM: Synechococcus sp.

<400> SEQUENCE: 68

Met Phe Gly Leu Ile Gly His Ser Thr Ser Phe Glu Ala Ala Arg Arg
 1               5                  10                  15

Lys Ala Ser Glu Leu Gly Phe Asp His Ile Ala Glu Gly Asp Leu Asp
                20                  25                  30

Val Trp Cys Ser Ala Pro Pro Gln Leu Val Glu His Val Glu Val Thr
            35                  40                  45

Ser Ala Thr Gly Lys Thr Ile Thr Gly Ala Tyr Ile Asp Ser Cys Phe
        50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Glu Trp Glu Arg Phe Thr Thr Gly
        115                 120                 125

Asn Thr His Thr Ala Trp Val Ile Ser Arg Gln Val Glu Asn Asn Ala
    130                 135                 140

Pro Leu Leu Gly Ile Asp Leu Ser Ser Ala Lys Val Ala Val Val Gly
145                 150                 155                 160

Ala Thr Gly Asp Ile Gly Ser Ala Val Cys Arg Trp Leu Ser Gln Arg
                165                 170                 175

Thr Gly Val Gly Glu Leu Leu Leu Val Ala Arg Gln Gln Gln Pro Leu
            180                 185                 190

Leu Asp Leu Gln Gln Glu Leu Gly Gly Arg Ile Leu Ser Leu Asp
        195                 200                 205

Glu Ala Leu Pro Glu Ala Asp Val Val Trp Val Ala Ser Met Pro
    210                 215                 220

Arg Thr Leu Glu Ile Asp Ala Ala Ser Leu Arg Lys Pro Cys Leu Met
225                 230                 235                 240

Ile Asp Gly Gly Tyr Pro Lys Asn Leu Asp Ala Lys Val Ala Ser Ala
                245                 250                 255

Gly Val His Val Leu Lys Gly Gly Ile Val Glu Phe Gly Ser Asp Ile
            260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Asp Phe Glu Glu Cys
    290                 295                 300

His Thr Asn Phe Ser Trp Gly Arg Asn Asn Ile Thr Leu Glu Lys Met
305                 310                 315                 320

Asp Phe Ile Gly Glu Ala Ser Val Arg His Gly Phe Ser Thr Leu Asn
                325                 330                 335

Leu Asn Pro Gln Pro Gln Ala Ala Val Ala
            340
```

<210> SEQ ID NO 69
<211> LENGTH: 346
<212> TYPE: PRT
<213> ORGANISM: Prochlorococcus marinus

<400> SEQUENCE: 69

```
Met Phe Gly Leu Ile Gly His Ser Thr Ser Phe Glu Asp Ala Lys Arg
 1               5                  10                  15

Lys Ala Leu Gly Leu Gly Tyr Asp His Ile Ala Gln Gly Asp Leu Asp
            20                  25                  30

Val Trp Cys Thr Ala Pro Pro Gln Leu Val Glu Asn Val Lys Val Val
        35                  40                  45

Ser Ala Ile Gly Lys Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Glu Ile Ser Ile Thr Ala Leu
                85                  90                  95

Gly Gly Phe Thr Ser Ile Ile Phe Glu Asn Phe Asn Leu Leu Gln Asn
            100                 105                 110

Gln Gln Val Arg Asn Thr Thr Leu Asp Trp Gln Arg Phe Thr Thr Gly
        115                 120                 125

Asn Thr His Thr Ala Trp Val Ile Cys Arg Gln Leu Glu Gln Asn Ala
    130                 135                 140

Pro Arg Ile Gly Ile Asp Leu Ser Lys Ser Lys Val Ala Val Val Gly
145                 150                 155                 160

Ala Thr Gly Asp Ile Gly Ser Ala Val Cys Arg Trp Leu Ser Asn Arg
                165                 170                 175

Thr Gly Val Ser Glu Leu Leu Leu Val Ala Arg Gln Gln Lys Pro Leu
            180                 185                 190

Leu Glu Leu Gln Ser Gln Leu Gly Gly Gly Arg Ile Leu Ser Leu Asp
        195                 200                 205

Asp Ala Leu Pro Glu Ala Asp Ile Val Ile Trp Val Ala Ser Met Pro
    210                 215                 220

Lys Thr Leu Glu Ile Asp Pro Ser Lys Ile Lys Arg Pro Cys Leu Met
225                 230                 235                 240

Ile Asp Gly Gly Tyr Pro Lys Asn Leu Gly Glu Lys Phe Ser Gly Pro
                245                 250                 255

Gly Ile His Val Leu Lys Gly Gly Ile Val Gln Phe Phe Lys Asp Ile
            260                 265                 270

Gly Trp Ser Met Met Glu Leu Ala Glu Met Glu Asn Pro Lys Arg Glu
        275                 280                 285

Met Phe Ala Cys Phe Ala Glu Ala Met Leu Leu Glu Phe Glu Asn Cys
    290                 295                 300

His Thr Asn Phe Ser Trp Gly Arg Asn Asn Ile Thr Leu Glu Lys Met
305                 310                 315                 320

Asp Phe Ile Gly Lys Ala Ser Glu Arg His Gly Phe Ser Ala Val Gly
                325                 330                 335

Leu Lys Ser Asn Ile Gln Thr Leu Thr Val
            340                 345
```

<210> SEQ ID NO 70
<211> LENGTH: 346
<212> TYPE: PRT

<213> ORGANISM: Prochlorococcus marinus

<400> SEQUENCE: 70

| | | | | | | | | | | | | | | | |
|---|---|---|---|---|---|---|---|---|---|---|---|---|---|---|---|
| Met | Phe | Gly | Leu | Ile | Gly | His | Ser | Thr | Ser | Phe | Glu | Asp | Ala | Lys | Arg |
| 1 | | | | 5 | | | | | 10 | | | | | 15 | |
| Lys | Ala | Ser | Met | Leu | Gly | Phe | Asp | His | Ile | Ala | Asp | Gly | Asp | Leu | Asp |
| | | | 20 | | | | | 25 | | | | | 30 | | |
| Val | Trp | Cys | Thr | Ala | Pro | Pro | Gln | Leu | Val | Glu | Asn | Val | Glu | Val | Lys |
| | | | 35 | | | | | 40 | | | | | 45 | | |
| Ser | Ala | Thr | Gly | Ile | Ser | Ile | Glu | Gly | Ser | Tyr | Ile | Asp | Ser | Cys | Phe |
| | 50 | | | | | 55 | | | | | 60 | | | | |
| Val | Pro | Glu | Met | Leu | Ser | Arg | Phe | Lys | Thr | Ala | Arg | Arg | Lys | Val | Leu |
| 65 | | | | | 70 | | | | | 75 | | | | | 80 |
| Asn | Ala | Met | Glu | Leu | Ala | Gln | Lys | Lys | Gly | Ile | Asn | Ile | Thr | Ala | Leu |
| | | | | 85 | | | | | 90 | | | | | 95 | |
| Gly | Gly | Phe | Thr | Ser | Ile | Ile | Phe | Glu | Asn | Phe | Asn | Leu | Leu | Gln | His |
| | | | 100 | | | | | 105 | | | | | 110 | | |
| Lys | Gln | Ile | Arg | Asn | Thr | Ser | Leu | Glu | Trp | Glu | Arg | Phe | Thr | Thr | Gly |
| | | | 115 | | | | | 120 | | | | | 125 | | |
| Asn | Thr | His | Thr | Ala | Trp | Val | Ile | Cys | Arg | Gln | Leu | Glu | Ile | Asn | Ala |
| | 130 | | | | | 135 | | | | | 140 | | | | |
| Pro | Arg | Ile | Gly | Ile | Asp | Leu | Lys | Lys | Ala | Thr | Val | Ala | Val | Ile | Gly |
| 145 | | | | | 150 | | | | | 155 | | | | | 160 |
| Ala | Thr | Gly | Asp | Ile | Gly | Ser | Ala | Val | Cys | Arg | Trp | Leu | Ile | Asn | Lys |
| | | | | 165 | | | | | 170 | | | | | 175 | |
| Thr | Gly | Ile | Ser | Glu | Leu | Leu | Met | Val | Ala | Arg | Gln | Gln | Glu | Pro | Leu |
| | | | 180 | | | | | 185 | | | | | 190 | | |
| Ala | Leu | Leu | Gln | Lys | Glu | Leu | Asp | Gly | Gly | Thr | Ile | Thr | Thr | Leu | Asp |
| | | | 195 | | | | | 200 | | | | | 205 | | |
| Lys | Ala | Leu | Pro | Gln | Ala | Asp | Ile | Val | Val | Trp | Val | Ala | Ser | Met | Pro |
| | 210 | | | | | 215 | | | | | 220 | | | | |
| Lys | Thr | Ile | Glu | Ile | Asp | Thr | Asp | Asn | Leu | Lys | Lys | Pro | Cys | Leu | Met |
| 225 | | | | | 230 | | | | | 235 | | | | | 240 |
| Ile | Asp | Gly | Gly | Tyr | Pro | Lys | Asn | Leu | Asp | Glu | Lys | Phe | Gln | Gly | Glu |
| | | | | 245 | | | | | 250 | | | | | 255 | |
| Asn | Ile | His | Val | Leu | Lys | Gly | Ile | Val | Glu | Phe | Phe | Asn | Asp | Ile |
| | | | 260 | | | | | 265 | | | | | 270 | | |
| Gly | Trp | Asn | Met | Met | Glu | Leu | Ala | Glu | Met | Gln | Asn | Pro | Gln | Arg | Glu |
| | | | 275 | | | | | 280 | | | | | 285 | | |
| Met | Phe | Ala | Cys | Phe | Ala | Glu | Ala | Met | Ile | Leu | Glu | Phe | Glu | Lys | Cys |
| | 290 | | | | | 295 | | | | | 300 | | | | |
| His | Thr | Asn | Phe | Ser | Trp | Gly | Arg | Asn | Asn | Ile | Ser | Leu | Glu | Lys | Met |
| 305 | | | | | 310 | | | | | 315 | | | | | 320 |
| Glu | Phe | Ile | Gly | Ala | Ala | Ser | Leu | Lys | His | Gly | Phe | Ser | Ala | Ile | Gly |
| | | | | 325 | | | | | 330 | | | | | 335 | |
| Leu | Asp | Lys | Gln | Pro | Lys | Val | Leu | Thr | Val | | | | | | |
| | | | 340 | | | | | 345 | | | | | | | |

<210> SEQ ID NO 71
<211> LENGTH: 348
<212> TYPE: PRT
<213> ORGANISM: Synechococcus sp.

<400> SEQUENCE: 71

| | | | | | | | | | | | | | | | |
|---|---|---|---|---|---|---|---|---|---|---|---|---|---|---|---|
| Met | Phe | Gly | Leu | Ile | Gly | His | Ser | Thr | Ser | Phe | Glu | Ala | Ala | Arg | Arg |
| 1 | | | | 5 | | | | | 10 | | | | | 15 | |

Lys Ala Leu Glu Leu Gly Phe Asp His Ile Ala Glu Gly Asp Leu Asp
            20                  25                  30

Val Trp Cys Ser Ala Pro Pro Gln Leu Val Glu His Leu Glu Val Thr
        35                  40                  45

Ser Leu Thr Gly Lys Lys Ile Glu Gly Ala Tyr Ile Asp Ser Cys Phe
50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Lys His
            100                 105                 110

Gln Thr Ile Arg Ser Thr Thr Leu Glu Trp Arg Phe Thr Thr Gly
        115                 120                 125

Asn Thr His Thr Ala Trp Val Ile Ser Arg Gln Val Glu Ile Asn Ala
130                 135                 140

Pro Leu Leu Gly Ile Asp Leu Ser Lys Ala Arg Val Ala Val Val Gly
145                 150                 155                 160

Ala Thr Gly Asp Ile Gly Ser Ala Val Cys Arg Trp Leu Thr Gln Arg
                165                 170                 175

Thr Gly Ile Lys Glu Leu Leu Met Val Ala Arg Gln Gln Pro Leu
            180                 185                 190

Lys Asp Leu Gln Gln Glu Leu Glu Gly Gly Arg Ile Leu Ser Leu Asp
            195                 200                 205

Glu Ala Leu Pro Glu Ala Asp Val Val Val Trp Val Ala Ser Met Pro
210                 215                 220

Arg Thr Leu Glu Ile Asp Ser Asp Arg Leu Gln Lys Pro Cys Leu Met
225                 230                 235                 240

Ile Asp Gly Gly Tyr Pro Lys Asn Leu Asp Ser Arg Val Ala Gly Gln
                245                 250                 255

Gly Val His Val Leu Lys Gly Gly Ile Val Glu Phe Val Ser Asp Ile
            260                 265                 270

Gly Trp Thr Met Met Glu Asn Ala Glu Trp Gln Met Glu Lys Pro Gln
            275                 280                 285

Arg Gln Met Phe Ala Cys Phe Ala Glu Ala Ile Leu Leu Glu Phe Glu
        290                 295                 300

Ala Cys His Thr Asn Phe Ser Trp Gly Arg Asn Asn Ile Thr Leu Glu
305                 310                 315                 320

Lys Met Asp Phe Ile Gly Ala Ala Ser Val Arg His Gly Phe Ser Thr
                325                 330                 335

Leu Asn Leu Gln Gly Gln Leu Gln Ala Ala Ala
            340                 345

<210> SEQ ID NO 72
<211> LENGTH: 346
<212> TYPE: PRT
<213> ORGANISM: Prochlorococcus marinus

<400> SEQUENCE: 72

Met Phe Gly Leu Ile Gly His Ser Thr Ser Phe Glu Asp Ala Lys Arg
1               5                   10                  15

Lys Ala Ser Met Leu Gly Phe Asp His Ile Ala Asp Gly Asp Leu Asp
            20                  25                  30

Val Trp Cys Thr Ala Pro Pro Gln Leu Val Glu Asn Val Glu Val Arg
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
 65                  70                  75                  80

Asn Ala Met Glu Leu Ala Gln Lys Lys Gly Ile Asn Ile Thr Ala Leu
                 85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Thr Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Thr Leu Asp
        195                 200                 205

Lys Ala Leu Pro Gln Ala Asp Ile Val Val Trp Val Ala Ser Met Pro
210                 215                 220

Lys Thr Ile Glu Ile Asp Thr Asp Asn Leu Lys Lys Pro Cys Leu Met
225                 230                 235                 240

Ile Asp Gly Gly Tyr Pro Lys Asn Leu Asp Glu Lys Phe Gln Gly Glu
                245                 250                 255

Asn Ile His Val Leu Lys Gly Gly Ile Val Lys Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345

<210> SEQ ID NO 73
<211> LENGTH: 346
<212> TYPE: PRT
<213> ORGANISM: Prochlorococcus marinus

<400> SEQUENCE: 73

Met Phe Gly Leu Ile Gly His Ser Thr Ser Phe Glu Asp Ala Lys Arg
 1               5                  10                  15

Lys Ala Ser Met Leu Gly Phe Asp His Ile Ala Asp Gly Asp Leu Asp
                 20                  25                  30

Val Trp Cys Thr Ala Pro Pro Gln Leu Val Glu Asn Val Glu Val Lys
             35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
 65                  70                  75                  80

```
Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Lys Gln Leu Glu Ile Asn Ala
130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Ile Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Ser Leu Asp
        195                 200                 205

Glu Ala Leu Pro Gln Ala Asp Ile Val Val Trp Val Ala Ser Met Pro
210                 215                 220

Lys Thr Ile Glu Ile Asn Thr Asp Asn Leu Gln Lys Pro Cys Leu Met
225                 230                 235                 240

Ile Asp Gly Gly Tyr Pro Lys Asn Leu Asp Glu Lys Phe Gln Gly Glu
                245                 250                 255

Asn Ile Tyr Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345

<210> SEQ ID NO 74
<211> LENGTH: 341
<212> TYPE: PRT
<213> ORGANISM: Synechococcus sp.

<400> SEQUENCE: 74

Met Phe Gly Leu Ile Gly His Leu Thr Ser Leu Ala His Ala Lys Arg
1               5                   10                  15

Val Ala Asp Lys Leu Gly Tyr Ser Glu Tyr Ala Glu Ser Asp Leu Glu
            20                  25                  30

Phe Trp Cys Met Ala Pro Pro Gln Val Val Asp Glu Ile Val Val Thr
        35                  40                  45

Ser Ile Thr Gly Gln Lys Ile Tyr Gly Gln Tyr Val Glu Ser Cys Phe
    50                  55                  60

Leu Pro Glu Met Leu Ala Gly Gly Arg Val Lys Ala Ala Cys Arg Lys
65                  70                  75                  80

Ile Leu Asn Ala Met Ala Leu Ala Gln Arg Arg Gly Leu Asn Ile Thr
                85                  90                  95

Thr Leu Gly Gly Phe Ser Ser Ile Ile Phe Glu Asn Phe Arg Leu Asp
            100                 105                 110
```

Thr Leu Arg Arg Val Arg Asn Ile Asp Leu Glu Ile Arg Arg Phe Thr
            115                 120                 125

Thr Gly Asn Thr His Thr Ala Tyr Ile Ile Cys Gln Gln Leu Gln Ala
        130                 135                 140

Ala Ala Gln Arg Tyr Ala Met Asp Leu Ala Ala Thr Val Ala Val
145                 150                 155                 160

Val Gly Ala Thr Gly Asp Ile Gly Ser Ala Ile Cys Gln Trp Leu Val
                165                 170                 175

Ala His Thr Ser Pro Ala Lys Leu Leu Ile Ala Arg Glu Arg Arg
            180                 185                 190

Arg Leu Glu Glu Leu Gln Ala Lys Leu Lys Gly Glu Val Cys Ser
        195                 200                 205

Leu Glu Glu Ala Leu Pro Arg Ala Asp Phe Ile Val Trp Val Ala Ser
        210                 215                 220

Met Ser Gln Gly Val Thr Leu Asp Pro Gln Val Leu Pro Asp Pro Cys
225                 230                 235                 240

Val Ile Ile Asp Gly Gly Tyr Pro Lys Asn Ile Ala Ser Lys Leu Gln
                245                 250                 255

Arg Lys Gly Leu Tyr Val Ile Asp Gly Met Val Glu His Ser Leu
        260                 265                 270

Asp Ile Glu Trp Asn Ile Met Gln Phe Leu Asn Val Ala Asn Pro Ala
        275                 280                 285

Arg Gln Leu Phe Ala Cys Phe Ala Glu Ala Met Leu Leu Glu Phe Glu
        290                 295                 300

Gly Leu Tyr Thr Asn Phe Ser Trp Gly Arg Asn Leu Ile Thr Leu Glu
305                 310                 315                 320

Lys Leu Asp Leu Ile Gly Gln Leu Ser Arg Lys His Gly Phe Arg Pro
                325                 330                 335

Leu Met Pro Glu Ala
            340

<210> SEQ ID NO 75
<211> LENGTH: 341
<212> TYPE: PRT
<213> ORGANISM: Synechococcus sp.

<400> SEQUENCE: 75

Met Phe Gly Leu Ile Gly His Leu Thr Ser Leu Ala His Ala Lys Arg
1               5                   10                  15

Val Ala Asp Lys Leu Gly Tyr Ser Glu Tyr Ala Glu Ser Asp Leu Glu
                20                  25                  30

Phe Trp Cys Met Ala Pro Pro Gln Val Val Asp Glu Ile Thr Val Thr
            35                  40                  45

Ser Ile Thr Gly Gln Lys Ile Tyr Gly Gln Tyr Val Glu Ser Cys Phe
    50                  55                  60

Leu Pro Glu Met Leu Ala Gly Gly Arg Val Lys Ala Ala Cys Arg Lys
65                  70                  75                  80

Val Leu Asn Ala Met Ala Leu Ala Gln Arg Gly Leu Asn Ile Thr
            85                  90                  95

Ala Leu Gly Gly Phe Ser Ser Ile Ile Phe Glu Thr Phe Arg Leu Asp
            100                 105                 110

Ser Leu Arg Arg Val Arg Asn Ile Asp Leu Glu Ile Gln Arg Phe Thr
            115                 120                 125

Thr Gly Asn Thr His Thr Ala Tyr Ile Ile Cys Gln Gln Leu Gln Leu
        130                 135                 140

```
Ala Ala Gln Arg Tyr Ala Met Asp Leu Ala Ala Thr Val Ala Val
145                 150                 155                 160

Val Gly Ala Thr Gly Asp Ile Gly Ser Ala Ile Cys Gln Trp Leu Val
            165                 170                 175

Ala His Thr His Leu Gly Lys Leu Leu Ile Ala Arg Glu Arg Arg
        180                 185                 190

Arg Leu Glu Glu Leu Gln Ala Lys Leu Lys Gln Gly Glu Ile Ser Ser
        195                 200                 205

Leu Glu Glu Ala Leu Pro Arg Ala Asp Phe Ile Val Trp Val Ala Ser
        210                 215                 220

Met Ser Gln Gly Met Ala Leu Asp Pro Gln Val Leu Pro Asp Pro Cys
225                 230                 235                 240

Val Ile Ile Asp Gly Gly Tyr Pro Lys Asn Ile Ala Ser Ser Leu Gln
            245                 250                 255

Arg Lys Gly Leu Tyr Val Ile Asp Gly Gly Met Val Glu His Ser Leu
        260                 265                 270

Asp Ile Glu Trp Asn Ile Met Gln Phe Leu Asn Val Ala Asn Pro Ala
        275                 280                 285

Arg Gln Leu Phe Ala Cys Phe Ala Glu Ser Met Leu Leu Glu Phe Glu
        290                 295                 300

Gly Leu Tyr Thr Asn Phe Ser Trp Gly Arg Asn Leu Ile Thr Leu Glu
305                 310                 315                 320

Lys Leu Asp Leu Ile Gly Gln Leu Ser Arg Lys His Gly Phe Arg Pro
                325                 330                 335

Leu Met Pro Glu Ala
            340

<210> SEQ ID NO 76
<211> LENGTH: 346
<212> TYPE: PRT
<213> ORGANISM: Prochlorococcus marinus

<400> SEQUENCE: 76

Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Arg Ile Gly Ile Asp Leu Lys Thr Ala Thr Val Ala Val Ile Gly
145                 150                 155                 160

Ala Thr Gly Asp Ile Gly Ser Ala Val Cys Arg Trp Leu Val Asn Lys
                165                 170                 175
```

```
Thr Gly Ile Ser Glu Leu Leu Met Val Ala Arg Gln Gln Pro Leu
            180                 185                 190

Thr Leu Leu Gln Lys Glu Leu Asp Gly Gly Thr Ile Lys Ser Leu Asp
    195                 200                 205

Glu Ala Leu Pro Gln Ala Asp Ile Val Val Trp Val Ala Ser Met Pro
    210                 215                 220

Lys Thr Ile Glu Ile Glu Ile Glu Asn Leu Lys Lys Pro Cys Leu Met
225                 230                 235                 240

Ile Asp Gly Gly Tyr Pro Lys Asn Leu Asp Glu Lys Phe Lys Gly Lys
                245                 250                 255

Asn Ile His Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345

<210> SEQ ID NO 77
<211> LENGTH: 231
<212> TYPE: PRT
<213> ORGANISM: Synechococcus elongatus

<400> SEQUENCE: 77

Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30

Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80

Gly Phe Ala Gln Lys Phe Phe Glu Arg Leu His Glu Asn Phe Lys Ala
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190

Met Glu Arg Glu Ser Leu Val Glu Asp Phe Met Ile Ala Tyr Gly Glu
        195                 200                 205
```

Ala Leu Glu Asn Ile Gly Phe Thr Thr Arg Glu Ile Met Arg Met Ser
    210                 215                 220

Ala Tyr Gly Leu Ala Ala Val
225                 230

<210> SEQ ID NO 78
<211> LENGTH: 254
<212> TYPE: PRT
<213> ORGANISM: Synechococcus elongatus

<400> SEQUENCE: 78

Met Arg Thr Pro Trp Asp Pro Pro Asn Pro Thr Phe Ser Leu Ser Ser
1               5                   10                  15

Val Ser Gly Asp Arg Arg Leu Met Pro Gln Leu Glu Ala Ser Leu Glu
            20                  25                  30

Leu Asp Phe Gln Ser Glu Ser Tyr Lys Asp Ala Tyr Ser Arg Ile Asn
        35                  40                  45

Ala Ile Val Ile Glu Gly Glu Gln Glu Ala Phe Asp Asn Tyr Asn Arg
    50                  55                  60

Leu Ala Glu Met Leu Pro Asp Gln Arg Asp Glu Leu His Lys Leu Ala
65                  70                  75                  80

Lys Met Glu Gln Arg His Met Lys Gly Phe Met Ala Cys Gly Lys Asn
                85                  90                  95

Leu Ser Val Thr Pro Asp Met Gly Phe Ala Gln Lys Phe Phe Glu Arg
            100                 105                 110

Leu His Glu Asn Phe Lys Ala Ala Ala Glu Gly Lys Val Val Thr
        115                 120                 125

Cys Leu Leu Ile Gln Ser Leu Ile Ile Glu Cys Phe Ala Ile Ala Ala
    130                 135                 140

Tyr Asn Ile Tyr Ile Pro Val Ala Asp Ala Phe Ala Arg Lys Ile Thr
145                 150                 155                 160

Glu Gly Val Val Arg Asp Glu Tyr Leu His Arg Asn Phe Gly Glu Glu
                165                 170                 175

Trp Leu Lys Ala Asn Phe Asp Ala Ser Lys Ala Glu Leu Glu Glu Ala
            180                 185                 190

Asn Arg Gln Asn Leu Pro Leu Val Trp Leu Met Leu Asn Glu Val Ala
        195                 200                 205

Asp Asp Ala Arg Glu Leu Gly Met Glu Arg Glu Ser Leu Val Glu Asp
    210                 215                 220

Phe Met Ile Ala Tyr Gly Glu Ala Leu Glu Asn Ile Gly Phe Thr Thr
225                 230                 235                 240

Arg Glu Ile Met Arg Met Ser Ala Tyr Gly Leu Ala Ala Val
                245                 250

<210> SEQ ID NO 79
<211> LENGTH: 231
<212> TYPE: PRT
<213> ORGANISM: Arthrospira maxima

<400> SEQUENCE: 79

Met Pro Gln Leu Glu Thr Ile Thr Glu Leu Asp Phe Gln Asn Glu Thr
1               5                   10                  15

Tyr Lys Asp Ala Tyr Ser Arg Ile Asn Ala Ile Val Ile Glu Gly Glu
            20                  25                  30

Gln Glu Ala Ser Asp Asn Tyr Ile Lys Leu Gly Glu Met Leu Pro Glu
        35                  40                  45

```
Glu Arg Glu Glu Leu Ile Arg Leu Ser Lys Met Glu Lys Arg His Lys
         50                  55                  60

Lys Gly Phe Gln Ala Cys Gly Arg Asn Leu Glu Val Thr Pro Asp Met
 65                  70                  75                  80

Asp Phe Gly Arg Glu Phe Phe Ala Lys Leu His Gly Asn Phe Gln Lys
                     85                  90                  95

Ala Ala Ala Glu Gly Lys Leu Val Thr Cys Leu Leu Ile Gln Ser Leu
                100                 105                 110

Ile Ile Glu Ser Phe Ala Ile Ala Ala Tyr Asn Ile Tyr Ile Pro Val
            115                 120                 125

Ala Asp Pro Phe Ala Arg Lys Ile Thr Glu Gly Val Val Lys Asp Glu
        130                 135                 140

Tyr Glu His Leu Asn Phe Gly Glu Glu Trp Leu Lys Ala His Phe Glu
145                 150                 155                 160

Glu Ser Lys Ala Glu Leu Glu Glu Ala Asn Arg Gln Asn Leu Pro Leu
                165                 170                 175

Val Trp Lys Met Leu Asn Gln Val Glu Lys Asp Ala Ser Ile Leu Gly
                180                 185                 190

Met Glu Lys Glu Ala Leu Ile Glu Asp Phe Met Ile Ala Tyr Gly Glu
            195                 200                 205

Ala Leu Ser Asn Ile Gly Phe Thr Thr Arg Asp Ile Met Arg Met Ser
        210                 215                 220

Ala Tyr Gly Leu Ala Gly Val
225                 230

<210> SEQ ID NO 80
<211> LENGTH: 239
<212> TYPE: PRT
<213> ORGANISM: Microcoleus chthonoplastes

<400> SEQUENCE: 80

Met Gln Thr Gly Glu Asn Leu Leu Met Gln Gln Leu Thr Val Ser Gln
 1               5                  10                  15

Glu Leu Asp Phe Asn Ser Glu Thr Tyr Lys Asp Ala Tyr Ser Arg Ile
                 20                  25                  30

Asn Ala Ile Val Ile Glu Gly Glu Gln Glu Ala His Gln Asn Tyr Ile
             35                  40                  45

Gln Leu Ala Glu Leu Leu Pro Asp Gln Lys Asp Glu Leu Thr Ser Leu
         50                  55                  60

Ala Lys Met Glu Asn Arg His Lys Lys Gly Phe Gln Ala Cys Gly Arg
 65                  70                  75                  80

Asn Leu Ser Val Thr Ala Asp Met Glu Phe Ala Lys Glu Tyr Phe Ser
                 85                  90                  95

Asp Leu His Gln Asn Phe Gln Thr Ala Ala Ala Ser Gly Asn Ile Val
                100                 105                 110

Thr Cys Leu Leu Ile Gln Ser Leu Ile Ile Glu Cys Phe Ala Ile Ala
            115                 120                 125

Ala Tyr Asn Ile Tyr Ile Pro Val Ala Asp Pro Phe Ala Arg Lys Ile
        130                 135                 140

Thr Glu Gly Val Val Lys Asp Glu Tyr Met His Leu Asn Phe Gly Glu
145                 150                 155                 160

Glu Trp Leu Lys Glu Asn Phe Gly Ala Ser Lys Thr Glu Leu Glu Gln
                165                 170                 175

Ala Asn Lys Gln Asn Leu Pro Leu Val Trp Arg Met Leu Asn Gln Val
                180                 185                 190
```

```
Glu Lys Asp Ala His Ile Leu Gly Met Glu Lys Asp Ala Leu Val Glu
        195                 200                 205

Asp Phe Met Ile Ala Tyr Gly Glu Ala Leu Ser Asn Ile Gly Phe Thr
    210                 215                 220

Thr Arg Asp Ile Met Arg Met Ser Ala Tyr Gly Leu Thr Ala Ala
225                 230                 235

<210> SEQ ID NO 81
<211> LENGTH: 231
<212> TYPE: PRT
<213> ORGANISM: Lyngbya sp.

<400> SEQUENCE: 81

Met Pro Gln Leu Glu Ala Ile Ala Glu Ile Asp Phe Asn Thr Asn Thr
1               5                   10                  15

Tyr Lys Asp Ala Tyr Ser Arg Ile Asn Ala Ile Val Ile Glu Gly Glu
            20                  25                  30

Gln Val Ala His Asp Asn Tyr Ile Lys Leu Gly Glu Met Leu Pro Asp
        35                  40                  45

Gln Lys Asp Glu Leu Val Arg Leu Ser Lys Met Glu Lys Arg His Met
    50                  55                  60

Lys Gly Phe Gln Ala Cys Gly Arg Asn Leu Glu Val Thr Ala Asp Met
65                  70                  75                  80

Asp Tyr Ala His Gln Phe Phe Ser Gln Leu His Gln Asn Phe Lys Asp
                85                  90                  95

Ala Ala Ala Gln Gly Lys Val Val Thr Cys Leu Leu Ile Gln Ser Leu
            100                 105                 110

Ile Ile Glu Ser Phe Ala Ile Ala Ala Tyr Asn Ile Tyr Ile Pro Val
        115                 120                 125

Ala Asp Pro Phe Ala Arg Lys Ile Thr Glu Gly Val Val Asp Asp Glu
    130                 135                 140

Tyr Met His Leu Asn Phe Gly Glu Glu Trp Leu Lys Ala His Phe Glu
145                 150                 155                 160

Glu Ser Lys Ala Glu Leu Gln Glu Ala Asn Ser Gln Asn Leu Pro Leu
                165                 170                 175

Val Trp Lys Met Leu Asn Glu Val Glu Asn Asp Ala His Ile Leu Gly
            180                 185                 190

Met Glu Lys Asp Ala Leu Val Glu Asp Phe Met Ile Ala Tyr Gly Glu
        195                 200                 205

Ala Leu Asn Asn Ile Gly Phe Thr Thr Arg Glu Ile Met Arg Met Ser
    210                 215                 220

Ala His Gly Leu Thr Thr Ala
225                 230

<210> SEQ ID NO 82
<211> LENGTH: 231
<212> TYPE: PRT
<213> ORGANISM: Nodularia spumigena

<400> SEQUENCE: 82

Met Gln Gln Leu Ala Ala Glu Leu Lys Ile Asp Phe Gln Ser Glu Lys
1               5                   10                  15

Tyr Lys Asp Ala Tyr Ser Arg Ile Asn Ala Ile Val Ile Glu Gly Glu
            20                  25                  30

Gln Glu Ala His Asp Asn Tyr Ile Thr Leu Gly Glu Met Leu Pro Glu
        35                  40                  45

Leu Lys Asp Glu Leu Ile Arg Leu Ser Lys Met Glu Ser Arg His Lys
```

```
            50                  55                  60
Lys Gly Phe Glu Ala Cys Gly Arg Asn Leu Ser Val Lys Pro Asp Met
 65                  70                  75                  80

Pro Phe Ala Gln Lys Phe Phe Ser Gly Leu His Glu Asn Phe Gln Lys
                 85                  90                  95

Ala Ala Ala Glu Gly Gln Val Val Thr Cys Leu Leu Ile Gln Ser Leu
                100                 105                 110

Ile Ile Glu Cys Phe Ala Ile Ala Ala Tyr Asn Ile Tyr Ile Pro Val
                115                 120                 125

Ala Asp Asp Phe Ala Arg Lys Ile Thr Glu Gly Val Val Lys Asp Glu
130                 135                 140

Tyr Ser His Leu Asn Phe Gly Glu Val Trp Leu Lys Glu Asn Phe Ala
145                 150                 155                 160

Gln Ser Lys Ala Glu Leu Glu Ala Ala Asn Arg Gln Asn Leu Pro Ile
                165                 170                 175

Val Trp Lys Met Leu Asn Glu Val Glu Asn Asp Ala His Val Leu Ala
                180                 185                 190

Met Glu Lys Glu Ala Leu Val Glu Asp Phe Met Ile Gln Tyr Gly Glu
                195                 200                 205

Thr Leu Ser Asn Ile Gly Phe Thr Thr Arg Asp Ile Met Lys Met Ser
210                 215                 220

Ala Tyr Gly Leu Thr Ala Ala
225                 230

<210> SEQ ID NO 83
<211> LENGTH: 231
<212> TYPE: PRT
<213> ORGANISM: Microcystis aeruginosa

<400> SEQUENCE: 83

Met Pro Glu Leu Ala Val Pro Leu Glu Leu Asp Phe Thr Ser Glu Thr
 1               5                  10                  15

Tyr Lys Ser Ala Tyr Ser Arg Ile Asn Ala Ile Val Ile Glu Gly Glu
                20                  25                  30

Tyr Glu Ala Asn Ser Asn Tyr Ile Gln Leu Ala Asp Ile Leu Thr Asp
                35                  40                  45

Asn Lys Glu Glu Leu His Arg Leu Ala Lys Met Glu Asn Arg His Met
50                  55                  60

Lys Gly Phe Gln Ala Cys Gly Gln Asn Leu Lys Ile Thr Pro Asp Met
65                  70                  75                  80

Asp Tyr Ala Arg Glu Phe Phe Ser Ser Leu His Asn Asn Phe Gln Ile
                85                  90                  95

Ala Tyr Ala Glu Gly Lys Val Val Thr Cys Leu Leu Ile Gln Ser Leu
                100                 105                 110

Ile Ile Glu Ala Phe Ala Ile Ala Ala Tyr Asn Ile Tyr Ile Pro Val
                115                 120                 125

Ala Asp Pro Phe Ala Arg Lys Ile Thr Glu Gly Val Val Lys Asp Glu
130                 135                 140

Tyr Leu His Leu Asn Phe Gly Glu Glu Trp Leu Lys Ala Asn Phe Glu
145                 150                 155                 160

Thr Ala Lys Glu Glu Leu Glu Ala Ala Asn Arg Ala Asn Leu Pro Ile
                165                 170                 175

Val Trp Arg Met Leu Asn Gln Val Glu Asn Asp Ala Arg Val Leu Gly
                180                 185                 190

Met Glu Lys Glu Ala Leu Val Glu Asp Phe Met Ile Ser Tyr Gly Glu
```

```
            195                 200                 205
Ala Leu Ser Asn Ile Gly Phe Ser Thr Arg Asp Ile Met Arg Met Ser
210                 215                 220

Ala Tyr Gly Leu Thr Ala Val
225                 230

<210> SEQ ID NO 84
<211> LENGTH: 231
<212> TYPE: PRT
<213> ORGANISM: Microcystis aeruginosa

<400> SEQUENCE: 84

Met Pro Glu Leu Ala Val Pro Leu Glu Leu Asp Phe Thr Ser Glu Thr
1               5                   10                  15

Tyr Lys Ser Ala Tyr Ser Arg Ile Asn Ala Ile Val Ile Glu Gly Glu
                20                  25                  30

Tyr Glu Ala Asn Ser Asn Tyr Ile Gln Leu Ala Asp Ile Leu Thr Asp
            35                  40                  45

Asn Lys Glu Glu Leu His Arg Leu Ala Lys Met Glu Asn Arg His Met
50                  55                  60

Lys Gly Phe Gln Ala Cys Gly Gln Asn Leu Gln Ile Thr Pro Asp Met
65                  70                  75                  80

Glu Tyr Ala Lys Glu Phe Phe Ser Ser Leu His Asn Asn Phe Gln Ile
                85                  90                  95

Ala Tyr Ala Glu Gly Lys Val Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Ser Val Val Lys Asp Glu
    130                 135                 140

Tyr Leu His Leu Asn Phe Gly Glu Glu Trp Leu Lys Ala Asn Phe Glu
145                 150                 155                 160

Thr Ala Lys Glu Glu Leu Glu Ala Ala Asn Arg Ala Asn Leu Pro Ile
                165                 170                 175

Val Trp Arg Met Leu Asn Gln Val Glu Asp Asp Ala Arg Val Leu Ala
            180                 185                 190

Met Glu Lys Glu Ala Leu Val Glu Asp Phe Met Ile Ser Tyr Gly Glu
        195                 200                 205

Ala Leu Asn Asn Ile Gly Phe Ser Thr Arg Asp Ile Met Arg Met Ser
    210                 215                 220

Ala Tyr Gly Leu Thr Ala Val
225                 230

<210> SEQ ID NO 85
<211> LENGTH: 231
<212> TYPE: PRT
<213> ORGANISM: Nostoc sp.

<400> SEQUENCE: 85

Met Gln Gln Val Ala Ala Asp Leu Glu Ile Asp Phe Lys Ser Glu Lys
1               5                   10                  15

Tyr Lys Asp Ala Tyr Ser Arg Ile Asn Ala Ile Val Ile Glu Gly Glu
                20                  25                  30

Gln Glu Ala Tyr Glu Asn Tyr Ile Gln Leu Ser Gln Leu Leu Pro Asp
            35                  40                  45

Asp Lys Glu Asp Leu Ile Arg Leu Ser Lys Met Glu Ser Arg His Lys
50                  55                  60
```

```
Lys Gly Phe Glu Ala Cys Gly Arg Asn Leu Gln Val Ser Pro Asp Met
 65                  70                  75                  80

Glu Phe Ala Lys Glu Phe Phe Ala Gly Leu His Gly Asn Phe Gln Lys
                 85                  90                  95

Ala Ala Ala Glu Gly Lys Ile Val Thr Cys Leu Leu Ile Gln Ser Leu
            100                 105                 110

Ile Ile Glu Cys Phe Ala Ile Ala Ala Tyr Asn Ile Tyr Ile Pro Val
            115                 120                 125

Ala Asp Asp Phe Ala Arg Lys Ile Thr Glu Gly Val Val Lys Asp Glu
            130                 135                 140

Tyr Ser His Leu Asn Phe Gly Glu Val Trp Leu Gln Lys Asn Phe Ala
145                 150                 155                 160

Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Ala Val Leu Ala
            180                 185                 190

Met Glu Lys Glu Ala Leu Val Glu Asp Phe Met Ile Gln Tyr Gly Glu
            195                 200                 205

Ala Leu Ser Asn Ile Gly Phe Thr Thr Arg Asp Ile Met Arg Met Ser
210                 215                 220

Ala Tyr Gly Leu Thr Ala Ala
225                 230

<210> SEQ ID NO 86
<211> LENGTH: 231
<212> TYPE: PRT
<213> ORGANISM: Anabaena variabilis

<400> SEQUENCE: 86

Met Gln Gln Val Ala Ala Asp Leu Glu Ile Asp Phe Lys Ser Glu Lys
 1               5                  10                  15

Tyr Lys Asp Ala Tyr Ser Arg Ile Asn Ala Ile Val Ile Glu Gly Glu
                 20                  25                  30

Gln Glu Ala Tyr Glu Asn Tyr Ile Gln Leu Ser Gln Leu Leu Pro Asp
             35                  40                  45

Asp Lys Glu Asp Leu Ile Arg Leu Ser Lys Met Glu Ser Arg His Lys
 50                  55                  60

Lys Gly Phe Glu Ala Cys Gly Arg Asn Leu Gln Val Ser Pro Asp Ile
 65                  70                  75                  80

Glu Phe Ala Lys Glu Phe Phe Ala Gly Leu His Gly Asn Phe Gln Lys
                 85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
            115                 120                 125

Ala Asp Asp Phe Ala Arg Lys Ile Thr Glu Gly Val Val Lys Asp Glu
            130                 135                 140

Tyr Ser His Leu Asn Phe Gly Glu Val Trp Leu Gln Lys Asn Phe Ala
145                 150                 155                 160

Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Ala Val Leu Ala
            180                 185                 190

Met Glu Lys Glu Ala Leu Val Glu Asp Phe Met Ile Gln Tyr Gly Glu
            195                 200                 205
```

Ala Leu Ser Asn Ile Gly Phe Thr Thr Arg Asp Ile Met Arg Met Ser
    210                 215                 220

Ala Tyr Gly Leu Thr Ala Ala
225                 230

<210> SEQ ID NO 87
<211> LENGTH: 231
<212> TYPE: PRT
<213> ORGANISM: Crocosphaera watsonii

<400> SEQUENCE: 87

Met Gln Glu Leu Ala Val Arg Ser Glu Leu Asp Phe Asn Ser Glu Thr
1               5                   10                  15

Tyr Lys Asp Ala Tyr Ser Arg Ile Asn Ala Ile Val Ile Glu Gly Glu
            20                  25                  30

Gln Glu Ala Tyr Glu Asn Tyr Ile Asp Met Gly Glu Leu Leu Pro Gly
        35                  40                  45

Asp Lys Asp Glu Leu Ile Arg Leu Ser Lys Met Glu Asn Arg His Lys
    50                  55                  60

Lys Gly Phe Gln Ala Cys Gly Lys Asn Leu Lys Val Thr Pro Asp Met
65                  70                  75                  80

Asp Tyr Ala Glu Arg Phe Phe Ser Gln Leu His Gly Asn Phe Gln Thr
                85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Asn Val Val Lys Asp Glu
    130                 135                 140

Tyr Ser His Leu Asn Phe Gly Glu Val Trp Leu Lys Glu Asn Phe Glu
145                 150                 155                 160

Ala Ser Lys Ala Glu Leu Gln Ala Asn Lys Glu Asn Leu Pro Ile
                165                 170                 175

Val Trp Gln Met Leu Asn Glu Val Glu Asp Ala Glu Ile Leu Gly
            180                 185                 190

Met Glu Lys Glu Ala Leu Val Glu Asp Phe Met Ile Ser Tyr Gly Glu
        195                 200                 205

Ala Leu Gly Asn Ile Gly Phe Ser Thr Arg Glu Ile Met Lys Met Ser
    210                 215                 220

Ala His Gly Leu Ala Ala Val
225                 230

<210> SEQ ID NO 88
<211> LENGTH: 251
<212> TYPE: PRT
<213> ORGANISM: Trichodesmium erythraeum

<400> SEQUENCE: 88

Met Pro Lys Leu Glu Ile Ile Pro Thr Met Asp Ser Gln Ser Glu Thr
1               5                   10                  15

Lys Leu Glu Lys Val Lys Ser Gln Ser Glu Gly Asp Gln Ile Asn Phe
            20                  25                  30

Glu Thr Glu Thr Tyr Lys Asp Ala Tyr Ser Arg Ile Asn Ala Ile Val
        35                  40                  45

Ile Glu Gly Glu Gln Glu Ala Tyr Lys Asn Tyr Ile Lys Leu Ala Glu
    50                  55                  60

Met Leu Pro Asp Glu Lys Asp Glu Leu Ile Lys Leu Ser Lys Met Glu
65                  70                  75                  80

Asn Arg His Lys Lys Gly Phe Glu Ala Cys Gly Arg Asn Leu His Val
            85                  90                  95

Thr Pro Asp Met Glu Phe Ala Lys Lys Phe Glu Pro Leu His Glu
        100                 105                 110

Asn Phe Gln Thr Ala Ala Ala Thr Gly Asn Val Val Thr Cys Leu Leu
        115                 120                 125

Ile Gln Ser Leu Ile Ile Glu Cys Phe Ala Ile Ala Ala Tyr Asn Ile
        130                 135                 140

Tyr Ile Pro Val Ala Asp Pro Phe Ala Arg Lys Ile Thr Glu Ser Val
145                 150                 155                 160

Val Lys Asp Glu Tyr Ser His Leu Asn Phe Gly Glu Val Trp Leu Lys
                165                 170                 175

Glu Tyr Phe Glu Asp Ser Lys Gln Glu Leu Gln Lys Ala Asn Arg Gln
            180                 185                 190

Asn Leu Pro Leu Val Trp Lys Met Leu Asn Gln Val Glu Lys Asp Ala
        195                 200                 205

Lys Thr Leu Glu Met Glu Lys Glu Ala Leu Ile Glu Asp Phe Met Ile
210                 215                 220

Ala Tyr Gly Glu Ala Leu Asn Asn Ile Gly Phe Thr Thr Gly Glu Ile
225                 230                 235                 240

Met Arg Met Ser Ala Tyr Gly Leu Ile Ala Ala
                245                 250

<210> SEQ ID NO 89
<211> LENGTH: 231
<212> TYPE: PRT
<213> ORGANISM: Synechococcus sp.

<400> SEQUENCE: 89

Met Gln Thr Leu Glu Val Ser Pro Ala Met Asp Phe Gln Ser Glu Thr
1               5                   10                  15

Tyr Lys Asp Ala Tyr Ser Arg Ile Asn Ala Ile Val Ile Glu Gly Glu
            20                  25                  30

Leu Glu Ala Asn Asn Asn Tyr Lys Gln Leu Ser Glu His Leu Gly Asp
        35                  40                  45

Phe Lys Asp Asp Leu Leu Lys Leu Ala Arg Met Glu Asn Arg His Met
50                  55                  60

Lys Gly Phe Gln Ala Cys Gly Lys Asn Leu Ser Val Asn Pro Asp Met
65                  70                  75                  80

Pro Phe Ala Lys Glu Phe Phe Ala Gln Leu His Asp Asn Phe Gln Thr
                85                  90                  95

Ala Leu Ala Glu Gly Lys Ile Val Thr Cys Leu Leu Ile Gln Ser Leu
            100                 105                 110

Ile Ile Glu Thr Phe Ala Ile Ser Ala Tyr Asn Ile Tyr Ile Pro Val
        115                 120                 125

Ala Asp Asp Phe Ala Arg Lys Ile Thr Glu Gly Val Val Lys Asp Glu
130                 135                 140

Tyr Met His Leu Asn Phe Gly Glu Glu Trp Leu Lys Ala Asn Phe Glu
145                 150                 155                 160

Ala Ser Lys Ala Glu Leu Glu Thr Ala Asn Arg Ala Asn Leu Pro Leu
            165                 170                 175

Ile Trp Lys Met Leu Asn Gln Val Glu Glu Asp Ala Ala Val Leu Gly
        180                 185                 190

-continued

Met Glu Lys Asp Ala Leu Ile Glu Asp Phe Met Ile Thr Tyr Gly Glu
        195                 200                 205

Ala Leu Ala Asn Ile Gly Phe Ser Ala Arg Asp Val Met Arg Leu Ser
    210                 215                 220

Ala Gln Gly Leu Ala Ala Val
225                 230

<210> SEQ ID NO 90
<211> LENGTH: 232
<212> TYPE: PRT
<213> ORGANISM: Nostoc azollae

<400> SEQUENCE: 90

Met Gln Gln Leu Val Glu Glu Ile Glu Lys Ile Asp Phe Gln Ser Glu
1               5                   10                  15

Lys Tyr Lys Asp Ala Tyr Ser Arg Ile Asn Ala Ile Val Ile Glu Gly
            20                  25                  30

Glu Gln Glu Ala His Gly Asn Tyr Ile Thr Leu Ala Lys Leu Leu Pro
        35                  40                  45

Glu Ser Lys Glu Glu Leu Met Arg Leu Ser Lys Met Glu Ser Arg His
    50                  55                  60

Lys Lys Gly Phe Glu Ala Cys Gly Arg Asn Leu Gln Val Thr Pro Asp
65                  70                  75                  80

Met Gln Phe Ala Lys Glu Phe Phe Ser Gly Leu His Gln Asn Phe Gln
                85                  90                  95

Thr Ala Ala Ala Ala Gly Asn Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160

Ala Glu Ser Lys Ala Glu Leu Asp Asp Ala Asn Arg Gln Asn Leu Pro
                165                 170                 175

Ile Val Trp Gln Met Leu Asn Gln Val Ala Asp Ala Arg Val Leu
            180                 185                 190

Ala Met Glu Lys Glu Ala Leu Val Glu Asp Phe Met Ile Gln Tyr Gly
        195                 200                 205

Glu Ala Leu Ser Asn Ile Gly Phe Thr Thr Arg Asp Ile Ile Arg Leu
    210                 215                 220

Ser Ala Tyr Gly Leu Ala Thr Val
225                 230

<210> SEQ ID NO 91
<211> LENGTH: 231
<212> TYPE: PRT
<213> ORGANISM: Synechocystis sp.

<400> SEQUENCE: 91

Met Pro Glu Leu Ala Val Arg Thr Glu Phe Asp Tyr Ser Ser Glu Ile
1               5                   10                  15

Tyr Lys Asp Ala Tyr Ser Arg Ile Asn Ala Ile Val Ile Glu Gly Glu
            20                  25                  30

Gln Glu Ala Tyr Ser Asn Tyr Leu Gln Met Ala Glu Leu Leu Pro Glu
        35                  40                  45

Asp Lys Glu Glu Leu Thr Arg Leu Ala Lys Met Glu Asn Arg His Lys

```
                50                  55                  60
Lys Gly Phe Gln Ala Cys Gly Asn Asn Leu Gln Val Asn Pro Asp Met
 65                  70                  75                  80

Pro Tyr Ala Gln Glu Phe Phe Ala Gly Leu His Gly Asn Phe Gln His
                 85                  90                  95

Ala Phe Ser Glu Gly Lys Val Val Thr Cys Leu Leu Ile Gln Ala Leu
                100                 105                 110

Ile Ile Glu Ala Phe Ala Ile Ala Ala Tyr Asn Ile Tyr Ile Pro Val
                115                 120                 125

Ala Asp Asp Phe Ala Arg Lys Ile Thr Glu Gly Val Val Lys Asp Glu
130                 135                 140

Tyr Thr His Leu Asn Tyr Gly Glu Glu Trp Leu Lys Ala Asn Phe Ala
145                 150                 155                 160

Thr Ala Lys Glu Glu Leu Glu Gln Ala Asn Lys Glu Asn Leu Pro Leu
                165                 170                 175

Val Trp Lys Met Leu Asn Gln Val Gln Gly Asp Ala Lys Val Leu Gly
                180                 185                 190

Met Glu Lys Glu Ala Leu Val Glu Asp Phe Met Ile Ser Tyr Gly Glu
                195                 200                 205

Ala Leu Ser Asn Ile Gly Phe Ser Thr Arg Glu Ile Met Arg Met Ser
210                 215                 220

Ser Tyr Gly Leu Ala Gly Val
225                 230

<210> SEQ ID NO 92
<211> LENGTH: 231
<212> TYPE: PRT
<213> ORGANISM: Cyanothece sp.

<400> SEQUENCE: 92

Met Gln Glu Leu Ala Leu Arg Ser Glu Leu Asp Phe Asn Ser Glu Thr
  1               5                  10                  15

Tyr Lys Asp Ala Tyr Ser Arg Ile Asn Ala Ile Val Ile Glu Gly Glu
                 20                  25                  30

Gln Glu Ala Tyr Gln Asn Tyr Leu Asp Met Ala Gln Leu Leu Pro Glu
                 35                  40                  45

Asp Glu Ala Glu Leu Ile Arg Leu Ser Lys Met Glu Asn Arg His Lys
 50                  55                  60

Lys Gly Phe Gln Ala Cys Gly Lys Asn Leu Asn Val Thr Pro Asp Met
 65                  70                  75                  80

Asp Tyr Ala Gln Gln Phe Phe Ala Glu Leu His Gly Asn Phe Gln Lys
                 85                  90                  95

Ala Lys Ala Glu Gly Lys Ile Val Thr Cys Leu Leu Ile Gln Ser Leu
                100                 105                 110

Ile Ile Glu Ala Phe Ala Ile Ala Ala Tyr Asn Ile Tyr Ile Pro Val
                115                 120                 125

Ala Asp Pro Phe Ala Arg Lys Ile Thr Glu Gly Val Val Lys Asp Glu
130                 135                 140

Tyr Thr His Leu Asn Phe Gly Glu Val Trp Leu Lys Glu His Phe Glu
145                 150                 155                 160

Ala Ser Lys Ala Glu Leu Glu Asp Ala Asn Lys Glu Asn Leu Pro Leu
                165                 170                 175

Val Trp Gln Met Leu Asn Gln Val Glu Lys Asp Ala Glu Val Leu Gly
                180                 185                 190

Met Glu Lys Glu Ala Leu Val Glu Asp Phe Met Ile Ser Tyr Gly Glu
```

```
                195                 200                 205

Ala Leu Ser Asn Ile Gly Phe Ser Thr Arg Glu Ile Met Lys Met Ser
210                 215                 220

Ala Tyr Gly Leu Arg Ala Ala
225                 230

<210> SEQ ID NO 93
<211> LENGTH: 231
<212> TYPE: PRT
<213> ORGANISM: Cyanothece sp.

<400> SEQUENCE: 93

Met Gln Glu Leu Ala Leu Arg Ser Glu Leu Asp Phe Asn Ser Glu Thr
1               5                   10                  15

Tyr Lys Asp Ala Tyr Ser Arg Ile Asn Ala Ile Val Ile Glu Gly Glu
                20                  25                  30

Gln Glu Ala His Gln Asn Tyr Ile Asp Met Ala Gln Leu Leu Pro Glu
            35                  40                  45

Asp Glu Ala Glu Leu Ile Arg Leu Ser Lys Met Glu Asn Arg His Lys
        50                  55                  60

Lys Gly Phe Gln Ala Cys Gly Lys Asn Leu Asp Val Thr Pro Asp Met
65                  70                  75                  80

Asp Tyr Ala Gln Gln Phe Phe Ser Gln Leu His Asn Asn Phe Gln Thr
                85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Thr His Leu Asn Phe Gly Glu Ile Trp Leu Lys Glu His Phe Glu
145                 150                 155                 160

Ala Ser Lys Ala Glu Leu Glu Glu Ala Asn Lys Lys Asn Leu Pro Ile
                165                 170                 175

Val Trp Gln Met Leu Asn Gln Val Glu Lys Asp Ala Glu Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Lys Met Ser
    210                 215                 220

Ser His Gly Leu Ser Ala Ala
225                 230

<210> SEQ ID NO 94
<211> LENGTH: 231
<212> TYPE: PRT
<213> ORGANISM: Cyanothece sp.

<400> SEQUENCE: 94

Met Pro Gln Val Gln Ser Pro Ser Ala Ile Asp Phe Tyr Ser Glu Thr
1               5                   10                  15

Tyr Gln Asp Ala Tyr Ser Arg Ile Asp Ala Ile Val Ile Glu Gly Glu
                20                  25                  30

Gln Glu Ala His Asp Asn Tyr Leu Lys Leu Thr Glu Leu Leu Pro Asp
            35                  40                  45

Cys Gln Glu Asp Leu Val Arg Leu Ala Lys Met Glu Ala Arg His Lys
        50                  55                  60
```

```
Lys Gly Phe Glu Ala Cys Gly Arg Asn Leu Lys Val Thr Pro Asp Met
 65                  70                  75                  80

Glu Phe Ala Gln Gln Phe Phe Ala Asp Leu His Asn Asn Phe Gln Lys
             85                  90                  95

Ala Ala Ala Ala Asn Lys Ile Ala Thr Cys Leu Val Ile Gln Ala Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Asn Val Val Lys Asp Glu
    130                 135                 140

Tyr Thr His Leu Asn Phe Gly Glu Glu Trp Leu Lys Ala Asn Phe Asp
145                 150                 155                 160

Ser Gln Arg Glu Glu Val Glu Ala Ala Asn Arg Glu Asn Leu Pro Ile
                165                 170                 175

Val Trp Arg Met Leu Asn Gln Val Glu Thr Asp Ala His Val Leu Gly
            180                 185                 190

Met Glu Lys Glu Ala Leu Val Glu Ser Phe Met Ile Gln Tyr Gly Glu
        195                 200                 205

Ala Leu Glu Asn Ile Gly Phe Ser Thr Arg Glu Ile Met Arg Met Ser
    210                 215                 220

Val Tyr Gly Leu Ser Ala Ala
225                 230

<210> SEQ ID NO 95
<211> LENGTH: 232
<212> TYPE: PRT
<213> ORGANISM: Nostoc punctiforme

<400> SEQUENCE: 95

Met Gln Gln Leu Thr Asp Gln Ser Lys Glu Leu Asp Phe Lys Ser Glu
1               5                   10                  15

Thr Tyr Lys Asp Ala Tyr Ser Arg Ile Asn Ala Ile Val Ile Glu Gly
            20                  25                  30

Glu Gln Glu Ala His Glu Asn Tyr Ile Thr Leu Ala Gln Leu Leu Pro
        35                  40                  45

Glu Ser His Asp Glu Leu Ile Arg Leu Ser Lys Met Glu Ser Arg His
    50                  55                  60

Lys Lys Gly Phe Glu Ala Cys Gly Arg Asn Leu Ala Val Thr Pro Asp
65                  70                  75                  80

Leu Gln Phe Ala Lys Glu Phe Phe Ser Gly Leu His Gln Asn Phe Gln
                85                  90                  95

Thr Ala Ala Ala Glu Gly Lys Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160

Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205
```

```
Glu Ala Leu Ser Asn Ile Gly Phe Ser Thr Arg Asp Ile Met Arg Leu
    210                 215                 220

Ser Ala Tyr Gly Leu Ile Gly Ala
225                 230

<210> SEQ ID NO 96
<211> LENGTH: 231
<212> TYPE: PRT
<213> ORGANISM: Acaryochloris marina

<400> SEQUENCE: 96

Met Pro Gln Thr Gln Ala Ile Ser Glu Ile Asp Phe Tyr Ser Asp Thr
1               5                   10                  15

Tyr Lys Asp Ala Tyr Ser Arg Ile Asp Gly Ile Val Ile Glu Gly Glu
                20                  25                  30

Gln Glu Ala His Glu Asn Tyr Ile Arg Leu Gly Glu Met Leu Pro Glu
            35                  40                  45

His Gln Asp Asp Phe Ile Arg Leu Ser Lys Met Glu Ala Arg His Lys
    50                  55                  60

Lys Gly Phe Glu Ala Cys Gly Arg Asn Leu Lys Val Thr Cys Asp Leu
65                  70                  75                  80

Asp Phe Ala Arg Arg Phe Phe Ser Asp Leu His Lys Asn Phe Gln Asp
                85                  90                  95

Ala Ala Ala Glu Asp Lys Val Pro Thr Cys Leu Val Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Ser Val Val Lys Asp Glu
130                 135                 140

Tyr Gln His Leu Asn Tyr Gly Glu Glu Trp Leu Lys Ala His Phe Asp
145                 150                 155                 160

Asp Val Lys Ala Glu Ile Gln Glu Ala Asn Arg Lys Asn Leu Pro Ile
                165                 170                 175

Val Trp Arg Met Leu Asn Glu Val Asp Lys Asp Ala Ala Val Leu Gly
            180                 185                 190

Met Glu Lys Glu Ala Leu Val Glu Asp Phe Met Ile Gln Tyr Gly Glu
        195                 200                 205

Ala Leu Ser Asn Ile Gly Phe Ser Thr Gly Ile Met Arg Met Ser
210                 215                 220

Ala Tyr Gly Leu Val Ala Ala
225                 230

<210> SEQ ID NO 97
<211> LENGTH: 231
<212> TYPE: PRT
<213> ORGANISM: Cyanothece sp.

<400> SEQUENCE: 97

Met Gln Glu Leu Val Gln Arg Ser Glu Leu Asp Phe Thr Asn Pro Thr
1               5                   10                  15

Tyr Lys Asp Ala Tyr Ser Arg Ile Asn Ala Ile Val Ile Glu Gly Glu
                20                  25                  30

Gln Glu Ala His Gln Asn Tyr Ile Asp Met Ala Gln Leu Leu Pro Glu
            35                  40                  45

His Gln Glu Glu Leu Ile Arg Leu Ser Lys Met Glu Asn Arg His Lys
    50                  55                  60
```

```
Lys Gly Phe Glu Ala Cys Gly Asn Asn Leu Ser Val Thr Pro Asp Met
 65                  70                  75                  80

Gln Tyr Ala Gln Glu Phe Phe Ser Ser Leu His Gly Asn Phe Gln Lys
                 85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Thr His Leu Asn Phe Gly Glu Val Trp Leu Gln Glu His Phe Glu
145                 150                 155                 160

Glu Ser Lys Ala Glu Leu Glu Glu Ala Asn Lys Ala Asn Leu Pro Ile
                165                 170                 175

Val Trp Glu Met Leu Asn Gln Val Glu Gly Asp Ala Lys Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Asp Ile Met Arg Met Ser
    210                 215                 220

Ser His Gly Leu Val Ala Ala
225                 230

<210> SEQ ID NO 98
<211> LENGTH: 231
<212> TYPE: PRT
<213> ORGANISM: Cyanothece sp.

<400> SEQUENCE: 98

Met Gln Glu Leu Val Gln Arg Ser Glu Leu Asp Phe Thr Asn Pro Thr
  1               5                  10                  15

Tyr Lys Asp Ala Tyr Ser Arg Ile Asn Ala Ile Val Ile Glu Gly Glu
             20                  25                  30

Gln Glu Ala His Gln Asn Tyr Ile Asp Met Ala Gln Leu Leu Pro Glu
         35                  40                  45

His Gln Glu Glu Leu Ile Arg Leu Ser Lys Met Glu Asn Arg His Lys
 50                  55                  60

Lys Gly Phe Glu Ala Cys Gly Asn Asn Leu Ser Val Thr Pro Asp Met
 65                  70                  75                  80

Gln Tyr Ala Gln Glu Phe Phe Ser Ser Leu His Gly Asn Phe Gln Lys
                 85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Thr His Leu Asn Phe Gly Glu Val Trp Leu Gln Glu His Phe Glu
145                 150                 155                 160

Glu Ser Lys Ala Glu Leu Glu Glu Ala Asn Lys Ala Asn Leu Pro Ile
                165                 170                 175

Val Trp Glu Met Leu Asn Gln Val Glu Gly Asp Ala Lys Val Leu Gly
            180                 185                 190

Met Glu Lys Glu Ala Leu Val Glu Asp Phe Met Ile Ser Tyr Gly Glu
        195                 200                 205
```

```
Ala Leu Ser Asn Ile Gly Phe Ser Thr Arg Asp Ile Met Arg Met Ser
        210                 215                 220

Ser His Gly Leu Val Ala Ala
225                 230
```

<210> SEQ ID NO 99
<211> LENGTH: 240
<212> TYPE: PRT
<213> ORGANISM: Synechococcus sp.

<400> SEQUENCE: 99

```
Met Asn Val Leu Pro Asn Thr Pro Gln Pro Leu Ala Asp Glu Gly Gly
1               5                   10                  15

Thr Thr Leu Asp Tyr Gly Ser Ala Val Tyr Arg Gln Ala Tyr Ser Arg
            20                  25                  30

Ile Asn Gly Ile Val Ile Glu Gly Glu Gln Glu Ala His Asp Asn Tyr
        35                  40                  45

Leu Lys Leu Ala Glu Met Leu Pro Glu Gly Ala Glu Leu His Lys
 50                  55                  60

Leu Ala Lys Met Glu Leu Arg His Met Lys Gly Phe Gln Ser Cys Gly
65                  70                  75                  80

Lys Asn Leu Gln Val Glu Pro Asp Arg Glu Phe Ala Arg Thr Phe Phe
                85                  90                  95

Ala Pro Leu Arg Asn Asn Phe Gln Lys Ala Ala Ala Gly Asp Leu
            100                 105                 110

Val Thr Cys Leu Val Ile Gln Ser Leu Ile Ile Glu Cys Phe Ala Ile
        115                 120                 125

Ala Ala Tyr Asn Ile Tyr Ile Pro Val Ala Asp Glu Phe Ala Arg Lys
130                 135                 140

Ile Thr Glu Gly Val Val Lys Asp Glu Tyr Leu His Leu Asn Phe Gly
145                 150                 155                 160

Glu Arg Trp Leu Gly Glu His Phe Gly Glu Val Lys Gly Gln Ile Glu
                165                 170                 175

Ala Ala Asn Ala Gln Asn Leu Pro Leu Val Trp Gln Met Leu Gln Gln
            180                 185                 190

Val Asp Gln Asp Val Glu Ala Ile Tyr Met Asp Arg Glu Ala Ile Val
        195                 200                 205

Glu Asp Phe Met Ile Ala Tyr Gly Glu Ala Leu Ala Asn Ile Gly Phe
    210                 215                 220

Ser Thr Arg Glu Val Met Arg Leu Ser Ala Gln Gly Leu Arg Ala Ala
225                 230                 235                 240
```

<210> SEQ ID NO 100
<211> LENGTH: 241
<212> TYPE: PRT
<213> ORGANISM: Synechococcus sp.

<400> SEQUENCE: 100

```
Met Ala Ser Ser Leu Leu Asp Pro Ala Val Asp Gly Thr Pro Val Leu
1               5                   10                  15

Asp Val Glu Leu Pro Asp Phe Thr Thr Glu Ala Tyr Lys Ser Ala Tyr
            20                  25                  30

Ser Arg Ile Asn Ala Ile Val Ile Glu Gly Gln Glu Ala His Asp
        35                  40                  45

Asn Tyr Ile Ser Leu Gly Thr Leu Ile Pro Asp Gln Ala Asp Glu Leu
 50                  55                  60

Ala Gln Leu Ala Arg Met Glu Met Lys His Met Lys Gly Phe Gln Ala
```

```
                65                  70                  75                  80
Cys Gly Lys Asn Leu Ser Val Glu Pro Asp Met Val Phe Ala Lys Glu
                    85                  90                  95
Phe Phe Ser Asp Leu His Gly Asn Phe Arg Ser Ala Leu Glu Glu Asn
                100                 105                 110
Lys Val Val Thr Cys Leu Val Ile Gln Ala Leu Met Ile Glu Ala Phe
                115                 120                 125
Ala Ile Ala Ala Tyr His Ile Tyr Ile Pro Val Ala Asp Pro Phe Ala
            130                 135                 140
Arg Lys Ile Thr Glu Gly Val Val Lys Asp Glu Tyr Thr His Leu Asn
145                 150                 155                 160
Tyr Gly Gln Glu Trp Leu Lys Ala Asn Phe Asp Ser Ser Arg Asp Glu
                165                 170                 175
Ile Ile Glu Ala Asn Lys Ala Asn Leu Pro Ile Ile Arg Arg Met Leu
                180                 185                 190
Glu Glu Val Ala Asp Asp Ala Ala Glu Leu Lys Met Glu Lys Glu Ser
                195                 200                 205
Leu Ile Glu Asp Phe Leu Ile Ala Tyr Gln Glu Ala Leu Met Asp Ile
            210                 215                 220
Gly Phe Asn Ser Arg Asp Leu Ala Arg Met Ser Ala Ala Ala Leu Val
225                 230                 235                 240
Ala

<210> SEQ ID NO 101
<211> LENGTH: 243
<212> TYPE: PRT
<213> ORGANISM: Synechococcus sp.

<400> SEQUENCE: 101

Met Pro Thr Pro Val Thr Ser Glu Val Ala Val Leu Asp Gly Gln Ala
1               5                   10                  15
Gly Ser Ala Gln Ala Leu Pro Asp Phe Ser Ser Glu Ala Tyr Lys Asp
                20                  25                  30
Ala Tyr Ser Arg Ile Asn Ala Ile Val Ile Glu Gly Glu Gln Glu Ala
            35                  40                  45
His Asp Asn Tyr Ile Ser Leu Gly Thr Leu Ile Pro Glu Gln Ala Asp
        50                  55                  60
Glu Leu Ala Arg Leu Ala Arg Met Glu Met Lys His Met Lys Gly Phe
65                  70                  75                  80
Met Ser Cys Gly Arg Asn Leu Gly Val Glu Ala Asp Met Pro Phe Ala
                85                  90                  95
Lys Glu Phe Phe Gly Pro Leu His Gly Asn Phe Gln Thr Ala Leu Lys
                100                 105                 110
Glu Gly Lys Val Val Thr Cys Leu Leu Ile Gln Ala Leu Leu Ile Glu
            115                 120                 125
Ala Phe Ala Ile Ser Ala Tyr His Ile Tyr Ile Pro Val Ala Asp Pro
        130                 135                 140
Phe Ala Arg Lys Ile Thr Glu Gly Val Val Lys Asp Glu Tyr Thr His
145                 150                 155                 160
Leu Asn Tyr Gly Gln Glu Trp Leu Lys Ala Asn Phe Glu Ala Ser Arg
                165                 170                 175
Glu Glu Leu Met Glu Ala Asn Lys Val Asn Leu Pro Leu Ile Arg Ser
                180                 185                 190
Met Leu Glu Gln Val Ala Lys Asp Ala Ala Val Leu Lys Met Glu Lys
            195                 200                 205
```

```
Glu Asp Leu Ile Glu Asp Phe Leu Ile Ala Tyr Gln Glu Ala Leu Glu
    210                 215                 220

Glu Ile Gly Phe Thr Ser Arg Asp Ile Ala Arg Met Ala Ala Ala Ala
225                 230                 235                 240

Leu Ser Ile

<210> SEQ ID NO 102
<211> LENGTH: 239
<212> TYPE: PRT
<213> ORGANISM: Synechococcus sp.

<400> SEQUENCE: 102

Met Thr Thr Leu Asn Ala Pro Glu Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Gly Ser Leu Ile Pro Asp Gln Lys Asp Glu Leu Ala Lys
50                  55                  60

Leu Ala Arg Met Glu Met Lys His Met Lys Gly Phe Thr Ser Cys Gly
65                  70                  75                  80

Arg Asn Leu Gly Val Glu Ala Asp Met Val Phe Ala Lys Lys Phe Phe
                85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Glu Glu
            180                 185                 190

Val Ala Ser Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
    210                 215                 220

Thr Ser Arg Asp Ile Ala Arg Met Ala Ala Ala Leu Ala Val
225                 230                 235

<210> SEQ ID NO 103
<211> LENGTH: 243
<212> TYPE: PRT
<213> ORGANISM: Synechococcus sp.

<400> SEQUENCE: 103

Met Pro Thr Pro Val Thr Ser Glu Val Ala Val Leu Asp Glu Gln Ala
1               5                   10                  15

Gly Ser Ala Ser Leu Leu Pro Asp Phe Ser Ser Glu Ala Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ser Leu Gly Thr Leu Ile Pro Asp Gln Ala Asp
```

```
            50                  55                  60
Glu Leu Ala Arg Leu Ala Arg Met Glu Met Lys His Met Lys Gly Phe
 65                  70                  75                  80

Thr Ser Cys Gly Arg Asn Leu Gly Val Asp Ala Asp Met Pro Phe Ala
                 85                  90                  95

Lys Thr Phe Phe Ala Pro Leu His Gly Asn Phe Gln Thr Ala Leu Lys
            100                 105                 110

Asp Gly Lys Val Val Thr Cys Leu Leu Ile Gln Ala Leu Leu Ile Glu
            115                 120                 125

Ala Phe Ala Ile Ser Ala Tyr His Ile Tyr Ile Pro Val Ala Asp Pro
        130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Asp Ala Ser Arg
                165                 170                 175

Glu Glu Leu Met Glu Ala Asn Lys Val Asn Leu Pro Leu Ile Arg Ser
            180                 185                 190

Met Leu Glu Gln Val Ala Glu Asp Ala Ala Val Leu Lys Met Glu Lys
        195                 200                 205

Glu Asp Leu Ile Glu Asp Phe Leu Ile Ala Tyr Gln Glu Ala Leu Glu
    210                 215                 220

Gln Ile Gly Phe Thr Ser Arg Asp Ile Ala Arg Met Ala Ala Ala Ala
225                 230                 235                 240

Leu Ala Val

<210> SEQ ID NO 104
<211> LENGTH: 239
<212> TYPE: PRT
<213> ORGANISM: Synechococcus sp.

<400> SEQUENCE: 104

Met Thr Thr Leu Asn Ala Pro Glu Ala Ala Val Val Glu Gly Leu Asp
 1               5                  10                  15

Ala Leu Pro Asp Phe Thr Thr Glu Ala Tyr Lys Asp Ala Tyr Ser Arg
             20                  25                  30

Ile Asn Ala Ile Val Ile Glu Gly Glu Gln Glu Ala His Asp Asn Tyr
         35                  40                  45

Ile Ser Leu Gly Thr Leu Ile Pro Asp Gln Lys Asp Glu Leu Ala Lys
     50                  55                  60

Leu Ala Arg Met Glu Met Lys His Met Lys Gly Phe Thr Ser Cys Gly
 65                  70                  75                  80

Arg Asn Leu Gly Val Glu Ala Asp Leu Ala Phe Ala Lys Lys Phe Phe
                 85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
            115                 120                 125

Ser Ala Tyr His Ile Tyr Ile Pro Val Ala Asp Pro Phe Ala Arg Lys
        130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Glu Asp
            180                 185                 190
```

Val Ala Ser Asp Ala Ala Val Leu His Met Glu Lys Glu Asp Leu Ile
            195                 200                 205

Glu Asp Phe Leu Ile Ala Tyr Gln Glu Ala Leu Gly Glu Ile Gly Phe
210                 215                 220

Thr Ser Arg Asp Ile Ala Arg Met Ala Ala Ala Leu Ala Val
225                 230                 235

<210> SEQ ID NO 105
<211> LENGTH: 243
<212> TYPE: PRT
<213> ORGANISM: Synechococcus sp.

<400> SEQUENCE: 105

Met Ala Pro Ala Asn Val Leu Pro Asn Thr Pro Ser Pro Thr Asp
1               5                   10                  15

Gly Gly Gly Thr Ala Leu Asp Tyr Ser Ser Pro Arg Tyr Arg Gln Ala
            20                  25                  30

Tyr Ser Arg Ile Asn Gly Ile Val Ile Glu Gly Glu Gln Glu Ala His
        35                  40                  45

Asp Asn Tyr Leu Lys Leu Ala Glu Met Leu Pro Glu Ala Ala Glu Glu
    50                  55                  60

Leu Arg Lys Leu Ala Lys Met Glu Leu Arg His Met Lys Gly Phe Gln
65                  70                  75                  80

Ala Cys Gly Lys Asn Leu Gln Val Glu Pro Asp Val Glu Phe Ala Arg
                85                  90                  95

Ala Phe Phe Ala Pro Leu Arg Asp Asn Phe Gln Ser Ala Ala Ala Ala
            100                 105                 110

Gly Asp Leu Val Ser Cys Phe Val Ile Gln Ser Leu Ile Ile Glu Cys
        115                 120                 125

Phe Ala Ile Ala Ala Tyr Asn Ile Tyr Ile Pro Val Ala Asp Asp Phe
    130                 135                 140

Ala Arg Lys Ile Thr Glu Gly Val Val Lys Asp Glu Tyr Leu His Leu
145                 150                 155                 160

Asn Phe Gly Glu Arg Trp Leu Gly Glu His Phe Ala Glu Val Lys Ala
                165                 170                 175

Gln Ile Glu Ala Ala Asn Ala Gln Asn Leu Pro Leu Val Arg Gln Met
            180                 185                 190

Leu Gln Gln Val Glu Ala Asp Val Glu Ala Ile Tyr Met Asp Arg Glu
        195                 200                 205

Ala Ile Val Glu Asp Phe Met Ile Ala Tyr Gly Glu Ala Leu Ala Ser
    210                 215                 220

Ile Gly Phe Asn Thr Arg Glu Val Met Arg Leu Ser Ala Gln Gly Leu
225                 230                 235                 240

Arg Ala Ala

<210> SEQ ID NO 106
<211> LENGTH: 239
<212> TYPE: PRT
<213> ORGANISM: Synechococcus sp.

<400> SEQUENCE: 106

Met Thr Thr Leu Asn Ala Pro Glu Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr

```
                    35                  40                  45
Ile Ser Leu Gly Ser Leu Ile Pro Asp Gln Lys Asp Glu Leu Ala Lys
 50                  55                  60
Leu Ala Arg Met Glu Met Lys His Met Lys Gly Phe Thr Ser Cys Gly
 65                  70                  75                  80
Arg Asn Leu Gly Val Glu Ala Asp Met Val Phe Ala Lys Thr Phe Phe
                 85                  90                  95
Glu Pro Leu His Gly Asn Phe Gln Ala Ala Leu Lys Glu Gly Lys Val
                100                 105                 110
Val Thr Cys Leu Leu Ile Gln Ala Leu Leu Ile Glu Ala Phe Ala Ile
                115                 120                 125
Ser Ala Tyr His Ile Tyr Ile Pro Val Ala Asp Pro Phe Ala Arg Lys
                130                 135                 140
Ile Thr Glu Gly Val Val Lys Asp Glu Tyr Thr His Leu Asn Tyr Gly
145                 150                 155                 160
Gln Glu Trp Leu Lys Ala Asn Phe Glu Ala Ser Lys Asp Glu Leu Phe
                165                 170                 175
Glu Ala Asn Lys Ala Asn Leu Pro Leu Ile Arg Ser Met Leu Glu Glu
                180                 185                 190
Val Ala Ser Asp Ala Ala Val Leu His Met Glu Lys Glu Asp Leu Ile
                195                 200                 205
Glu Asp Phe Leu Ile Ala Tyr Gln Glu Ala Leu Gly Glu Ile Gly Phe
                210                 215                 220
Thr Ser Arg Asp Ile Ala Arg Met Ala Ala Ala Leu Ala Val
225                 230                 235

<210> SEQ ID NO 107
<211> LENGTH: 239
<212> TYPE: PRT
<213> ORGANISM: Synechococcus sp.

<400> SEQUENCE: 107

Met Thr Thr Leu Asn Ala Pro Glu Ala Ser Val Met Glu Gly Gln Asp
 1               5                  10                  15
Ala Leu Pro Asp Phe Thr Thr Glu Ala Tyr Lys Asp Ala Tyr Ser Arg
                 20                  25                  30
Ile Asn Ala Ile Val Ile Glu Gly Glu Gln Ala His Asp Asn Tyr
                 35                  40                  45
Ile Ser Leu Gly Thr Leu Ile Pro Asp Gln Ala Glu Glu Leu Ala Arg
 50                  55                  60
Leu Ala Arg Met Glu Met Lys His Met Lys Gly Phe Thr Ser Cys Gly
 65                  70                  75                  80
Arg Asn Leu Gly Val Gln Ala Asp Met Ala Phe Ala Arg Lys Phe Phe
                 85                  90                  95
Glu Pro Leu His Gly Asn Phe Gln Ser Ala Leu Lys Glu Gly Lys Val
                100                 105                 110
Val Thr Cys Leu Leu Ile Gln Ala Leu Leu Ile Glu Ala Phe Ala Ile
                115                 120                 125
Ser Ala Tyr His Ile Tyr Ile Pro Val Ala Asp Pro Phe Ala Arg Lys
                130                 135                 140
Ile Thr Glu Gly Val Val Lys Asp Glu Tyr Thr His Leu Asn Tyr Gly
145                 150                 155                 160
Gln Glu Trp Leu Lys Ala Asn Phe Glu Ala Ser Lys Glu Glu Leu Phe
                165                 170                 175
Glu Ala Asn Lys Ala Asn Leu Pro Leu Ile Arg Ser Met Leu Glu Asp
```

-continued

```
                180                 185                 190
Val Ala Ala Asp Ala Ala Val Leu His Met Glu Lys Glu Asp Leu Ile
            195                 200                 205

Glu Asp Phe Leu Ile Ala Tyr Asn Glu Ala Leu Ser Glu Ile Gly Phe
        210                 215                 220

Ser Ser Arg Asp Ile Ala Arg Met Ala Ala Ala Leu Ala Leu
225                 230                 235

<210> SEQ ID NO 108
<211> LENGTH: 242
<212> TYPE: PRT
<213> ORGANISM: Synechococcus sp.

<400> SEQUENCE: 108

Met Pro Thr Leu Asp Ser Thr Leu Val Ala Val Leu Asp Asp Gln Gln
1               5                   10                  15

Gly Leu Ala Glu Leu Pro Asp Phe Thr Thr Asp Ala Tyr Lys Asp Ala
            20                  25                  30

Tyr Ser Arg Ile Asn Ala Ile Val Ile Glu Gly Glu Lys Glu Ala His
        35                  40                  45

Asp Asn Tyr Leu Ser Leu Gly Thr Leu Ile Pro Glu Gln Ala Glu Glu
    50                  55                  60

Leu Ala Lys Leu Ala Lys Met Glu Met Lys His Met Lys Gly Phe Thr
65                  70                  75                  80

Ala Cys Ala Lys Asn Leu Asp Val Val Ala Asp Met Pro Phe Ala Gln
                85                  90                  95

Glu Phe Phe Ala Pro Leu His Gly Asn Phe Gln Ser Ala Leu Lys Glu
            100                 105                 110

Gly Lys Val Val Thr Cys Leu Leu Ile Gln Ala Leu Leu Ile Glu Ala
        115                 120                 125

Phe Ala Ile Ser Ala Tyr His Ile Tyr Ile Pro Val Ala Asp Pro Phe
    130                 135                 140

Ala Arg Lys Ile Thr Glu Gly Val Val Lys Asp Glu Tyr Thr His Leu
145                 150                 155                 160

Asn Tyr Gly Gln Glu Trp Leu Lys Ala Asn Phe Glu Ala Ser Arg Asp
                165                 170                 175

Glu Leu Met Glu Ala Asn Lys Val Asn Leu Pro Leu Ile Arg Ser Met
            180                 185                 190

Leu Glu Gln Val Ala Ala Asp Ala Ser Val Leu His Met Glu Lys Glu
        195                 200                 205

Asp Leu Ile Glu Asp Phe Leu Ile Ala Tyr Gln Glu Ala Leu Asn Glu
    210                 215                 220

Ile Gly Phe Ser Ser Arg Asp Ile Ala Arg Met Ala Ala Ala Ala Leu
225                 230                 235                 240

Ser Ile

<210> SEQ ID NO 109
<211> LENGTH: 239
<212> TYPE: PRT
<213> ORGANISM: Synechococcus sp.

<400> SEQUENCE: 109

Met Thr Thr Leu Asn Ala Pro Asp Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30
```

```
Ile Asn Ala Ile Val Ile Glu Gly Glu Gln Glu Ala His Asp Asn Tyr
            35                  40                  45

Ile Ala Leu Gly Thr Leu Ile Pro Asp Gln Lys Asp Glu Leu Ala Arg
 50                  55                  60

Leu Ala Arg Met Glu Met Lys His Met Lys Gly Phe Thr Ser Cys Gly
 65                  70                  75                  80

Arg Asn Leu Gly Val Lys Ala Asp Met Val Phe Ala Lys Thr Phe Phe
                 85                  90                  95

Glu Pro Leu His Arg Asn Phe Gln Ser Ala Leu Gln Glu Gly Lys Val
                100                 105                 110

Val Thr Cys Leu Leu Ile Gln Ala Leu Leu Ile Glu Ala Phe Ala Ile
            115                 120                 125

Ser Ala Tyr His Ile Tyr Ile Pro Val Ala Asp Pro Phe Ala Arg Lys
        130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Asp Asp
                180                 185                 190

Val Ala Gly Asp Ala Ala Val Leu His Met Glu Lys Glu Asp Leu Ile
            195                 200                 205

Glu Asp Phe Leu Ile Ala Tyr Gln Glu Ala Leu Gly Glu Ile Gly Phe
        210                 215                 220

Thr Ser Arg Asp Ile Ala Arg Met Ala Ala Ala Leu Ala Val
225                 230                 235

<210> SEQ ID NO 110
<211> LENGTH: 253
<212> TYPE: PRT
<213> ORGANISM: Synechococcus sp.

<400> SEQUENCE: 110

Met Pro Ser Leu Glu Thr Thr Ile Ala Ala Ser Glu Thr Ala Ser Ala
 1               5                  10                  15

Ser Ala Ser Met Ala Val Gly Gly Ser Val Glu Gln Asp Leu Gly Leu
                20                  25                  30

Pro Asp Phe Ser Ser Ser Thr Tyr Lys Asp Ala Tyr Ser Arg Ile Asn
            35                  40                  45

Ala Ile Val Ile Glu Gly Glu Gln Glu Ala His Asp Asn Tyr Ile Ser
 50                  55                  60

Leu Gly His Leu Ile Pro Asp Gln Ala Glu Glu Leu Glu Arg Leu Ala
 65                  70                  75                  80

Arg Met Glu Leu Lys His Lys Lys Gly Phe Thr Ala Cys Ala Lys Asn
                 85                  90                  95

Leu Ser Val Ile Ala Asp Met Asp Phe Ala Lys Glu Phe Phe Ser Pro
                100                 105                 110

Leu His Gly Asn Phe Gln Ala Ala Leu Ala Glu Gly Lys Val Val Thr
            115                 120                 125

Cys Leu Leu Ile Gln Ala Ile Leu Ile Glu Ala Phe Ala Ile Ser Ala
        130                 135                 140

Tyr His Ile Tyr Ile Pro Val Ala Asp Pro Phe Ala Arg Lys Ile Thr
145                 150                 155                 160

Glu Gly Val Val Lys Asp Glu Tyr Thr His Leu Asn Tyr Gly Gln Glu
                165                 170                 175
```

```
Trp Leu Lys Ala Asn Leu Glu Ser Ser Arg Gly Glu Leu Glu Gln Ala
            180                 185                 190

Asn Arg Val Asn Leu Pro Leu Val Arg Lys Met Leu Glu Gln Val Ala
            195                 200                 205

Gly Asp Ala Ala Val Leu His Met Asp Gln Glu Asp Leu Met Ala Asp
210                 215                 220

Phe Met Thr Ser Tyr Gln Glu Ala Leu Thr Asp Ile Gly Phe Thr Thr
225                 230                 235                 240

Arg Glu Ile Ala Lys Met Ala Thr Ala Ala Leu Leu Gly
                245                 250

<210> SEQ ID NO 111
<211> LENGTH: 235
<212> TYPE: PRT
<213> ORGANISM: Gloeobacter violaceus

<400> SEQUENCE: 111

Met Asn Arg Thr Ala Pro Ser Ser Ala Ala Leu Asp Tyr Arg Ser Asp
1               5                   10                  15

Thr Tyr Arg Asp Ala Tyr Ser Arg Ile Asn Ala Ile Val Leu Glu Gly
            20                  25                  30

Glu Arg Glu Ala His Ala Asn Tyr Leu Thr Leu Ala Glu Met Leu Pro
        35                  40                  45

Asp His Ala Glu Ala Leu Lys Lys Leu Ala Met Glu Asn Arg His
    50                  55                  60

Phe Lys Gly Phe Gln Ser Cys Ala Arg Asn Leu Glu Val Thr Pro Asp
65                  70                  75                  80

Asp Pro Phe Ala Arg Ala Tyr Phe Glu Gln Leu Asp Gly Asn Phe Gln
                85                  90                  95

Gln Ala Ala Ala Glu Gly Asp Leu Thr Thr Cys Met Val Ile Gln Ala
            100                 105                 110

Leu Ile Ile Glu Cys Phe Ala Ile Ala Ala Tyr Asn Val Tyr Ile Pro
        115                 120                 125

Val Ala Asp Ala Phe Ala Arg Lys Val Thr Glu Gly Val Val Lys Asp
130                 135                 140

Glu Tyr Thr His Leu Asn Phe Gly Gln Gln Trp Leu Lys Glu Arg Phe
145                 150                 155                 160

Val Thr Val Arg Glu Gly Ile Glu Arg Ala Asn Ala Gln Asn Leu Pro
                165                 170                 175

Ile Val Trp Arg Met Leu Asn Ala Val Glu Ala Asp Thr Glu Val Leu
            180                 185                 190

Gln Met Asp Lys Glu Ala Ile Val Glu Asp Phe Met Ile Ala Tyr Gly
        195                 200                 205

Glu Ala Leu Gly Asp Ile Gly Phe Ser Met Arg Asp Val Met Lys Met
    210                 215                 220

Ser Ala Arg Gly Leu Ala Ser Ala Pro Arg Gln
225                 230                 235

<210> SEQ ID NO 112
<211> LENGTH: 243
<212> TYPE: PRT
<213> ORGANISM: Synechococcus sp.

<400> SEQUENCE: 112

Met Pro Thr Leu Asn Ser Pro Glu Val Ala Ile Ser Asp Gln Asp
1               5                   10                  15

Gly Ser Ala Ser Gln Leu Pro Asp Phe Ser Ser Ala Ala Tyr Lys Asp
```

```
                    20                  25                  30
Ala Tyr Ser Arg Ile Asn Ala Ile Val Ile Glu Gly Glu Gln Glu Ala
                35                  40                  45

His Asp Asn Tyr Ile Ser Leu Gly Thr Leu Ile Pro Asp Gln Ala Asp
 50                  55                  60

Glu Leu Lys Gly Leu Ala Arg Met Glu Met Lys His Met Lys Gly Phe
65                  70                  75                  80

Thr Ala Cys Gly Asn Asn Leu Gly Val Thr Ala Asp Met Asp Phe Ala
                85                  90                  95

Arg Thr Phe Phe Ala Pro Leu His Gly Asn Phe Gln Lys Ala Met Lys
                100                 105                 110

Glu Gly Lys Val Val Thr Cys Leu Leu Ile Gln Ala Leu Leu Ile Glu
                115                 120                 125

Ala Phe Ala Ile Ser Ala Tyr His Ile Tyr Ile Pro Val Ala Asp Pro
                130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Glu Ala Ser Lys
                165                 170                 175

Asp Glu Leu Met Glu Ala Asn Lys Val Asn Leu Pro Leu Ile Arg Ser
                180                 185                 190

Met Leu Glu Glu Val Ala Lys Asp Ala Ala Val Leu His Met Glu Lys
                195                 200                 205

Glu Asp Leu Ile Glu Asp Phe Leu Ile Ala Tyr Gln Glu Ala Leu Asn
                210                 215                 220

Glu Ile Gly Phe Ser Ser Arg Asp Ile Ala Arg Met Ala Ala Ala Ala
225                 230                 235                 240

Leu Ala Val

<210> SEQ ID NO 113
<211> LENGTH: 243
<212> TYPE: PRT
<213> ORGANISM: Synechococcus sp.

<400> SEQUENCE: 113

Met Pro Thr Leu Glu Thr Ser Glu Val Ala Val Leu Glu Asp Ser Met
1               5                   10                  15

Ala Ser Gly Ser Arg Leu Pro Asp Phe Thr Ser Glu Ala Tyr Lys Asp
                20                  25                  30

Ala Tyr Ser Arg Ile Asn Ala Ile Val Ile Glu Gly Glu Gln Glu Ala
                35                  40                  45

His Asp Asn Tyr Ile Ala Leu Gly Thr Leu Ile Pro Glu Gln Lys Asp
 50                  55                  60

Glu Leu Ala Arg Leu Ala Arg Met Glu Met Lys His Met Lys Gly Phe
65                  70                  75                  80

Thr Ser Cys Gly Arg Asn Leu Gly Val Glu Ala Asp Leu Pro Phe Ala
                85                  90                  95

Lys Glu Phe Phe Ala Pro Leu His Gly Asn Phe Gln Ala Ala Leu Gln
                100                 105                 110

Glu Gly Lys Val Val Thr Cys Leu Leu Ile Gln Ala Leu Leu Ile Glu
                115                 120                 125

Ala Phe Ala Ile Ser Ala Tyr His Ile Tyr Ile Pro Val Ala Asp Pro
                130                 135                 140

Phe Ala Arg Lys Ile Thr Glu Gly Val Val Lys Asp Glu Tyr Thr His
145                 150                 155                 160
```

```
Leu Asn Tyr Gly Gln Glu Trp Leu Lys Ala Asn Phe Glu Ala Ser Lys
                165                 170                 175

Asp Glu Leu Met Glu Ala Asn Lys Ala Asn Leu Pro Leu Ile Arg Ser
            180                 185                 190

Met Leu Glu Gln Val Ala Ala Asp Ala Ala Val Leu Gln Met Glu Lys
        195                 200                 205

Glu Asp Leu Ile Glu Asp Phe Leu Ile Ala Tyr Gln Glu Ala Leu Cys
210                 215                 220

Glu Ile Gly Phe Ser Ser Arg Asp Ile Ala Arg Met Ala Ala Ala Ala
225                 230                 235                 240

Leu Ala Val

<210> SEQ ID NO 114
<211> LENGTH: 239
<212> TYPE: PRT
<213> ORGANISM: Synechococcus sp.

<400> SEQUENCE: 114

Met Thr Thr Leu Asn Ala Pro Glu Ala Pro Val Leu Glu Gly Gln Asp
1               5                   10                  15

Ala Leu Pro Asp Phe Thr Thr Ala Ala Tyr Lys Asp Ala Tyr Ser Arg
            20                  25                  30

Ile Asn Ala Ile Val Ile Glu Gly Glu Gln Ala His Asp Asn Tyr
        35                  40                  45

Ile Ser Leu Gly Thr Leu Ile Pro Glu Gln Ala Glu Glu Leu Lys Arg
    50                  55                  60

Leu Ala Arg Met Glu Met Lys His Met Lys Gly Phe Thr Ser Cys Gly
65                  70                  75                  80

Arg Asn Leu Gly Val Glu Ala Asp Leu Pro Phe Ala Lys Lys Phe Phe
                85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asn Glu Leu Phe
                165                 170                 175

Glu Ala Asn Lys Ala Asn Leu Pro Leu Ile Arg Ser Met Leu Glu Asp
            180                 185                 190

Val Ala Ala Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
210                 215                 220

Thr Ser Arg Asp Ile Ala Arg Met Ala Ala Ala Leu Ala Val
225                 230                 235

<210> SEQ ID NO 115
<211> LENGTH: 243
<212> TYPE: PRT
<213> ORGANISM: Prochlorococcus marinus

<400> SEQUENCE: 115

Met Pro Thr Leu Glu Met Pro Glu Ala Ala Val Leu Asp Ser Thr Val
```

```
                1               5                      10                     15
Gly Ser Ser Glu Ala Leu Pro Asp Phe Thr Ser Asp Ala Tyr Lys Asp
                    20                  25                  30

Ala Tyr Ser Arg Ile Asn Ala Ile Val Ile Glu Gly Glu Gln Glu Ala
                    35                  40                  45

His Asp Asn Tyr Ile Ala Ile Gly Thr Leu Leu Pro Asp His Val Glu
    50                  55                  60

Glu Leu Lys Arg Leu Ala Lys Met Glu Met Arg His Lys Lys Gly Phe
65                      70                  75                  80

Thr Ala Cys Gly Lys Asn Leu Gly Val Thr Ala Asp Met Asp Phe Ala
                    85                  90                  95

Arg Glu Phe Phe Ala Pro Leu Arg Asp Asn Phe Gln Thr Ala Leu Glu
                    100                 105                 110

Gln Gly Lys Thr Pro Thr Cys Leu Leu Ile Gln Ala Leu Leu Ile Glu
                    115                 120                 125

Ala Phe Ala Ile Ser Ala Tyr His Thr Tyr Ile Pro Val Ser Asp Pro
        130                 135                 140

Phe Ala Arg Lys Ile Thr Glu Gly Val Val Lys Asp Glu Tyr Thr His
145                     150                 155                 160

Leu Asn Tyr Gly Glu Ala Trp Leu Lys Ala Asn Leu Glu Ser Cys Arg
                    165                 170                 175

Glu Glu Leu Leu Glu Ala Asn Arg Glu Asn Leu Pro Leu Ile Arg Arg
                    180                 185                 190

Met Leu Asp Gln Val Ala Gly Asp Ala Ala Val Leu Gln Met Asp Lys
                    195                 200                 205

Glu Asp Leu Ile Glu Asp Phe Leu Ile Ala Tyr Gln Glu Ser Leu Thr
        210                 215                 220

Glu Ile Gly Phe Asn Thr Arg Glu Ile Thr Arg Met Ala Ala Ala Ala
225                     230                 235                 240

Leu Val Ser

<210> SEQ ID NO 116
<211> LENGTH: 249
<212> TYPE: PRT
<213> ORGANISM: Cyanobium sp.

<400> SEQUENCE: 116

Met Ala Ser Val Ala His Pro Ala Val Ala Val Gln Pro Ala Thr Lys
1               5                   10                  15

Pro Ala Asp Thr Ala Ala Glu Arg Gly Asp Gly Leu Pro Asp Phe Ser
                    20                  25                  30

Ser Asp Thr Tyr Lys Asp Ala Tyr Ser Arg Ile Asn Ala Ile Val Ile
                    35                  40                  45

Glu Gly Glu Gln Glu Ala His Asp Asn Tyr Ile Ala Leu Gly Thr Leu
    50                  55                  60

Ile Pro Asp Gln Ala Asp Glu Leu Ala Lys Leu Ala Arg Met Glu Leu
65                      70                  75                  80

Lys His Met Lys Gly Phe Thr Ala Cys Ala Asn Asn Leu Gly Val Thr
                    85                  90                  95

Ala Asp Met Pro Phe Ala Lys Glu Phe Phe Ala Pro Leu His Gly Asn
                    100                 105                 110

Phe Gln Arg Ala Leu Ala Glu Gly Lys Val Thr Thr Cys Leu Leu Ile
                    115                 120                 125

Gln Ala Ile Leu Ile Glu Ala Phe Ala Ile Ser Ala Tyr His Ile Tyr
        130                 135                 140
```

```
Ile Pro Val Ala Asp Pro Phe Ala Arg Arg Ile Thr Glu Gly Val Val
145                 150                 155                 160

Lys Asp Glu Tyr Thr His Leu Asn Tyr Gly Gln Trp Leu Lys Ala
            165                 170                 175

Asn Leu Ala Asp Val Arg Glu Glu Leu Glu Gln Ala Asn Arg Glu Asn
            180                 185                 190

Leu Pro Leu Val Arg Lys Met Leu Glu Gln Val Ala Gly Asp Ala Ala
        195                 200                 205

Val Leu Gln Met Asp Lys Glu Asp Leu Met Ala Asp Phe Leu Ser Ser
    210                 215                 220

Tyr Gln Glu Ala Leu Met Asp Ile Gly Phe Thr Gly Arg Glu Ile Ala
225                 230                 235                 240

Lys Leu Ala Ala Ala Leu Val Gly
                245

<210> SEQ ID NO 117
<211> LENGTH: 243
<212> TYPE: PRT
<213> ORGANISM: Prochlorococcus marinus

<400> SEQUENCE: 117

Met Pro Thr Leu Glu Met Pro Val Ala Val Leu Asp Ser Thr Val
1               5                   10                  15

Gly Ser Ser Glu Ala Leu Pro Asp Phe Thr Ser Asp Arg Tyr Lys Asp
            20                  25                  30

Ala Tyr Ser Arg Ile Asn Ala Ile Val Ile Glu Gly Gly Gln Glu Ala
        35                  40                  45

His Asp Asn Tyr Ile Ala Ile Gly Thr Leu Leu Pro Asp His Val Glu
50                  55                  60

Glu Leu Lys Arg Leu Ala Lys Met Glu Met Arg His Lys Lys Gly Phe
65                  70                  75                  80

Thr Ala Cys Gly Lys Asn Leu Gly Val Glu Ala Asp Met Asp Phe Ala
                85                  90                  95

Arg Glu Phe Phe Ala Pro Leu Arg Asp Asn Phe Gln Thr Ala Leu Gly
            100                 105                 110

Gln Gly Lys Thr Pro Thr Cys Leu Leu Ile Gln Ala Leu Leu Ile Glu
        115                 120                 125

Ala Phe Ala Ile Ser Ala Tyr His Thr Tyr Ile Pro Val Ser Asp Pro
130                 135                 140

Phe Ala Arg Lys Ile Thr Glu Gly Val Val Lys Asp Glu Tyr Thr His
145                 150                 155                 160

Leu Asn Tyr Gly Glu Ala Trp Leu Lys Ala Asn Leu Glu Ser Cys Arg
                165                 170                 175

Glu Glu Leu Leu Glu Ala Asn Arg Glu Asn Leu Pro Leu Ile Arg Arg
            180                 185                 190

Met Leu Asp Gln Val Ala Gly Asp Ala Ala Val Leu Gln Met Asp Lys
        195                 200                 205

Glu Asp Leu Ile Glu Asp Phe Leu Ile Ala Tyr Gln Glu Ser Leu Thr
    210                 215                 220

Glu Ile Gly Phe Asn Thr Arg Glu Ile Thr Arg Met Ala Ala Ala Ala
225                 230                 235                 240

Leu Val Ser

<210> SEQ ID NO 118
<211> LENGTH: 239
```

```
<212> TYPE: PRT
<213> ORGANISM: Synechococcus sp.

<400> SEQUENCE: 118

Met Pro Thr Leu Asn Ala Pro Glu Val Ser Val Leu Glu Gly Gln Asp
1               5                   10                  15

Ala Leu Pro Asp Phe Thr Thr Ala Glu Tyr Lys Asp Ala Tyr Ser Arg
            20                  25                  30

Ile Asn Ala Ile Val Ile Glu Gly Glu Gln Ala His Asp Asn Tyr
        35                  40                  45

Ile Ser Leu Gly Thr Leu Ile Pro Glu Gln Ala Asp Glu Leu Ser Arg
    50                  55                  60

Leu Ala Arg Met Glu Met Lys His Met Lys Gly Phe Thr Ala Cys Ala
65                  70                  75                  80

Arg Asn Leu Gly Val Glu Ala Asp Met Pro Phe Ala Lys Asp Phe Phe
                85                  90                  95

Gly Pro Leu His Gly Asn Phe Gln Val Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Met Phe
                165                 170                 175

Ala Ala Asn Lys Ala Asn Leu Pro Leu Ile Arg Ser Met Leu Glu Gly
            180                 185                 190

Val Ala Ala Asp Ala Ala Val Leu His Met Glu Lys Glu Asp Leu Ile
        195                 200                 205

Glu Asp Phe Leu Ile Ala Tyr Gln Glu Ala Leu Asn Glu Ile Gly Phe
210                 215                 220

Ser Ser Arg Asp Ile Ala Lys Met Ala Ala Ala Leu Ala Ile
225                 230                 235

<210> SEQ ID NO 119
<211> LENGTH: 251
<212> TYPE: PRT
<213> ORGANISM: Prochlorococcus marinus

<400> SEQUENCE: 119

Met His Asn Glu Leu Lys Ile Thr Asp Met Gln Thr Leu Glu Ser Asn
1               5                   10                  15

Lys Lys Thr Ile Glu Glu Ser Thr Asn Ser Ile Ser Leu Asp Leu Pro
            20                  25                  30

Asp Phe Thr Thr Asp Ser Tyr Lys Asp Ala Tyr Ser Arg Ile Asn Ala
        35                  40                  45

Ile Val Ile Glu Gly Glu Gln Glu Ala His Asp Asn Tyr Ile Ser Ile
    50                  55                  60

Ala Thr Leu Ile Pro Asn Glu Leu Glu Leu Thr Lys Leu Ala Arg
65                  70                  75                  80

Met Glu Met Lys His Lys Lys Gly Phe Thr Ala Cys Gly Arg Asn Leu
                85                  90                  95

Asp Val Val Ala Asp Met Glu Phe Ala Lys Lys Phe Phe Ser Lys Leu
            100                 105                 110

His Gly Asn Phe Gln Val Ala Leu Lys Lys Gly Asn Val Thr Thr Cys
```

```
                        115                 120                 125
Leu Leu Ile Gln Ala Ile Leu Ile Glu Ala Phe Ala Ile Ser Ala Tyr
130                 135                 140

Asn Val Tyr Ile Arg Val Ala Asp Pro Phe Ala Lys Lys Ile Thr Glu
145                 150                 155                 160

Gly Val Val Lys Asp Glu Tyr Leu His Leu Asn Tyr Gly Gln Gln Trp
                165                 170                 175

Leu Lys Glu Asn Leu Ser Thr Cys Lys Asp Glu Leu Met Glu Ala Asn
            180                 185                 190

Lys Val Asn Leu Pro Leu Ile Lys Lys Met Leu Asp Glu Val Ala Asp
        195                 200                 205

Asp Ala Ser Val Leu Ala Met Asp Arg Glu Glu Leu Met Glu Glu Phe
    210                 215                 220

Met Ile Ala Tyr Gln Asp Thr Leu Met Glu Ile Gly Leu Asp Asn Arg
225                 230                 235                 240

Glu Ile Ala Arg Met Ala Met Ala Ala Ile Val
                245                 250

<210> SEQ ID NO 120
<211> LENGTH: 229
<212> TYPE: PRT
<213> ORGANISM: Synechococcus sp.

<400> SEQUENCE: 120

Met Leu Glu Gly Gln Asp Ala Leu Pro Asp Phe Thr Thr Ala Glu Tyr
1               5                   10                  15

Lys Asp Ala Tyr Ser Arg Ile Asn Ala Ile Val Ile Glu Gly Glu Gln
                20                  25                  30

Glu Ala His Asp Asn Tyr Ile Ser Leu Gly Thr Leu Ile Pro Glu Gln
            35                  40                  45

Ala Glu Glu Leu Ser Arg Leu Ala Arg Met Glu Met Lys His Met Lys
        50                  55                  60

Gly Phe Thr Ala Cys Ala Arg Asn Leu Gly Val Glu Ala Asp Met Pro
65                  70                  75                  80

Phe Ala Lys Glu Phe Phe Gly Pro Leu His Gly Asn Phe Gln Val Ala
                85                  90                  95

Leu Lys Glu Gly Lys Val Val Thr Cys Leu Leu Ile Gln Ala Leu Leu
            100                 105                 110

Ile Glu Ala Phe Ala Ile Ser Ala Tyr His Ile Tyr Ile Pro Val Ala
        115                 120                 125

Asp Pro Phe Ala Arg Lys Ile Thr Glu Gly Val Val Lys Asp Glu Tyr
    130                 135                 140

Thr His Leu Asn Tyr Gly Gln Glu Trp Leu Lys Ala Asn Phe Glu Ala
145                 150                 155                 160

Ser Lys Asp Glu Met Phe Ala Ala Asn Lys Ala Asn Leu Pro Leu Ile
                165                 170                 175

Arg Ser Met Leu Glu Gly Val Ala Ala Asp Ala Val Leu His Met
            180                 185                 190

Glu Lys Glu Asp Leu Ile Glu Asp Phe Leu Ile Ala Tyr Gln Glu Ala
        195                 200                 205

Leu Asn Glu Ile Gly Phe Ser Ser Arg Asp Ile Ala Lys Met Ala Ala
    210                 215                 220

Ala Ala Leu Ala Ile
225
```

```
<210> SEQ ID NO 121
<211> LENGTH: 251
<212> TYPE: PRT
<213> ORGANISM: Prochlorococcus marinus

<400> SEQUENCE: 121

Met His Asn Glu Leu Lys Ile Thr Asp Met Gln Thr Leu Glu Ser Asn
1               5                   10                  15

Lys Lys Thr Ile Glu Glu Ser Ile Asn Pro Ile Ser Leu Asp Leu Pro
            20                  25                  30

Asp Phe Thr Thr Asp Ser Tyr Lys Asp Ala Tyr Ser Arg Ile Asn Ala
        35                  40                  45

Ile Val Ile Glu Gly Glu Gln Glu Ala His Asp Asn Tyr Ile Ser Ile
50                  55                  60

Ala Thr Leu Ile Pro Asn Glu Val Glu Leu Thr Lys Leu Ala Arg
65                  70                  75                  80

Met Glu Met Lys His Lys Lys Gly Phe Thr Ala Cys Gly Arg Asn Leu
                85                  90                  95

Gly Val Val Ala Asp Met Asp Phe Ala Lys Lys Phe Ser Lys Leu
            100                 105                 110

His Gly Asn Phe Gln Val Ala Leu Glu Lys Gly Asn Leu Thr Thr Cys
        115                 120                 125

Leu Leu Ile Gln Ala Ile Leu Ile Glu Ala Phe Ala Ile Ser Ala Tyr
    130                 135                 140

Asn Val Tyr Ile Arg Val Ala Asp Pro Phe Ala Lys Lys Ile Thr Glu
145                 150                 155                 160

Gly Val Val Lys Asp Glu Tyr Leu His Leu Asn Tyr Gly Gln Glu Trp
                165                 170                 175

Leu Lys Glu Asn Leu Ser Thr Cys Lys Glu Glu Leu Met Glu Ala Asn
            180                 185                 190

Lys Val Asn Leu Pro Leu Ile Lys Lys Met Leu Asp Glu Val Ala Asp
        195                 200                 205

Asp Ala Ser Val Leu Ala Met Asp Lys Glu Glu Leu Met Glu Glu Phe
    210                 215                 220

Met Ile Ala Tyr Gln Asp Thr Leu Met Glu Ile Gly Leu Asp Asn Arg
225                 230                 235                 240

Glu Ile Ala Arg Met Ala Met Ala Ala Ile Val
                245                 250

<210> SEQ ID NO 122
<211> LENGTH: 238
<212> TYPE: PRT
<213> ORGANISM: Prochlorococcus marinus

<400> SEQUENCE: 122

Met Gln Thr Leu Glu Ser Asn Lys Lys Thr Asn Leu Glu Asn Ser Ile
1               5                   10                  15

Asp Leu Pro Asp Phe Thr Thr Asp Ser Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Ala Thr Leu Ile Pro Asn Glu Leu Glu Glu Leu Thr Lys
    50                  55                  60

Leu Ala Lys Met Glu Leu Lys His Lys Arg Gly Phe Thr Ala Cys Gly
65                  70                  75                  80

Arg Asn Leu Gly Val Gln Ala Asp Met Ile Phe Ala Lys Glu Phe Phe
                85                  90                  95
```

Ser Lys Leu His Gly Asn Phe Gln Val Ala Leu Ser Asn Gly Lys Thr
            100                 105                 110

Thr Thr Cys Leu Leu Ile Gln Ala Ile Leu Ile Glu Ala Phe Ala Ile
            115                 120                 125

Ser Ala Tyr His Val Tyr Ile Arg Val Ala Asp Pro Phe Ala Lys Lys
    130                 135                 140

Ile Thr Gln Gly Val Val Lys Asp Glu Tyr Leu His Leu Asn Tyr Gly
145                 150                 155                 160

Gln Glu Trp Leu Lys Glu Asn Leu Ala Thr Cys Lys Asp Glu Leu Met
                165                 170                 175

Glu Ala Asn Lys Val Asn Leu Pro Leu Ile Lys Lys Met Leu Asp Gln
            180                 185                 190

Val Ser Glu Asp Ala Ser Val Leu Ala Met Asp Arg Glu Glu Leu Met
            195                 200                 205

Glu Glu Phe Met Ile Ala Tyr Gln Asp Thr Leu Leu Glu Ile Gly Leu
    210                 215                 220

Asp Asn Arg Glu Ile Ala Arg Met Ala Met Ala Ala Ile Val
225                 230                 235

<210> SEQ ID NO 123
<211> LENGTH: 242
<212> TYPE: PRT
<213> ORGANISM: Prochlorococcus marinus

<400> SEQUENCE: 123

Met Pro Thr Leu Glu Ser Ser Glu Val Ala Val Ile Ser Asp Leu Glu
1               5                   10                  15

Gly Arg Asp Gly Ser Leu Pro Asp Phe Thr Thr Glu Gln Tyr Lys Asp
            20                  25                  30

Ala Tyr Ser Arg Ile Asn Ala Ile Val Ile Glu Gly Glu Lys Glu Ala
        35                  40                  45

His Asp Asn Tyr Val Ala Ile Gly Thr Val Ile Pro Glu Lys Ala Asp
    50                  55                  60

Glu Leu Lys Lys Leu Ala Ile Met Glu Leu Arg His Met Lys Gly Phe
65                  70                  75                  80

Thr Ala Cys Gly Lys Asn Leu Gly Val Val Ala Asp Met Glu Phe Ala
            85                  90                  95

Gln Arg Phe Phe Ala Pro Leu His Gly Asn Phe Gln Lys Ala Leu Glu
            100                 105                 110

Asn Gly Lys Ile Thr Thr Cys Phe Leu Ile Gln Ala Ile Leu Ile Glu
            115                 120                 125

Ala Phe Ala Ile Ser Ala Tyr His Val Tyr Ile Arg Val Ala Asp Pro
    130                 135                 140

Phe Ala Lys Lys Ile Thr Glu Gly Val Val Lys Asp Glu Tyr Leu His
145                 150                 155                 160

Leu Asn Tyr Gly Gln Glu Trp Leu Lys Ala Asn Leu Ala Thr Cys Lys
                165                 170                 175

Asp Glu Leu Ile Ala Ala Asn Lys Glu Asn Leu Pro Leu Ile Asn Ser
            180                 185                 190

Met Leu Asp Gln Val Ala Asn Asp Ala Gln Val Leu Tyr Met Glu Lys
            195                 200                 205

Glu Glu Leu Met Glu Glu Phe Met Ile Ala Tyr Gln Asp Ser Leu Met
    210                 215                 220

Glu Ile Gly Leu Asp Ala Arg Glu Ile Ala Arg Met Ala Leu Ala Ala
225                 230                 235                 240

Ile Ala

<210> SEQ ID NO 124
<211> LENGTH: 241
<212> TYPE: PRT
<213> ORGANISM: Prochlorococcus marinus

<400> SEQUENCE: 124

| Met | Gln | Ala | Phe | Ala | Ser | Asn | Asn | Leu | Thr | Val | Glu | Lys | Glu | Leu |
| 1 | | | | 5 | | | | | 10 | | | | | 15 |

Ser Ser Asn Ser Leu Pro Asp Phe Thr Ser Glu Ser Tyr Lys Asp Ala
            20                  25                  30

Tyr Ser Arg Ile Asn Ala Val Val Ile Glu Gly Glu Gln Glu Ala Tyr
        35                  40                  45

Ser Asn Phe Leu Asp Leu Ala Lys Leu Ile Pro Glu His Ala Asp Glu
    50                  55                  60

Leu Val Arg Leu Gly Lys Met Glu Lys Lys His Met Asn Gly Phe Cys
65                  70                  75                  80

Ala Cys Gly Arg Asn Leu Ala Val Lys Pro Asp Met Pro Phe Ala Lys
                85                  90                  95

Thr Phe Phe Ser Lys Leu His Asn Asn Phe Leu Glu Ala Phe Lys Val
            100                 105                 110

Gly Asp Thr Thr Thr Cys Leu Leu Ile Gln Cys Ile Leu Ile Glu Ser
        115                 120                 125

Phe Ala Ile Ser Ala Tyr His Val Tyr Ile Arg Val Ala Asp Pro Phe
    130                 135                 140

Ala Lys Arg Ile Thr Glu Gly Val Val Gln Asp Glu Tyr Leu His Leu
145                 150                 155                 160

Asn Tyr Gly Gln Glu Trp Leu Lys Ala Asn Leu Glu Thr Val Lys Lys
                165                 170                 175

Asp Leu Met Arg Ala Asn Lys Glu Asn Leu Pro Leu Ile Lys Ser Met
            180                 185                 190

Leu Asp Glu Val Ser Asn Asp Ala Glu Val Leu His Met Asp Lys Glu
        195                 200                 205

Glu Leu Met Glu Glu Phe Met Ile Ala Tyr Gln Asp Ser Leu Leu Glu
    210                 215                 220

Ile Gly Leu Asp Asn Arg Glu Ile Ala Arg Met Ala Leu Ala Ala Val
225                 230                 235                 240

Ile

<210> SEQ ID NO 125
<211> LENGTH: 241
<212> TYPE: PRT
<213> ORGANISM: Prochlorococcus marinus

<400> SEQUENCE: 125

| Met | Gln | Ala | Phe | Ala | Ser | Asn | Asn | Leu | Thr | Val | Glu | Lys | Glu | Leu |
| 1 | | | | 5 | | | | | 10 | | | | | 15 |

Ser Ser Asp Ser Leu Pro Asp Phe Thr Ser Glu Ser Tyr Lys Asp Ala
            20                  25                  30

Tyr Ser Arg Ile Asn Ala Val Val Ile Glu Gly Glu Gln Glu Ala Tyr
        35                  40                  45

Ser Asn Phe Leu Asp Leu Ala Lys Leu Ile Pro Glu His Ala Asp Glu
    50                  55                  60

Leu Val Arg Leu Gly Lys Met Glu Lys Lys His Met Asn Gly Phe Cys
65                  70                  75                  80

```
Ala Cys Gly Arg Asn Leu Ala Val Lys Pro Asp Met Pro Phe Ala Lys
                85                  90                  95

Thr Phe Phe Ser Lys Leu His Asn Asn Phe Leu Glu Ala Phe Lys Val
            100                 105                 110

Gly Asp Thr Thr Thr Cys Leu Leu Ile Gln Cys Ile Leu Ile Glu Ser
            115                 120                 125

Phe Ala Ile Ser Ala Tyr His Val Tyr Ile Arg Val Ala Asp Pro Phe
        130                 135                 140

Ala Lys Arg Ile Thr Glu Gly Val Val Gln Asp Glu Tyr Leu His Leu
145                 150                 155                 160

Asn Tyr Gly Gln Glu Trp Leu Lys Ala Asn Leu Glu Thr Val Lys Lys
                165                 170                 175

Asp Leu Met Arg Ala Asn Lys Glu Asn Leu Pro Leu Ile Lys Ser Met
            180                 185                 190

Leu Asp Glu Val Ser Asn Asp Ala Glu Val Leu His Met Asp Lys Glu
            195                 200                 205

Glu Leu Met Glu Glu Phe Met Ile Ala Tyr Gln Asp Ser Leu Leu Glu
        210                 215                 220

Ile Gly Leu Asp Asn Arg Glu Ile Ala Arg Met Ala Leu Ala Ala Val
225                 230                 235                 240

Ile

<210> SEQ ID NO 126
<211> LENGTH: 237
<212> TYPE: PRT
<213> ORGANISM: Prochlorococcus marinus

<400> SEQUENCE: 126

Met Gln Thr Leu Thr Asn Gln Val Ala Ser Ala Asp Glu Leu Asp Asn
1               5                   10                  15

Leu Pro Asp Phe Ser Ser Ser Gln Tyr Lys Asp Ala Tyr Ser Arg Ile
                20                  25                  30

Asn Ala Ile Val Ile Glu Gly Glu Lys Glu Ala His Asp Asn Tyr Met
            35                  40                  45

Ser Ile Gly Thr Leu Ile Pro Asp Lys Ala Asp Glu Leu Lys Lys Leu
        50                  55                  60

Ala Val Met Glu Leu Lys His Met Arg Gly Phe Thr Ala Cys Gly Lys
65                  70                  75                  80

Asn Leu Gly Val Lys Ala Asp Ile Pro Phe Ala Glu Lys Phe Phe Ser
                85                  90                  95

Pro Leu His Gly Asn Phe Gln Lys Ala Phe Lys Glu Glu Asn Leu Thr
            100                 105                 110

Thr Cys Phe Leu Ile Gln Ala Ile Leu Ile Glu Ala Phe Ala Ile Ser
        115                 120                 125

Ala Tyr His Val Tyr Ile Arg Val Ala Asp Pro Phe Ala Lys Lys Ile
        130                 135                 140

Thr Glu Asn Val Val Lys Asp Glu Tyr Leu His Leu Asn Tyr Gly Gln
145                 150                 155                 160

Gln Trp Leu Lys Ala Asn Leu Asp Thr Cys Lys Glu Glu Leu Met Lys
                165                 170                 175

Ala Asn Lys Glu Asn Leu Pro Leu Ile Lys Ser Met Leu Asp Gln Val
            180                 185                 190

Ala Asp Asp Ala Cys Ser Leu Ser Met Asp Lys Glu Glu Leu Met Glu
        195                 200                 205
```

-continued

Glu Phe Met Ile Ala Tyr Gln Asp Ser Leu Leu Glu Ile Gly Leu Asp
                210                 215                 220

Ser Arg Glu Ile Ala Arg Met Ala Leu Ala Ala Leu Val
225                 230                 235

<210> SEQ ID NO 127
<211> LENGTH: 243
<212> TYPE: PRT
<213> ORGANISM: Prochlorococcus marinus

<400> SEQUENCE: 127

Met Gln Thr Leu Glu Ser Asn Lys Asn Ile Gln Ile Gly Ser Ser Pro
1               5                   10                  15

Glu Ser Asp Ser Ala Asn Leu Pro Asp Phe Thr Thr Asp Ala Tyr Lys
                20                  25                  30

Asp Ala Tyr Ser Arg Ile Asn Ala Ile Val Ile Glu Gly Glu Gln Glu
            35                  40                  45

Ala Tyr Asp Asn Tyr Ile Ser Ile Ala Thr Leu Leu Pro Asn Asp Ser
        50                  55                  60

Glu Glu Leu Thr Lys Leu Ala Lys Met Glu Leu Lys His Lys Arg Gly
65                  70                  75                  80

Phe Thr Ala Cys Gly Lys Asn Leu Gly Val Glu Ala Asp Met Ser Phe
                85                  90                  95

Ala Lys Glu Phe Phe Ser Lys Leu His Gly Asn Phe Gln Ala Ala Leu
                100                 105                 110

Lys Asn Glu Ser Leu Thr Thr Cys Leu Leu Ile Gln Ala Ile Leu Ile
            115                 120                 125

Glu Ala Phe Ala Ile Ser Ala Tyr His Val Tyr Ile Arg Val Ala Asp
        130                 135                 140

Pro Phe Ala Lys Lys Ile Thr Gln Gly Val Val Asn Asp Glu Tyr Leu
145                 150                 155                 160

His Leu Asn Tyr Gly Glu Lys Trp Leu Lys Glu Asn Leu Ser Thr Cys
                165                 170                 175

Lys Asp Glu Leu Ile Ala Ala Asn Lys Val Asn Leu Pro Ile Ile Lys
                180                 185                 190

Lys Met Leu Asp Gln Val Ala Asp Ala Ala Thr Leu Ala Met Asp
            195                 200                 205

Lys Glu Glu Leu Met Glu Glu Phe Met Ile Ala Tyr Gln Asp Ala Leu
        210                 215                 220

Leu Glu Met Gly Leu Asp Asn Arg Glu Ile Ala Arg Met Ala Met Ala
225                 230                 235                 240

Ala Ile Val

<210> SEQ ID NO 128
<211> LENGTH: 250
<212> TYPE: PRT
<213> ORGANISM: Prochlorococcus marinus

<400> SEQUENCE: 128

Met Asn Lys Ser Leu Thr Asp Met Gln Thr Leu Glu Ser Lys Lys Asp
1               5                   10                  15

Ile Gln Leu Glu Gly Ser Thr Asp Asn Asp Ser Ala Asn Leu Pro Asp
                20                  25                  30

Phe Thr Thr Asp Ala Tyr Lys Asp Ala Tyr Ser Arg Ile Asn Ala Ile
            35                  40                  45

Val Ile Glu Gly Glu Gln Glu Ala Tyr Asp Asn Tyr Ile Ser Ile Ala
        50                  55                  60

```
                        -continued

Thr Leu Leu Pro Asn Asp Ser Glu Glu Leu Thr Lys Leu Ala Lys Met
65                  70                  75                  80

Glu Leu Lys His Lys Arg Gly Phe Thr Ala Cys Gly Lys Asn Leu Gly
                85                  90                  95

Val Glu Ala Asp Met Pro Phe Ala Lys Glu Phe Phe Ser Lys Leu His
            100                 105                 110

Gly Asn Phe Gln Ile Ala Leu Lys Asp Gly Asn Leu Thr Thr Cys Leu
        115                 120                 125

Leu Ile Gln Ala Ile Leu Ile Glu Ala Phe Ala Ile Ser Ala Tyr His
    130                 135                 140

Val Tyr Ile Arg Val Ala Asp Pro Phe Ala Lys Lys Ile Thr Gln Gly
145                 150                 155                 160

Val Val Asn Asp Glu Tyr Leu His Leu Asn Tyr Gly Glu Lys Trp Leu
                165                 170                 175

Lys Glu Asn Leu His Thr Cys Lys Asp Glu Leu Ile Ala Ala Asn Lys
            180                 185                 190

Val Asn Leu Pro Leu Ile Lys Lys Met Leu Asp Gln Val Ala Glu Asp
        195                 200                 205

Ala Ala Thr Leu Ser Met Asp Lys Glu Glu Leu Met Glu Glu Phe Met
    210                 215                 220

Ile Ala Tyr Gln Asp Ala Leu Leu Glu Met Gly Leu Asp Asn Arg Glu
225                 230                 235                 240

Ile Ala Arg Met Ala Met Ala Ala Ile Val
                245                 250
```

METHODS AND COMPOSITIONS FOR THE RECOMBINANT BIOSYNTHESIS OF N-ALKANES

CROSS-REFERENCE TO RELATED APPLICATIONS

This application is a continuation application of U.S. patent application Ser. No. 12/759,657 filed on Apr. 13, 2010, which claims the benefit of U.S. Provisional Patent Application No. 61/224,463, filed Jul. 9, 2009 and U.S. Provisional Patent Application No. 61/228,937, filed Jul. 27, 2009, the disclosures of which are incorporated herein by reference.

REFERENCE TO SEQUENCE LISTING

The instant application contains a Sequence Listing which has been submitted via EFS-Web and is hereby incorporated by reference in its entirety. Said ASCII copy, created on Sep. 10, 2010, is named 17191US_SeqList.txt, lists 128 sequences, and is 337 kb in size.

FIELD OF THE INVENTION

The present disclosure relates to methods for conferring alkane-producing properties to a heterotrophic or photoautotrophic host, such that the modified host can be used in the commercial production of bioalkanes.

BACKGROUND OF THE INVENTION

Many existing photoautotrophic organisms (i.e., plants, algae, and photosynthetic bacteria) are poorly suited for industrial bioprocessing and have therefore not demonstrated commercial viability. Such organisms typically have slow doubling times (3-72 hrs) compared to industrialized heterotrophic organisms such as *Escherichia coli* (20 minutes), reflective of low total productivities. While a desire for the efficient biosynthetic production of fuels has led to the development of photosynthetic microorganisms which produce alkyl esters of fatty acids, a need still exists for methods of producing hydrocarbons, e.g., alkanes, using photosynthetic organisms.

SUMMARY OF THE INVENTION

The present invention provides, in certain embodiments, isolated polynucleotides comprising or consisting of nucleic acid sequences selected from the group consisting of the coding sequences for AAR and ADM enzymes, nucleic acid sequences that are codon-optimized variants of these sequences, and related nucleic acid sequences and fragments.

An AAR enzyme refers to an enzyme with the amino acid sequence of the SYNPCC7942_1594 protein (SEQ ID NO: 6) or a homolog thereof, wherein a SYNPCC7942_1594 homolog is a protein whose BLAST alignment (i) covers >90% length of SYNPCC7942_1594, (ii) covers >90% of the length of the matching protein, and (iii) has >50% identity with SYNPCC7942_1594 (when optimally aligned using the parameters provided herein), and retains the functional activity of SYNPCC7942_1594, i.e., the conversion of an acyl-ACP to an alkanal. An ADM enzyme refers to an enzyme with the amino acid sequence of the SYNPCC7942_1593 protein (SEQ ID NO: 8) or a homolog thereof, wherein a SYNPCC7942_1593 homolog is defined as a protein whose amino acid sequence alignment (i) covers >90% length of SYNPCC7942_1593, (ii) covers >90% of the length of the matching protein, and (iii) has >50% identity with SYNPCC7942_1593 (when aligned using the preferred parameters provided herein), and retains the functional activity of SYNPCC7942_1593, i.e., the conversion of an n-alkanal to an (n−1)-alkane. Exemplary AAR and ADM enzymes are listed in Table 1 and Table 2, respectively. Genes encoding AAR or ADM enzymes are referred to herein as AAR genes or ADM genes, respectively.

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

While Applicants refer herein to a putative alkanal decarboxylative monooxygenase activity, Applicants do so without intending to be bound to any particular reaction mechanism unless expressly set forth. For example, whether the enzyme encoded by SYNPCC7942_1594 or any other ADM gene carries out a decarbonylase or a decarboxylase reaction does not affect the utility of Applicants' invention, unless expressly set forth herein to the contrary.

The present invention further provides isolated polypeptides comprising or consisting of polypeptide sequences selected from the group consisting of the sequences listed in Table 1 and Table 2, and related polypeptide sequences, fragments and fusions. Antibodies that specifically bind to the isolated polypeptides of the present invention are also contemplated.

The present invention also provides methods for expressing a heterologous nucleic acid sequence encoding AAR and ADM in a host cell lacking catalytic activity for AAR and ADM (thereby conferring n-alkane producing capability in the host cell), or for expressing a nucleic acid encoding AAR and ADM in a host cell which comprises native AAR and/or ADM activity (thereby enhancing n-alkane producing capability in the host cell).

In addition, the present invention provides methods for producing carbon-based products of interest using the AAR and ADM genes, proteins and host cells described herein. For example, in one embodiment the invention provides a method for producing hydrocarbons, comprising: (i) culturing an engineered cyanobacterium in a culture medium, wherein said engineered cyanobacterium comprises a recombinant AAR enzyme and a recombinant ADM enzyme; and (ii) exposing said engineered cyanobacterium to light and carbon dioxide, wherein said exposure results in the conversion of said carbon dioxide by said engineered cynanobacterium into n-alkanes, wherein at least one of said n-alkanes is selected from the group consisting of n-tridecane, n-tetradecane, n-pentadecane, n-hexadecane, and n-heptadecane, and wherein the amount of said n-alkanes produced is between 0.1% and 5% dry cell weight and at least two times the amount produced by an otherwise identical cyanobacterium, cultured under identical conditions, but lacking said recombinant AAR and ADM enzymes.

In a related embodiment, the amount on n-alkanes produced by the engineered cyanobacterium is at least 0.1%, 0.2%, 0.3%, 0.4%, 0.5%, 0.6%, 0.7%, 0.8%, 0.9%, or 1%, and at least two times the amount produced by an otherwise identical cyanobacterium, cultured under identical conditions, but lacking said recombinant AAR and ADM enzymes.

In a related embodiment, at least one of said recombinant enzymes is heterologous with respect to said engineered cyanobacterium. In another embodiment, said cyanobacterium does not synthesize alkanes in the absence of the expression of one or both of the recombinant enzymes. In another embodiment, at least one of said recombinant AAR or ADM enzymes is not heterologous to said engineered cyanobacterium.

In another related embodiment of the method, said engineered cyanobacterium further produces at least one n-alkene or n-alkanol. In yet another embodiment, the engineered cyanobacterium produces at least one n-alkene or n-alkanol selected from the group consisting of n-pentadecene, n-heptadecene, and 1-octadecanol. In a related embodiment, said n-alkanes comprise predominantly n-heptadecane, n-pentadecane or a combination thereof. In a related embodiment, more n-heptadecane and/or n-pentadecane are produced than all other n-alkane products combined. In yet another related embodiment, more n-heptadecane and/or n-pentadecane are produced by the engineered cyanobacterium than any other n-alkane or n-alkene produced by the engineered cyanobacterium. In yet another related embodiment, at least one n-pentadecene produced by said engineered cyanobacterium is selected from the group consisting of cis-3-heptadecene and cis-4-pentadecene. In yet another related embodiment, at least one n-heptadecene produced by said engineered cyanobacterium is selected from the group consisting of cis-4-pentadecene, cis-6-heptadecene, cis-8-heptadecene, cis-9-heptadecene, and cis, cis-heptadec-di-ene.

In yet another related embodiment, the invention further provides a step of isolating at least one n-alkane, n-alkene or n-alkanol from said engineered cyanobacterium or said culture medium. In yet another related embodiment, the engineered cyanobacterium is cultured in a liquid medium. In yet another related embodiment, the engineered cyanobacterium is cultured in a photobioreactor.

In another related embodiment, the AAR and/or ADM enzymes are encoded by a plasmid. In yet another related embodiment, the AAR and/or ADM enzymes are encoded by recombinant genes incorporated into the genome of the engineered cyanobacterium. In yet another related embodiment, the AAR and/or ADM enzymes are encoded by genes which are present in multiple copies in said engineered cyanobacterium. In yet another related embodiment, the recombinant AAR and/or ADM enzymes are encoded by genes which are part of an operon, wherein the expression of said genes is controlled by a single promoter. In yet another related embodiment, the recombinant AAR and/or ADM enzymes are encoded by genes which are expressed independently under the control of separate promoters. In yet another related embodiment, expression of the recombinant AAR and/or ADM enzymes in an engineered cyanobacterium is controlled by a promoter selected from the group consisting of a cI promoter, a cpcB promoter, a lacI-trc promoter, an EM7 promoter, and a aphII promoter.

In yet another related embodiment, the cyanobacterium species that is engineered to express recombinant AAR and/or ADM enzymes produces less than 0.1% DCW n-heptadecane or n-pentadecane in the absence of said recombinant AAR and/or ADM enzymes. In another related embodiment, the engineered cyanobacterium of the method is a thermophile. In yet another related embodiment, the engineered cyanobacterium of the method is selected from the group consisting of an engineered *Synechococcus* sp. PCC7002 and an engineered *Thermosynechococcus elongatus* BP-1.

In yet another related embodiment, the recombinant AAR and/or ADM enzymes are selected from the group of enzymes listed in Table 1 and Table 2, respectively. In yet another related embodiment, the recombinant AAR enzymes are selected from the group consisting of SYNPCC7942_1594, tll1312, and PMT9312_0533. In yet another related embodiment, the recombinant ADM enzymes are selected from the group consisting of SYNPCC7942_1593, tll1313, and PMT9312_0532. In yet another related embodiment, the recombinant AAR enzymes have the amino acid sequences of SEQ ID NO:10 and SEQ ID NO:12, respectively. In certain embodiments, the recombinant AAR and ADM enzymes are encoded by SEQ ID NOs: 9 and 11, respectively.

In yet another related embodiment, the method comprising culturing the engineered cyanobacterium in the presence of an antibiotic, wherein said antibiotic selects for the presence of a recombinant gene encoding an AAR and/or ADM enzyme. In certain embodiments, the antibiotic is spectinomycin or kanamycin. In related embodiments, the amount of spectinomycin in the culture media is between 100 and 700 µg/ml, e.g., 100, 200, 300, 400, 500, 600, or 700 µg/ml of spectinomycin can be added to the culture media. In certain embodiments, the amount of spectinomycin added is about 600 µg/ml, and the amount of n-alkanes produced by the engineered cyanobacterium is at least about 3%, 4% or 5% DCW.

In another embodiment, the method for producing hydrocarbons comprises culturing an cyanobacterium expressing recombinant AAR and/or ADM enzymes in the presence of an exogenous substrate for one or both enzymes. In a related embodiment, the substrate is selected from the group consisting of an acyl-ACP, an acyl-CoA, a fatty aldehyde, a fatty alcohol, and a fatty ester.

In yet another embodiment, the invention provides a composition comprising an n-alkane produced by any of the recombinant biosynthetic methods described herein. In yet another embodiment, the invention provides a composition comprising an n-alkene or n-alkanol produced by any of the recombinant biosynthetic methods described herein.

In certain embodiments, the invention provides an engineered host cell for producing an n-alkane, wherein said cell comprises one or more recombinant protein activities selected from the group consisting of an acyl-CoA reductase activity, an acyl-ACP reductase activity, an alkanal decarboxylative monooxygenase activity, and an electron donor activity. In related embodiments, the host cell comprises a recombinant acyl-ACP reductase activity, a recombinant alkanal decarboxylative monooxygenase activity, and a recombinant electron donor activity. In other embodiments, the host cell comprises a recombinant acyl-ACP reductase activity and a recombinant alkanal decarboxylative monooxygenase activity. In certain embodiments, the electron donor activity is a ferredoxin. In certain related embodiments, the host cell is capable of photosynthesis. In still other related embodiments, the host cell is a cyanobacterium. In still other embodiments, the host cell is a gram-negative, a gram-positive bacteria, or a yeast cell.

In other embodiments, the invention provides an isolated or recombinant polynucleotide comprising or consisting of a nucleic acid sequence selected from the group consisting of: (a) SEQ ID NOs:1, 3, 5, 7, 9, 11, 13 or 14; (b) a nucleic acid sequence that is a degenerate variant of SEQ ID NOs: 1, 3, 5, 7, 9, 11, 13 or 14; (c) a nucleic acid sequence at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO: 1, 3, 5, 7, 9, 11, 13 or 14; (d) a nucleic acid sequence that encodes a polypeptide having the amino acid sequence of SEQ ID NO:2, 4, 6, 8, 10 or 12; (e) a nucleic acid sequence that encodes a polypeptide at least 50%, at least 60%, at least 70%, at least 80%, at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO:2, 4, 6, 8, 10, or 12; and (f) a nucleic acid sequence that hybridizes under stringent conditions to SEQ ID NOs: 1, 3, 5, 7, 9, 11, 13 or 14. In related embodiments, the nucleic acid sequence encodes a polypeptide having acyl-ACP reductase activity or alkanal decarboxylative monooxygenase activity.

In yet another embodiment, the invention provides an isolated, soluble polypeptide with alkanal decarboxylative monooxygenase activity wherein, in certain related embodiments, the polypeptide has an amino acid sequence of one of the proteins listed in Table 2. In related embodiments, the polypeptide has the amino acid sequence of SEQ ID NO: 4, 8 or 12.

In yet another embodiment, the invention provides a method for synthesizing an n-alkane from an acyl-ACP in vitro, comprising: contacting an acyl-ACP with a recombinant acyl-ACP reductase, wherein said acyl-ACP reductase converts said acyl-ACP to an n-alkanal; then contacting said n-alkanal with a recombinant, soluble alkanal decarboxylative monooxygenase in the presence of an electron donor, wherein said alkanal decarboxylative monooxygenase converts said acyl-ACP to an n-alkane. In a related embodiment, the invention provides a method for synthesizing an n-alkane from an n-alkanal in vitro, comprising: contacting said n-alkanal with a recombinant, soluble alkanal decarboxylative monooxygenase in the presence of an electron donor, wherein said alkanal decarboxylative monooxygenase converts said acyl-ACP to an n-alkane. In certain related embodiments, the electron donor is a ferredoxin protein.

In another embodiment, the invention provides engineered cyanobacterial cells comprising recombinant AAR and ADM enzymes, wherein said cells comprise between 0.1% and 5%, between 1% and 5%, or between 2% and 5% dry cell weight n-alkanes, wherein said n-alkanes are predominantly n-pentadecane, n-heptadecane, or a combination thereof.

DETAILED DESCRIPTION OF THE INVENTION

Figure 1A:
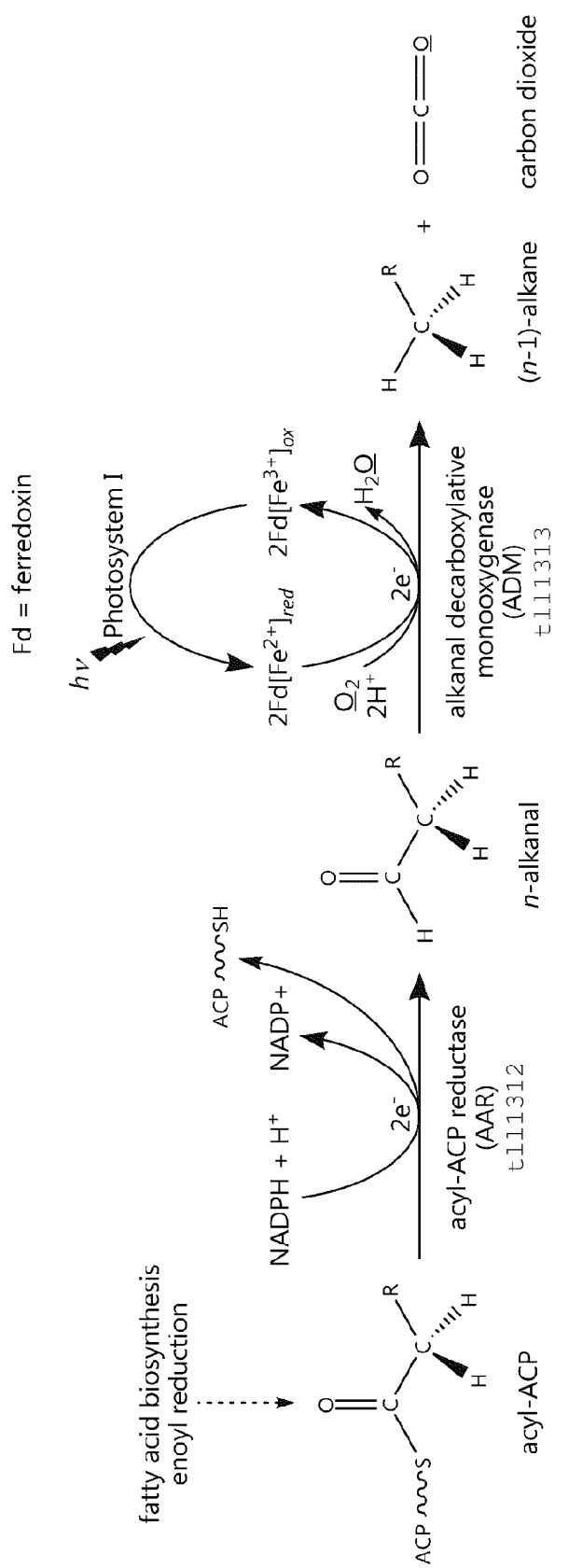
FIG. 1 depicts, in panel A, an enzymatic pathway for the production of n-alkanes based on the sequential activity of (1) an AAR enzyme (e.g., tll1312); and (2) an ADM enzyme (e.g., tll1313); B, Biosynthesis of n-alkanal via acyl-CoA. Acyl-CoAs are typically intermediates of fatty acid degradation; C, Biosynthesis of n-alkanal via acyl-ACP. Acyl-ACP's are typically intermediates of fatty acid biosynthesis. Note the three different types of ACP reductase: (i) β-ketoacyl-ACP reductase, (ii) enoyl-ACP reductase, and (iii) acyl-ACP reductase. Acyl-ACP reductase, a new enzyme, generates the substrate for alkanal decarboxylative monooxygenase. CoA, coenzyme A; ACP, acyl carrier protein; D, an alternative acyl-CoA-mediated alkane biosynthetic pathway. See additional discussion in Example 1, herein.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); Handbook of Biochemistry: Section A Proteins, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" organic molecule (e.g., an alkane, alkene, or alkanal) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); and "oligonucleotide-directed mutagenesis" (a process which enables the generation of site-specific mutations in any cloned DNA segment of interest; see, e.g., Reidhaar-Olson and Sauer, Science 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

Deletion: The removal of one or more nucleotides from a nucleic acid molecule or one or more amino acids from a protein, the regions on either side being joined together.

Knock-out: A gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab').sub.2, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications*, (Marasco, ed., Springer-Verlag New York, Inc., 1998), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic." See, e.g., Jones, Amino Acid and Peptide Synthesis, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, J. *Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the present invention may be used to produce an equivalent effect and are therefore envisioned to be part of the present invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. Even more preferred are muteins having at least 90% overall sequence homology to the wild-type protein.

In an even more preferred embodiment, a mutein exhibits at least 95% sequence identity, even more preferably 98%, even more preferably 99% and even more preferably 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

"Percent dry cell weight" refers to a measurement of hydrocarbon production obtained as follows: a defined volume of culture is centrifuged to pellet the cells. Cells are washed then dewetted by at least one cycle of microcentrifugation and aspiration. Cell pellets are lyophilized overnight, and the tube containing the dry cell mass is weighed again such that the mass of the cell pellet can be calculated within ±0.1 mg. At the same time cells are processed for dry cell weight determination, a second sample of the culture in question is harvested, washed, and dewetted. The resulting cell pellet, corresponding to 1-3 mg of dry cell weight, is then extracted by vortexing in approximately 1 ml acetone plus butylated hydroxytolune (BHT) as antioxidant and an internal standard, e.g., n-heptacosane. Cell debris is then pelleted by centrifugation and the supernatant (extractant) is taken for analysis by GC. For accurate quantitation of n-alkanes, flame ionization detection (FID) was used as opposed to MS total ion count. n-Alkane concentrations in the biological extracts were calculated using calibration relationships between GC-FID peak area and known concentrations of authentic n-alkane standards. Knowing the volume of the extractant, the resulting concentrations of the n-alkane species in the extractant, and the dry cell weight of the cell pellet extracted, the percentage of dry cell weight that comprised n-alkanes can be determined.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

"Carbon-based Products of Interest" include alcohols such as ethanol, propanol, isopropanol, butanol, fatty alcohols, fatty acid esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, $\epsilon$-caprolactone, isoprene, caprolactam, rubber; commodity chemicals such as lactate, Docosahexaenoic acid (DHA), 3-hydroxypropionate, $\gamma$-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

Biofuel: A biofuel refers to any fuel that derives from a biological source. Biofuel can refer to one or more hydrocarbons, one or more alcohols, one or more fatty esters or a mixture thereof.

Hydrocarbon: The term generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

Alkanes, also known as paraffins, are chemical compounds that consist only of the elements carbon (C) and hydrogen (H) (i.e., hydrocarbons), wherein these atoms are linked together exclusively by single bonds (i.e., they are saturated compounds) without any cyclic structure. n-Alkanes are linear, i.e., unbranched, alkanes. Together, AAR and ADM enzymes function to synthesize n-alkanes from acyl-ACP molecules.

Accordingly, the present invention provides isolated nucleic acid molecules for genes encoding AAR and ADM enzymes, and variants thereof. Exemplary full-length nucleic acid sequences for genes encoding AAR are presented as SEQ ID NOs: 1, 5, and 13, and the corresponding amino acid sequences are presented as SEQ ID NOs: 2, 6, and 10, respectively. Exemplary full-length nucleic acid sequences for genes encoding ADM are presented as SEQ ID NOs: 3, 7, 14, and the corresponding amino acid sequences are presented as SEQ ID NOs: 4, 8, and 12, respectively. Additional nucleic acids provided by the invention include any of the genes encoding the AAR and ADM enzymes in Table 1 and Table 2, respectively.

In one embodiment, the present invention provides an isolated nucleic acid molecule having a nucleic acid sequence comprising or consisting of a gene coding for AAR and ADM, and homologs, variants and derivatives thereof expressed in a host cell of interest. The present invention also provides a nucleic acid molecule comprising or consisting of a sequence which is a codon-optimized version of the AAR and ADM genes described herein (e.g., SEQ ID NO: 9 and SEQ ID NO: 11, which are optimized for the expression of the AAR and ADM genes of *Prochlorococcus marinus* MIT 9312 in *Synechoccocus* sp. PCC 7002). In a further embodiment, the present invention provides a nucleic acid molecule and homologs, variants and derivatives of the molecule comprising or consisting of a sequence which is a variant of the AAR or ADM gene having at least 76% identity to the wild-type gene. The nucleic acid sequence can be preferably 80%, 85%, 90%, 95%, 98%, 99%, 99.9% or even higher identity to the wild-type gene.

In another embodiment, the nucleic acid molecule of the present invention encodes a polypeptide having the amino acid sequence of SEQ ID NO:2, 4, 6, 8, 10 or 12. Preferably, the nucleic acid molecule of the present invention encodes a polypeptide sequence of at least 50%, 60, 70%, 80%, 85%, 90% or 95% identity to SEQ ID NO:2, 4, 6, 8, 10 or 12 and the identity can even more preferably be 96%, 97%, 98%, 99%, 99.9% or even higher.

The present invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip: Tools and Technology*, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip: Tools and Technology*, Schena (ed.), Eaton Publishing Company/BioTechniques Books Division (2000) (ISBN: 1881299376), the disclosure of each of which is incorporated herein by reference in its entirety.

As is well known in the art, enzyme activities can be measured in various ways. For example, the pyrophosphorolysis of OMP may be followed spectroscopically (Grubmeyer et al., (1993) *J. Biol. Chem.* 268:20299-20304). Alternatively, the activity of the enzyme can be followed using chromatographic techniques, such as by high performance liquid chromatography (Chung and Sloan, (1986) *J. Chromatogr.* 371:71-81). As another alternative the activity can be indirectly measured by determining the levels of product made from the enzyme activity. These levels can be measured with techniques including aqueous chloroform/methanol extraction as known and described in the art (Cf. M. Kates (1986) *Techniques of Lipidology; Isolation, analysis and identification of Lipids.* Elsevier Science Publishers, New York (ISBN: 0444807322)). More modern techniques include using gas chromatography linked to mass spectrometry (Niessen, W. M. A. (2001). *Current practice of gas chromatography-mass spectrometry.* New York, N.Y.: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G (1997) *Am. Chem. Soc. Symp. Series,* 666: 172-208), titration for determining free fatty acids (Komers (1997) *Fett/Lipid,* 99(2): 52-54), enzymatic methods (Bailer (1991) *Fresenius J. Anal. Chem.* 340(3): 186), physical property-based methods, wet chemical methods, etc. can be used to analyze the levels and the identity of the product produced by the organisms of the present invention. Other methods and techniques may also be suitable for the measurement of enzyme activity, as would be known by one of skill in the art.

Vectors

Also provided are vectors, including expression vectors, which comprise the above nucleic acid molecules of the present invention, as described further herein. In a first embodiment, the vectors include the isolated nucleic acid molecules described above. In an alternative embodiment, the vectors of the present invention include the above-described nucleic acid molecules operably linked to one or more expression control sequences. The vectors of the instant invention may thus be used to express an AAR and/or ADM polypeptide contributing to n-alkane producing activity by a host cell.

Vectors useful for expression of nucleic acids in prokaryotes are well known in the art.

Isolated Polypeptides

According to another aspect of the present invention, isolated polypeptides (including muteins, allelic variants, fragments, derivatives, and analogs) encoded by the nucleic acid molecules of the present invention are provided. In one embodiment, the isolated polypeptide comprises the polypeptide sequence corresponding to SEQ ID NO:2, 4, 6, 8 10 or 12. In an alternative embodiment of the present invention, the isolated polypeptide comprises a polypeptide sequence at least 85% identical to SEQ ID NO:2, 4, 6, 8, 10 or 12. Preferably the isolated polypeptide of the present invention has at least 50%, 60, 70%, 80%, 85%, 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to SEQ ID NO:2, 4, 6, 8, 10 or 12.

According to other embodiments of the present invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cell Transformants

In another aspect of the present invention, host cells transformed with the nucleic acid molecules or vectors of the present invention, and descendants thereof, are provided. In some embodiments of the present invention, these cells carry the nucleic acid sequences of the present invention on vectors, which may but need not be freely replicating vectors. In other embodiments of the present invention, the nucleic acids have been integrated into the genome of the host cells.

In a preferred embodiment, the host cell comprises one or more AAR or ADM encoding nucleic acids which express AAR or ADM in the host cell.

In an alternative embodiment, the host cells of the present invention can be mutated by recombination with a disruption, deletion or mutation of the isolated nucleic acid of the present invention so that the activity of the AAR and/or ADM protein(s) in the host cell is reduced or eliminated compared to a host cell lacking the mutation.

Selected or Engineered Microorganisms for the Production of Carbon-Based Products of Interest Microorganism: Includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

A variety of host organisms can be transformed to produce a product of interest. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure-tolerant organisms include piezophiles, which tolerate pressure of 130 MPa. Weight-tolerant organisms include barophiles. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt-tolerant organisms include halophiles (e.g., 2-5 M NaCl) *Halobacteriacea* and *Dunaliella salina*. pH-tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas-tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spennatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis, and Zygonium. A partial list of cyanobacteria that can be engineered to express recombinant AAR and ADM enzymes is also provided in Table 1 and Table 2, herein. Additional cyanobacteria include members of the genus Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Synechocystis, Cyanocystis, Dermocarpella, Stanieria, Xenococcus, Chroococcidiopsis, Myxosarcina, Arthrospira, Borzia, Crinalium, Geitlerinemia, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Cyanospira, Cylindrospermopsis, Cylindrospermum, Nodularia, Nostoc, Scylonema, Calothrix, Rivularia, Tolypothrix, Chlorogloeopsis, Fischerella, Geitieria, Iyengariella, Nostochopsis, Stigonema and Thermosynechococcus.

Green non-sulfur bacteria include but are not limited to the following genera: Chloroflexus, Chloronema, Oscillochloris, Heliothrix, Herpetosiphon, Roseiflexus, and Thermomicrobium.

Green sulfur bacteria include but are not limited to the following genera:

Chlorobium, Clathrochloris, and Prosthecochloris.

Purple sulfur bacteria include but are not limited to the following genera: Allochromatium, Chromatium, Halochromatium, Isochromatium, Marichromatium, Rhodovulum, Thermochromatium, Thiocapsa, Thiorhodococcus, and Thiocystis, Purple non-sulfur bacteria include but are not limited to the following genera: Phaeospirillum, Rhodobaca, Rhodobacter, Rhodomicrobium, Rhodopila, Rhodopseudomonas, Rhodothalassium, Rhodospirillum, Rodovibrio, and Roseospira.

Aerobic chemolithotrophic bacteria include but are not limited to nitrifying bacteria such as Nitrobacteraceae sp., Nitrobacter sp., Nitrospina sp., Nitrococcus sp., Nitrospira sp., Nitrosomonas sp., Nitrosococcus sp., Nitrosospira sp., Nitrosolobus sp., Nitrosovibrio sp.; colorless sulfur bacteria such as, Thiovulum sp., Thiobacillus sp., Thiomicrospira sp., Thiosphaera sp., Thermothrix sp.; obligately chemolithotrophic hydrogen bacteria such as Hydrogenobacter sp., iron and manganese-oxidizing and/or depositing bacteria such as Siderococcus sp., and magnetotactic bacteria such as Aquaspirillum sp.

Archaeobacteria include but are not limited to methanogenic archaeobacteria such as Methanobacterium sp., Methanobrevibacter sp., Methanothermus sp., Methanococcus sp., Methanomicrobium sp., Methanospirillum sp., Methanogenium sp., Methanosarcina sp., Methanolobus sp., Methanothrix sp., Methanococcoides sp., Methanoplanus sp.; extremely thermophilic S-Metabolizers such as Thermoproteus sp., Pyrodictium sp., Sulfolobus sp., Acidianus sp. and other microorganisms such as, Bacillus subtilis, Saccharomyces cerevisiae, Streptomyces sp., Ralstonia sp., Rhodococcus sp., Corynebacteria sp., Brevibacteria sp., Mycobacteria sp., and oleaginous yeast.

Preferred organisms for the manufacture of n-alkanes according to the methods disclosed herein include: Arabidopsis thaliana, Panicum virgatum, Miscanthus giganteus, and Zea mays (plants); Botryococcus braunii, Chlamydomonas reinhardtii and Dunaliela salina (algae); Synechococcus sp PCC 7002, Synechococcus sp. PCC 7942, Synechocystis sp. PCC 6803, Thermosynechococcus elongatus BP-1 (cyanobacteria); Chlorobium tepidum (green sulfur bacteria), Chloroflexus auranticus (green non-sulfur bacteria); Chromatium tepidum and Chromatium vinosum (purple sulfur bacteria); Rhodospirillum rubrum, Rhodobacter capsulatus, and Rhodopseudomonas palusris (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix carbon dioxide bacteria such as Escherichia coli, Acetobacter aceti, Bacillus subtilis, yeast and fungi such as Clostridium ljungdahlii, Clostridium thermocellum, Penicillium chrysogenum, Pichia pastoris, Saccharomyces cerevisiae, Schizosaccharomyces pombe, Pseudomonas fluorescens, or Zymomonas mobilis.

A suitable organism for selecting or engineering is autotrophic fixation of $CO_2$ to products. This would cover photosynthesis and methanogenesis. Acetogenesis, encompassing the three types of $CO_2$ fixation; Calvin cycle, acetyl-CoA pathway and reductive TCA pathway is also covered. The capability to use carbon dioxide as the sole source of cell carbon (autotrophy) is found in almost all major groups of prokaryotes. The $CO_2$ fixation pathways differ between groups, and there is no clear distribution pattern of the four presently-known autotrophic pathways. See, e.g., Fuchs, G. 1989. Alternative pathways of autotrophic $CO_2$ fixation, p. 365-382. In H. G. Schlegel, and B. Bowien (ed.), Autotrophic bacteria. Springer-Verlag, Berlin, Germany. The reductive pentose phosphate cycle (Calvin-Bassham-Benson cycle) represents the $CO_2$ fixation pathway in almost all aerobic autotrophic bacteria, for example, the cyanobacteria.

For producing n-alkanes via the recombinant expression of AAR and/or ADM enzymes, an engineered cyanobacteria, e.g., a *Synechococcus* or *Thermosynechococcus* species, is preferred. Other preferred organisms include *Synechocystis, Klebsiella oxytoca, Escherichia coli* or *Saccharomyces cerevisiae*. Other prokaryotic, archaea and eukaryotic host cells are also encompassed within the scope of the present invention.

Carbon-Based Products of Interest: Hydrocarbons & Alcohols

In various embodiments of the invention, desired hydrocarbons and/or alcohols of certain chain length or a mixture thereof can be produced. In certain aspects, the host cell produces at least one of the following carbon-based products of interest: 1-dodecanol, 1-tetradecanol, 1-pentadecanol, n-tridecane, n-tetradecane, 15:1 n-pentadecane, n-pentadecane, 16:1 n-hexadecene, n-hexadecane, 17:1 n-heptadecene, n-heptadecane, 16:1 n-hexadecen-ol, n-hexadecan-1-ol and n-octadecen-1-ol, as shown in the Examples herein. In other aspects, the carbon chain length ranges from $C_{10}$ to $C_{20}$. Accordingly, the invention provides production of various chain lengths of alkanes, alkenes and alkanols suitable for use as fuels & chemicals.

In preferred aspects, the methods provide culturing host cells for direct product secretion for easy recovery without the need to extract biomass. These carbon-based products of interest are secreted directly into the medium. Since the invention enables production of various defined chain length of hydrocarbons and alcohols, the secreted products are easily recovered or separated. The products of the invention, therefore, can be used directly or used with minimal processing.

Fuel Compositions

In various embodiments, compositions produced by the methods of the invention are used as fuels. Such fuels comply with ASTM standards, for instance, standard specifications for diesel fuel oils D 975-09b, and Jet A, Jet A-1 and Jet B as specified in ASTM Specification D. 1655-68. Fuel compositions may require blending of several products to produce a uniform product. The blending process is relatively straightforward, but the determination of the amount of each component to include in a blend is much more difficult. Fuel compositions may, therefore, include aromatic and/or branched hydrocarbons, for instance, 75% saturated and 25% aromatic, wherein some of the saturated hydrocarbons are branched and some are cyclic. Preferably, the methods of the invention produce an array of hydrocarbons, such as $C_{13}$-$C_{17}$ or $C_{10}$-$C_{15}$ to alter cloud point. Furthermore, the compositions may comprise fuel additives, which are used to enhance the performance of a fuel or engine. For example, fuel additives can be used to alter the freezing/gelling point, cloud point, lubricity, viscosity, oxidative stability, ignition quality, octane level, and flash point. Fuels compositions may also comprise, among others, antioxidants, static dissipater, corrosion inhibitor, icing inhibitor, biocide, metal deactivator and thermal stability improver.

In addition to many environmental advantages of the invention such as $CO_2$ conversion and renewable source, other advantages of the fuel compositions disclosed herein include low sulfur content, low emissions, being free or substantially free of alcohol and having high cetane number.

Carbon Fingerprinting

Biologically-produced carbon-based products, e.g., ethanol, fatty acids, alkanes, isoprenoids, represent a new commodity for fuels, such as alcohols, diesel and gasoline. Such biofuels have not been produced using biomass but use CO2 as its carbon source. These new fuels may be distinguishable from fuels derived form petrochemical carbon on the basis of dual carbon-isotopic fingerprinting. Such products, derivatives, and mixtures thereof may be completely distinguished from their petrochemical derived counterparts on the basis of $^{14}C$ (fM) and dual carbon-isotopic fingerprinting, indicating new compositions of matter.

There are three naturally occurring isotopes of carbon: $^{12}C$, $^{13}C$, and $^{14}C$. These isotopes occur in above-ground total carbon at fractions of 0.989, 0.011, and $10^{-12}$, respectively. The isotopes $^{12}C$ and $^{13}C$ are stable, while $^{14}C$ decays naturally to $^{14}N$, a beta particle, and an anti-neutrino in a process with a half-life of 5730 years. The isotope $^{14}C$ originates in the atmosphere, due primarily to neutron bombardment of $^{14}N$ caused ultimately by cosmic radiation. Because of its relatively short half-life (in geologic terms), $^{14}C$ occurs at extremely low levels in fossil carbon. Over the course of 1 million years without exposure to the atmosphere, just 1 part in $10^{50}$ will remain $^{14}C$.

The $^{13}C$:$^{12}C$ ratio varies slightly but measurably among natural carbon sources. Generally these differences are expressed as deviations from the $^{13}C$:$^{12}C$ ratio in a standard material. The international standard for carbon is Pee Dee Belemnite, a form of limestone found in South Carolina, with a $^{13}C$ fraction of 0.0112372. For a carbon source a, the deviation of the $^{13}C$:$^{12}C$ ratio from that of Pee Dee Belemnite is expressed as: $\delta_a=(R_a/(R_s))-1$, where $R_a=^{13}C$:$^{12}C$ ratio in the natural source, and $R_s=^{13}C$:$^{12}C$ ratio in Pee Dee Belemnite, the standard. For convenience, $\delta_a$ is expressed in parts per thousand, or ‰. A negative value of $\delta_a$ shows a bias toward $^{12}C$ over $^{13}C$ as compared to Pee Dee Belemnite. Table A shows $\delta_a$ and $^{14}C$ fraction for several natural sources of carbon.

TABLE A

13C:12C variations in natural carbon sources

| Source | $-\delta_a$ (‰) | References |
|---|---|---|
| Underground coal | 32.5 | Farquhar et al. (1989) Plant Mol. Biol., 40: 503-37 |
| Fossil fuels | 26 | Farquhar et al. (1989) Plant Mol. Biol., 40: 503-37 |
| Ocean DIC* | 0-1.5 | Goericke et al. (1994) Chapter 9 in Stable Isotopes in Ecology and Environmental Science, by K. Lajtha and R. H. Michener, Blackwell Publishing; Ivlev (2010) Separation Sci. Technol. 36: 1819-1914 |
| Atmospheric CO2 | 6-8 | Ivlev (2010) Separation Sci. Technol. 36: 1819-1914; Farquhar et al. (1989) Plant Mol. Biol., 40: 503-37 |
| Freshwater DIC* | 6-14 | Dettman et al. (1999) Geochim. Cosmochim. Acta 63: 1049-1057 |
| Pee Dee Belemnite | 0 | Ivlev (2010) Separation Sci. Technol. 36: 1819-1914 |

*DIC = dissolved inorganic carbon

Biological processes often discriminate among carbon isotopes. The natural abundance of $^{14}C$ is very small, and hence discrimination for or against $^{14}C$ is difficult to measure. Biological discrimination between $^{13}C$ and $^{12}C$, however, is well-documented. For a biological product p, we can define similar quantities to those above: $\delta_p=(R_p/R_s)-1$, where $R_p=^{13}C$:$^{12}C$ ratio in the biological product, and $R_s=^{13}C$:$^{12}C$ ratio in Pee Dee Belemnite, the standard. Table B shows measured deviations in the $^{13}C$:$^{12}C$ ratio for some biological products.

TABLE B $^{13}C:^{12}C$ variation in selected biological products

| Product | $-\delta_p$(‰) | $-D$(‰)* | References |
|---|---|---|---|
| Plant sugar/starch from atmospheric $CO_2$ | 18-28 | 10-20 | Ivlev (2010) Separation Sci. Technol. 36: 1819-1914 |
| Cyanobacterial biomass from marine DIC | 18-31 | 16.5-31 | Goericke et al. (1994) Chapter 9 in Stable Isotopes in Ecology and Environmental Science, by K. Lajtha and R. H. Michener, Blackwell Publishing; Sakata et al. (1997) Geochim. Cosmochim. Acta, 61: 5379-89 |
| Cyanobacterial lipid from marine DIC | 39-40 | 37.5-40 | Sakata et al. (1997) Geochim. Cosmochim. Acta, 61: 5379-89 |
| Algal lipid from marine DIC | 17-28 | 15.5-28 | Goericke et al. (1994) Chapter 9 in Stable Isotopes in Ecology and Environmental Science, by K. Lajtha and R. H. Michener, Blackwell Publishing; Abelseon et al. (1961) Proc. Natl. Acad. Sci., 47: 623-32 |
| Algal biomass from freshwater DIC | 17-36 | 3-30 | Marty et al. (2008) Limnol. Oceanogr.: Methods 6: 51-63 |
| *E. coli* lipid from plant sugar | 15-27 | near 0 | Monson et al. (1980) J. Biol. Chem., 255: 11435-41 |
| Cyanobacterial lipid from fossil carbon | 63.5-66 | 37.5-40 | — |
| Cyanobacterial biomass from fossil carbon | 42.5-57 | 16.5-31 | — |

*D = discrimination by a biological process in its utilization of $^{12}C$ vs. $^{13}C$ (see text)

Table B introduces a new quantity, D. This is the discrimination by a biological process in its utilization of $^{12}C$ vs. $^{13}C$. We define D as follows: $D=(R_p/R_a)-1$. This quantity is very similar to $\delta_a$ and $\delta_p$, except we now compare the biological product directly to the carbon source rather than to a standard. Using D, we can combine the bias effects of a carbon source and a biological process to obtain the bias of the biological product as compared to the standard. Solving for $\delta_p$, we obtain: $\delta_p=(D)(\delta_a)+D+\delta_a$, and, because $(D)(\delta_a)$ is generally very small compared to the other terms, $\delta_p \approx \delta_a+D$.

For a biological product having a production process with a known D, we may therefore estimate $\delta_p$ by summing $\delta_a$ and D. We assume that D operates irrespective of the carbon source. This has been done in Table B for cyanobacterial lipid and biomass produced from fossil carbon. As shown in the Table A and Table B, above, cyanobacterial products made from fossil carbon (in the form of, for example, flue gas or other emissions) will have a higher ($\delta_p$ than those of comparable biological products made from other sources, distinguishing them on the basis of composition of matter from these other biological products. In addition, any product derived solely from fossil carbon will have a negligible fraction of $^{14}C$, while products made from above-ground carbon will have a $^{14}C$ fraction of approximately $10^{-12}$.

Accordingly, in certain aspects, the invention provides various carbon-based products of interest characterized as $-\delta_p$(‰) of about 63.5 to about 66 and $-D$(‰) of about 37.5 to about 40.

Antibodies

In another aspect, the present invention provides isolated antibodies, including fragments and derivatives thereof that bind specifically to the isolated polypeptides and polypeptide fragments of the present invention or to one or more of the polypeptides encoded by the isolated nucleic acids of the present invention. The antibodies of the present invention may be specific for linear epitopes, discontinuous epitopes or conformational epitopes of such polypeptides or polypeptide fragments, either as present on the polypeptide in its native conformation or, in some cases, as present on the polypeptides as denatured, as, e.g., by solubilization in SDS. Among the useful antibody fragments provided by the instant invention are Fab, Fab', Fv, F(ab')$_2$, and single chain Fv fragments.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies of the present invention will discriminate over adventitious binding to unrelated polypeptides by at least two-fold, more typically by at least 5-fold, typically by more than 10-fold, 25-fold, 50-fold, 75-fold, and often by more than 100-fold, and on occasion by more than 500-fold or 1000-fold.

Typically, the affinity or avidity of an antibody (or antibody multimer, as in the case of an IgM pentamer) of the present invention for a polypeptide or polypeptide fragment of the present invention will be at least about $1\times10^{-6}$ M, typically at least about $5\times10^{-7}$ M, usefully at least about $1\times10^{-7}$ M, with affinities and avidities of $1\times10^{-8}$ M, $5\times10^{-9}$ M, $1\times10^{-10}$ M and even stronger proving especially useful.

The isolated antibodies of the present invention may be naturally-occurring forms, such as IgG, IgM, IgD, IgE, and IgA, from any mammalian species. For example, antibodies are usefully obtained from species including rodents—typically mouse, but also rat, guinea pig, and hamster—lagomorphs, typically rabbits, and also larger mammals, such as sheep, goats, cows, and horses. The animal is typically affirmatively immunized, according to standard immunization protocols, with the polypeptide or polypeptide fragment of the present invention.

Virtually all fragments of 8 or more contiguous amino acids of the polypeptides of the present invention may be used effectively as immunogens when conjugated to a carrier, typically a protein such as bovine thyroglobulin, keyhole limpet hemocyanin, or bovine serum albumin, conveniently using a bifunctional linker. Immunogenicity may also be conferred by fusion of the polypeptide and polypeptide fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. See, e.g., Tam et al., *Proc. Natl. Acad. Sci. USA* 85:5409-5413 (1988); Posnett et al., *J. Biol. Chem.* 263, 1719-1725 (1988).

Protocols for immunization are well-established in the art. Such protocols often include multiple immunizations, either with or without adjuvants such as Freund's complete adjuvant and Freund's incomplete adjuvant. Antibodies of the present invention may be polyclonal or monoclonal, with polyclonal antibodies having certain advantages in immuno-histochemical detection of the proteins of the present invention and monoclonal antibodies having advantages in identifying and distinguishing particular epitopes of the proteins of the present invention. Following immunization, the antibodies of the present invention may be produced using any art-accepted technique. Host cells for recombinant antibody production—either whole antibodies, antibody fragments, or antibody derivatives—can be prokaryotic or eukaryotic. Prokaryotic hosts are particularly useful for producing phage displayed antibodies, as is well known in the art. Eukaryotic cells, including mammalian, insect, plant and fungal cells are also useful for expression of the antibodies, antibody fragments, and antibody derivatives of the present invention. Antibodies of the present invention can also be prepared by cell free translation.

The isolated antibodies of the present invention, including fragments and derivatives thereof, can usefully be labeled. It is, therefore, another aspect of the present invention to provide labeled antibodies that bind specifically to one or more of the polypeptides and polypeptide fragments of the present invention. The choice of label depends, in part, upon the desired use. In some cases, the antibodies of the present invention may usefully be labeled with an enzyme. Alternatively, the antibodies may be labeled with colloidal gold or with a fluorophore. For secondary detection using labeled avidin, streptavidin, captavidin or neutravidin, the antibodies of the present invention may usefully be labeled with biotin. When the antibodies of the present invention are used, e.g., for Western blotting applications, they may usefully be labeled with radioisotopes, such as $^{33}$P, $^{32}$P, $^{35}$S, $^{3}$H and $^{125}$I. As would be understood, use of the labels described above is not restricted to any particular application.

The following examples are for illustrative purposes and are not intended to limit the scope of the present invention.

Example 1

A pathway for the enzymatic synthesis of n-alkanes. An enzymatic process for the production of n-alkanes in, e.g., cyanobacteria is shown in FIG. 1A based on the sequential activity of (1) an AAR enzyme, e.g., tll1312, an acyl-ACP reductase; and (2) an ADM enzyme, e.g., tll1313, a putative alkanal decarboxylative monooxygenase, that uses reduced ferredoxin as electron donor. The AAR activity is distinct from the relatively well characterized acyl-CoA reductase activity exhibited by proteins such as Acr1 from *Acinetobacter calcoaceticus* (Reiser S and Somerville C (1997) *J. Bacteriol.* 179:2969-2975). A membranous ADM activity has previously been identified in insect microsomal preparations (Reed J R et al. (1994) *Proc. Natl. Acad. Sci. USA* 91:10000-10004; Reed J R et al. (1995) *Musca domestica. Biochemistry* 34:16221-16227).

Figure 1B:
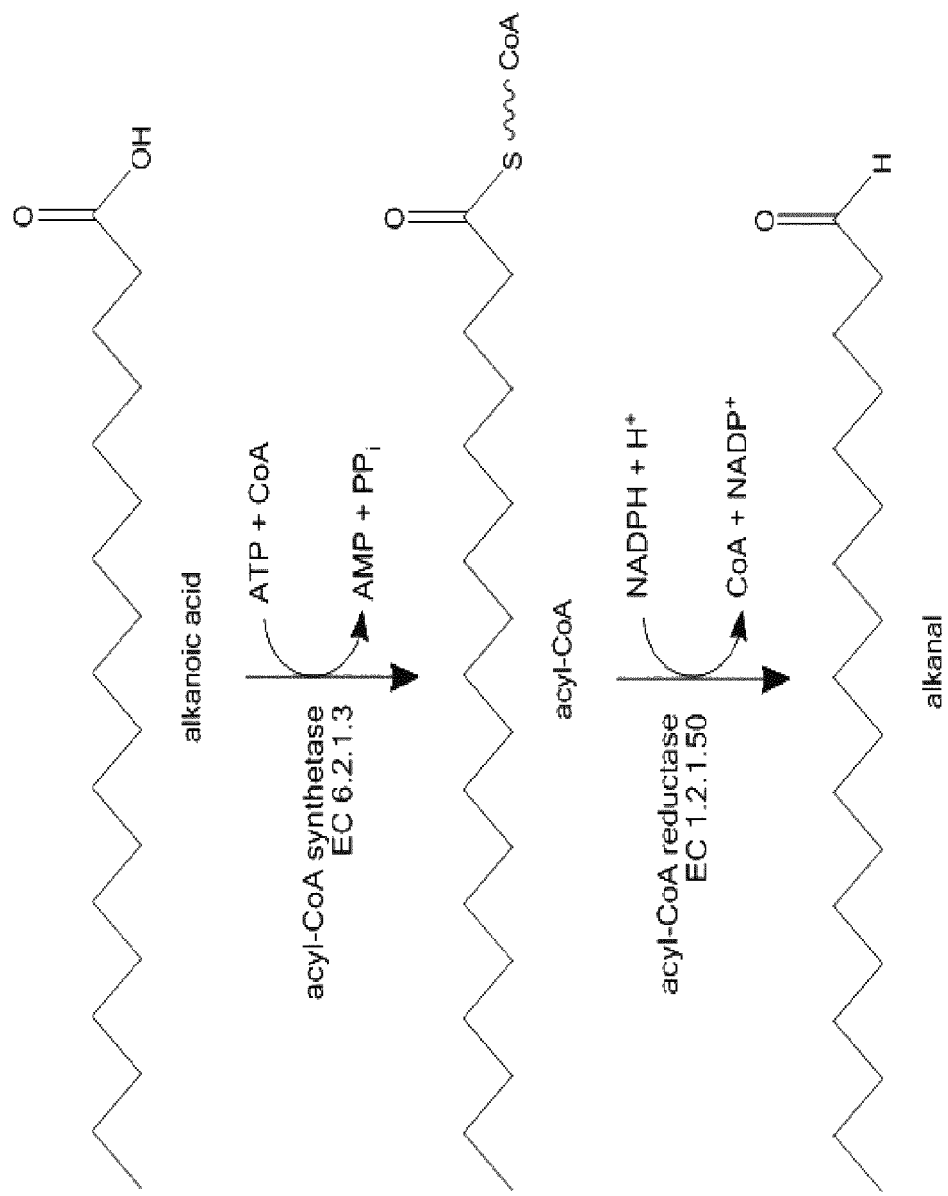
Figure 1C:
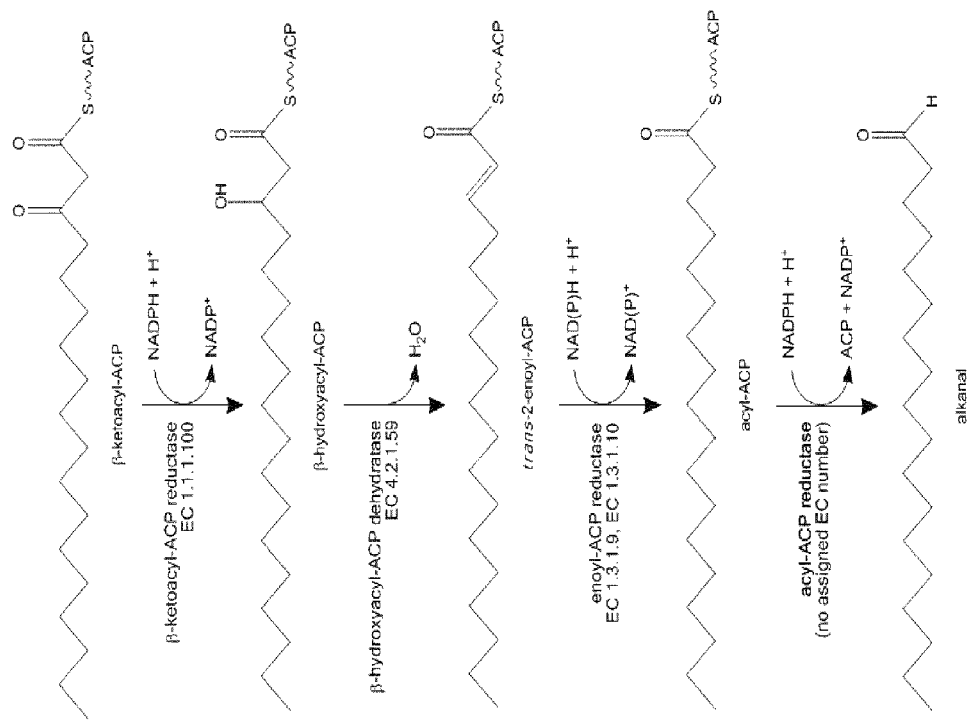

FIGS. 1B and 1C summarize the names and activities of the enzymes involved in the biosynthesis of n-alkanals. FIG. 1B depicts the relatively well characterized acyl-CoA reductase activity (EC 1.2.1.50) exhibited by proteins such as Acr1 from *Acinetobacter calcoaceticus*. In FIG. 1C, the two well-known ACP-related reductases that are involved in fatty acid biosynthesis, β-ketoacyl-ACP reductase (EC 1.1.1.100) and enoyl-ACP reductase (EC 1.3.1.9, 1.3.1.10), are contrasted with the acyl-ACP reductase (AAR) (no EC number yet assigned) believed to be involved in the biosynthetic pathway for n-alkanes in cyanobacteria. The key difference between AAR and acyl-CoA reductase (EC 1.2.1.50) is that ACP is the acyl carrier rather than coenzyme A. Supporting this distinction, it has been shown that acyl-CoA reductase Acr1 from *Acinetobacter calcoaceticus* can only generate alkanals from acyl-CoA and not acyl-ACP (Resier S and Somerville C (1997) *J. Bacteriol.* 179: 2969-2975).

ADM also lacks a presently assigned EC number. An alkanal monooxygenase (EC 1.14.14.3), often referred to as luciferase, is known to catalyze the conversion of n-alkanal to n-alkanoic acid. This activity is distinct from the ADM activity (n-alkanal to (n−1)-alkane) proposed herein, although both use n-alkanal and molecular oxygen as substrates.

Cyanobacterial AAR and ADM homologs for production of n-alkanes. In this example, homologs of cyanobacterial AAR and ADM genes (e.g., homologs of *Synechococcus elongatus* PCC 7942 SYNPCC7942_1594 and/or SYNPCC7942_1593 protein, respectively) are identified using a BLAST search. These proteins can be expressed in a variety of organisms (bacteria, yeast, plant, etc.) for the purpose of generating and isolating n-alkanes and other desired carbon-based products of interest from the organisms. A search of the non-redundant BLAST protein database revealed counterparts for each protein in other cyanobacteria.

To determine the degree of similarity among homologs of the *Synechococcus elongatus* PCC 7942 SYNPCC7942_1594 protein, the 341-amino acid protein sequence was queried using BLAST (http://blast.ncbi.nlm.nih.gov/) against the "nr" non-redundant protein database. Homologs were taken as matching proteins whose alignments (i) covered >90% length of SYNPCC7942_1594, (ii) covered >90% of the length of the matching protein, and (iii) had >50% identity with SYNPCC7942_1594 (Table 1).

TABLE 1

Protein homologs of SYNPCC7942_1594 (AAR)

| Organism | SEQ ID NO: | Homolog accession # | BLAST Score, E-value |
|---|---|---|---|
| *Synechococcus elongatus* PCC 7942 | 6 | (SYNPCC7942_1594) | n/a |
| *Synechococcus elongatus* PCC 7942 [cyanobacteria] taxid 1140 | 23 | YP_400611.1 | 706, 0.0 |
| *Synechococcus elongatus* PCC 6301 [cyanobacteria] taxid 269084 | 24 | YP_170761.1 | 706, 0.0 |
| *Anabaena variabilis* ATCC 29413 [cyanobacteria] taxid 240292 | 25 | YP_323044.1 | 538, 4e−151 |
| *Nostoc* sp. PCC 7120 [cyanobacteria] taxid 103690 | 26 | NP_489324.1 | 535, 3e−150 |
| '*Nostoc azollae*' 0708 [cyanobacteria] taxid 551115 | 27 | ZP_03763674.1 | 533, 1e−149 |
| *Cyanothece* sp. PCC 7425 [cyanobacteria] taxid 395961 | 28 | YP_002481152.1 | 526, 9e−148 |
| *Nodularia spumigena* CCY 9414 [cyanobacteria] taxid 313624 | 29 | ZP_01628095.1 | 521, 3e−146 |
| *Lyngbya* sp. PCC 8106 [cyanobacteria] taxid 313612 | 30 | ZP_01619574.1 | 520, 6e−146 |
| *Nostoc punctiforme* PCC 73102 [cyanobacteria] taxid 63737 | 31 | YP_001865324.1 | 520, 7e−146 |
| *Trichodesmium erythraeum* IMS101 [cyanobacteria] taxid 203124 | 32 | YP_721978.1 | 517, 6e−145 |
| *Thermosynechococcus elongatus* BP-1 [cyanobacteria] taxid 197221 | 2 | NP_682102.1 | 516, 2e−144 |
| *Acaryochloris marina* MBIC11017 [cyanobacteria] taxid 329726 | 33 | YP_001518341.1 | 512, 2e−143 |
| *Cyanothece* sp. PCC 8802 [cyanobacteria] taxid 395962 | 34 | ZP_03142196.1 | 510, 8e−143 |
| *Cyanothece* sp. PCC 8801 [cyanobacteria] taxid 41431 | 35 | YP_002371106.1 | 510, 8e−143 |
| *Microcoleus chthonoplastes* PCC 7420 [cyanobacteria] taxid 118168 | 36 | YP_002619867.1 | 509, 2e−142 |
| *Arthrospira maxima* CS-328 [cyanobacteria] taxid 513049 | 37 | ZP_03273554.1 | 507, 7e−142 |
| *Synechocystis* sp. PCC 6803 [cyanobacteria] taxid 1148 | 38 | NP_442146.1 | 504, 5e−141 |
| *Cyanothece* sp. CCY 0110 [cyanobacteria] taxid 391612 | 39 | ZP_01728620.1 | 501, 4e−140 |
| *Synechococcus* sp. PCC 7335 [cyanobacteria] taxid 91464 | 40 | YP_002711557.1 | 500, 1e−139 |
| *Cyanothece* sp. ATCC 51142 [cyanobacteria] taxid 43989 | 41 | YP_001802846.1 | 489, 2e−136 |
| *Gloeobacter violaceus* PCC 7421 [cyanobacteria] taxid 251221 | 42 | NP_926091.1 | 487, 7e−136 |
| *Microcystis aeruginosa* NIES-843 [cyanobacteria] taxid 449447 | 43 | YP_001660322.1 | 486, 1e−135 |
| *Crocosphaera watsonii* WH 8501 [cyanobacteria] taxid 165597 | 44 | ZP_00516920.1 | 486, 1e−135 |
| *Microcystis aeruginosa* PCC 7806 [cyanobacteria] taxid 267872 | 45 | emb|CAO90781.1 | 484, 8e−135 |

TABLE 1-continued

| Protein homologs of SYNPCC7942_1594 (AAR) | | | |
|---|---|---|---|
| Organism | SEQ ID NO: | Homolog accession # | BLAST Score, E-value |
| *Synechococcus* sp. WH 5701 [cyanobacteria] taxid 69042 | 46 | ZP_01085337.1 | 471, 4e−131 |
| *Synechococcus* sp. RCC307 [cyanobacteria] taxid 316278 | 47 | YP_001227841.1 | 464, 8e−129 |
| uncultured marine type-A *Synechococcus* GOM 3O6 [cyanobacteria] taxid 364150 | 48 | gb|ABD96327.1 | 462, 2e−128 |
| *Synechococcus* sp. WH 8102 [cyanobacteria] taxid 84588 | 49 | NP_897828.1 | 462, 2e−128 |
| *Synechococcus* sp. WH 7803 [cyanobacteria] taxid 32051 | 50 | YP_001224378.1 | 459, 2e−127 |
| uncultured marine type-A *Synechococcus* GOM 5D20 [cyanobacteria] taxid 364154 | 51 | gb|ABD96480.1 | 458, 3e−127 |
| *Synechococcus* sp. WH 7805 [cyanobacteria] taxid 59931 | 52 | ZP_01123215.1 | 457, 5e−127 |
| uncultured marine type-A *Synechococcus* 5B2 [cyanobacteria] taxid 359140 | 53 | gb|ABB92249.1 | 457, 8e−127 |
| *Synechococcus* sp. RS9917 [cyanobacteria] taxid 221360 | 54 | ZP_01079773.1 | 456, 2e−126 |
| *Synechococcus* sp. CC9902 [cyanobacteria] taxid 316279 | 55 | YP_377636.1 | 454, 6e−126 |
| *Prochlorococcus marinus* subsp. *marinus* str. CCMP1375 [cyanobacteria] taxid 167539 | 56 | NP_874926.1 | 453, 9e−126 |
| *Prochlorococcus marinus* str. MIT 9313 [cyanobacteria] taxid 74547 | 57 | NP_895058.1 | 453, 1e−125 |
| uncultured marine type-A *Synechococcus* GOM 3M9 [cyanobacteria] taxid 364149 | 58 | gb|ABD96274.1 | 452, 2e−125 |
| uncultured marine type-A *Synechococcus* GOM 4P21 [cyanobacteria] taxid 364153 | 59 | gb|ABD96442.1 | 452, 2e−125 |
| *Synechococcus* sp. BL107 [cyanobacteria] taxid 313625 | 60 | ZP_01469469.1 | 452, 2e−125 |
| *Cyanobium* sp. PCC 7001 [cyanobacteria] taxid 180281 | 61 | YP_002597253.1 | 451, 4e−125 |
| *Prochlorococcus marinus* str. NATL1A [cyanobacteria] taxid 167555 | 62 | YP_001014416.1 | 449, 2e−124 |
| *Prochlorococcus marinus* str. MIT 9515 [cyanobacteria] taxid 167542 | 63 | YP_001010913.1 | 447, 6e−124 |
| *Synechococcus* sp. CC9605 [cyanobacteria] taxid 110662 | 64 | YP_381056.1 | 447, 8e−124 |
| *Prochlorococcus marinus* str. MIT 9211 [cyanobacteria] taxid 93059 | 65 | YP_001550421.1 | 446, 2e−123 |
| *Prochlorococcus marinus* subsp. *pastoris* str. CCMP1986 [cyanobacteria] taxid 59919 | 66 | NP_892651.1 | 446, 2e−123 |
| *Prochlorococcus marinus* str. MIT 9301 [cyanobacteria] taxid 167546 | 67 | YP_001090783.1 | 445, 3e−123 |
| *Synechococcus* sp. RS9916 [cyanobacteria] | 68 | ZP_01472595.1 | 445, 3e−123 |

TABLE 1-continued

Protein homologs of SYNPCC7942_1594 (AAR)

| Organism | SEQ ID NO: | Homolog accession # | BLAST Score, E-value |
|---|---|---|---|
| taxid 221359 | | | |
| *Prochlorococcus marinus* str. NATL2A [cyanobacteria] taxid 59920 | 69 | YP_293055.1 | 445, 4e−123 |
| *Prochlorococcus marinus* str. MIT 9202 [cyanobacteria] taxid 93058 | 70 | YP_002673377.1 | 444, 7e−123 |
| *Synechococcus* sp. CC9311 [cyanobacteria] taxid 64471 | 71 | YP_731192.1 | 443, 1e−122 |
| *Prochlorococcus marinus* str. MIT 9215 [cyanobacteria] taxid 93060 | 72 | YP_001483815.1 | 442, 2e−122 |
| *Prochlorococcus marinus* str. AS9601 [cyanobacteria] taxid 146891 | 73 | YP_001008982.1 | 442, 3e−122 |
| *Synechococcus* sp. JA-3-3Ab [cyanobacteria] taxid 321327 | 74 | YP_473896.1 | 441, 5e−122 |
| *Synechococcus* sp. JA-2-3B'a(2-13) [cyanobacteria] taxid 321332 | 75 | YP_478638.1 | 440, 8e−122 |
| *Prochlorococcus marinus* str. MIT 9312 [cyanobacteria] taxid 74546 | 76 | YP_397030.1 | 436, 1e−120 |

To determine the degree of similarity among homologs of the *Synechococcus elongatus* PCC 7942 SYNPCC7942_1593 protein, the 231 amino acid protein sequence was queried using BLAST (http://blast.ncbi.nlm.nih.gov/) against the "nr" non-redundant protein database. Homologs were taken as matching proteins whose alignments (i) covered >90% length of SYNPCC7942_1593, (ii) covered >90% of the length of the matching protein, (iii) and had >50% identity with SYNPCC7942_1593 (Table 2).

TABLE 2

Protein homologs of SYNPCC7942_1593 (ADM)

| Organism | SEQ ID NO: | Homolog accession # | BLAST Score, E-value |
|---|---|---|---|
| *Synechococcus elongatus* PCC 7942 [cyanobacteria] | 8 | (SYNPCC7942_1593) | n/a |
| *Synechococcus elongatus* PCC 7942 [cyanobacteria] taxid 1140 | 77 | YP_400610.1 | 475, 1e−132 |
| *Synechococcus elongatus* PCC 6301 [cyanobacteria] taxid 269084 | 78 | YP_170760.1 | 475, 2e−132 |
| *Arthrospira maxima* CS-328 [cyanobacteria] taxid 513049 | 79 | ZP_03273549.1 | 378, 3e−103 |
| *Microcoleus chthonoplastes* PCC 7420 [cyanobacteria] taxid 118168 | 80 | YP_002619869.1 | 376, 1e−102 |
| *Lyngbya* sp. PCC 8106 [cyanobacteria] taxid 313612 | 81 | ZP_01619575.1 | 374, 5e−102 |
| *Nodularia spumigena* CCY 9414 [cyanobacteria] taxid 313624 | 82 | ZP_01628096.1 | 369, 1e−100 |
| *Microcystis aeruginosa* NIES-843 [cyanobacteria] taxid 449447 | 83 | YP_001660323.1 | 367, 5e−100 |
| *Microcystis aeruginosa* PCC 7806 [cyanobacteria] taxid 267872 | 84 | emb|CAO90780.1 | 364, 3e−99 |
| *Nostoc* sp. PCC 7120 [cyanobacteria] taxid 103690 | 85 | NP_489323.1 | 363, 1e−98 |
| *Anabaena variabilis* ATCC 29413 [cyanobacteria] taxid 240292 | 86 | YP_323043.1 | 362, 2e−98 |

TABLE 2-continued

Protein homologs of SYNPCC7942_1593 (ADM)

| Organism | SEQ ID NO: | Homolog accession # | BLAST Score, E-value |
|---|---|---|---|
| *Crocosphaera watsonii* WH 8501 [cyanobacteria] taxid 165597 | 87 | ZP_00514700.1 | 359, 1e-97 |
| *Trichodesmium erythraeum* IMS101 [cyanobacteria] taxid 203124 | 88 | YP_721979.1 | 358, 2e-97 |
| *Synechococcus* sp. PCC 7335 [cyanobacteria] taxid 91464 | 89 | YP_002711558.1 | 357, 6e-97 |
| '*Nostoc azollae*' 0708 [cyanobacteria] taxid 551115 | 90 | ZP_03763673.1 | 355, 3e-96 |
| *Synechocystis* sp. PCC 6803 [cyanobacteria] taxid 1148 | 91 | NP_442147.1 | 353, 5e-96 |
| *Cyanothece* sp. ATCC 51142 [cyanobacteria] taxid 43989 | 92 | YP_001802195.1 | 352, 2e-95 |
| *Cyanothece* sp. CCY 0110 [cyanobacteria] taxid 391612 | 93 | ZP_01728578.1 | 352, 2e-95 |
| *Cyanothece* sp. PCC 7425 [cyanobacteria] taxid 395961 | 94 | YP_002481151.1 | 350, 7e-95 |
| *Nostoc punctiforme* PCC 73102 [cyanobacteria] taxid 63737 | 95 | YP_001865325.1 | 349, 1e-94 |
| *Acaryochloris marina* MBIC11017 [cyanobacteria] taxid 329726 | 96 | YP_001518340.1 | 344, 4e-93 |
| *Cyanothece* sp. PCC 8802 [cyanobacteria] taxid 395962 | 97 | ZP_03142957.1 | 342, 1e-92 |
| *Cyanothece* sp. PCC 8801 [cyanobacteria] taxid 41431 | 98 | YP_002370707.1 | 342, 1e-92 |
| *Thermosynechococcus elongatus* BP-1 [cyanobacteria] taxid 197221 | 4 | NP_682103.1 | 332, 2e-89 |
| *Synechococcus* sp. JA-2-3B'a(2-13) [cyanobacteria] taxid 321332 | 99 | YP_478639.1 | 319, 1e-85 |
| *Synechococcus* sp. RCC307 [cyanobacteria] taxid 316278 | 100 | YP_001227842.1 | 319, 1e-85 |
| *Synechococcus* sp. WH 7803 [cyanobacteria] taxid 32051 | 101 | YP_001224377.1 | 313, 8e-84 |
| *Synechococcus* sp. WH 8102 [cyanobacteria] taxid 84588 | 102 | NP_897829.1 | 311, 3e-83 |
| *Synechococcus* sp. WH 7805 [cyanobacteria] taxid 59931 | 103 | ZP_01123214.1 | 310, 6e-83 |
| uncultured marine type-A *Synechococcus* GOM 3O12 [cyanobacteria] taxid 364151 | 104 | gb|ABD96376.1 | 309, 1e-82 |
| *Synechococcus* sp. JA-3-3Ab [cyanobacteria] taxid 321327 | 105 | YP_473897.1 | 309, 1e-82 |
| uncultured marine type-A *Synechococcus* GOM 3O6 [cyanobacteria] taxid 364150 | 106 | gb|ABD96328.1 | 309, 1e-82 |
| uncultured marine type-A *Synechococcus* GOM 3M9 [cyanobacteria] taxid 364149 | 107 | gb|ABD96275.1 | 308, 2e-82 |
| *Synechococcus* sp. CC9311 [cyanobacteria] taxid 64471 | 108 | YP_731193.1 | 306, 7e-82 |
| uncultured marine type-A *Synechococcus* 5B2 [cyanobacteria] taxid 359140 | 109 | gb|ABB92250.1 | 306, 9e-82 |

TABLE 2-continued

Protein homologs of SYNPCC7942_1593 (ADM)

| Organism | SEQ ID NO: | Homolog accession # | BLAST Score, E-value |
|---|---|---|---|
| *Synechococcus* sp. WH 5701 [cyanobacteria] taxid 69042 | 110 | ZP_01085338.1 | 305, 3e−81 |
| *Gloeobacter violaceus* PCC 7421 [cyanobacteria] taxid 251221 | 111 | NP_926092.1 | 303, 8e−81 |
| *Synechococcus* sp. RS9916 [cyanobacteria] taxid 221359 | 112 | ZP_01472594.1 | 303, 9e−81 |
| *Synechococcus* sp. RS9917 [cyanobacteria] taxid 221360 | 113 | ZP_01079772.1 | 300, 6e−80 |
| *Synechococcus* sp. CC9605 [cyanobacteria] taxid 110662 | 114 | YP_381055.1 | 300, 7e−80 |
| *Prochlorococcus marinus* str. MIT 9303 [cyanobacteria] taxid 59922 | 115 | YP_001016795.1 | 294, 4e−78 |
| *Cyanobium* sp. PCC 7001 [cyanobacteria] taxid 180281 | 116 | YP_002597252.1 | 294, 6e−78 |
| *Prochlorococcus marinus* str. MIT 9313 [cyanobacteria] taxid 74547 | 117 | NP_895059.1 | 291, 3e−77 |
| *Synechococcus* sp. CC9902 [cyanobacteria] taxid 316279 | 118 | YP_377637.1 | 289, 1e−76 |
| *Prochlorococcus marinus* str. MIT 9301 [cyanobacteria] taxid 167546 | 119 | YP_001090782.1 | 287, 5e−76 |
| *Synechococcus* sp. BL107 [cyanobacteria] taxid 313625 | 120 | ZP_01469468.1 | 287, 6e−76 |
| *Prochlorococcus marinus* str. AS9601 [cyanobacteria] taxid 146891 | 121 | YP_001008981.1 | 286, 2e−75 |
| *Prochlorococcus marinus* str. MIT 9312 [cyanobacteria] taxid 74546 | 12 | YP_397029.1 | 282, 1e−74 |
| *Prochlorococcus marinus* subsp. *pastoris* str. CCMP1986 [cyanobacteria] taxid 59919 | 122 | NP_892650.1 | 280, 9e−74 |
| *Prochlorococcus marinus* str. MIT 9211 [cyanobacteria] taxid 93059 | 123 | YP_001550420.1 | 279, 2e−73 |
| *Prochlorococcus marinus* str. NATL2A [cyanobacteria] taxid 59920 | 124 | YP_293054.1 | 276, 9e−73 |
| *Prochlorococcus marinus* str. NATL1A [cyanobacteria] taxid 167555 | 125 | YP_001014415.1 | 276, 9e−73 |
| *Prochlorococcus marinus* subsp. *marinus* str. CCMP1375 [cyanobacteria] taxid 167539 | 126 | NP_874925.1 | 276, 1e−72 |
| *Prochlorococcus marinus* str. MIT 9515 [cyanobacteria] taxid 167542 | 127 | YP_001010912.1 | 273, 6e−72 |
| *Prochlorococcus marinus* str. MIT 9215 [cyanobacteria] taxid 93060 | 128 | YP_001483814.1 | 273, 9e−72 |

The amino acid sequences referred to in the Table, as those sequences appeared in the NCBI database on Jul. 9, 2009, by accession number are incorporated by reference herein.

An AAR enzyme from Table 1, and/or an ADM enzyme from Table 2, or both can be expressed in a host cell of interest, wherein the host may be a heterologous host or the native host, i.e., the species from which the genes were originally derived. In one embodiment, the invention provides a method of imparting n-alkane synthesis capability in a heterologous organism, lacking native homologs of AAR and/or ADM, by engineering the organism to express a gene encoding one of the enzymes listed in Table 1 or Table 2. Also provided are methods of modulating n-alkane synthesis in an organism which already expresses one or both of the AAR and ADM enzymes by increasing the expression of the native enzymes, or by augmenting native gene expression by the recombinant expression of heterologous AAR and/or ADM enzymes. In addition, the invention provides methods of modulating the degree of alkane synthesis by varying certain parameters, including the identity and/or compatibility of electron donors, culture conditions, promoters for expressing AAR and/or ADM enzymes, and the like.

If the host lacks a suitable electron donor or lacks sufficient levels of a suitable electron donor to achieve production of the desired amount of n-alkane, such electron donor may also be introduced recombinantly. Guidelines for optimizing electron donors for the reaction catalyzed by the recombinant ADM proteins described herein may be summarized as follows:

1. In cyanobacteria, electrons are shuttled from photosystem I to ferredoxin and from ferredoxin to the ADM enzyme.
2. In bacteria that lack photosystem I, electrons can be shuttled from NADPH to ferredoxin via the action of ferredoxin-NADP+ reductase (EC 1.18.1.2) and from ferredoxin to the ADM enzyme.
3. In bacteria that lack photosystem I, electrons can be shuttled from NADPH to flavodoxin via the action of ferredoxin-NADP+ reductase (EC 1.18.1.2) and from flavodoxin to the ADM enzyme.
4. In bacteria that lack photosystem I, electrons can be shuttled from NADH to ferredoxin via the action of *Trichomonas vaginalis* NADH dehydrogenase and from ferredoxin to the ADM enzyme.
5. In all bacteria, electrons can be shuttled from pyruvate to ferredoxin by the action of pyruvate:ferredoxin oxidoreductase (EC 1.2.7.1), and from ferredoxin to the ADM enzyme.

In addition to the in vivo production of n-alkanes discussed above, AAR and ADM proteins encoded by the genes listed in Tables 1 and 2 can be purified. When incubated in vitro with an appropriate electron donor (e.g., a ferredoxin, as discussed above), the proteins will catalyze the enzymatic synthesis of n-alkanes in vitro from appropriate starting materials (e.g., an acyl-ACP or n-alkanal).

Figure 1D:
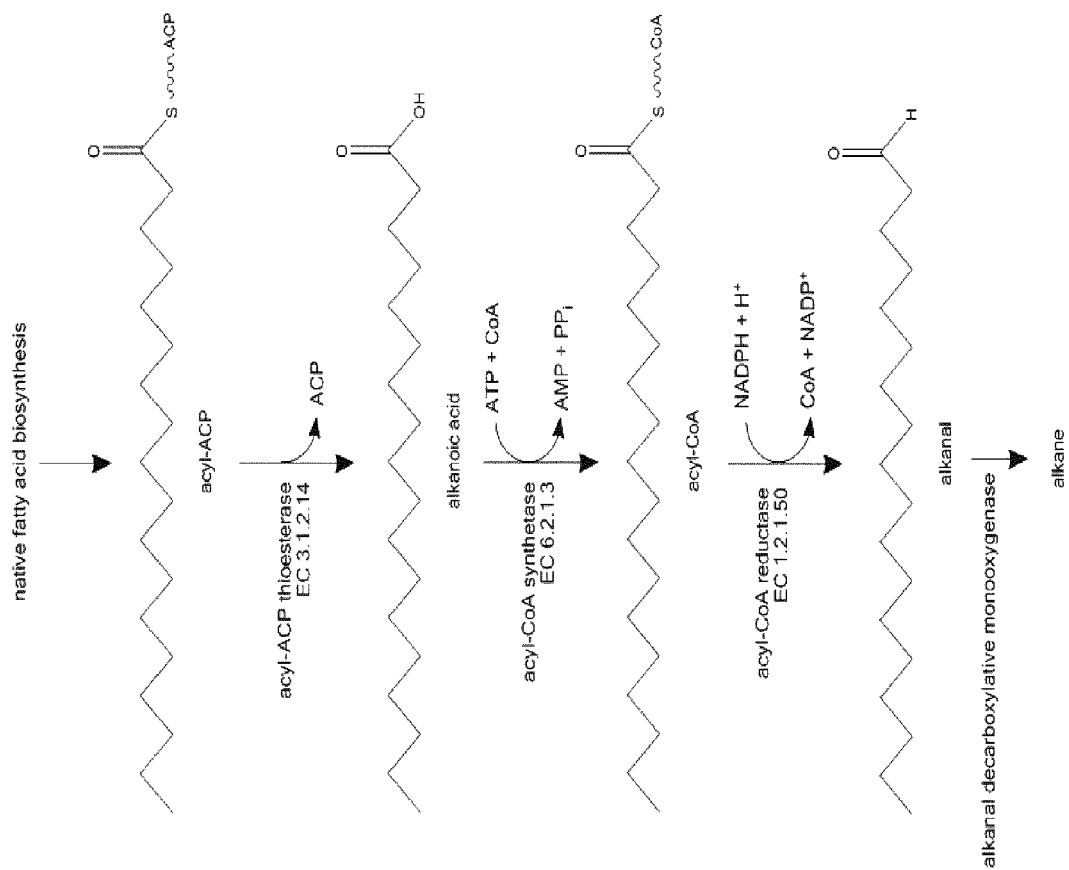

In addition to the pathways for n-alkane synthesis described above, the invention also provides an alternative pathway, namely, acyl-CoA→n-alkanal→(n−1)-alkane, via the successive activities of acyl-CoA reductase (ACR) and ADM. Normally, acyl-CoA is the first intermediate in metabolic pathways of fatty acid oxidation; thus, upon import into the cell, exogenously added free fatty acids are converted to acyl-CoAs by acyl-CoA synthetase (FIG. 1B). Acyl-CoA can also be derived purely biosynthetically as follows: acyl-ACP→free fatty acid→acyl-CoA, via the activities of cytoplasmic acyl-ACP thioesterase (EC 3.1.2.14; an example is leader-signal-less *E. coli* TesA) and the endogenous and/or heterologous acyl-CoA synthetase. Thus, in one embodiment, the invention provides a method for the biosynthesis of n-alkanes via the pathway: acyl-ACP→intracellular free fatty acid→acyl-CoA→n-alkanal→(n−1)-alkane (FIG. 1D), catalyzed by the successive activities of acyl-ACP thioesterase, acyl-CoA synthetase, acyl-CoA reductase, and ADM. For example, the acyl-CoA reductase Acr1 from *Acinetobacter calcoaceticus* and the ADM from *Synechococcus* sp. PCC7942 (SYNPCC7942_1593) can be used to transform *E. coli*, which is cultured in the presence of exogenous free fatty acids. The free fatty acids are taken up by the cells as acyl-CoA, which are then converted to n-alkanal by Acr1, and thence to (n−1)-alkane by ADM.

Example 2

Production of n-Alkanes, n-Alkenes, and Fatty Alcohols in *Escherichia coli* K-12 Through Heterologous Expression of *Synechococcus elongatus* PCC7942 SYNPCC7942_1593 (adm) and SYNPCC7942_1594 (aar)

The natural SYNPCC7942_1593-SYNPCC7942_1594 operonic sequence was PCR-amplified from the genomic DNA of *Synechococcus elongatus* PCC7942 and cloned into the pAQ1 homologous recombination vector pJB5 via NdeI and EcoRI. The resulting plasmid was denoted pJB823. This construct placed the SYNPCC7942_1593-SYNPCC7942_1594 operon under the transcriptional control of the constitutive aphII promoter. The sequence of pJB823 is provided as SEQ ID NO: 15. The intracellular hydrocarbon products of *E. coli* K-12 EPI400™ (Epicentre) harboring pJB823, JCC1076, were compared to those of EPI400™ harboring pJB5, the control strain JCC9a, by gas chromatography-mass spectrometry (GC-MS). Clonal cultures of JCC9a and JCC1076 were grown overnight at 37° C. in Luria Broth (LB) containing 2% glucose, 100 µg/ml carbenicillin, 50 µg/ml spectinomycin, 50 µg/ml streptomycin, and 1× CopyCutter Induction Solution (Epicentre). For each strain, 15 ml of saturated culture was collected by centrifugation. Cell pellets were washed thoroughly by three cycles of resuspension in Milli-Q water and microcentrifugation, and then dewetted as much as possible by three cycles of microcentrifugation and aspiration. Cell pellets were then extracted by vortexing for five minutes in 0.8 ml acetone containing 100 µg/ml butylated hydroxytoluene (BHT; a general antioxidant) and 100 µg/ml ethyl arachidate (EA; an internal reporter of extraction efficiency). Cell debris was pelleted by centrifugation, and 700 µl extractant was pipetted into a GC vial. These JCC9a and JCC1067 acetone samples, along with authentic standards, were then analyzed by GC-MS.

The gas chromatograph was an Agilent 7890A GC equipped with a 5975C electron-impact mass spectrometer. Liquid samples (1.0 µl) were injected into the GC with a 7683 automatic liquid sampler equipped with a 10 µl syringe. The GC inlet temperature was 290° C. and split-less injection was used. The capillary column was an Agilent HP-5MS (30 m×0.25 mm×0.25 µm). The carrier gas was helium at a flow rate of 1.0 ml/min. The GC oven temperature program was 50° C., hold 1 min/10° C. per min to 290° C./hold 9 min. The GC-MS interface temperature was 290° C. The MS source temperature was 230° C., and the quadrapole temperature was 150° C. The mass range was 25-600 amu. MS fragmentation spectra were matched against the NIST MS database, 2008 version.

Peaks present in the total-ion GC-MS chromatograms were chemically assigned in one of two ways. In the first, assignment was done by ensuring that both the retention time and the fragmentation mass spectrum corresponded to the retention time and fragmentation mass spectrum, respectively, of an authentic standard—this is referred to as "Method 1", and is essentially unambiguous. In the absence of authentic standards, only a tentative chemical assignment can be reached; this was done by collectively integrating the following data for the peak in question: (i) the structure of the fragmentation spectrum, especially with regard to the weight of the molecular ion, and to the degree to which it resembled a hydrocarbon-characteristic "envelope" mass spectrum, (ii) the retention time, especially with regard to its qualitative compatibility with the assigned compound, e.g., cis-unsaturated n-alkenes elute slightly before their saturated n-alkane counterparts, and (iii) the likelihood that the assigned compound is chemically compatible with the operation of the AAR-ADM and related pathways in the host organism in question, e.g., fatty aldehydes generated by AAR are expected to be converted to the corresponding fatty alcohols by host dehydrogenases in *E. coli* if they are not acted upon sufficiently quickly by ADM. This second approach to peak assignment is referred to as "Method 2". In the total-ion GC-MS chromatogram in FIG. 2, as well as in all such chromatograms in subsequent figures, peaks chemically assigned by Method 1 are labeled in regular font, whereas those assigned by Method 2 are labeled in italic font.

Figure 2:
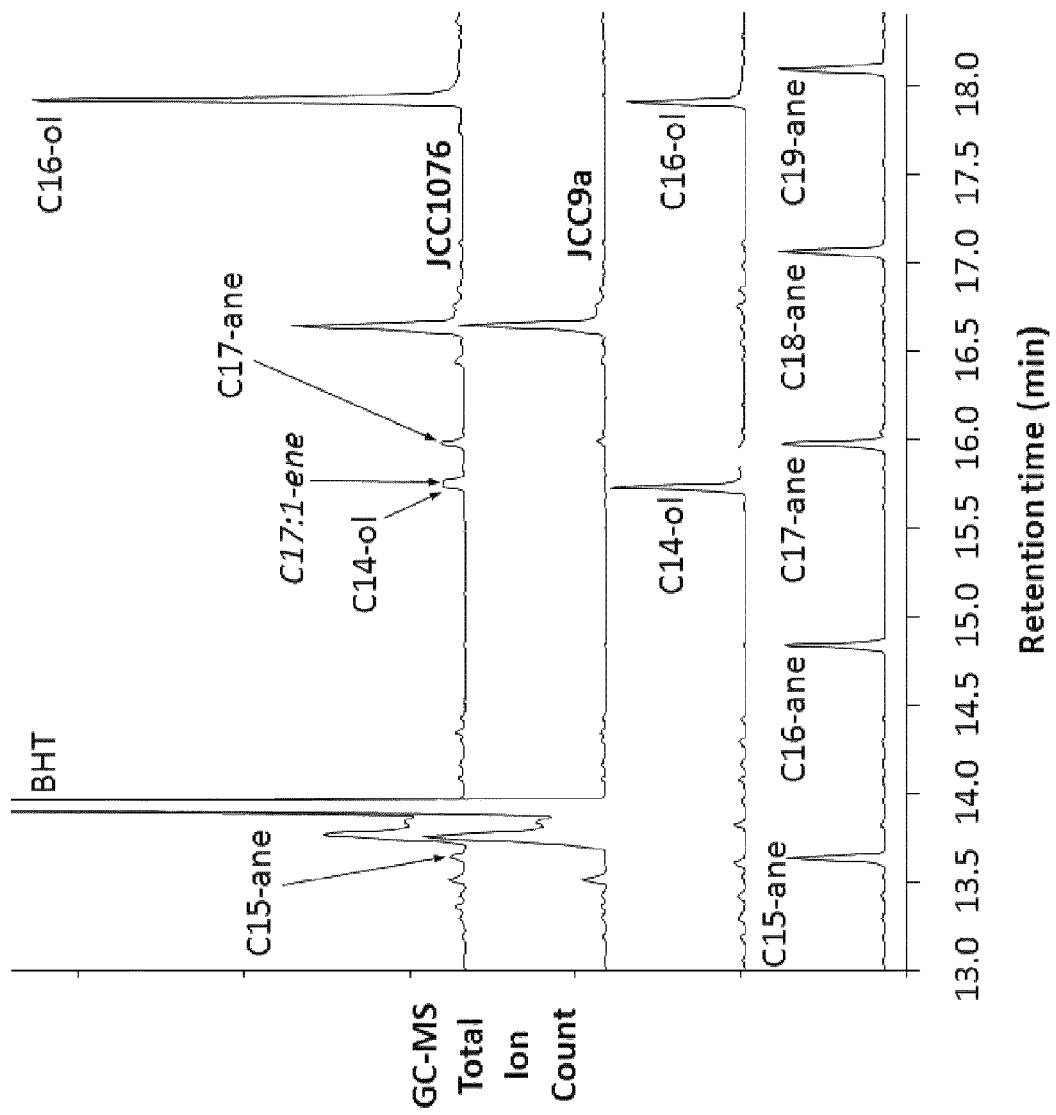
FIG. 2 represents 0-to-2700000-count total ion chromatograms of JCC9a and JCC1076 BHT (butylated hydroxytoluene)-acetone cell pellet extracts, as well as n-alkane and 1-alkanol authentic standards. Peaks assigned by Method 1 are identified in regular font, those by Method 2 in italic font.
Figure 3A:
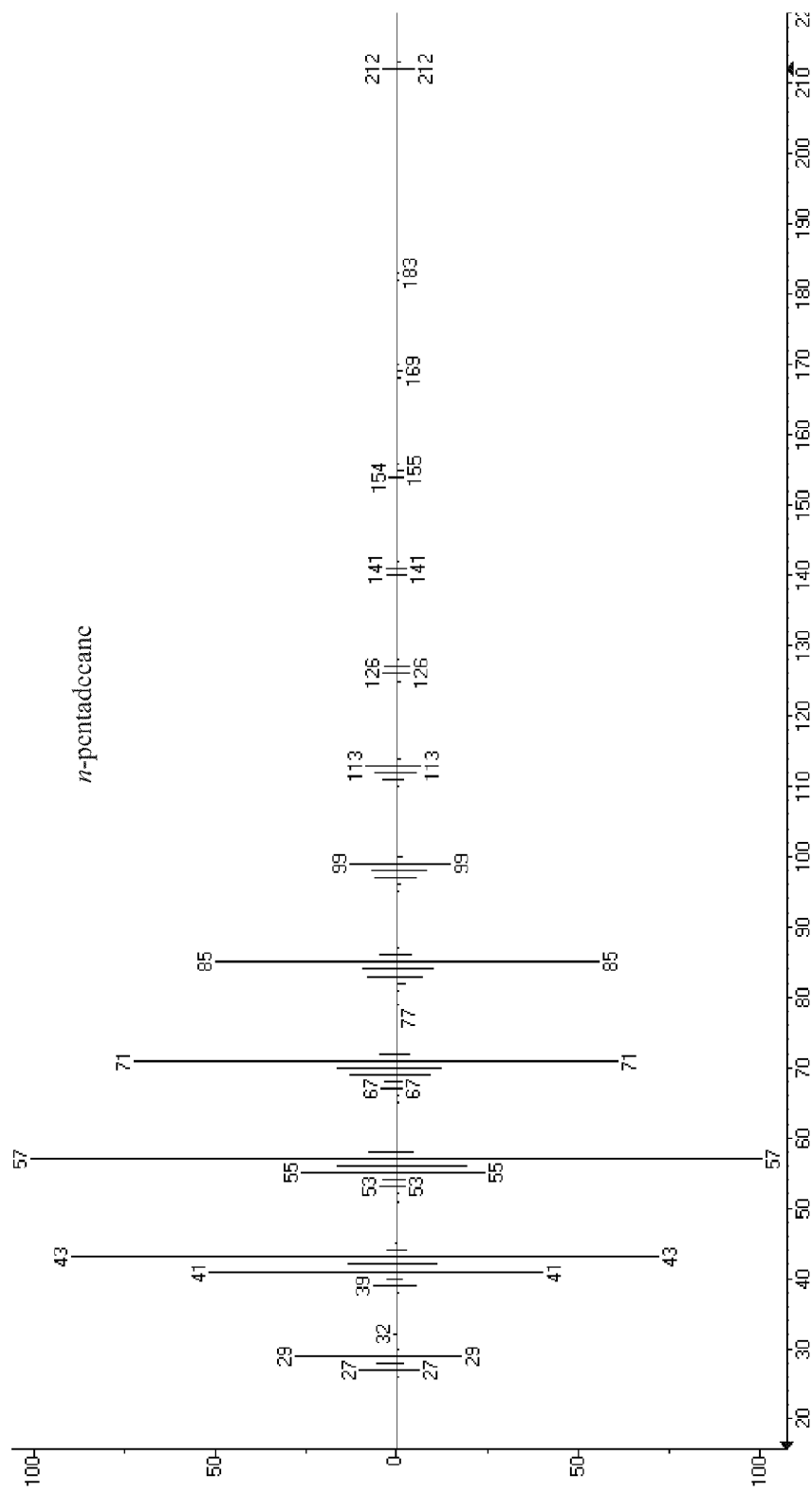
FIG. 3 depicts MS fragmentation spectra of JCC1076 peaks assigned by Method 1 (top mass spectrum of each panel), plotted against their respective NIST library hits (bottom mass spectrum of each panel). A, n-pentadecane; B, 1-tetradecanol; C, n-heptadecane; D, 1-hexadecanol.
Figure 3B:
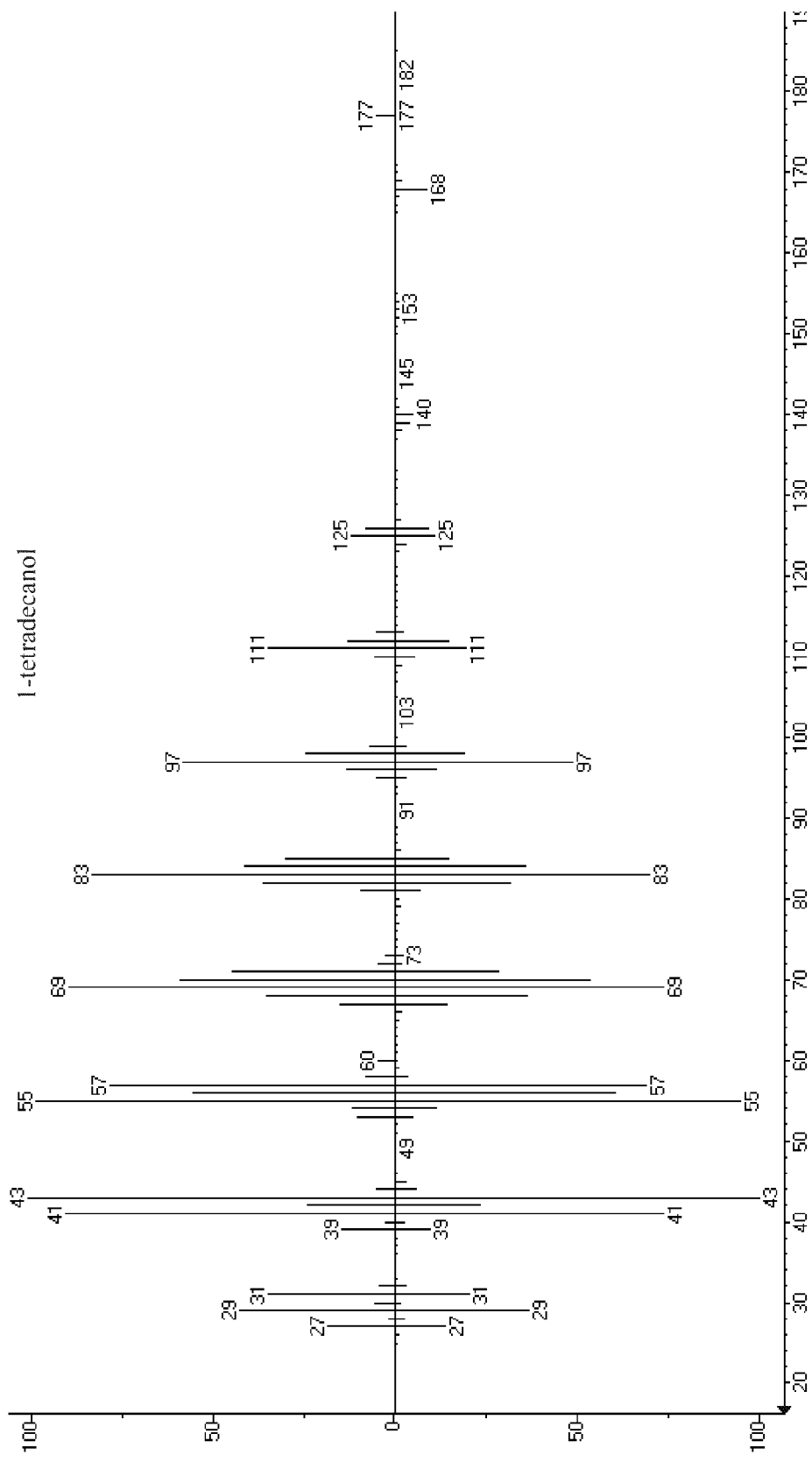
Figure 3C:
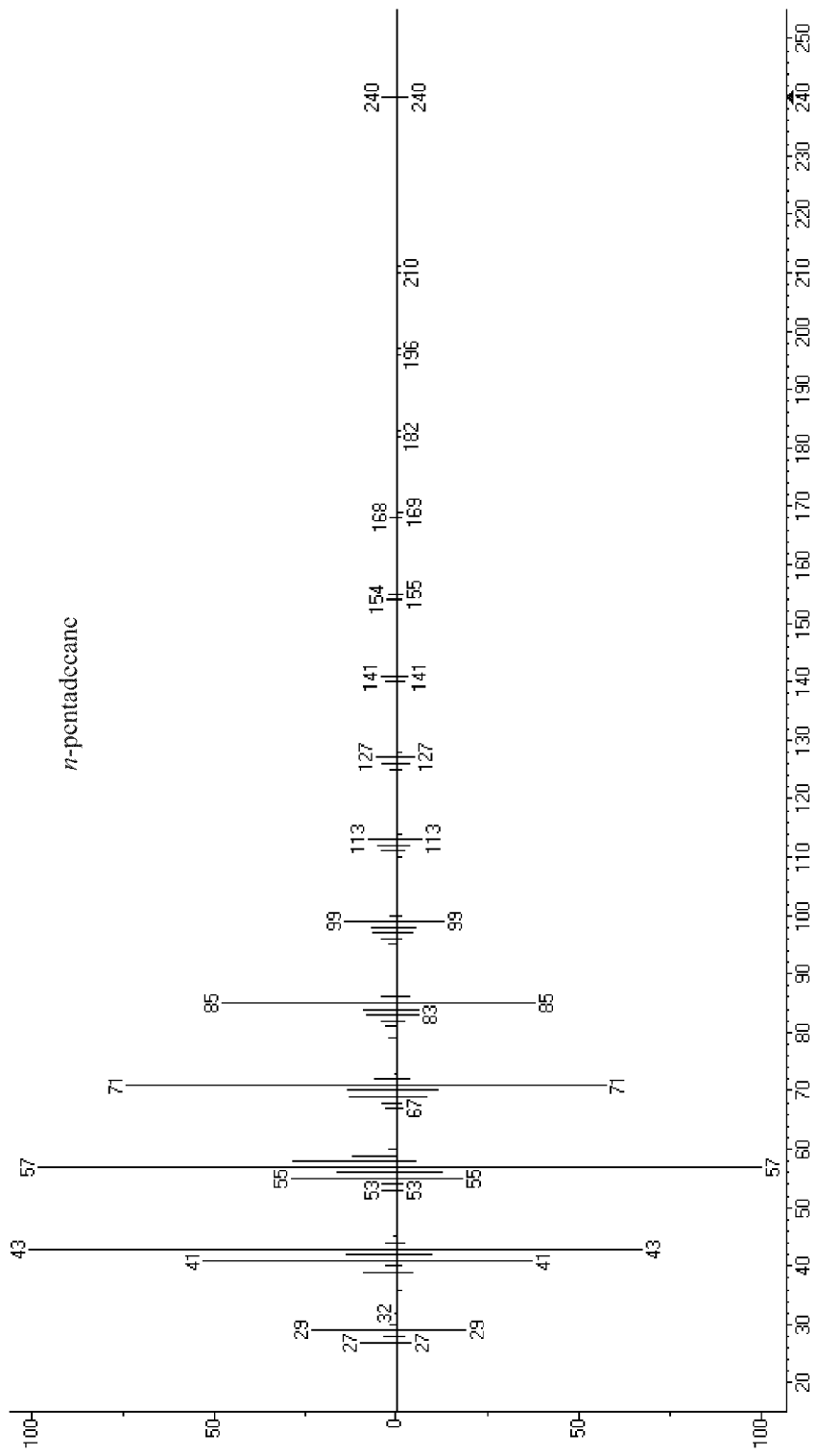
Figure 3D:
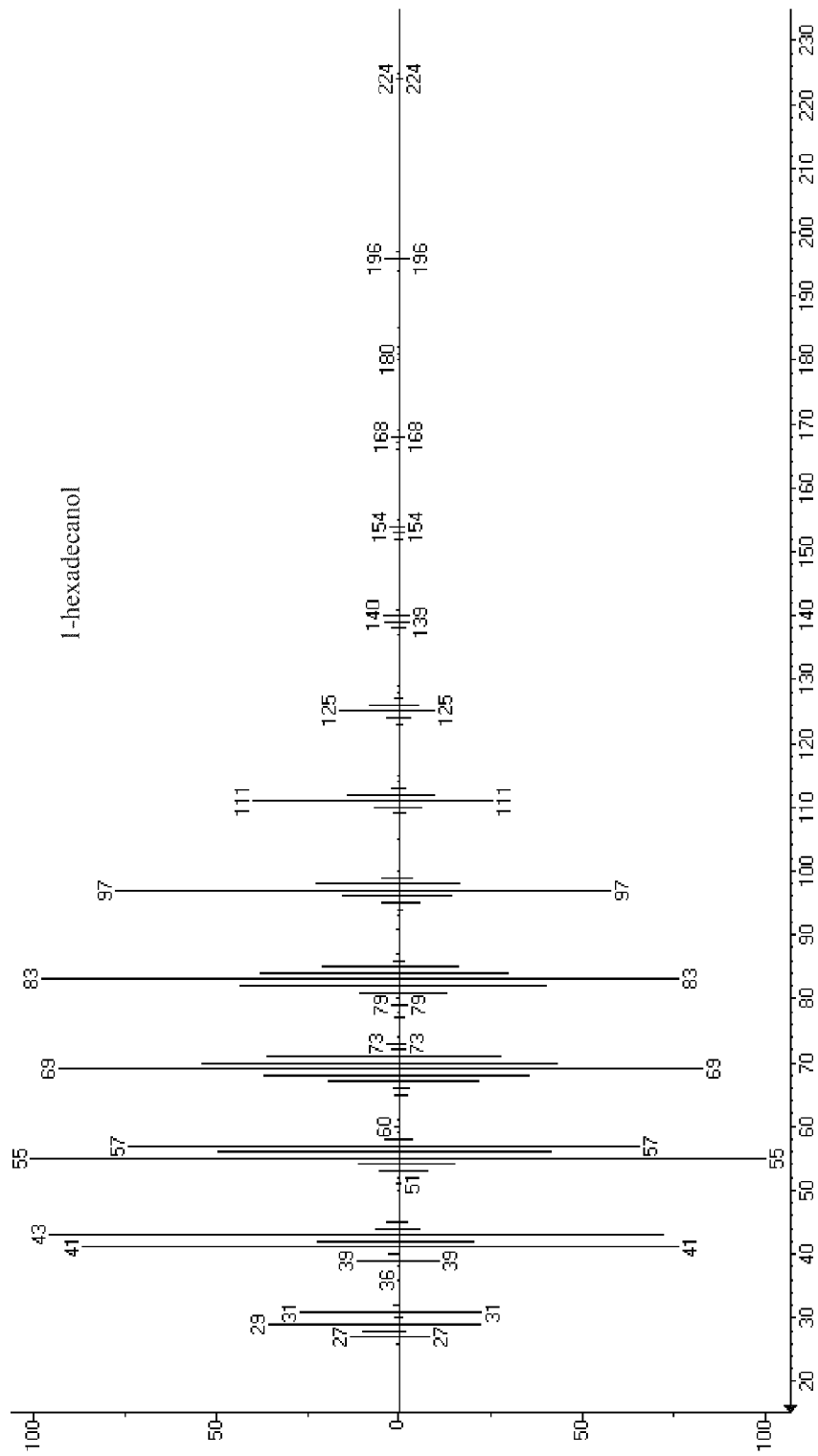

Total ion chromatograms (TICs) of JCC9a and JCC1076 acetone cell pellet extractants are shown in FIG. 2. The TICs of $C_8$-$C_{20}$ n-alkane authentic standards (Sigma 04070), as well as 1-tetradecanol (Sigma 185388) plus 1-hexadecanol (Sigma 258741) plus 1-octadecanol (Sigma 258768), are also shown. Hydrocarbons identified in JCC1076, but not in control strain JCC9a, are detailed in Table 3. These hydrocarbons are n-pentadecane (1), 1-tetradecanol (1), n-heptadecene (2), n-heptadecane (1), and 1-hexadecanol (1), where the number in parentheses indicates the GC-MS peak assignment method. MS fragmentation spectra of the Method 1 peaks are shown in FIG. 3, plotted against their respective library hits.

TABLE 3

Hydrocarbons detected by GC-MS in acetone cell pellet extractants of JCC1076 but not JCC9a, in increasing order of retention time.

| Compound | JCC9a | JCC1076 | GC-MS Peak Assigment | Candidate isomer |
| --- | --- | --- | --- | --- |
| n-pentadecane | − | + | Method 1 | |
| 1-tetradecanol | − | + | Method 1 | |
| n-heptadecene | − | + | Method 2 (envelope-type MS with molecular ion mass 238) | cis-7-heptadecene |
| n-pentadecane | − | + | Method 1 | |
| 1-hexadecanol | − | + | Method 1 | |

"−" not detected;
"+" detected.

The formation of these five products is consistent with both the expected incomplete operation, i.e., acyl-ACP→fatty aldehyde→fatty alcohol, and expected complete operation, i.e., acyl-ACP→fatty aldehyde→alkane/alkene, of the AAR-ADM pathway in *E. coli*, whose major straight-chain acyl-ACPs include 12:0, 14:0, 16:0, 18:0, 16:1Δ9cis, and 18:1Δ11cis acyl groups (Heipieper H J (2005); *Appl Environ Microbiol* 71:3388). Assuming that n-heptadecene (2) is derived 18:1Δ11cis-ACP, it would correspond to cis-7-heptadecene. Indeed, an n-heptadecene isomer was identified as the highest-confidence MS fragmentation library hit at that retention time, with the expected molecular ion of molecular weight 238; also, as expected, it elutes slightly before n-heptadecane.

Example 3

Production of n-Alkanes, n-Alkenes, and Fatty Alcohols in *Escherichia coli* B Through Heterologous Expression of *Synechococcus elongatus* PCC7942 SYNPCC7942_1593 (adm) and SYNPCC7942_1594 (aar)

The natural SYNPCC7942_1593-SYNPCC7942_1594 operonic sequence was excised from pJB823 using NdeI and EcoRI, and cloned into the commercial expression vector pCDFDuet™-1 (Novagen) cut with via NdeI and MfeI. The resulting plasmid was denoted pJB855 (SEQ ID NO: 16). This construct placed the SYNPCC7942_1593-SYN-PCC7942_1594 operon under the transcriptional control of the inducible T7lacO promoter.

Figure 4A:
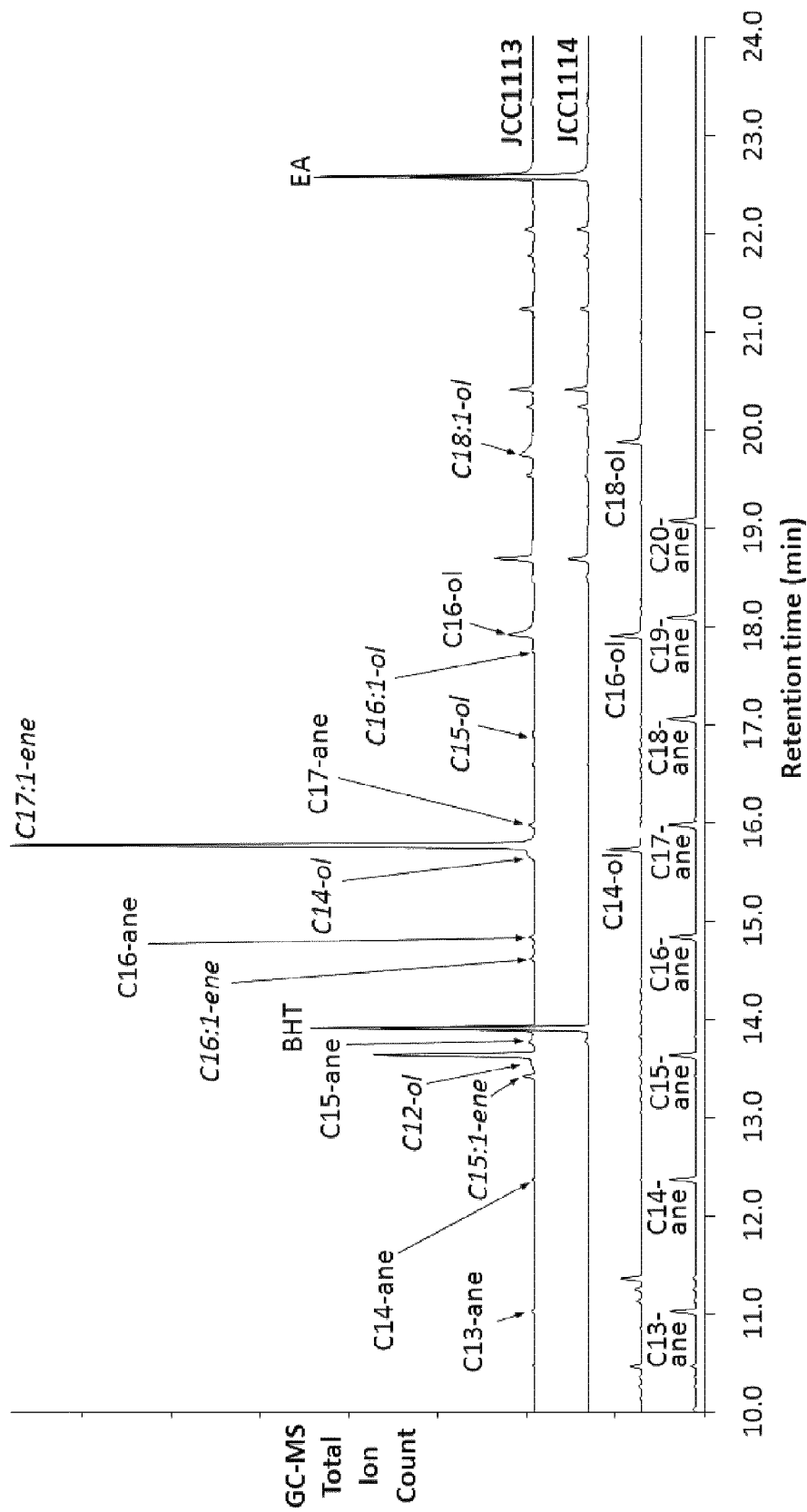
FIG. 4A represents 0-to-7500000-count total ion chromatograms for the BHT-acetone extracts of JCC1113 and JCC1114 cell pellets, as well as $C_{13}$-$C_{20}$ n-alkane and $C_{14}$, $C_{16}$, and $C_{18}$ n-alkanol authentic standards; B, represents 0-to-720000-count total ion chromatograms for BHT-acetone extracts of JCC1113 and JCC1114 cell pellets, as well as the n-alkane and n-alkanol authentic standards mentioned in 4A.
Figure 4B:
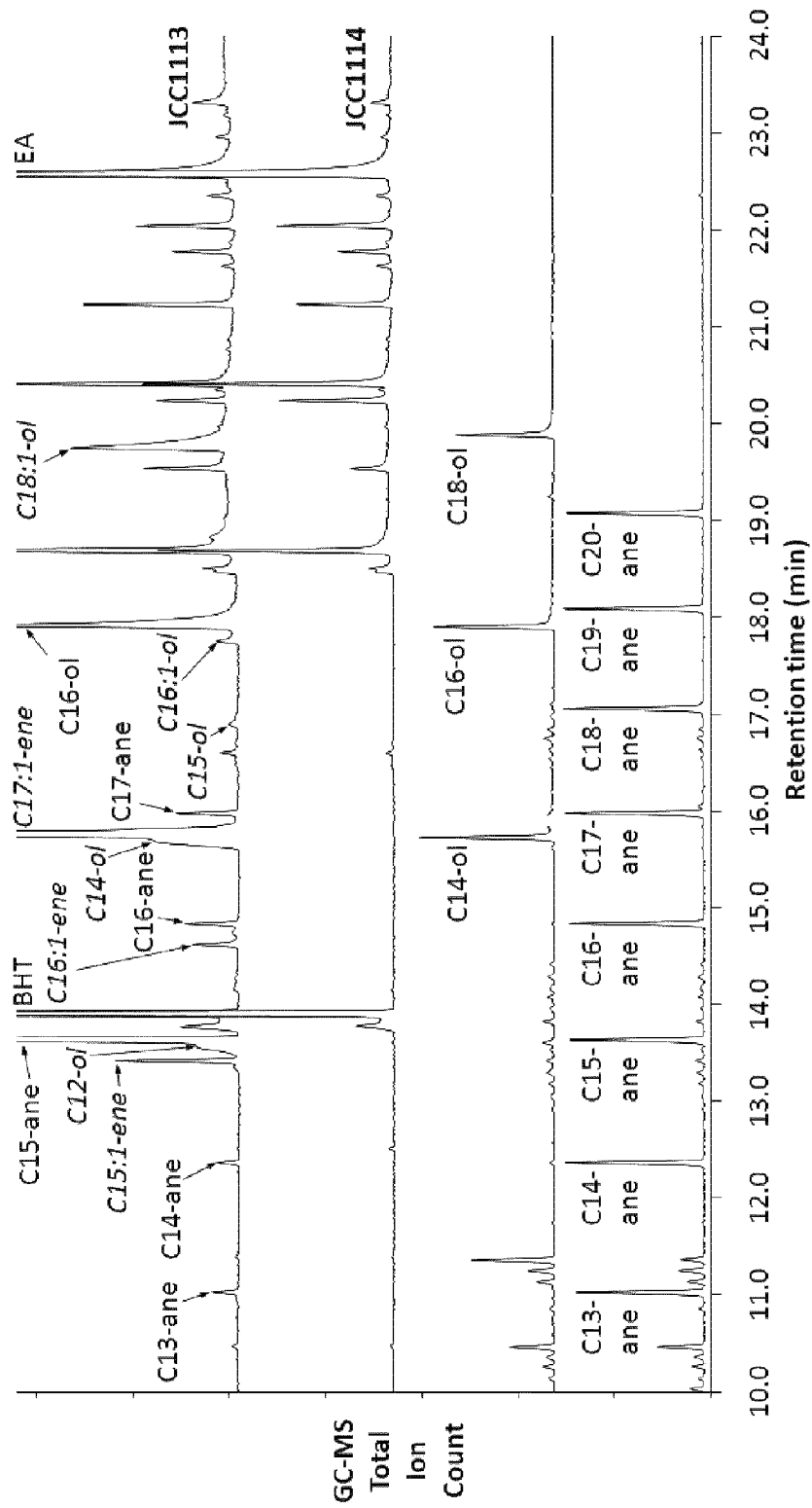
Figure 5A:
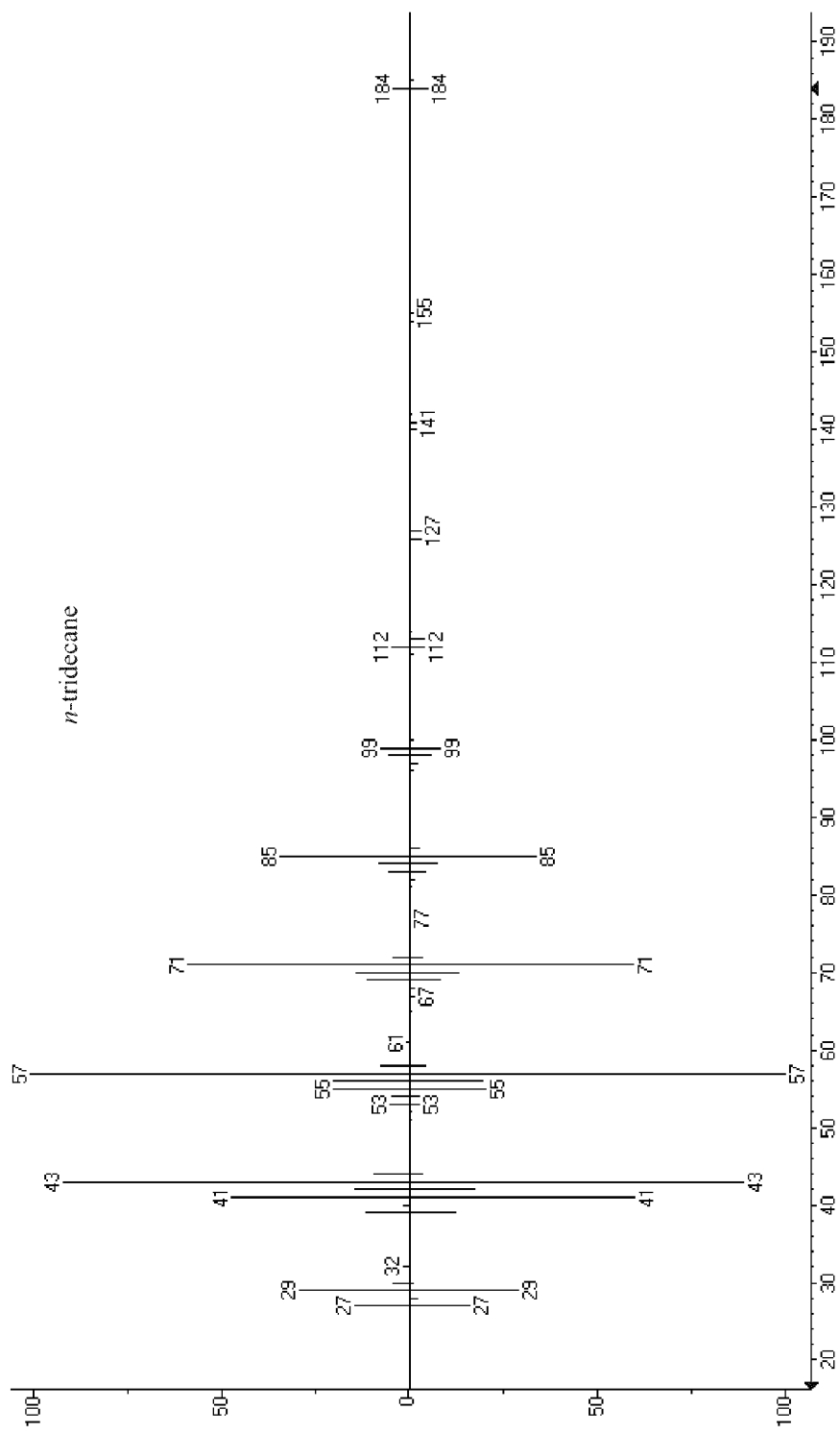
FIG. 5 depicts MS fragmentation spectra of JCC1113 peaks assigned by Method 1 (top mass spectrum of each panel), plotted against their respective NIST library hits (bottom mass spectrum of each panel). A, n-tridecane; B, n-tetradecane; C, n-pentadecane; D, n-hexadecane; E, n-heptadecane; F, 1-hexadecanol.
Figure 5B:
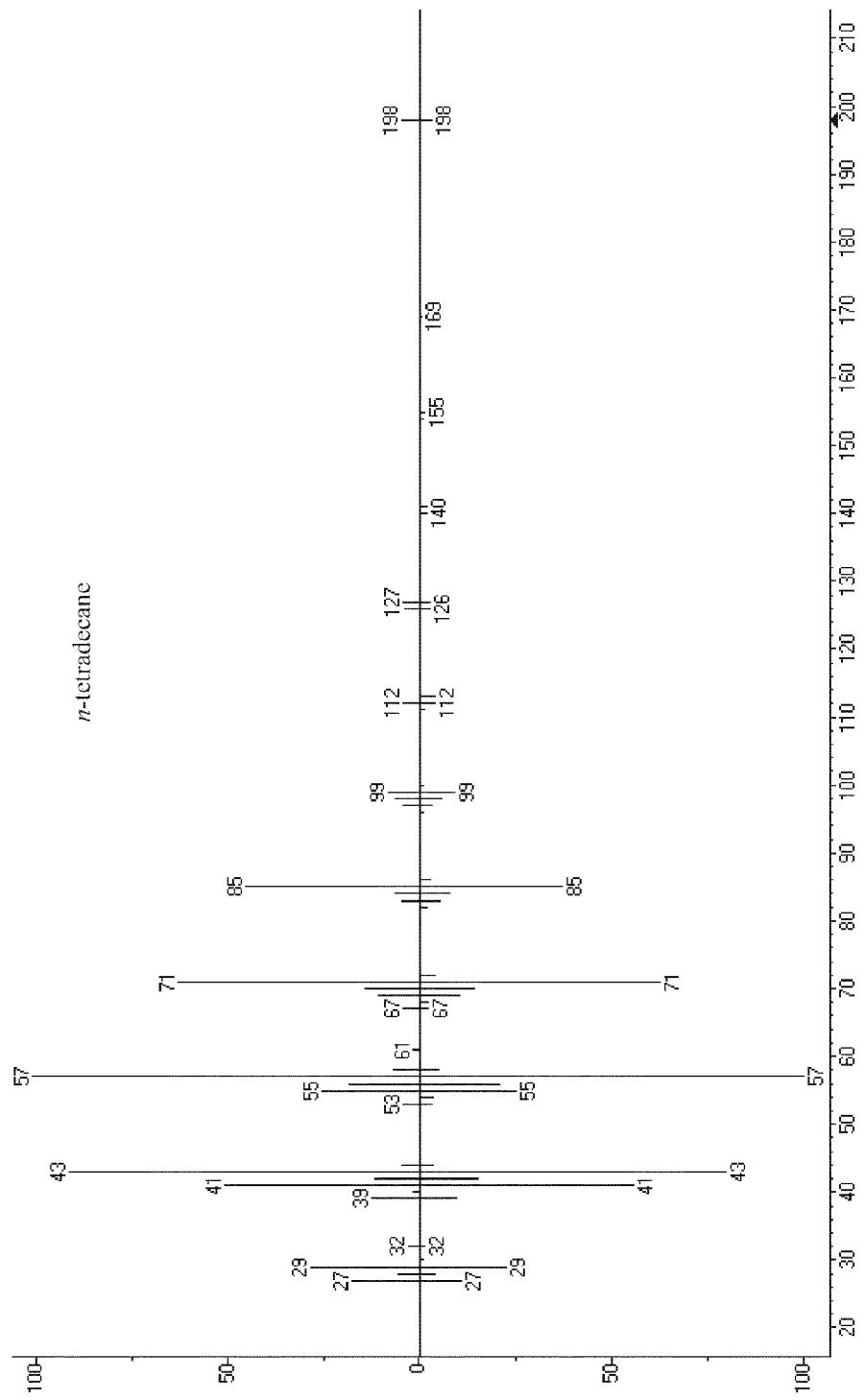
Figure 5C:
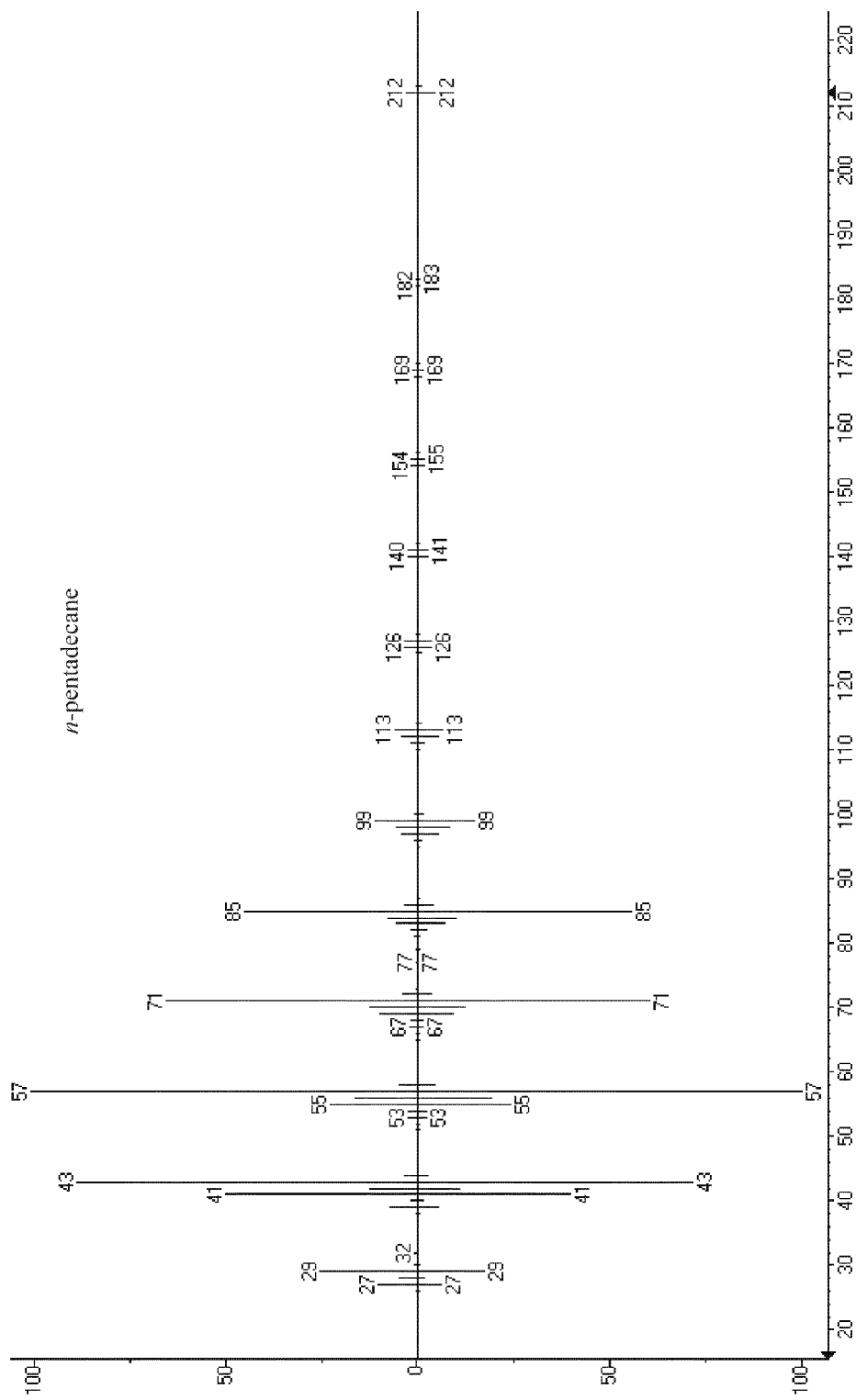
Figure 5D:
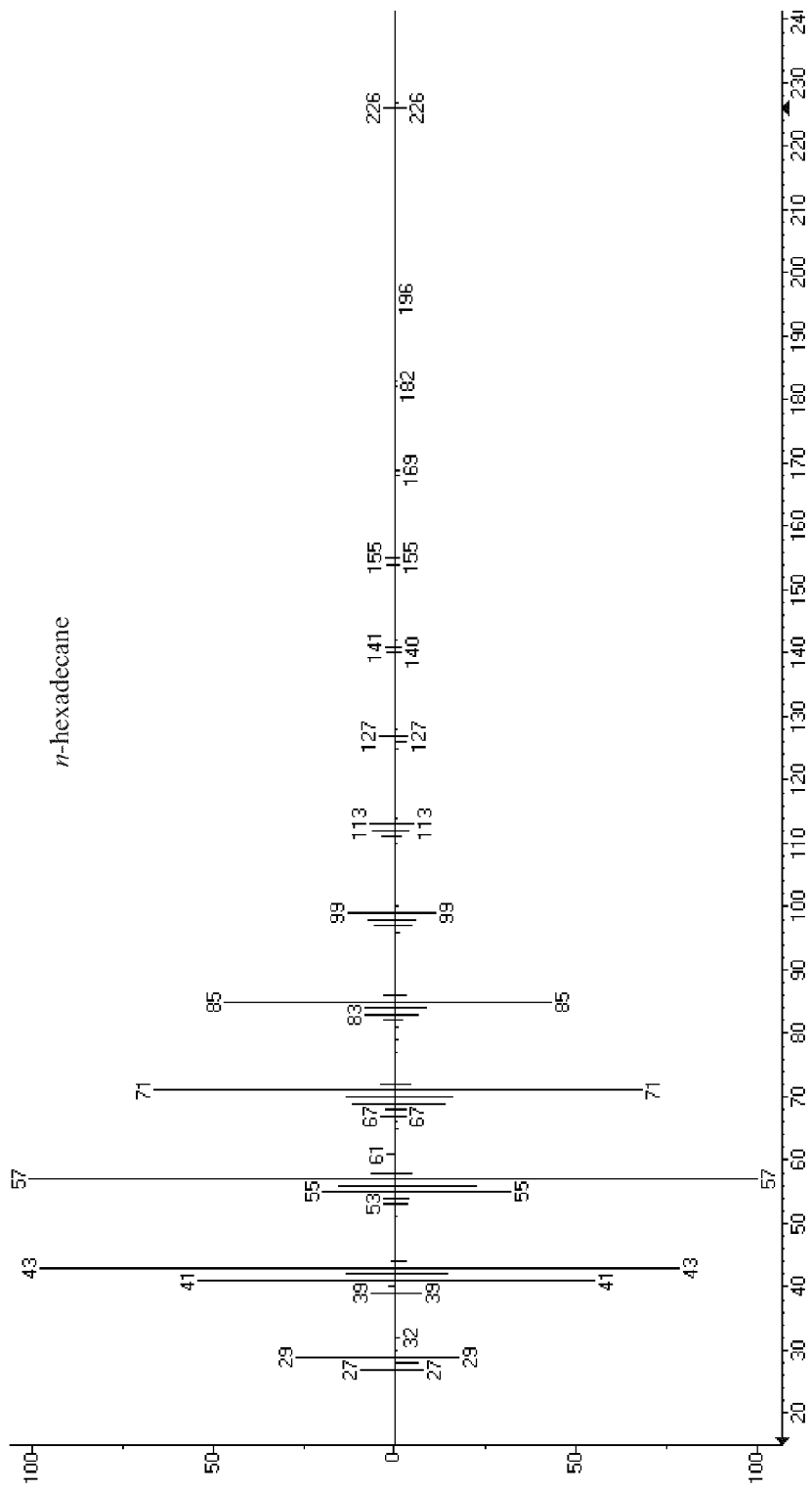
Figure 5E:
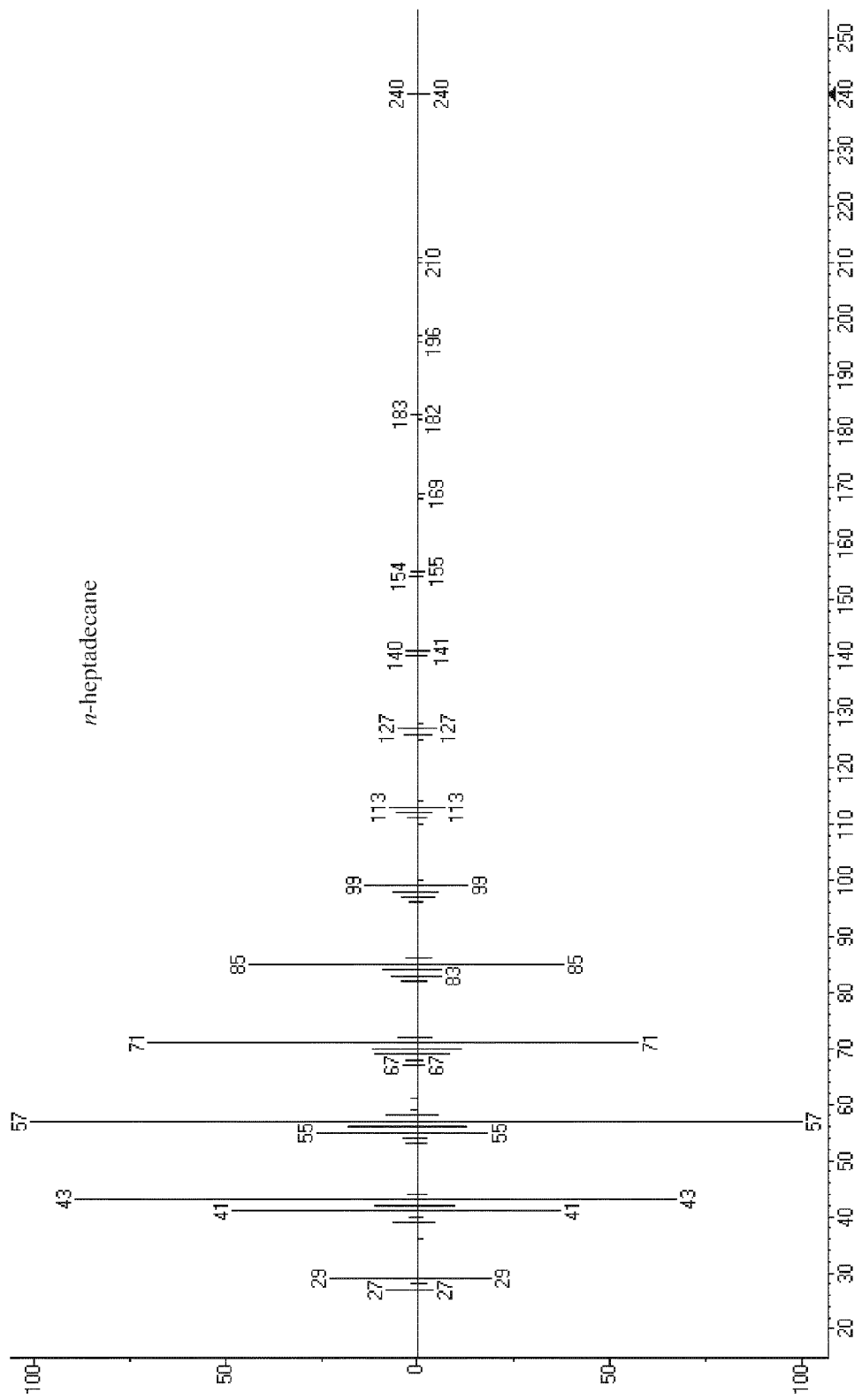
Figure 5F:
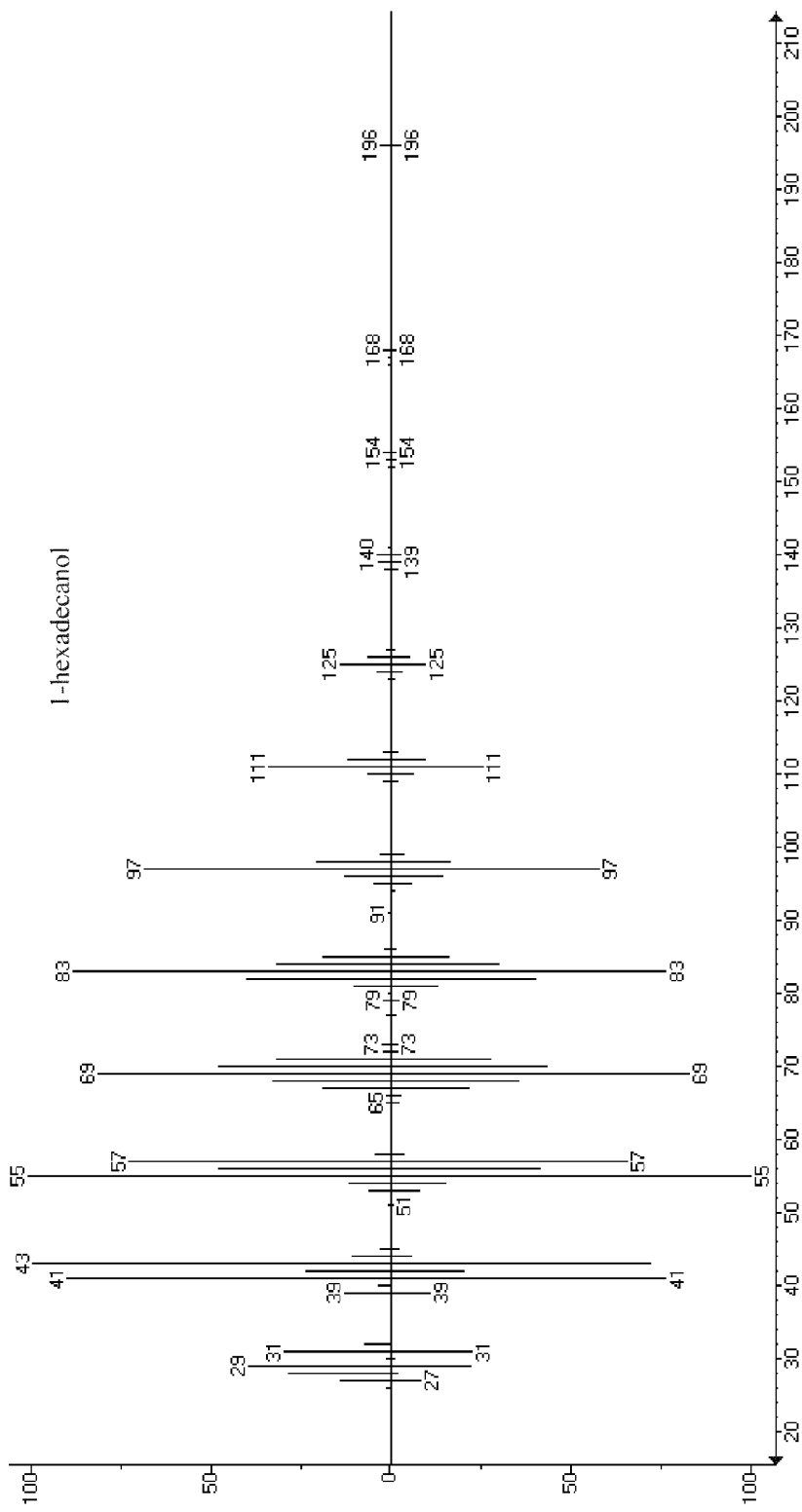

The intracellular hydrocarbon products of *E. coli* BL21 (DE3) (Novagen) harboring pJB855, JCC1113, were compared to those of *E. coli* BL21(DE3) harboring pCDFDuet™-1, the control strain JCC114, by gas chromatography-mass spectrometry (GC-MS). Starter clonal cultures of JCC1114 and JCC1113 were grown overnight at 37° C. in M9 minimal medium supplemented with 6 mg/l $FeSO_4 \cdot 7H_2O$, 50 µg/ml spectinomycin, and 2% glucose as carbon source; this medium is referred to M9fs. Each starter culture was used to inoculate a 32 ml culture of M9fs at an initial $OD_{600}$ of 0.1. Inoculated cultures were grown at 37° C. at 300 rpm until an $OD_{600}$ of 0.4 has been reached, at which point IPTG was added to a final concentration of 1 mM. After addition of inducer, cultures were grown under the same conditions for an additional 17 hours. For each strain, 12 ml of saturated culture was then collected by centrifugation. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 5 minutes in 0.7 ml acetone containing 20 µg/ml BHT and 20 µg/ml EA. Cell debris was pelleted by centrifugation, and 600 µl supernatant was pipetted into a GC vial. These JCC1114 and JCC1113 samples, along with authentic standards, were then analyzed by GC-MS as described in Example 2. The TICs of JCC1114 and JCC1113 acetone cell pellet extractants are shown in FIG. 4; n-alkane and 1-alkanol standards are as in Example 2. Hydrocarbons identified in JCC1113, but not in control strain JCC1114, are detailed in Table 4.

TABLE 4

Hydrocarbons detected by GC-MS in acetone cell pellet extractants of JCC1113 but not JCC1114 in increasing order of retention time.

| Compound | JCC1114 | JCC1113 | GC-MS Peak Assigment | Candidate isomer |
| --- | --- | --- | --- | --- |
| n-tridecane | − | + | Method 1 | |
| n-tetradecane | − | + | Method 1 | |
| n-pentadecene | − | + | Method 2 (envelope-type MS with molecular ion mass 210) | cis-7-pentadecene |
| 1-dodecanol | − | + | Method 2 | |
| n-pentadecane | − | + | Method 1 | |
| n-hexadecene | − | + | Method 2 (envelope-type MS with molecular ion mass 224) | cis-8-hexadecene |
| n-hexadecane | − | + | Method 1 | |
| 1-tetradecanol | − | + | Method 1 | |
| n-heptadecene | − | + | Method 2 (envelope-type MS with molecular ion mass 238) | cis-7-heptadecene |
| n-heptadecane | − | + | Method 1 | |
| 1-pentadecanol | − | + | Method 2 | |

TABLE 4-continued

Hydrocarbons detected by GC-MS in acetone cell pellet extractants of JCC1113 but not JCC1114 in increasing order of retention time.

| Compound | JCC1114 | JCC1113 | GC-MS Peak Assigment | Candidate isomer |
|---|---|---|---|---|
| 1-hexadecenol | − | + | Method 2 | cis-9-hexadecen-1-ol |
| 1-hexadecanol | − | + | Method 1 | |
| 1-octadecenol | − | + | Method 2 (envelope-type MS with molecular ion mass 250) | cis-11-octadecen-1-ol |

"−" not detected;
"+" detected.

These hydrocarbons are n-tridecane (1), n-tetradecane (1), n-pentadecene (2), 1-dodecanol (2), n-pentadecane (1), n-hexadecene (2), n-hexadecane (1), 1-tetradecanol (1), n-heptadecene (2), n-heptadecane (1), 1-pentadecanol (2), 1-hexadecenol (2), 1-hexadecanol (1), and 1-octadecenol (2), where the number in parentheses indicates the GC-MS peak assignment method. MS fragmentation spectra of Method 1 peaks are shown in FIG. 5, plotted against their respective library hits. The major products were n-pentadecane and n-heptadecene.

The formation of these fourteen products is consistent with both the expected incomplete operation, i.e., acyl-ACP→fatty aldehyde→fatty alcohol, and expected complete operation, i.e., acyl-ACP→fatty aldehyde→alkane/alkene, of the Aar-Adm pathway in *E. coli*, whose major straight-chain acyl-ACPs include 12:0, 14:0, 16:0, 18:0, 16:1Δ9cis, and 18:1Δ11 cis acyl groups (Heipieper H J (2005). Adaptation of *Escherichia coli* to Ethanol on the Level of Membrane Fatty Acid Composition. *Appl Environ Microbiol* 71:3388). Assuming that n-pentadecene (2) is derived 16:1Δ9cis-ACP, it would correspond to cis-7-pentadecene. Indeed, an n-pentadecene isomer was identified as the highest-confidence MS fragmentation library hit at that retention time, with the expected molecular ion of molecular weight 210; also, as expected, it elutes slightly before n-pentadecane. With respect to 1-dodecanol (2), a sufficiently clean fragmentation spectrum could not be obtained for that peak due to the overlapping, much larger n-pentadecane (1) peak. Its presence, however, is consistent with the existence of 12:0-ACP in *E. coli*, and its retention time is exactly that extrapolated from the relationship between 1-alkanol carbon number and observed retention time, for the 1-tetradecanol, 1-hexadecanol, and 1-octadecanol authentic standards that were run. Assuming that n-hexadecene (2) is derived from the trace-level unsaturated 17:1Δ9cis acyl group expected in the *E. coli* acyl-ACP population due to rare acyl chain initiation with propionyl-CoA as opposed to malonyl-CoA, it would correspond to cis-8-hexadecene. Indeed, an n-hexadecene isomer was identified as the highest-confidence MS fragmentation library hit at that retention time, with the expected molecular ion of molecular weight 224; also, as expected, it elutes slightly before n-hexadecane. Assuming that n-heptadecene (2) is derived 18:1Δ11cis-ACP, it would correspond to cis-7-heptadecene. Indeed, an n-heptadecene isomer was identified as the highest-confidence MS fragmentation library hit at that retention time, with the expected molecular ion of molecular weight 238; also, as expected, it elutes slightly before n-heptadecane. With respect to 1-pentadecanol (2), a sufficiently clean fragmentation spectrum could not be obtained for that peak due to its low abundance. Its presence, however, is consistent with the existence of trace-level 15:0 acyl group expected in the *E. coli* acyl-ACP population due to rare acyl chain initiation with propionyl-CoA as opposed to malonyl-CoA, and its retention time is exactly that interpolated from the relationship between 1-alkanol carbon number and observed retention time, for the 1-tetradecanol, 1-hexadecanol, and 1-octadecanol authentic standards that were run. In addition, 1-pentadecanol was identified as the highest-confidence MS fragmentation library hit at that retention time in acetone extracts of JCC1170, a BL21(DE3) derivative that expresses Aar without Adm (see Example 4). With respect to 1-hexadecenol (2), a sufficiently clean fragmentation spectrum could not be obtained for that peak due to its low abundance; however, assuming that it is derived 16:1Δ9cis-ACP, it would correspond to cis-9-hexadecen-1-ol. Also, as expected, it elutes slightly before 1-hexadecanol. Finally, assuming that n-octadecenol (2) is derived 18:11Δ9cis-ACP, it would correspond to cis-11-octadecen-1-ol. Indeed, an n-octadecen-1-ol isomer was identified as the highest-confidence MS fragmentation library hit at that retention time, with the expected molecular ion of molecular weight 250; also, as expected, it elutes slightly before 1-octadecanol.

Example 4

Production of Fatty Alcohols in *Escherichia coli* B Through Heterologous Expression of *Synechococcus elongatus* SYNPCC7942_1594 (aar) without Co-Expression of SYNPCC7942_1593 (adm)

In order to test the hypothesis that both AAR and ADM are required for alkane biosynthesis, as well as the prediction that expression of AAR alone should result in the production of fatty alcohols only in *E. coli* (due to non-specific dehydrogenation of the fatty aldehydes generated), expression constructs containing just SYNPCC7942_1593 (ADM) and just SYNPCC7942_1594 (AAR), were created. Accordingly, the SYNPCC7942_1593 and SYNPCC7942_1594 coding sequences were individually PCR-amplified and cloned via NdeI and MfeI into the commercial expression vector pCDFDuet™-1 (Novagen). The resulting plasmids were denoted pJB881 (SYNPCC7942_1593 only) and pJB882 (SYNPCC7942_1594 only); in each construct, the coding sequence was placed under the transcriptional control of the inducible T7lacO promoter.

The intracellular hydrocarbon products of *E. coli* BL21 (DE3) (Novagen) harboring pJB881, JCC1169, and of *E. coli* BL21(DE3) (Novagen) harboring pJB882, JCC1170, were compared to those of *E. coli* BL21(DE3) harboring pCDF-Duet™-1, the negative control strain JCC114, as well as to the positive control SYNPCC7942_1593-SYNPCC7942_1594 strain JCC1113 (Example 3), by gas chromatography-mass spectrometry (GC-MS). Clonal cultures of JCC1169, JCC1170, JCC1114, and JCC1113 were grown, extracted, and analyzed by GC-MS as described in Example 3, with the following exception: the JCC1170 culture was grown overnight in M9fs medium without IPTG, because the culture did not grow if IPTG was added. Presumably, this was due to the toxic over-accumulation of fatty alcohols that occurred even in the absence of inducer.

Figure 6:
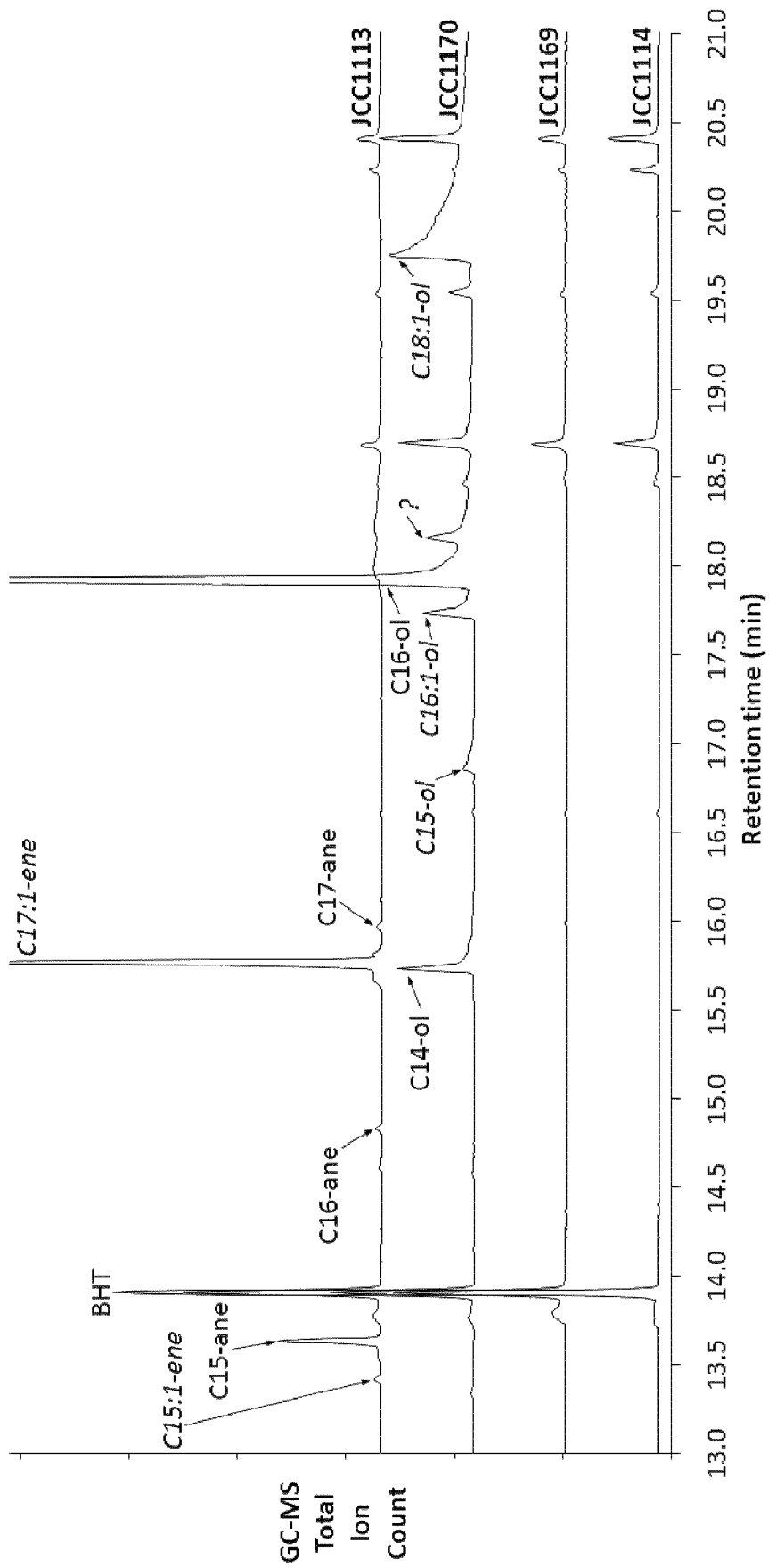
FIG. 6 represents 0-to-6100000-count total ion chromatograms of JCC1170 and JCC1169 BHT-acetone cell pellet extracts versus those of the control strains JCC1113 and JCC1114. No hydrocarbon products were observed in JCC1169. The unidentified peak in JCC1170 is likely cis-11-octadecenal.

The TICs of JCC1169, JCC1170, JCC1114, and JCC1113 acetone cell pellet extractants are shown in FIG. 6; n-alkane and 1-alkanol standard traces have been omitted. Hydrocarbons identified in JCC1170, but not in control strain JCC1114, are detailed in Table 5.

TABLE 5

Hydrocarbons detected by GC-MS in acetone cell pellet extractants of JCC1170 but not JCC1114 in increasing order of retention time.

| Compound | JCC1114 | JCC1170 | GC-MS Peak Assigment | Candidate isomer |
|---|---|---|---|---|
| 1-tetradecanol | − | + | Method 1 | |
| 1-pentadecanol | − | + | Method 2 (envelope-type MS with molecular ion mass 182) | |
| 1-hexadecenol | − | + | Method 2 (envelope-type MS with molecular ion mass 222) | cis-9-hexadecen-1-ol |
| 1-hexadecanol | − | + | Method 1 | |
| 1-octadecenol | − | + | Method 2 (envelope-type MS with molecular ion mass 250) | cis-11-octadecen-1-ol |

"−" not detected.
"+" detected.

Figure 7A:
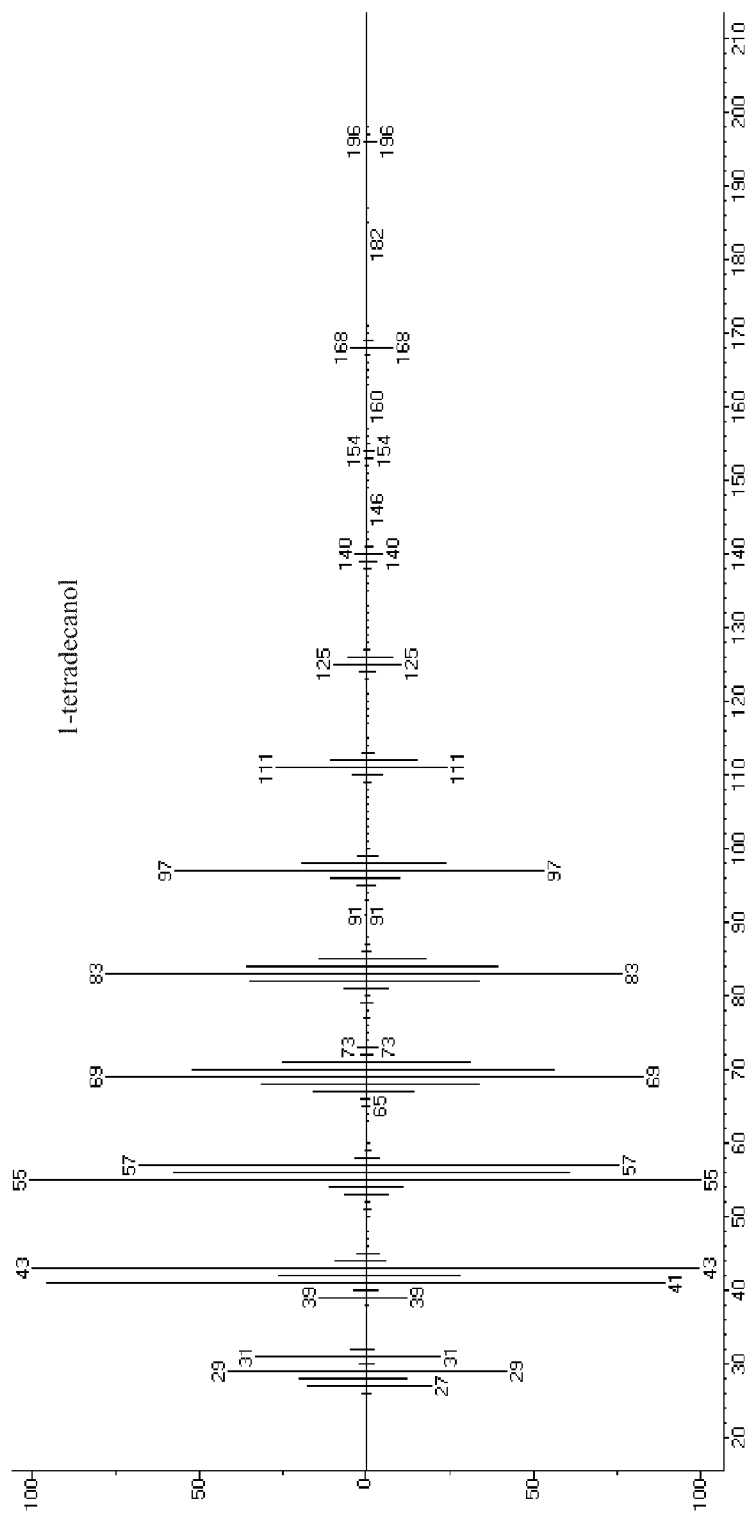
FIG. 7 depicts MS fragmentation spectra of JCC1170 peaks assigned by Method 1 (top mass spectrum of each panel), plotted against their respective NIST library hits (bottom mass spectrum of each panel). A, 1-tetradecanol; B, 1-hexadecanol.
Figure 7B:
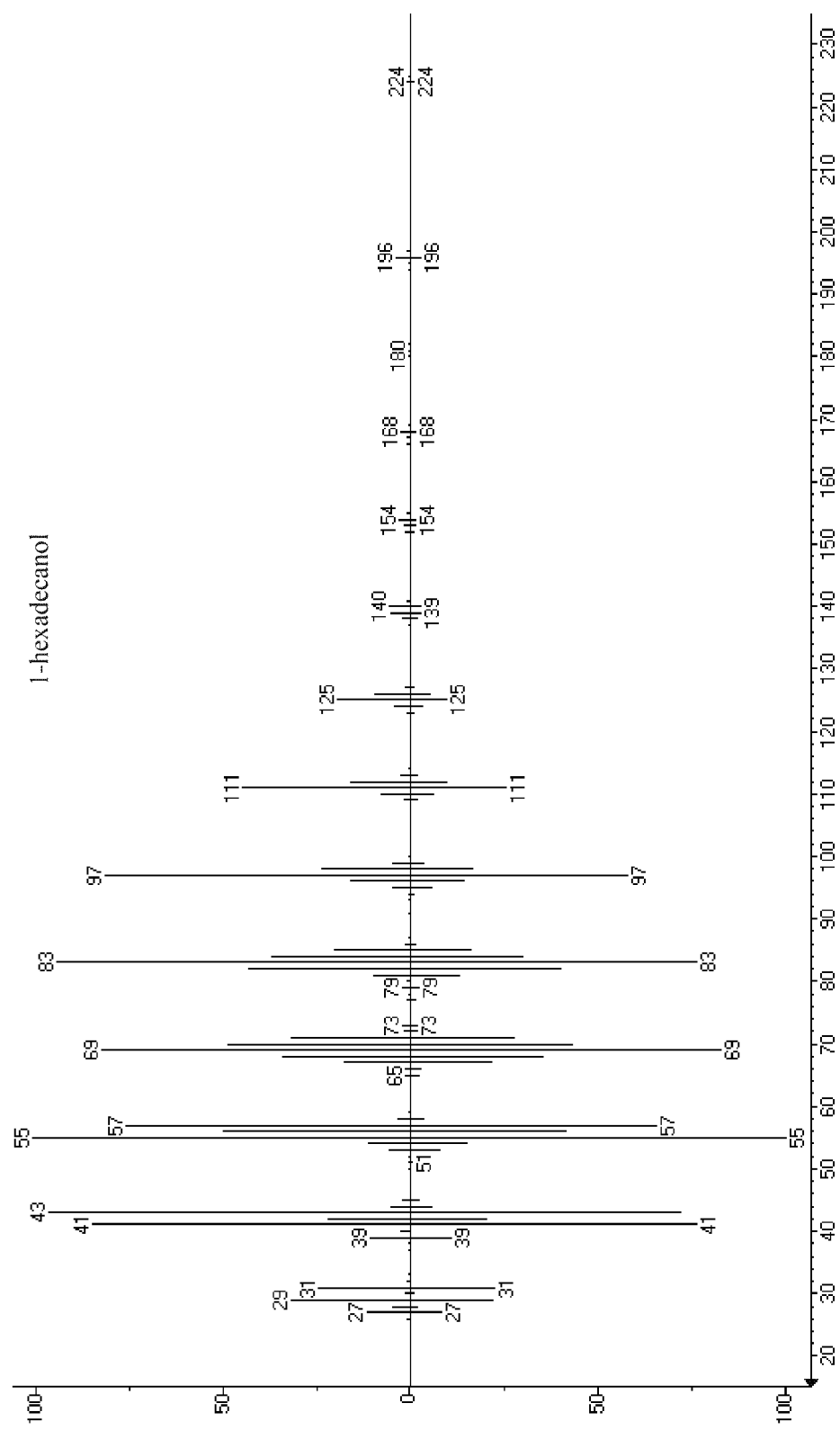

These hydrocarbons are 1-tetradecanol (1), 1-pentadecanol (2), 1-hexadecenol (2), 1-hexadecanol (1), and 1-ocadecenol (2), where the number in parentheses indicates the GC-MS peak assignment method. MS fragmentation spectra of Method 1 peaks are shown in FIG. 7, plotted against their respective library hits. No hydrocarbons were identified in JCC1169, whose trace was indistinguishable from that of JCC1114, as expected owing to absence of fatty aldehyde substrate generation by AAR.

The lack of production of alkanes, alkenes, and fatty alkanols in JCC1169, the production of only fatty alcohols in JCC1170, and the production of alkanes, alkenes, and fatty alkanols in JCC1113 (as discussed in Example 3) are all consistent with the proposed mechanism of alkane biosynthesis by AAR and ADM in *E. coli*. Thus, the formation of the five fatty alcohols in JCC1170 is consistent with only AAR being active, and active on the known straight-chain acyl-ACPs (see Example 3). With respect to 1-pentadecanol (2), its presence is consistent with the existence of trace-level 15:0 acyl group expected in the *E. coli* acyl-ACP population due to rare acyl chain initiation with propionyl-CoA as opposed to malonyl-CoA and its retention time is exactly that interpolated from the relationship between 1-alkanol carbon number and observed retention time, for the 1-tetradecanol, 1-hexadecanol, and 1-octadecanol authentic standards that were run. Most importantly, the 1-pentadecanol (2) peak exhibits an envelope-type fragmentation mass spectrum, with the expected molecular ion of molecular weight 182. Unlike in the case of JCC1113, a clean fragmentation spectrum from the candidate 1-hexadecenol peak could now be obtained due to increased abundance. The top library hit was a 1-hexadecenol with the expected molecular ion of molecular weight 222. Assuming that it is derived from 16:1Δ9cis hexadecenyl-ACP, the isomeric assignment would be cis-9-hexadecen-1-ol; also, as expected, it elutes slightly before 1-hexadecanol. Assuming that n-octadecenol (2) is derived 18:11Δ9cis-ACP, it would correspond to cis-11-octadecen-1-ol. Indeed, an n-octadecen-1-ol isomer was identified as the highest-confidence MS fragmentation library hit at that retention time, with the expected molecular ion of molecular weight 250; also, as expected, it elutes slightly before 1-octadecanol. There is also an unidentified side peak in JCC1170 that elutes in the tail of 1-hexadecenol and whose fragmentation mass spectrum was not sufficiently clean to enable possible identification. It is hypothesized that this could be the primary $C_{1-8}$ aldehyde product expected of AAR-only activity in *E. coli*, i.e., cis-11-octadecenal.

Example 5

Production of n-Alkanes, n-Alkenes, and Fatty Alcohol in *Synechococcus* sp. PCC 7002 Through Heterologous Expression of *Synechococcus elongatus* PCC7942 SYNPCC7942_1593 (adm) and SYNPCC7942_1594 (aar)

In order to test whether heterologous expression of AAR and ADM would lead to the desired alkane biosynthesis in a cyanobacterial host, the SYNPCC7942_1593-SYNPCC7942_1594 operon was expressed in *Synechococcus* sp. PCC 7002 (JCC138). Accordingly, plasmid pJB823 was transformed into JCC138, generating strain JCC1160. The sequence and annotation of this plasmid is provided as SEQ ID NO: 15, and described in Example 2. In this construct, the SYNPCC7942_1593-SYNPCC7942_1594 operon is placed under the transcriptional control of the constitutive aphII promoter. 500 base pair upstream and downstream homology regions direct homologous recombinational integration into the native high-copy pAQ1 plasmid of JCC138, and an aadA gene permits selection of transformants by virtue of their resistance to spectinomycin.

To test the effect of potentially stronger promoters, constructs directly analogous to pJB823 were also generated that substituted the aphII promoter with the following: the promoter of cro from lambda phage (PcI), the promoter of cpcB from *Synechocystis* sp. PCC 6803 (PcpcB), the trc promoter along with an upstream copy of a promoter-lacI cassette (PlacI-trc), the synthetic EM7 promoter (PEM7). Promoters were exchanged via the NotI and NdeI sites flanking the promoter upstream of the SYNPCC7942_1593-SYNPCC7942_1594 operon in the pJB823 vector. The corresponding final plasmids were as follows: pJB886 (PcI), pJB887 (PcpcB), pJB889 (PlacI-trc), pJB888 (PEM7), and pJB823 (PaphII). These sequences of pJB886, pJB887, pJB889, and pJB888 are identical to the sequence of pJB823 except in the region between the NotI and NdeI sites, where they differ according to the promoter used. The sequences of the different promoter regions are provided as SEQ ID NO: 19 (PcI), SEQ ID NO: 20 (PcpcB), SEQ ID NO: 21 (PlacI-trc), and SEQ ID NO: 22 (PEM7). The sequence of the PaphII promoter is presented in SEQ ID NO: 15.

pJB886, pJB887, pJB889, pJB888, pJB823, as well as pJB5 (the empty pAQ1 targeting vector that entirely lacked the SYNPCC7942_1593-SYNPCC7942_1594 operonic sequence) were naturally transformed into JCC138 using a standard cyanobacterial transformation protocol, generating strains JCC1221 (PcI), JCC1220 (PcpcB), JCC1160b (PlacI-trc), JCC1160a (PEM7), JCC1160 (PaphII), and JCC879 (pJB5), respectively. Briefly, 5-10 µg of plasmid DNA was added to 1 ml of neat JCC138 culture that had been grown to an $OD_{730}$ of approximately 1.0. The cell-DNA mixture was incubated at 37° C. for 4 hours in the dark with gentle mixing, plated onto A+ plates, and incubated in a photoincubator (Percival) for 24 hours, at which point spectinomycin was underlaid to a final concentration of 50 µg/ml. Spectinomycin-resistant colonies appeared after 5-8 days of further incubation under 24 hr-light conditions (~100 µmol photons $m^{-2}$ $s^{-1}$). Following one round of colony purification on A+ plates supplemented with 100 µg/ml spectinomycin, single colonies of each of the six transformed strains were grown in test-tubes for 4-8 days at 37° C. at 150 rpm in 3% $CO_2$-enriched air at ~100 µmol photons $m^{-2}$ $s^{-1}$ in a Multitron II (Infors) shaking photoincubator. The growth medium used for liquid culture was A+ with 200 µg/ml spectinomycin.

In order to compare the intracellular hydrocarbon products of strains JCC1221, JCC1220, JCC1160b, JCC1160a, JCC1160, and JCC879, 24 $OD_{730}$-ml worth of cells (~2.4× $10^9$ cells) of each strain was collected from the aforementioned test-tube cultures by centrifugation. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 5 minutes in 0.7 ml acetone containing 20 µg/ml BHT and 20 µg/ml EA. Cell debris was pelleted by centrifugation, and 600 µl supernatant was pipetted into a GC vial. The six extractants, along with authentic standards, were then analyzed by GC-MS as described in Example 2.

Figure 8A:
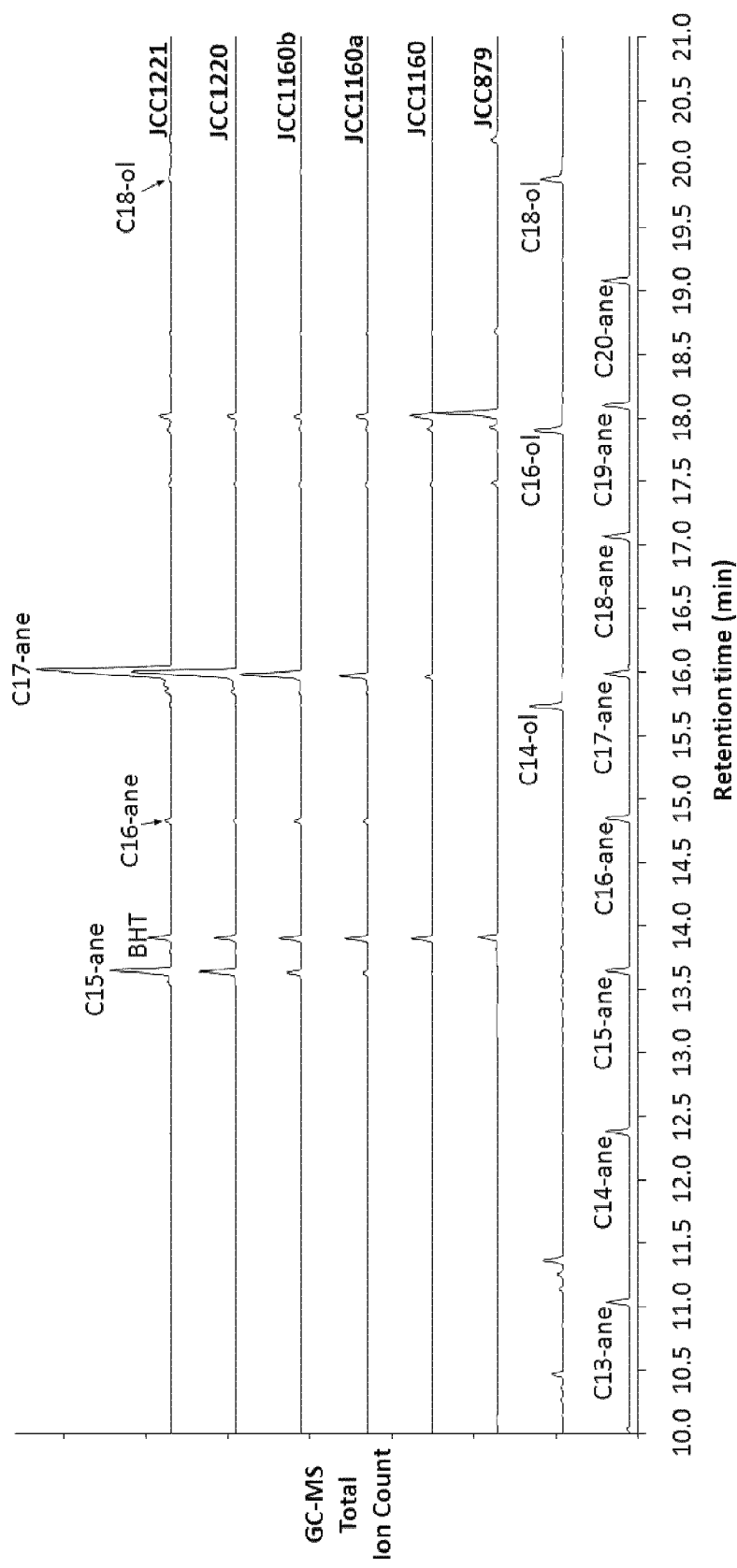
FIG. 8A represents 0-to-75000000-count total ion chromatograms for BHT-acetone extracts of JCC1221, JCC1220, JCC1160b, JCC1160a, JCC1160 and JCC879 cell pellets, as well as $C_{13}$-$C_{20}$ n-alkane and $C_{14}$, $C_{16}$, and $C_{18}$ n-alkanol authentic standards. The doublet around 18.0 minutes corresponds to nonadec-di-ene and 1-nonadecene, respectively (data not shown), n-alkenes that are naturally produced by JCC138; 8B represents 0-to-2250000-count total ion chromatograms for BHT-acetone extracts of JCC1221 and JCC879 cell pellets, as well as the n-alkane and n-alkanol authentic standards mentioned in 8A.
Figure 8B:
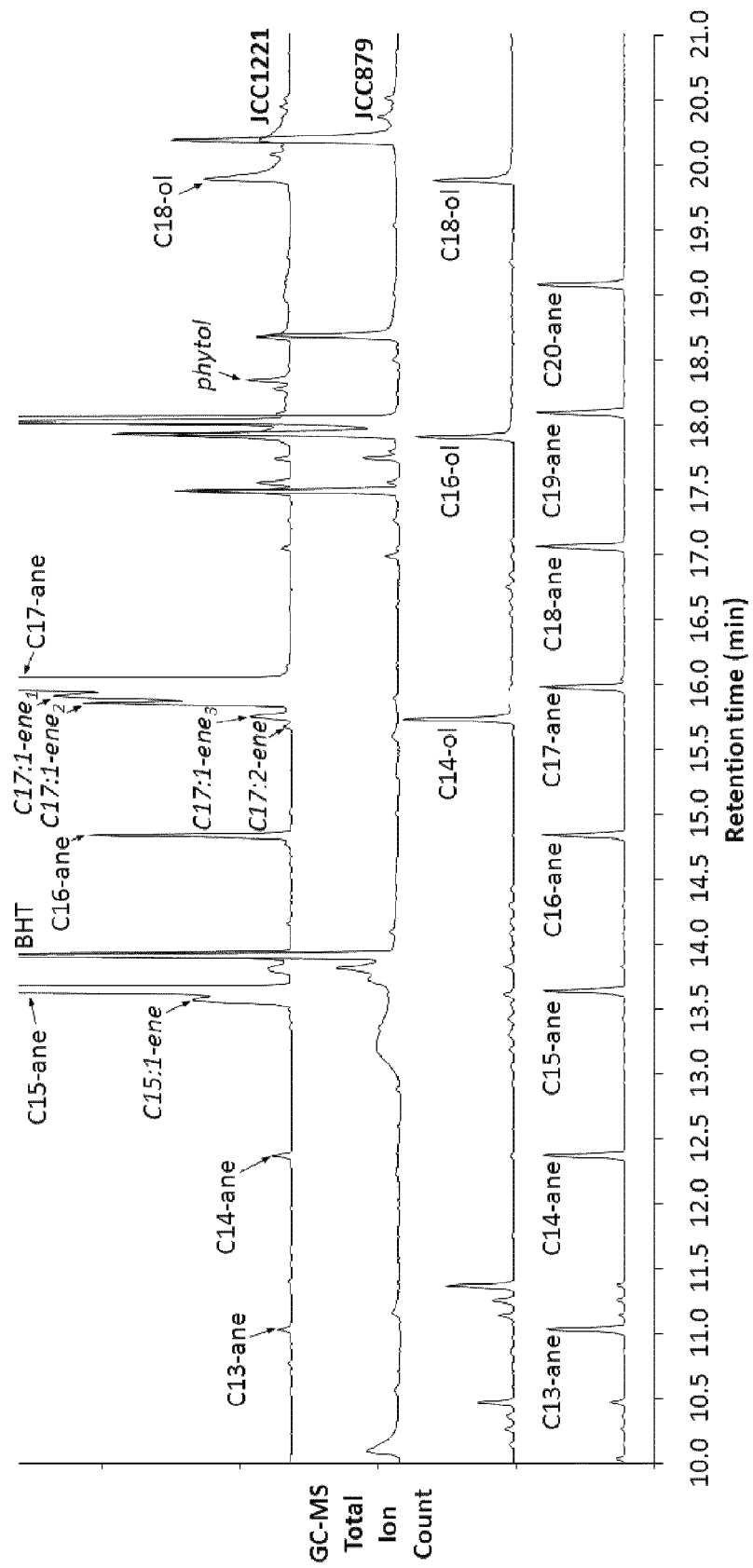
Figure 9A:
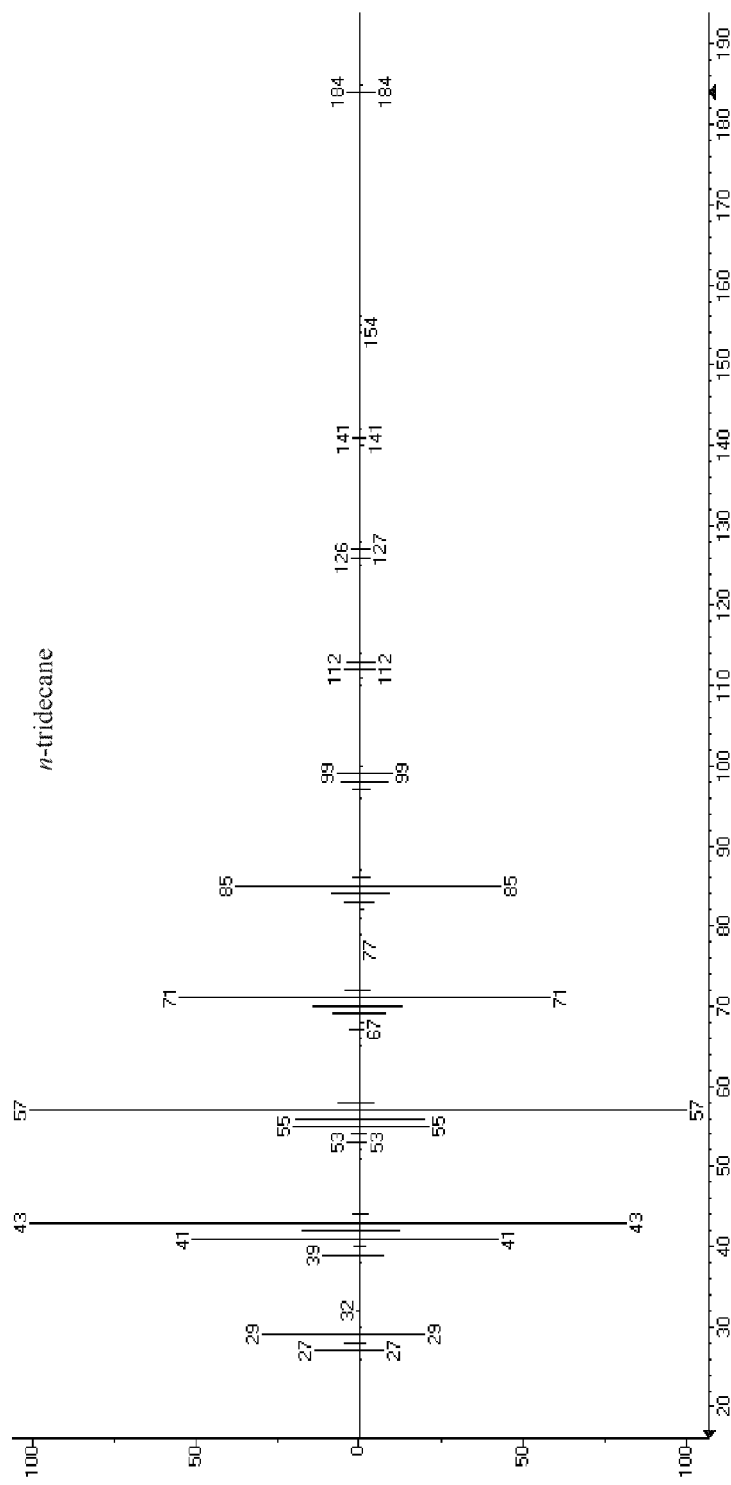
FIG. 9 depicts MS fragmentation spectra of JCC1221 peaks assigned by Method 1 (top mass spectrum of each panel), plotted against their respective NIST library hits (bottom mass spectrum of each panel). A, n-tridecane; B, n-tetradecane; C, n-pentadecane; D, n-hexadecane; E, n-heptadecane; F, 1-octadecanol.
Figure 9B:
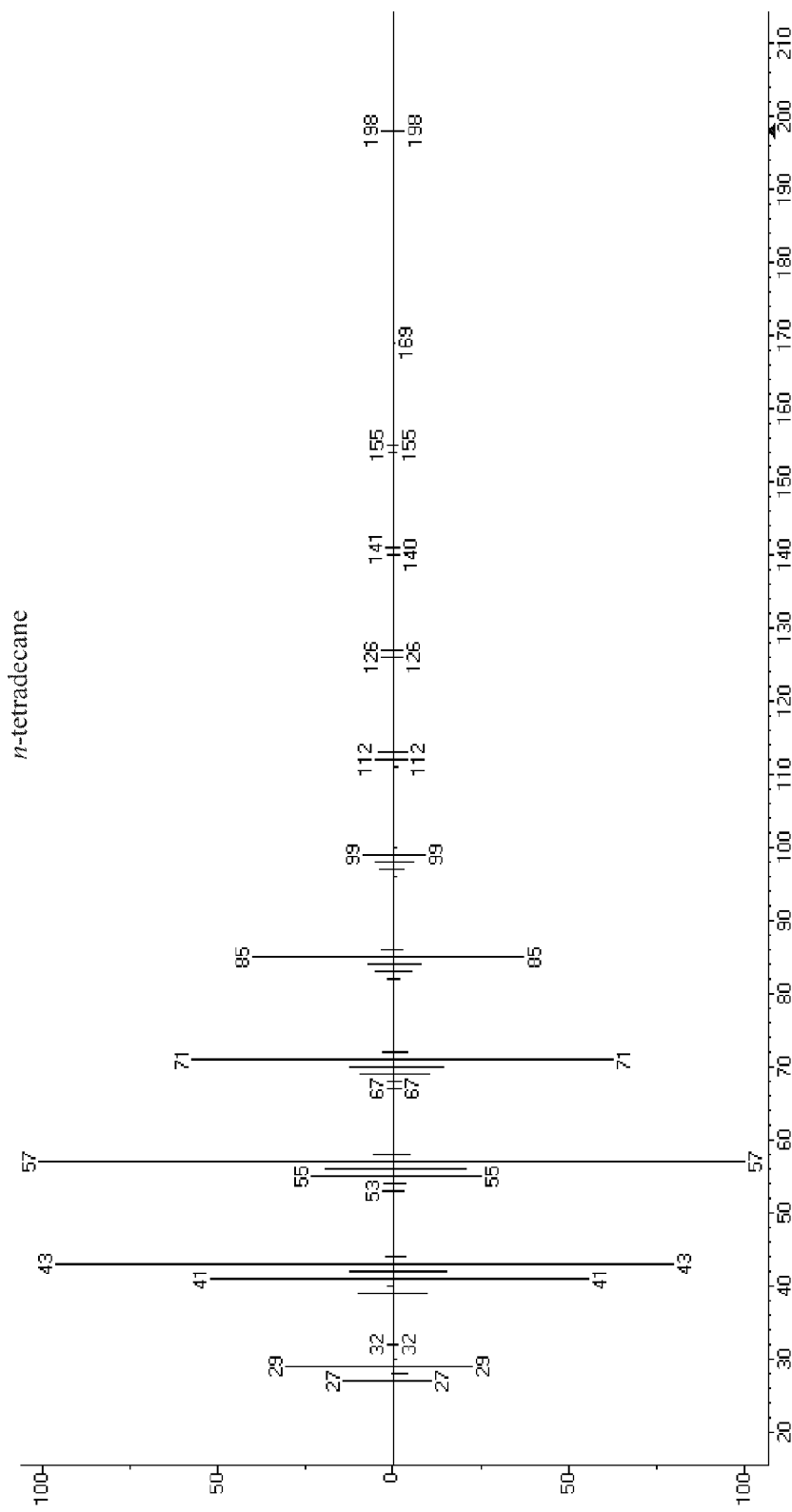
Figure 9C:
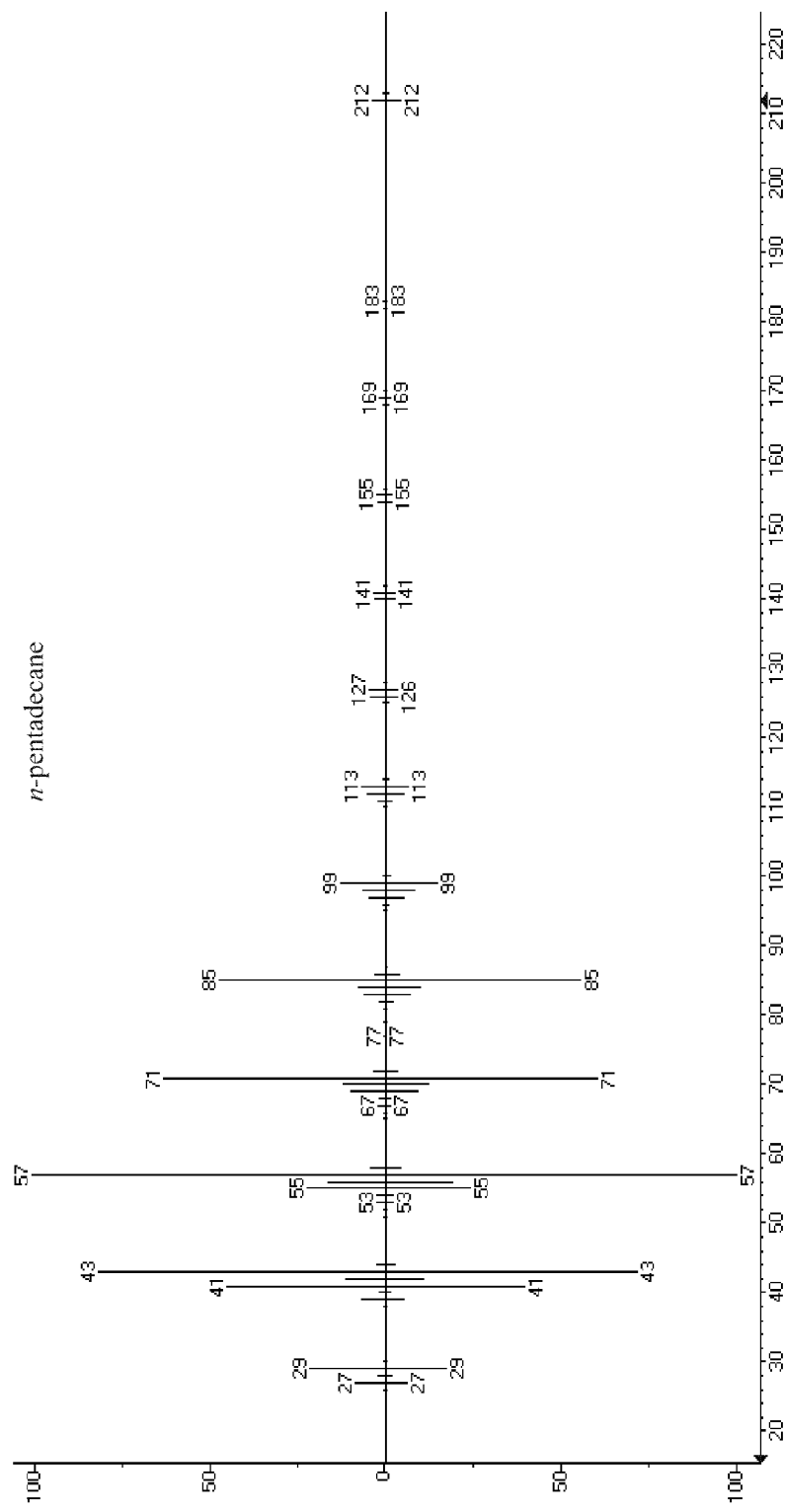
Figure 9D:
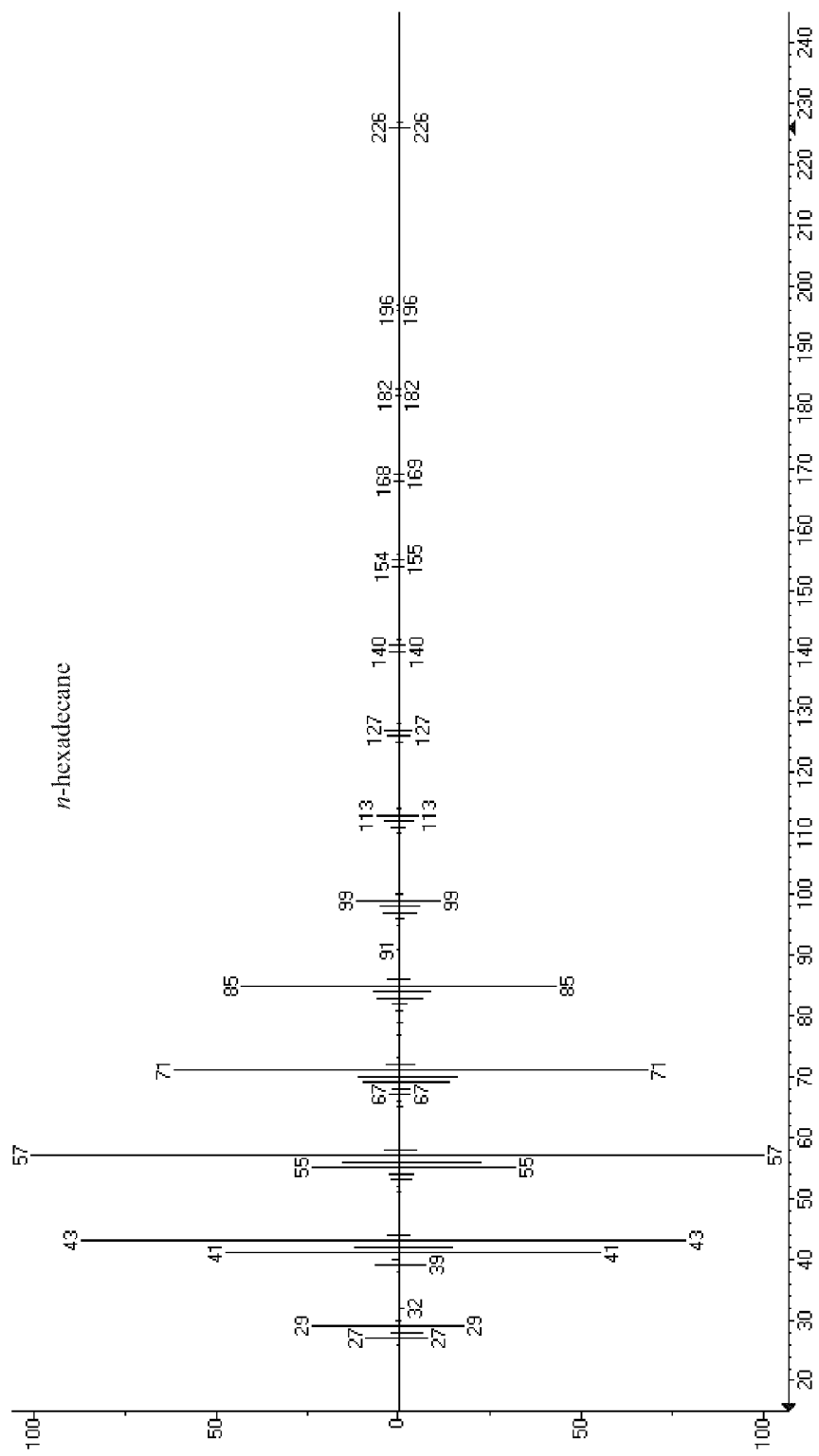
Figure 9E:
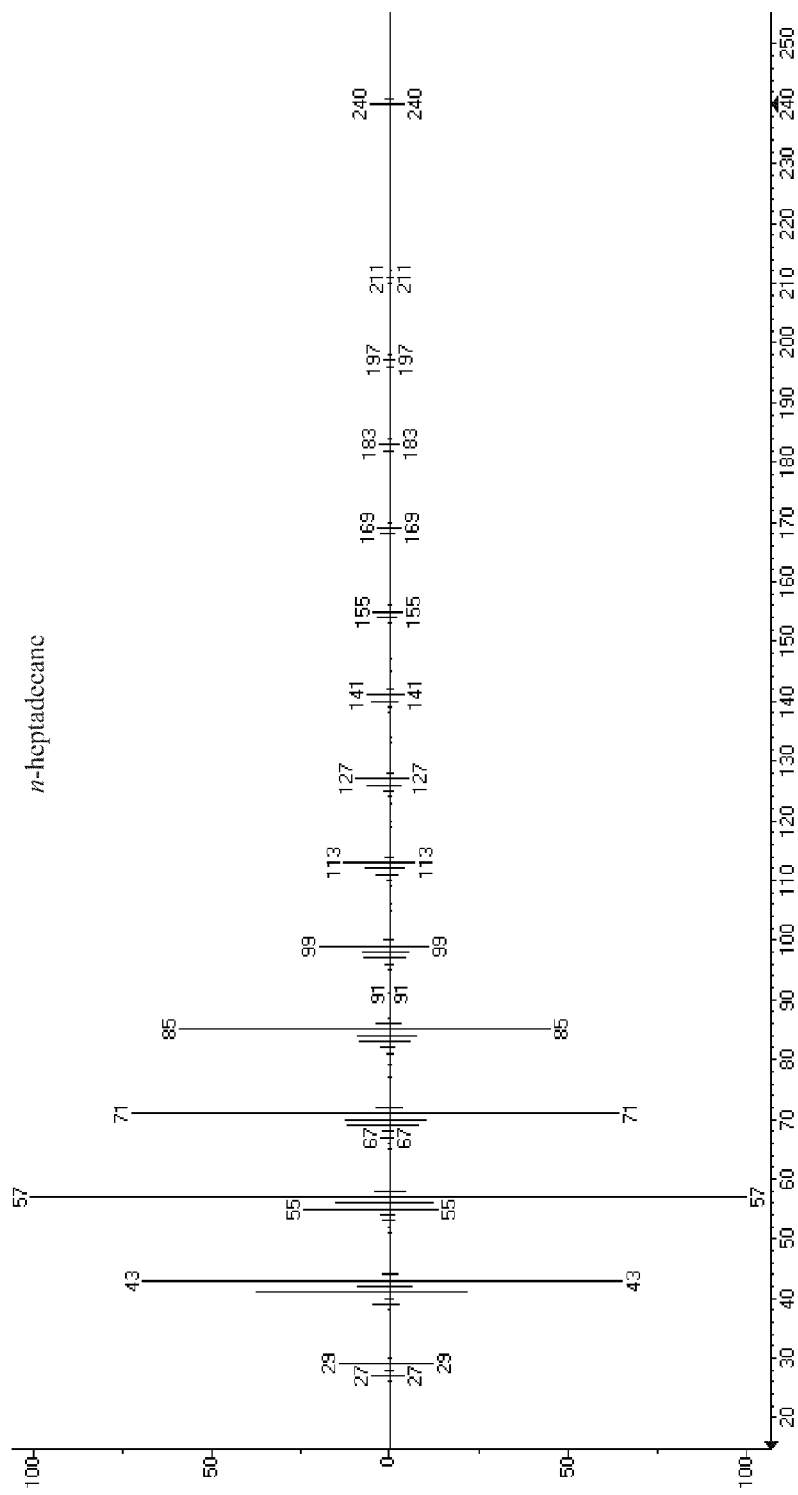
Figure 9F:
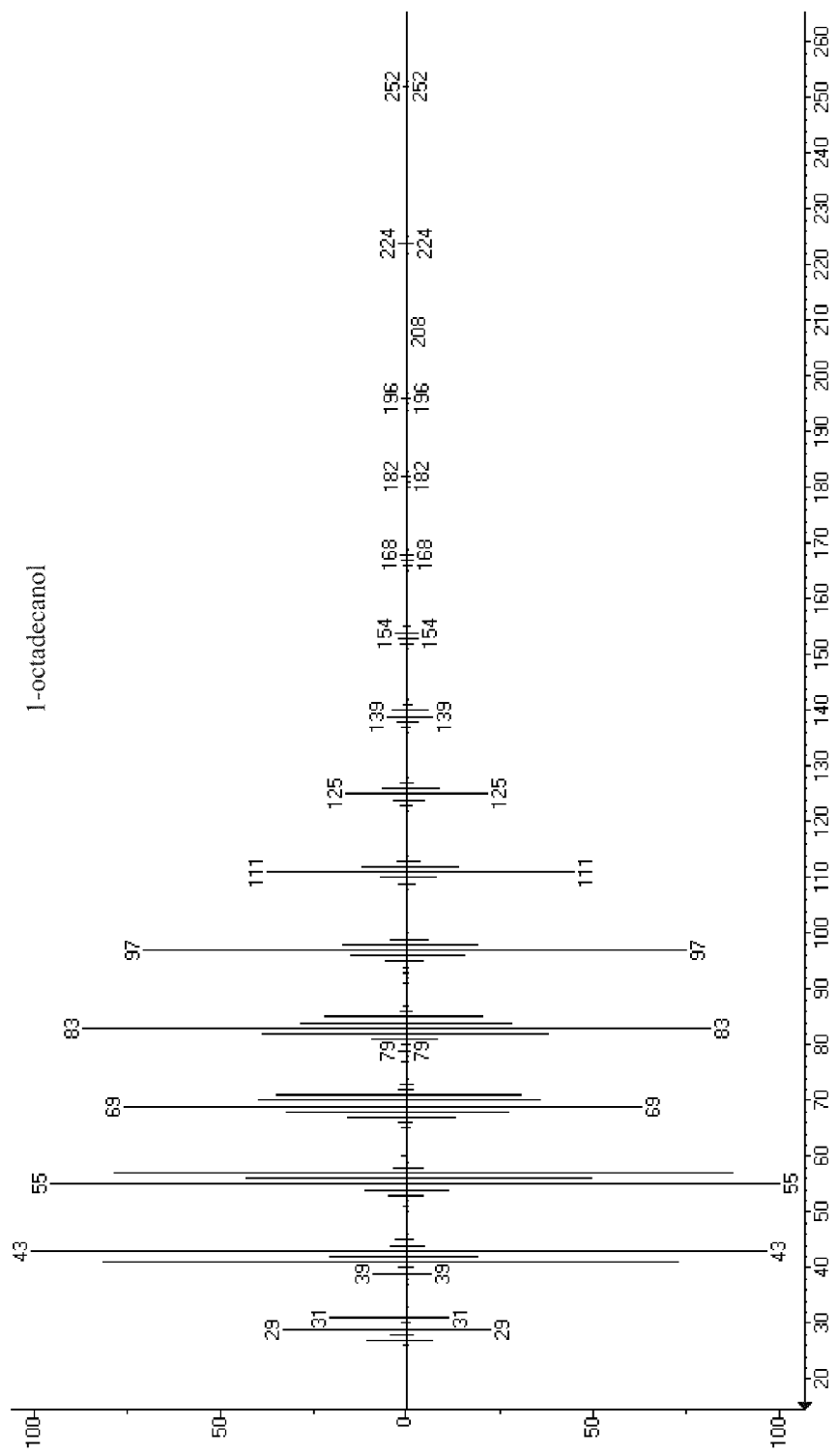

The TICs of JCC1221, JCC1220, JCC1160b, JCC1160a, JCC1160, and JCC879 acetone cell pellet extractants are shown in FIG. 8; n-alkane and 1-alkanol standards are as in Example 2. Consistent with a range of promoter strengths, and with function of the AAR-ADM pathway, there was a range of hydrocarbon accumulation, the order of accumulation being PcI>PcpcB>PlacI-trc>PEM7>PaphII (FIG. 8A).

In JCC1160, approximately 0.2% of dry cell weight was found as n-alkanes and n-alkan-1-ol (excluding n-nonadec-1-ene). Of this 0.2%, approximately three-quarters corresponded to n-alkanes, primary products being n-heptadecane and n-pentadecane. These hydrocarbons were not detected in JCC879. The data are summarized in Table 6A.

TABLE 6A

Hydrocarbons detected in acetone extracts of JCC1160 and JCC879.

| Compound | Approximate % of dry cell weight | |
|---|---|---|
| | JCC879 | JCC1160 |
| n-pentadecane | not detected | 0.024% |
| n-hexadecane | nd | 0.004% |
| n-heptadecane | nd | 0.110% |
| n-octadecan-1-ol | nd | 0.043% |
| Total | | 0.181% |
| % of products that are n-alkanes | | 76% |

The highest accumulator was JCC1221 (PcI). Hydrocarbons identified in JCC1221, but not in control strain JCC879, are detailed in Table 6B, Table 6C and FIG. 8B. These hydrocarbons are n-tridecane (1), n-tetradecane (1), n-pentadecene (2), n-pentadecane (1), n-hexadecane (1), n-heptadec-di-ene (2), three isomers of n-heptadecene (2), n-heptadecane (1), and 1-ocadecanol (1), where the number in parentheses indicates the GC-MS peak assignment method.

TABLE 6B n-Alkanes quantitated in acetone extract of JCC1221

| Compound | % of JCC1221 dry cell weight |
|---|---|
| n-tridecane | <0.001% |
| n-tetradecane | 0.0064% |
| n-pentadecane | 0.40% |
| n-hexadecane | 0.040% |
| n-heptadecane | 1.2% |
| Total | 1.67% |

MS fragmentation spectra of Method 1 peaks are shown in FIG. 9, plotted against their respective library hits. The only alkanes/alkenes observed in JCC879 were 1-nonadecene and a smaller amount of nonadec-di-ene, alkenes that are known to be naturally synthesized by JCC138 (Winters K et al. (1969) *Science* 163:467-468). The major products observed in JCC1221 were n-pentadecane (~25%) and n-heptadecane (~75%); all others were in relatively trace levels.

The formation of n-pentadecane and n-heptadecane in JCC1221, as well as the nine other trace hydrocarbon products, is consistent with the virtually complete operation of the ADM-AAR pathway in JCC138, i.e., 16:0 hexadecyl-ACP→n-hexadecanal→n-pentadecane and 18:0 octadecyl-ACP→n-octadecanal→n-heptadecane. Indeed it is known that the major acyl-ACP species in this organism are $C_{16:0}$ and $C_{18:0}$ (Murata N et al. (1992) *Plant Cell Physiol* 33:933-941). Relatively much less fatty alcohol is produced relative to AAR-ADM expression in *E. coli* (Example 3), as expected given the presence in JCC138 of a cyanobacterial ferredoxin/ferredoxin-NADPH reductase system that can regenerate the di-iron active site of ADM, thereby preventing the accumulation of hexadecanal and octadecanal that could in turn be non-specifically dehydrogenated to the corresponding 1-alkanols. Thus, in JCC1221, only a very small 1-octadecanol (1) peak is observed (FIG. 8).

The other trace hydrocarbons seen in JCC1221 are believed to be unsaturated isomers of n-pentadecane and n-heptadecane (Table 6C). It is hypothesized that all these alkenes are generated by desaturation events following the production of the corresponding alkanes by the SYN-PCC7942_1593 Adm. This contrasts with the situation in *E. coli*, where double bonds are introduced into the growing acyl chain while it is linked to the acyl carrier protein (Example 3). JCC138 is known to have a variety of position-specific acyl-lipid desaturases that, while nominally active only on fatty acids esterified to glycerolipids, could potentially act on otherwise unreactive alkanes produced nonphysiologically by the action of AAR and ADM. JCC138 desaturases, i.e., DesA, DesB, and DesC, introduce cis double bonds at the Δ9, Δ12, and Δ15 positions of $C_{18}$ acyl chains, and at the Δ9 and Δ12 positions of $C_{16}$ acyl chains (Murata N and Wada H (1995) *Biochem J*. 308:1-8). The candidate n-pentadecene peak is believed to be cis-4-pentadecene (Table 6C).

Assuming also that heptadecane could also serve as a substrate for JCC138 desaturases, and that it would be desaturated at positions analogous to the Δ9, Δ12, and Δ15 of the $C_{18}$ acyl moiety, there are four theoretically possible mono-unsaturated isomers: cis-3-heptadecene, cis-6-heptadecene, cis-8-heptadecene, and cis-9-heptadecene. These isomers do not include the single n-heptadecene species nominally observed in *E. coli*, cis-7-heptadecene (Example 2). It is believed that the three peaks closest to the n-heptadecane peak—denoted by subscripts 1, 2, and 3 in Table 6C and FIG. 8B—encompass at least three of these four mono-unsaturated heptadecane isomers. Consistent with this, n-heptadecene$_2$ and n-heptadecene$_3$ peaks have the expected molecular ions of mass 238 in their envelope-type fragmentation spectra. There are many isomeric possibilities, accordingly, for the putative cis,cis-heptadec-di-ene peak, which has an envelope-type fragmentation spectrum with the expected molecular ions of mass 236. As expected, all putative heptadecene species elute slightly before n-heptadecane.

TABLE 6C

Alkane and alkenes detected by GC-MS in acetone cell pellet extractants of JCC1221 but not JCC879 in increasing order of retention time.

| Compound | JCC879 | JCC1221 | GC-MS Peak Assigment | Candidate isomer |
|---|---|---|---|---|
| n-tridecane | − | + | Method 1 | |
| n-tetradecane | − | + | Method 1 | |
| n-pentadecene | − | + | Method 2 | cis-4-pentadecene |
| n-pentadecane | − | + | Method 1 | |
| n-hexadecane | − | + | Method 1 | |
| n-heptadec-di-ene | − | + | Method 2 (envelope-type MS with molecular ion mass 236) | cis,cis-heptadec-di-ene |
| n-heptadecene$_3$ | − | + | Method 2 (envelope-type MS with molecular ion mass 238) | cis-[3/6/8/9]-heptadecene |
| n-heptadecene$_2$ | − | + | Method 2 (envelope-type MS with molecular ion mass 238) | cis-[3/6/8/9]-heptadecene |
| n-heptadecene$_1$ | − | + | Method 2 | cis-[3/6/8/9]-heptadecene |
| n-heptadecane | − | + | Method 1 | |
| 1-octadecanol | − | + | Method 1 | |

"−", not detected;
"+", detected.

Example 6

Intracellular Accumulation of n-Alkanes to up to 5% of Dry Cell Weight in *Synechococcus* sp. PCC 7002 Through Heterologous Expression of *Synechococcus elongatus* PCC7942 SYNPCC7942_1593 (adm) and SYNPCC7942_1594 (aar)

In order to quantitate more accurately the level of intracellular accumulation of n-alkane products in the alkanogen JCC1221 (Example 5), the levels of n-pentadecane and n-heptadecane, as well as the relatively trace products n-tetradecane and n-hexadecane, were quantified with respect to dry cell weight (DCW). Based on the hypothesis that the extent of n-alkane production could correlate positively with the level of SYNPCC7942_1593-SYNPCC7942_1594 operon expression, the DCW-normalized n-alkane levels of JCC1221 were determined as a function of the spectinomycin concentration of the growth medium. The rationale was that the higher the spectinomycin selective pressure, the higher the relative copy number of pAQ1, and the more copies of the aadA-linked SYNPCC7942_1593-SYNPCC7942_1594 operon.

A clonal starter culture of JCC1221 was grown up in A+ medium supplemented with 100 µg/ml spectinomycin in for 7 days at 37° C. at 150 rpm in 3% $CO_2$-enriched air at ~100 µmol photons $m^{-2} s^{-1}$ in a Multitron II (Infors) shaking photoincubator. At this point, this culture was used to inoculate triplicate 30 ml JB2.1 medium (PCT/US2009/006516) flask cultures supplemented with 100, 200, 300, 400, or 600 µg/ml spectinomycin. JB2.1 medium consists of 18.0 g/l sodium chloride, 5.0 g/l magnesium sulfate heptahydrate, 4.0 g/l sodium nitrate, 1.0 g/l Tris, 0.6 g/l potassium chloride, 0.3 g/l calcium chloride (anhydrous), 0.2 g/l potassium phosphate monobasic, 34.3 mg/l boric acid, 29.4 mg/l EDTA (disodium salt dihydrate), 14.1 mg/l iron (III) citrate hydrate, 4.3 mg/l manganese chloride tetrahydrate, 315.0 µg/l zinc chloride, 30.0 µg/l molybdenum (VI) oxide, 12.2 µg/l cobalt (II) chloride hexahydrate, 10.0 µg/l vitamin $B_{12}$, and 3.0 µg/l copper (II) sulfate pentahydrate. The 15 cultures were grown for 10 days at 37° C. at 150 rpm in 3% $CO_2$-enriched air at ~100 µmol photons $m^{-2} s^{-1}$ in a Multitron II (Infors) shaking photoincubator.

For each culture, 5-10 ml was used for dry cell weight determination. To do so, a defined volume of culture—corresponding to approximately 20 mg DCW—was centrifuged to pellet the cells. Cells were transferred to a pre-weighed eppendorf tube, and then washed by 2 cycles of resuspension in Milli-Q water and microcentrifugation, and dewetted by 3 cycles of microcentrifugation and aspiration. Wet cell pellets were frozen at −80° C. for two hours and then lyophilized overnight, at which point the tube containing the dry cell mass was weighed again such that the mass of the cell pellet could be calculated within ±0.1 mg. In addition, for each culture, 0.3-0.8 ml was used for acetone extraction of the cell pellet for GC analysis. To do so, a defined volume of culture—corresponding to approximately 1.4 mg DCW—was microcentrifuged to pellet the cells. Cells were then washed by 2 cycles of resuspension in Milli-Q water and microcentrifugation, and then dewetted by 4 cycles of microcentrifugation and aspiration. Dewetted cell pellets were then extracted by vortexing for 1 minute in 1.0 ml acetone containing 50 µg/ml BHT and 160 µg/ml n-heptacosane internal standard (Sigma 51559). Cell debris was pelleted by centrifugation, and 700 µl supernatant was pipetted into a GC vial.

Concentrations of n-tetradecane, n-pentadecane, n-hexadecane, and n-heptadecane in the fifteen extractants were quantitated by gas chromatography/flame ionization detection (GC/FID). Unknown n-alkane peak areas in biological samples were converted to concentrations via linear calibration relationships determined between known n-tetradecane, n-pentadecane, n-hexadecane, and n-heptadecane authentic standard concentrations and their corresponding GC-FID peak areas. Standards were obtained from Sigma. GC-FID conditions were as follows. An Agilent 7890A GC/FID equipped with a 7683 series autosampler was used. 1 µl of each sample was injected into the GC inlet (split 5:1, pressure: 20 psi, pulse time: 0.3 min, purge time: 0.2 min, purge flow: 15 ml/min) and an inlet temperature of 280° C. The column was a HP-5MS (Agilent, 30 m×0.25 mm×0.25 µm) and the carrier gas was helium at a flow of 1.0 ml/min. The GC oven temperature program was 50° C., hold one minute; 10° C./min increase to 280° C.; hold ten minutes. n-Alkane production was calculated as a percentage of the DCW extracted in acetone.

Figure 10:
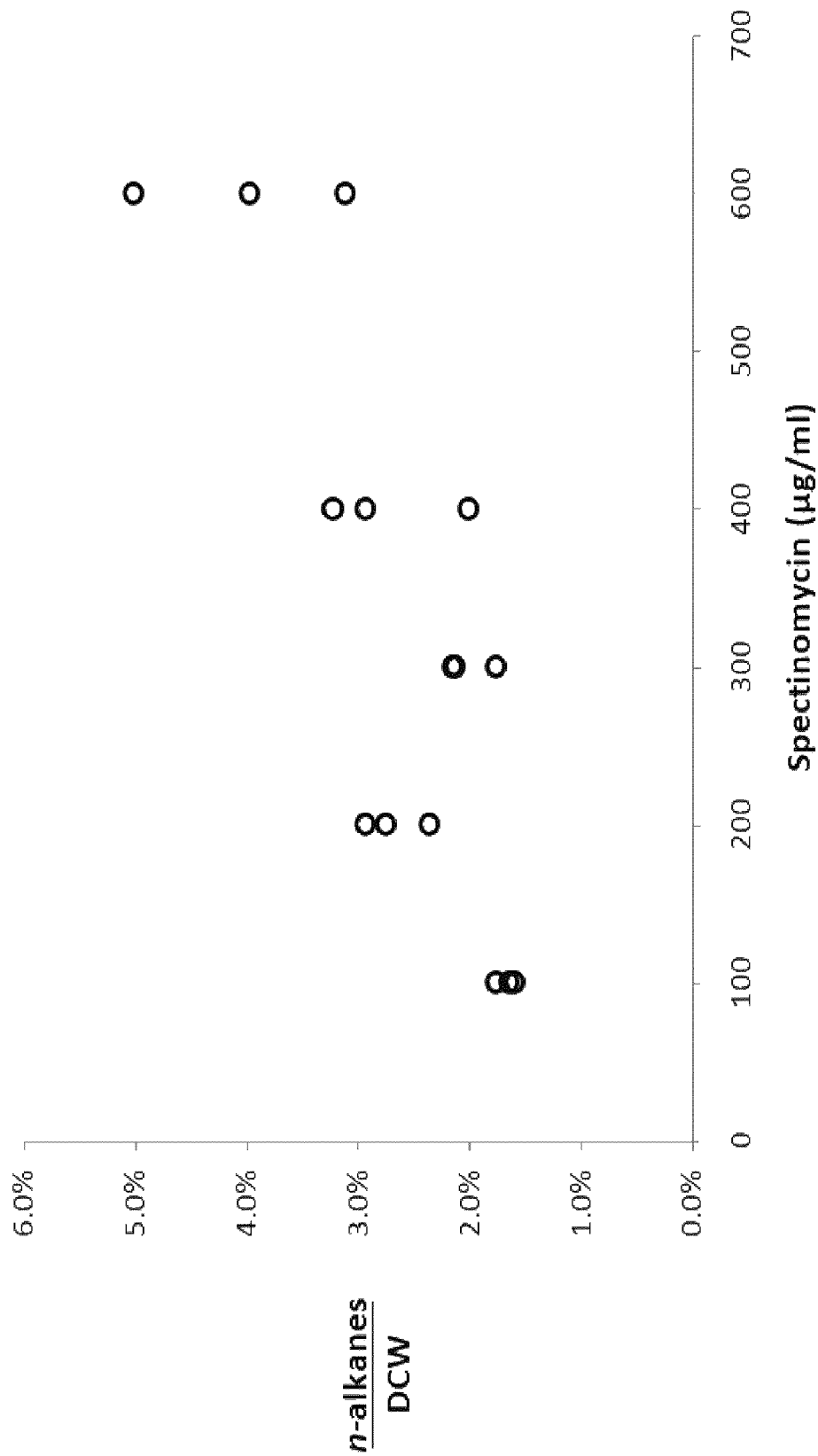
FIG. 10 depicts intracellular n-alkane production as a function of spectinomycin concentration in JCC1221.

Consistent with scaling between pAQ1 selective pressure and the extent of intracellular n-alkane production in JCC1221, there was a roughly positive relationship between the % n-alkanes with respect to DCW and spectinomycin concentration (FIG. 10). For all JCC1221 cultures, n-alkanes were ~25% n-pentadecane and ~75% n-heptadecane. The minimum n-alkane production was ~1.8% of DCW at 100 µg/ml spectinomycin and 5.0% in one of the 600 µg/ml spectinomycin cultures.

Example 7

Production of n-Alkanes in *Synechococcus* sp. PCC 7002 Through Heterologous Expression of *Prochlorococcus marinus* MIT 9312 PMT9312_0532 (adm) and PMT9312_0533 (aar)

This candidate Adm/Aar pair from *Prochlorococcus marinus* MIT9312 was selected for functional testing by heterologous expression in JCC138 because of the relatively low amino acid homology ($\leq 62\%$) of these proteins to their *Synechococcus elongatus* PCC7942 counterparts, SYNPCC7942_1593 and SYNPCC7942_1594. Specifically, the 252-amino acid protein PMT9312_0532 exhibits only 62% amino acid identity with the 232 amino acid protein SYNPCC7942_1593, wherein amino acids 33-246 of the former are aligned with amino acids 11-224 of the latter. The 347 amino acid protein PMT9312_0533 exhibits only 61% amino acid identity with the 342 amino acid protein SYNPCC7942_1594, wherein amino acids 1-337 of the former are aligned with amino acids 1-339 of the latter.

A codon- and restriction-site-optimized version of the PMT9312_0532-PMT9312_0533 operon was synthesized by DNA2.0 (Menlo Park, Calif.), flanked by NdeI and EcoRI sites. The operon was cloned into the pAQ1 homologous recombination vector pJB5 via NdeI and EcoRI, such that the PMT9312_0532-PMT9312_0533 operon was placed under transcriptional control of the aphII promoter. The sequence of the pJB947 vector is provided as SEQ ID NO: 17.

pJB947 was transformed into JCC138 as described in Example 5, generating strain JCC1281. The hydrocarbon products of this strain were compared to those of the negative control strain JCC879, corresponding to JCC138 transformed with empty pJB5 (see Example 5). Eight $OD_{730}$-ml worth of cells (~8×10$^8$ cells) of each strain was collected by centrifugation, having been grown in A+ medium supplemented with 200 µg/ml spectinomycin as described in Example 5. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 5 minutes in 0.7 ml acetone containing 20 µg/ml BHT and 20 µg/ml EA. Cell debris was pelleted by centrifugation, and 600 µl supernatant was pipetted into a GC vial. Samples were analyzed by GC-MS as described in Example 5.

Figure 11:
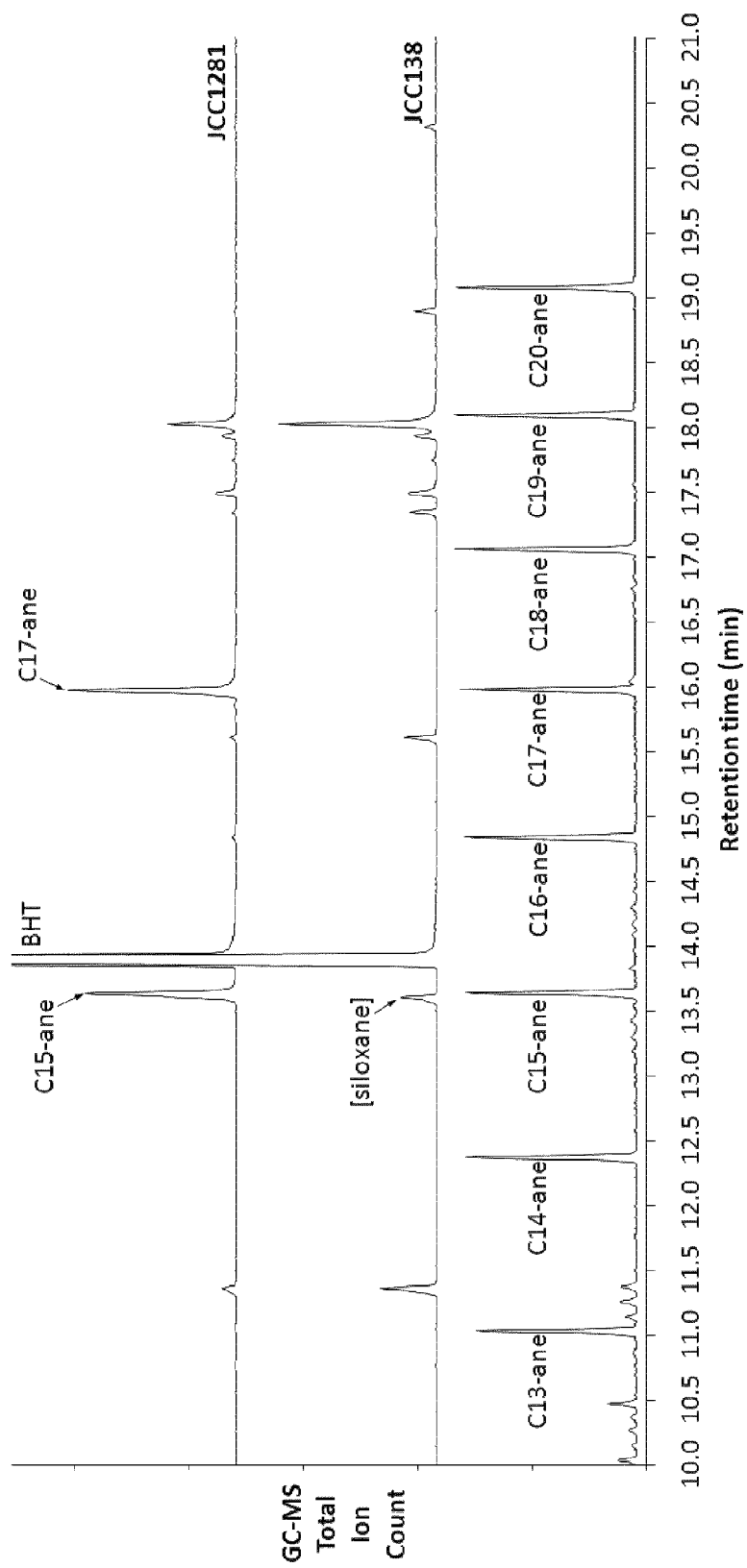
FIG. 11 represents 0-to-1080000-count total ion chromatograms of the JCC1281 BHT-acetone cell pellet extractant versus that of the control strain JCC138, as well as of authentic standard n-alkanes.
Figure 12A:
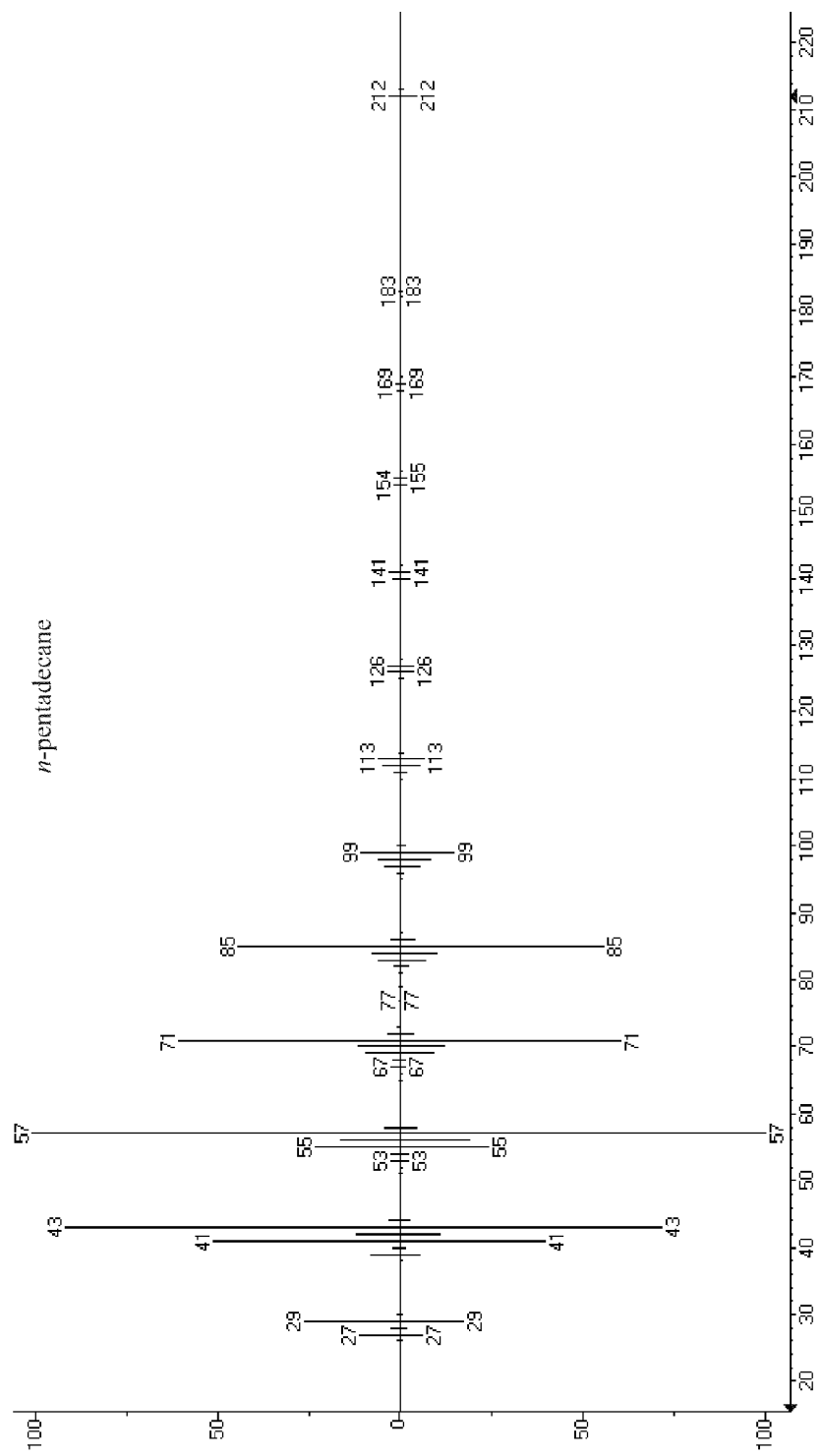
FIG. 12 depicts MS fragmentation spectra of JCC1281 peaks assigned by Method 1 (top mass spectrum of each panel), plotted against their respective NIST library hits (bottom mass spectrum of each panel). A, n-pentadecane; B, n-heptadecane.
Figure 12B:
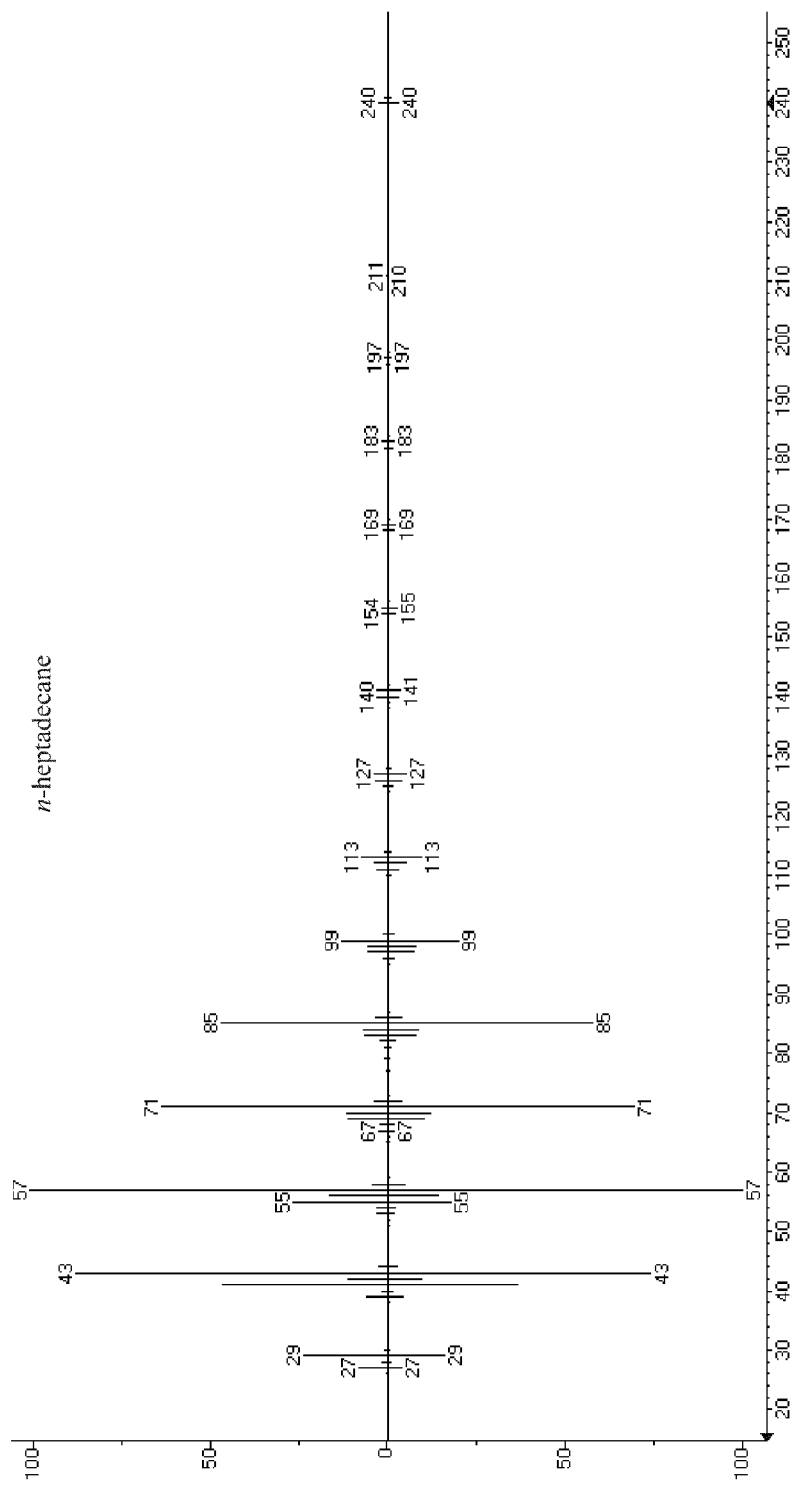

The TICs of JCC1281 and JCC879 acetone cell pellet extractants are shown in FIG. 11; n-alkane standards are as in Example 6. Hydrocarbons identified in JCC1281, but not in control strain JCC879, were n-pentadecane (1) and n-heptadecane (1), where the number in parentheses indicates the GC-MS peak assignment method. MS fragmentation spectra of Method 1 peaks are shown in FIG. 12, plotted against their respective library hits (as noted in Example 5, the only alkanes/alkenes observed in JCC879 were 1-nonadecene and a smaller amount of nonadec-di-ene, alkenes that are known to be naturally synthesized by JCC138). The amount of n-alkanes produced in JCC1281 is at least 0.1% dry cell weight, and at least 2-two times higher than the amount produced by JCC879. The ratio of n-pentadecane:n-heptadecane (~40%:~60%) in JCC1281 was higher than that observed in JCC1221 (~25%:~75%), suggesting that the PMT9312_0532 (ADM) and/or the PMT9312_0533 (AAR) exhibit higher activity towards the $C_{16}$ substrates relative to $C_{18}$ substrates, compared to SYNPCC7942_1593 (ADM) and/or SYNPCC7942_1594 (AAR).

Example 8

Augmentation of Native n-Alkane Production in *Thermosynechococcus elongatus* BP-1 by Overexpression of the Native tll1313 (adm)-tll1312 (aar) Operon Genes encoding *Thermosynechococcus elongatus* BP-1 tll1312 (AAR) and tll1313 (ADM) are incorporated into one or more plasmids (e.g., pJB5 derivatives), comprising promoters of differing strength. The plasmids are used to transform *Thermosynechococcus elongatus* BP-1. Overexpression of the genes in the transformed cells are measured as will the amount of n-alkanes, particularly heptadecane, produced by the transformed cells, in a manner similar to that described in Example 3. The n-alkanes and other carbon-based products of interest can also be isolated from the cell or cell culture, as needed.

Figure 13A:
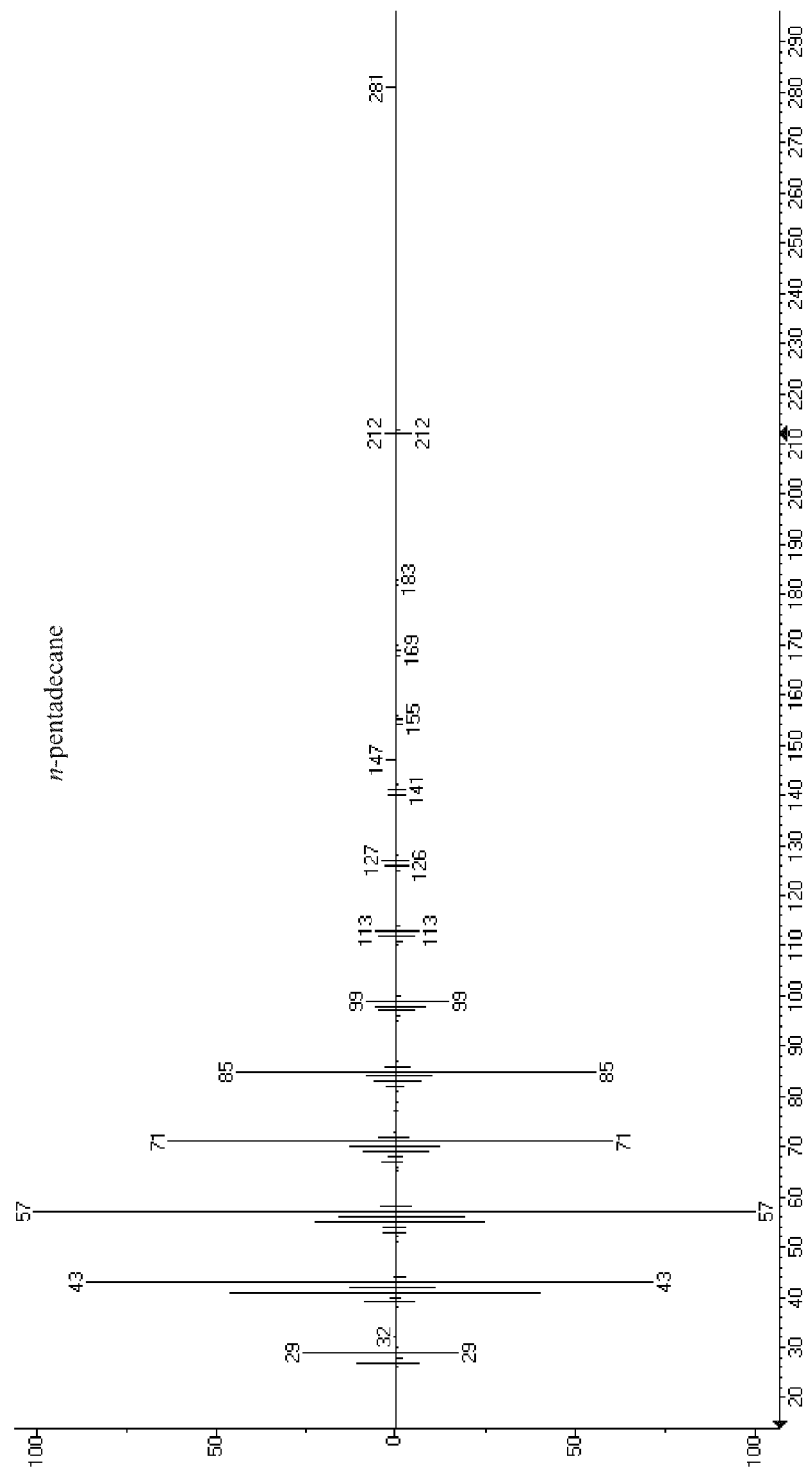
FIG. 13 depicts MS fragmentation spectra of JCC3 peaks assigned by Method 1 (top mass spectrum of each panel), plotted against their respective NIST library hits (bottom mass spectrum of each panel). A, n-pentadecane; B, n-hexadecane; C, n-heptadecane.
Figure 13B:
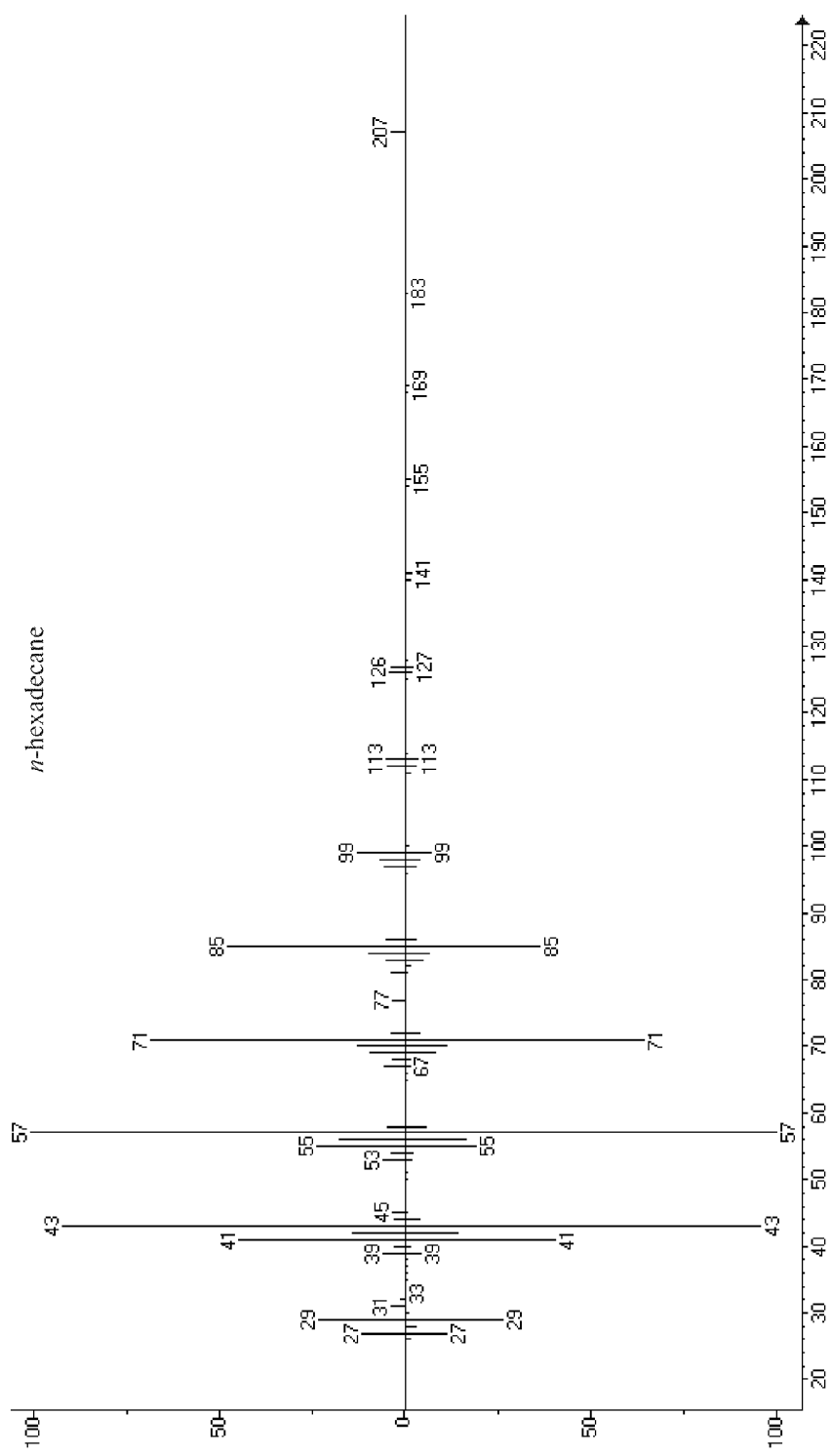
Figure 13C:
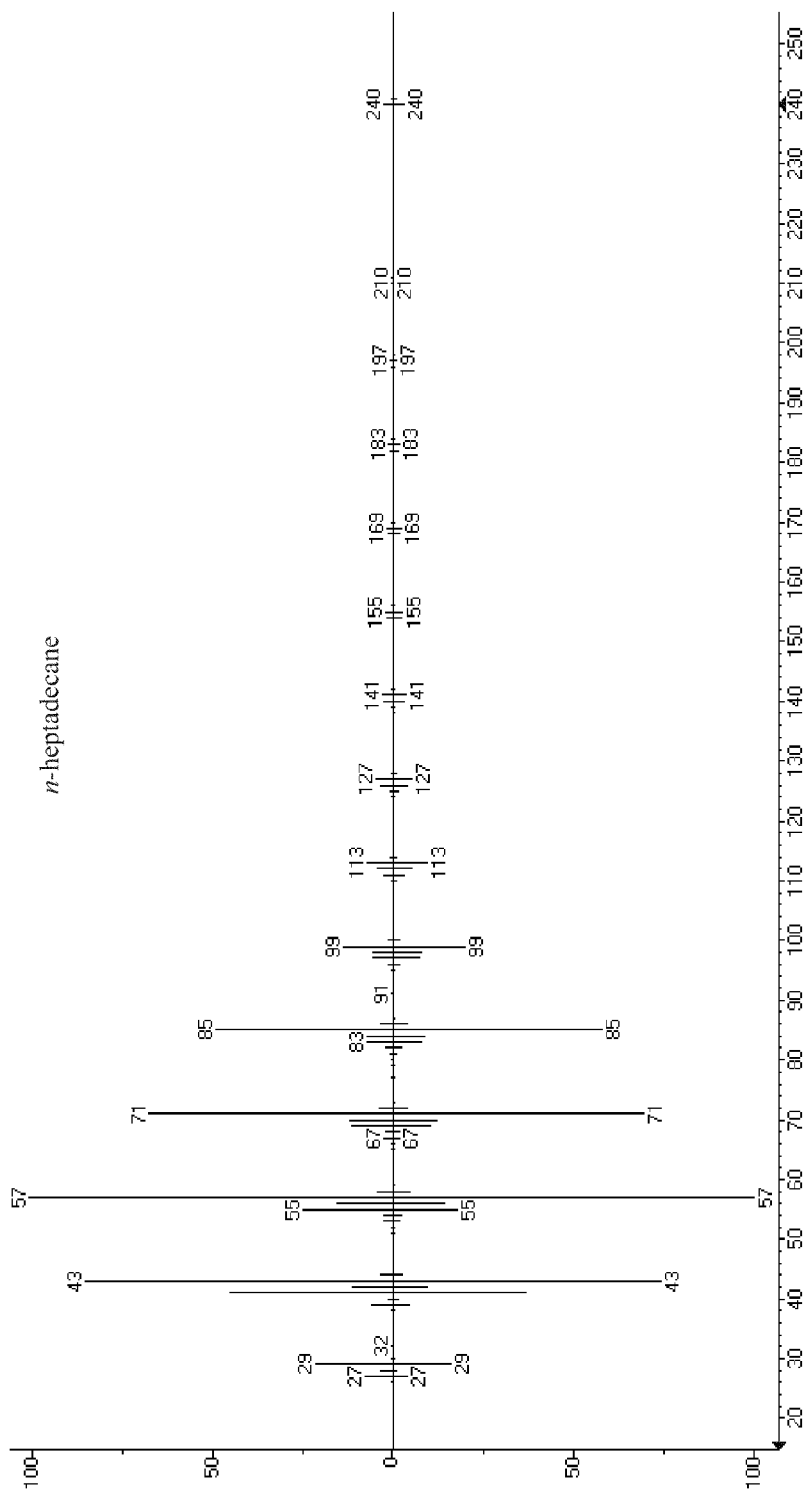

Wild-type *Thermosynechococcus elongatus* BP-1, referred to as JCC3, naturally produces n-heptadecane as the major intracellular hydrocarbon product, with traces of n-hexadecane and n-pentadecane. These n-alkanes were identified by GC-MS using Method 1; fragmentation spectra are shown in FIG. 13. Briefly, a colony of JCC3 was grown in B-HEPES medium to a final $OD_{730}$ of ~4, at which point 5 $OD_{730}$-ml worth of cells was harvested, extracted in acetone, and analyzed by GC-MS as detailed in Example 5.

In an effort to augment this n-alkane production, the native 1111313-1111312 operonic sequence from this organism was PCR-amplified and cloned into the *Thermosynechococcus elongatus* BP-1 chromosomal integration vector pJB825. This construct places the tll1313-tll1312 operon under the transcriptional control of the constitutive cI promoter. The sequence of the resulting plasmid, pJB825t, is shown in SEQ ID NO:18.

pJB825 and pJB825t were naturally transformed into JCC3 using a standard cyanobacterial transformation protocol, generating strains JCC1084 and JCC1084t, respectively. Briefly, 25 µg of plasmid DNA was added to 0.5 ml of concentrated JCC3 culture ($OD_{730}$~100) that had originally been grown to an $OD_{730}$ of approximately 1.0 in B-HEPES at 45° C. in 3% $CO_2$-enriched air at ~100 µmol photons $m^{-2} s^{-1}$ in a Multitron II (Infors) shaking photoincubator. The cell-DNA mixture was incubated at 37° C. for 4 hours in the dark with gentle mixing, made up to 7 ml with fresh B-HEPES medium, and then incubated under continuous light conditions (~100 µmol photons $m^{-2} s^{-1}$) for 20 hours at 45° C. at 150 rpm in 3% $CO_2$-enriched air at ~100 µmol photons $m^{-2} s^{-1}$ in a Multitron II (Infors) shaking photoincubator. At this point, cells were collected by centrifugation and serial dilutions were mixed with molten top agar and plated on the surface of B-HEPES plates supplemented with 60 µg/ml kanamycin. Transformant colonies appeared in the top agar layer within around 7 days upon incubation in a photoincubator (Percival) in 1% $CO_2$-enriched air at continuous ~100 µmol photons $m^{-2} s^{-1}$ irradiance. Single colonies of JCC1084 and JCC1084t were then grown up in triplicate to an $OD_{730}$ of ~6 in B-HEPES/60 µg/ml kanamycin liquid culture, and their intracellular hydrocarbon products quantitated by GC-FID.

3.5 $OD_{730}$-ml worth of cells (~$3.5 \times 10^8$ cells) of each replicate culture of each strain was collected by centrifugation. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 1 minutes in 0.7 ml acetone containing 20 µg/ml BHT and 20 µg/ml n-heptacosane. Cell debris was pelleted by centrifugation, and 600 µl supernatant was pipetted into a GC vial. The two extractants, along with authentic $C_8$-$C_{20}$ n-alkane authentic standards (Sigma 04070), were then analyzed by GC coupled with flame ionization detection (FID) as described in Example 6. Quantitation of n-pentadecane, n-hexadecane, and n-heptadecane by GC-FID, and dry cell weights were taken as described in Example 6.

Figure 14:
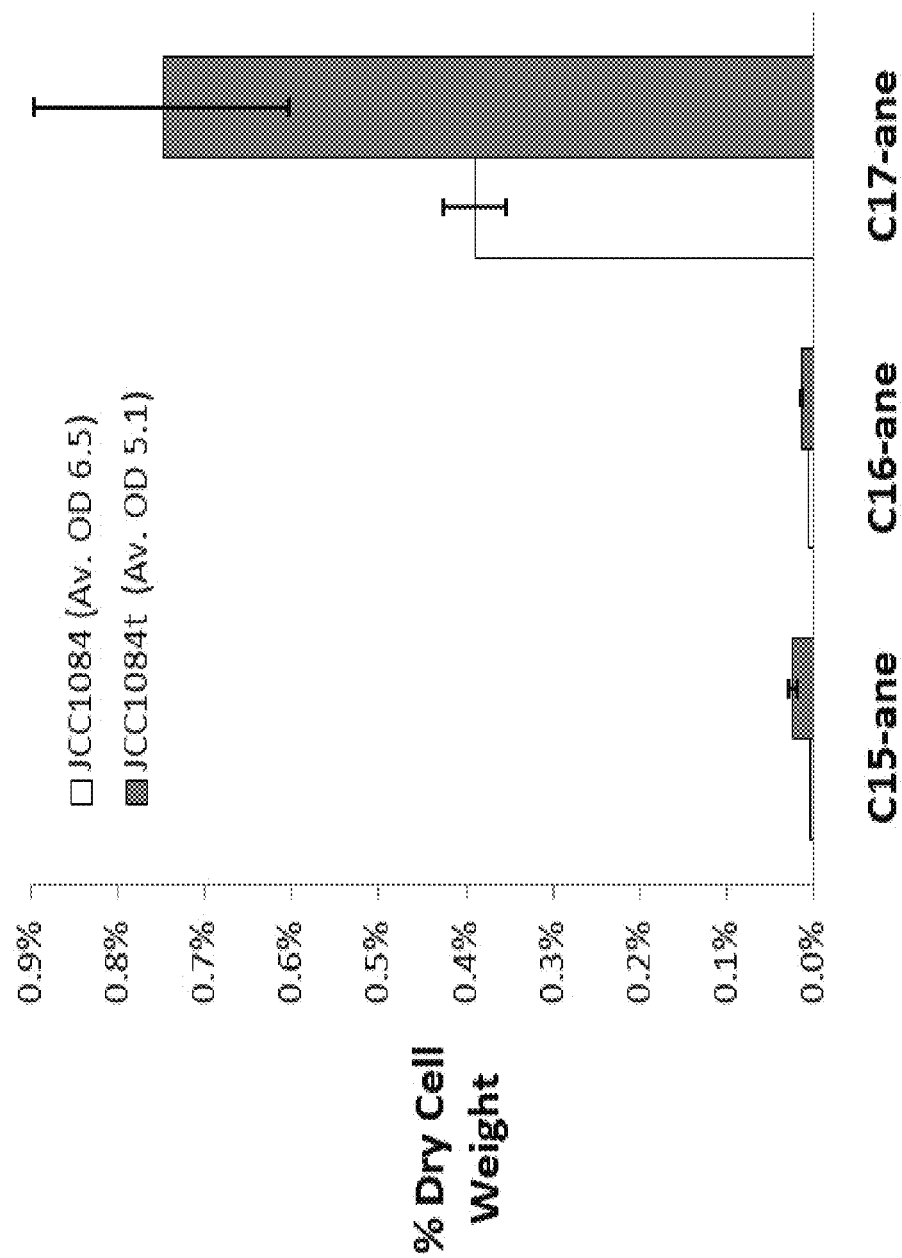
FIG. 14 depicts enhanced intracellular production of n-alkanes in JCC1084t compared to the control strain JCC1084. Error bars represent standard deviation of three independent observations.

Consistent with increased expression of tll1313-tll1312 in JCC1084t relative to the control strain JCC1084, n-pentadecane, n-hexadecane, and n-heptadecane were ~500%, ~100%, and ~100% higher, respectively, in JCC1084t relative to their % DCW levels in JCC1084 (FIG. 14). The total n-alkane concentration in both strains was less than 1%. The n-alkane concentration in JCC1084t was at least 0.62% and at least twice as much n-alkane was produced relative to JCC1084.

Example 9

Comparison of Intracellular Hydrocarbon Products of JCC1113 (a Derivative of *E. coli*) and JCC1221 (a Derivative of *Synechococcus* sp. PCC 7002), Both Strains Heterologously Expressing *Synechococcus elongatus* SYNPCC7942_1593 (adm) and SYNPCC7942_1594 (aar)

Figure 15:
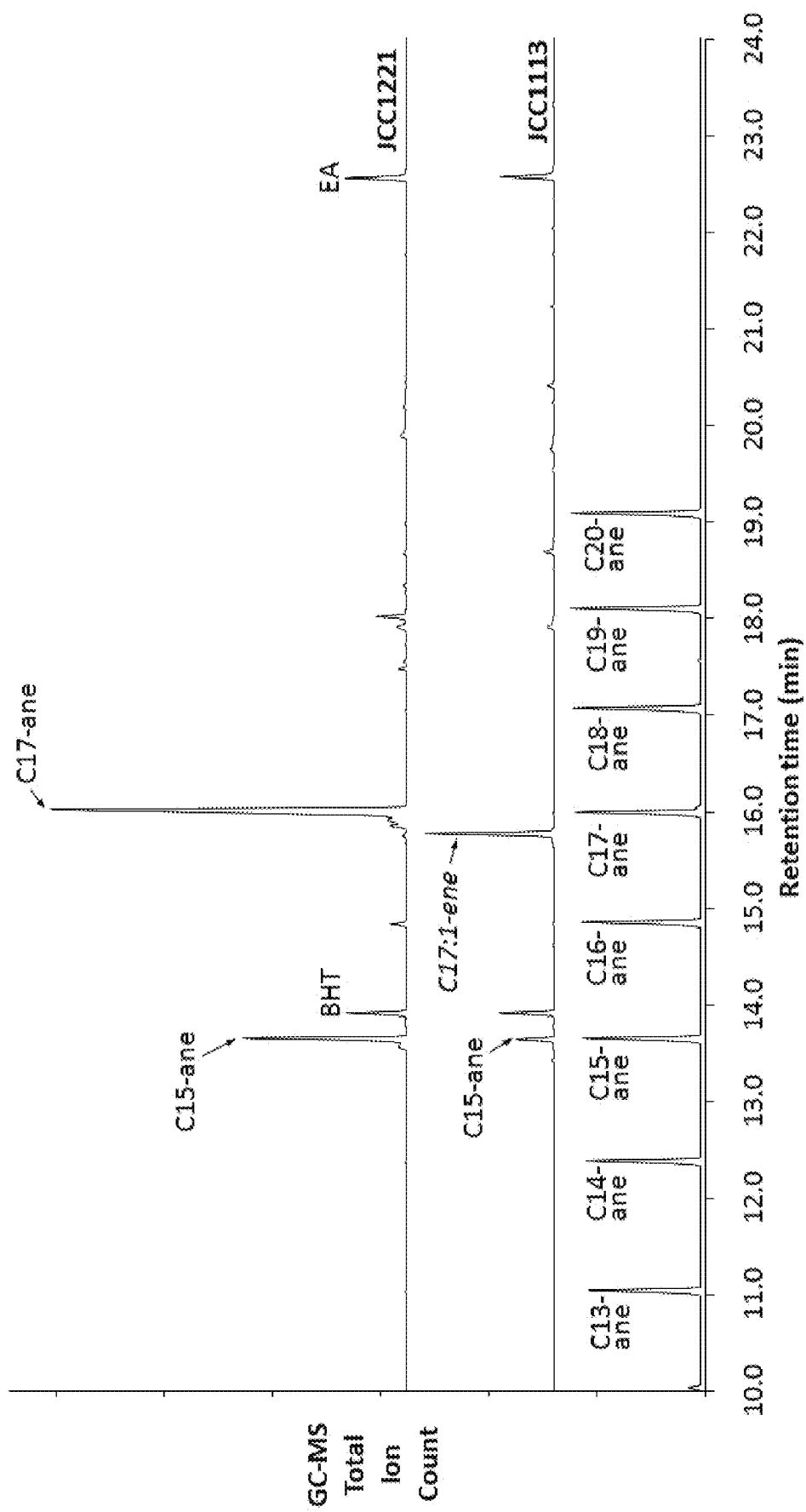
FIG. 15 represents 0-to-31500000-count total ion chromatograms of JCC1113 and JCC1221 BHT-acetone cell pellet extracts, as well as authentic n-alkane standards.

GC-MS TICs of JCC1113 and JCC1221 acetone cell pellet extractants are shown in FIG. 15, along with the TIC of $C_8$-$C_{20}$ n-alkane authentic standards (Sigma 04070). These two strains are derived from *E. coli* BL21(DE3) and *Synechococcus* sp. PCC7002, respectively, and are described in detail in Examples 3 and 5, respectively. JCC1113 synthesizes predominantly n-heptadecene and n-pentadecane, whereas JCC1221 synthesizes predominantly n-heptadecane and n-pentadecane. This figure visually emphasizes the different retention times of the n-heptadecene isomer produced in JCC1113 and n-heptadecane produced in JCC1221.

Example 10

Production of Hydrocarbons in Yeast

The methods of the invention can be performed in a number of lower eukaryotes such as *Saccharomyces cerevisiae, Trichoderma reesei, Aspergillus nidulans* and *Pichia pastoris*. Engineering such organisms may include optimization of genes for efficient transcription and/or translation of the encoded protein. For instance, because the ADM and AAR genes introduced into a fungal host are of cyanobacterial origin, it may be necessary to optimize the base pair composition. This includes codon optimization to ensure that the cellular pools of tRNA are sufficient. The foreign genes (ORFs) may contain motifs detrimental to complete transcription/translation in the fungal host and, thus, may require substitution to more amenable sequences. The expression of each introduced protein can be followed both at the transcriptional and translational stages by well known Northern and Western blotting techniques, respectively.

Use of various yeast expression vectors including genes encoding activities which promote the ADM or AAR pathways, a promoter, a terminator, a selectable marker and targeting flanking regions. Such promoters, terminators, selectable markers and flanking regions are readily available in the art. In a preferred embodiment, the promoter in each case is selected to provide optimal expression of the protein encoded by that particular ORF to allow sufficient catalysis of the desired enzymatic reaction. This step requires choosing a promoter that is either constitutive or inducible, and provides regulated levels of transcription. In another embodiment, the terminator selected enables sufficient termination of transcription. In yet another embodiment, the selectable/counterselectable markers used are unique to each ORF to enable the subsequent selection of a fungal strain that contains a specific combination of the ORFs to be introduced. In a further embodiment, the locus to which relevant plasmid construct (encoding promoter, ORF and terminator) is localized, is determined by the choice of flanking region.

The engineered strains can be transformed with a range of different genes for production of carbon-based products of interest, and these genes are stably integrated to ensure that the desired activity is maintained throughout the fermentation process. Various combinations of enzyme activities can be engineered into the fungal host such as the ADM, ADR pathways while undesired pathways are attenuated or knocked out.

A number of embodiments of the invention have been described. Nevertheless, it will be understood that various modifications may be made without departing from the spirit and scope of the invention. All publications, patents and other references mentioned herein are hereby incorporated by reference in their entirety.

INFORMAL SEQUENCE LISTING

SEQ ID NO: 1
*ThermoSynechococcus elongatus* BP-1; tl11312 (AAR)
nucleic acid sequence
ATGTTTGGATTAATTGGTCATCTGACGAGTCTGGAGCACGCCCAAGCCGTTGCCCATCAGTTGGG

TTACCCCGAATATGCCGATCAAGGCTTGGAATTTTGGTGTATGGCACCGCCGCAGATCGTCGATG

AGATTACGGTGACGAGCGTAACGGGCAAAACTATCTATGGCAAATACGTTGAGTCCTGCTTTTTA

CCAGAGATGCTGGCCAACCAGCGGGTGAAGGCAGCGACTCGCAAAGTTATTAACGCCATGGCCCA

TGCCCAAAAGCACAACATTGACATTACGGCCTTGGGGGGCTTCTCCTCGATCATCTTTGAGAACT

TTGATCTGGAGAAAATGTCCCACATTCGCAACATTGAACTGGACTTTCGCCGCTTTACAACGGGG

AATACCCATACCGCCTATATCATCTGCCAACAAATTGAGCAGGCGGCGCCCCAAGTGGGGATTGA

TTTGCGGCAGGCAACCGTGGCTGTTTGTGGGGCTACGGGGGATATTGGTAGTGCCGTCTGCCGTT

GGTTGAATACCTGTTTAGATGTGCAAGATCTCTTACTCGTAGCACGGAATCGCGATCGCCTGCTG

GAGCTACAGGCGGAATTGGGACGGGGGAAAATCCTCGACTTGATGGAGGCGCTGCCCCTTGCCGA

TATTGTGGTTTGGGTGGCCAGTATGCCCAAGGGAGTTGAGCTGAGCATTGAGCAGTTAAAACGCC

CCTCCCTGATGATTGATGGTGGTTATCCCAAAAATATGGCCACCAAAATTCAGCACCCCCAGATT

CATGTTCTCAATGGTGGCATTGTCGAGCATGCCCTCGACATTGACTGGAAAATTATGGAAATTGT

GAATATGGATGTGCCCTCGCGGCAGATGTTTGCCTGTTTTGCAGAGGCTATGCTTTTAGAGTTCG

AGGGCTGGCACACCAATTTCTCTTGGGGACGCAATCAAATCACTGTGGAAAAGATGCAGCAAATT

GGTGAGGTCTCCCGTAAACATGGATTTCAGCCACTACTGTTGAATCCTCAGTAA (SEQ ID

NO: 1)

SEQ ID NO: 2
*ThermoSynechococcus elongatus* BP-1 tl11312 (AAR)
amino acid sequence
MFGLIGHLTSLEHAQAVAHQLGYPEYADQGLEFWCMAPPQIVDEITVTSVTGKTIYGKYVESCFL

PEMLANQRVKAATRKVINAMAHAQKHNIDITALGGFSSIIFENFDLEKMSHIRNIELDFRRFTTG

NTHTAYIICQQIEQAAPQVGIDLRQATVAVCGATGDIGSAVCRWLNTCLDVQDLLLVARNRDRLL

ELQAELGRGKILDLMEALPLADIVVWVASMPKGVELSIEQLKRPSLMIDGGYPKNMATKIQHPQI

HVLNGGIVEHALDIDWKIMEIVNMDVPSRQMFACFAEAMLLEFEGWHTNFSWGRNQITVEKMQQI

GEVSRKHGFQPLLLNPQ (SEQ ID NO: 2)

SEQ ID NO: 3
*ThermoSynechococcus elongatus* BP-1 tl11313 (ADM)
nucleic acid sequence
ATGACAACGGCTACCGCTACACCTGTTTTGGACTACCATAGCGATCGCTACAAGGATGCCTACAG

CCGCATTAACGCCATTGTCATTGAAGGTGAACAGGAAGCTCACGATAACTATATCGATTTAGCCA

AGCTGCTGCCACAACACCAAGAGGAACTCACCCGCCTTGCCAAGATGGAAGCTCGCCACAAAAAG

GGGTTTGAGGCCTGTGGTCGCAACCTGAGCGTAACGCCAGATATGGAATTTGCCAAAGCCTTCTT

TGAAAAACTGCGCGCTAACTTTCAGAGGGCTCTGGCCGGAGGGAAAAACTGCGACTTGTCTTCTGA

TTCAAGCTTTGATCATCGAATCCTTTGCGATCGCGGCCTACAACATCTACATCCCAATGGCGGAT

CCTTTCGCCCGTAAAATTACTGAGAGTGTTGTTAAGGACGAATACAGCCACCTCAACTTTGGCGA

AATCTGGCTCAAGGAACACTTTGAAAGCGTCAAAGGAGAGCTCGAAGAAGCCAATCGCGCCAATT

TACCCTTGGTCTGGAAAATGCTCAACCAAGTGGAAGCAGATGCCAAAGTGCTCGGCATGGAAAAA

GATGCCCTTGTGGAAGACTTCATGATTCAGTACAGTGGTGCCCTAGAAAATATCGGCTTTACCAC

CCGCGAAATTATGAAGATGTCAGTTTATGGCCTCACTGGGGCATAA (SEQ ID NO: 3)

SEQ ID NO: 4
ThermoSynechococcus elongatus BP-1 tll1313 (ADM)
amino acid sequence
MTTATATPVLDYHSDRYKDAYSRINAIVIEGEQEAHDNYIDLAKLLPQHQEELTRLAKMEARHKK

GFEACGRNLSVTPDMEFAKAFFEKLRANFQRALAEGKTATCLLIQALIIESFAIAAYNIYIPMAD

PFARKITESVVKDEYSHLNFGEIWLKEHFESVKGELEEANRANLPLVWKMLNQVEADAKVLGMEK

DALVEDFMIQYSGALENIGFTTREIMKMSVYGLTGA (SEQ ID NO: 4)

SEQ ID NO: 5
Synechococcus elongatus PCC 7942; SYNPCC7942_1594 (AAR)
nucleic acid sequence
ATGTTCGGTCTTATCGGTCATCTCACCAGTTTGGAGCAGGCCCGCGACGTTTCTCGCAGGATGG

GCTACGACGAATACGCCGATCAAGGATTGGAGTTTTGGAGTAGCGCTCCTCCTCAAATCGTTGA

TGAAATCACAGTCACCAGTGCCACAGGCAAGGTGATTCACGGTCGCTACATCGAATCGTGTTTC

TTGCCGGAAATGCTGGCGGCGCGCCGCTTCAAAACAGCCACGCGCAAAGTTCTCAATGCCATGT

CCCATGCCCAAAAACACGGCATCGACATCTCGGCCTTGGGGGGCTTTACCTCGATTATTTTCGA

GAATTTCGATTTGGCCAGTTTGCGGCAAGTGCGCGACACTACCTTGGAGTTTGAACGGTTCACC

ACCGGCAATACTCACACGGCCTACGTAATCTGTAGACAGGTGGAAGCCGCTGCTAAAACGCTGG

GCATCGACATTACCCAAGCGACAGTAGCGGTTGTCGGCGCGACTGGCGATATCGGTAGCGCTGT

CTGCCGCTGGCTCGACCTCAAACTGGGTGTCGGTGATTTGATCCTGACGGCGCGCAATCAGGAG

CGTTTGGATAACCTGCAGGCTGAACTCGGCCGGGGCAAGATTCTGCCCTTGGAAGCCGCTCTGC

CGGAAGCTGACTTTATCGTGTGGGTCGCCAGTATGCCTCAGGGCGTAGTGATCGACCCAGCAAC

CCTGAAGCAACCCTGCGTCCTAATCGACGGGGGCTACCCCAAAAACTTGGGCAGCAAAGTCCAA

GGTGAGGGCATCTATGTCCTCAATGGCGGGGTAGTTGAACATTGCTTCGACATCGACTGGCAGA

TCATGTCCGCTGCAGAGATGGCGCGGCCCGAGCGCCAGATGTTTGCCTGCTTTGCCGAGGCGAT

GCTCTTGGAATTTGAAGGCTGGCATACTAACTTCTCCTGGGGCCGCAACCAAATCACGATCGAG

AAGATGGAAGCGATCGGTGAGGCATCGGTGCGCCACGGCTTCCAACCCTTGGCATTGGCAATTT

GA (SEQ ID NO: 5)

SEQ ID NO: 6
Synechococcus elongatus PCC 7942; SYNPCC7942_1594 (AAR)
amino acid sequence
MFGLIGHLTSLEQARDVSRRMGYDEYADQGLEFWSSAPPQIVDEITVTSATGKVIHGRYIESCFL

PEMLAARRFKTATRKVLNAMSHAQKHGIDISALGGFTSIIFENFDLASLRQVRDTTLEFERFTTG

NTHTAYVICRQVEAAAKTLGIDITQATVAVVGATGDIGSAVCRWLDLKLGVGDLILTARNQERLD

NLQAELGRGKILPLEAALPEADFIVWVASMPQGVVIDPATLKQPCVLIDGGYPKNLGSKVQGEGI

YVLNGGVVEHCFDIDWQIMSAAEMARPERQMFACFAEAMLLEFEGWHTNFSWGRNQITIEKMEAI

GEASVRHGFQPLALAI (SEQ ID NO: 6)

SEQ ID NO: 7
Synechococcus elongatus PCC 7942; SYNPCC7942_1593 (ADM)
nucleic acid sequence
ATGCCGCAGCTTGAAGCCAGCCTTGAACTGGACTTTCAAAGCGAGTCCTACAAAGACGCTTACAG

CCGCATCAACGCGATCGTGATTGAAGGCGAACAAGAGGCGTTCGACAACTACAATCGCCTTGCTG

AGATGCTGCCCGACCAGCGGGATGAGCTTCACAAGCTAGCCAAGATGGAACAGCGCCACATGAAA

GGCTTTATGGCCTGTGGCAAAAATCTCTCCGTCACTCCTGACATGGGTTTTGCCCAGAAATTTTT

CGAGCGCTTGCACGAGAACTTCAAAGCGGCGGCTGCGGAAGGCAAGGTCGTCACCTGCCTACTGA

TTCAATCGCTAATCATCGAGTGCTTTGCGATCGCGGCTTACAACATCTACATCCCAGTGGCGGAT

GCTTTTGCCCGCAAAATCACGGAGGGGGTCGTGCGCGACGAATACCTGCACCGCAACTTCGGTGA

AGAGTGGCTGAAGGCGAATTTTGATGCTTCCAAAGCCGAACTGGAAGAAGCCAATCGTCAGAACC

```
TGCCCTTGGTTTGGCTAATGCTCAACGAAGTGGCCGATGATGCTCGCGAACTCGGGATGGAGCGT

GAGTCGCTCGTCGAGGACTTTATGATTGCCTACGGTGAAGCTCTGGAAAACATCGGCTTCACAAC

GCGCGAAATCATGCGTATGTCCGCCTATGGCCTTGCGGCCGTTTGA (SEQ ID NO: 7)
```

```
                                                         SEQ ID NO: 8
Synechococcus elongatus PCC 7942; SYNPCC7942_1593 (ADM)
amino acid sequence
MPQLEASLELDFQSESYKDAYSRINAIVIEGEQEAFDNYNRLAEMLPDQRDELHKLAKMEQRHMK

GFMACGKNLSVTPDMGFAQKFFERLHENFKAAAAEGKVVTCLLIQSLIIECFAIAAYNIYIPVAD

AFARKITEGVVRDEYLHRNFGEEWLKANFDASKAELEEANRQNLPLVWLMLNEVADDARELGMER

ESLVEDFMIAYGEALENIGFTTREIMRMSAYGLAAV (SEQ ID NO: 8)
```

```
                                                         SEQ ID NO: 9
Prochlorococcus marinus MIT9312 PMT9312_0533 (AAR)
optimized nucleic acid sequence
ATGTTTGGTCTGATTGGTCATAGCACCAGCTTTGAGGACGCAAAGCGCAAGGCGAGCCTGCTGGG

TTTCGACCACATCGCGGATGGCGATCTGGATGTGTGGTGTACCGCACCGCCGCAACTGGTTGAAA

ACGTGGAAGTCAAAAGCGCGACGGGTATCAGCATTGAAGGTAGCTATATCGATAGCTGCTTCGTG

CCGGAGATGCTGAGCCGCTTCAAGACCGCGCGTCGTAAAGTTCTGAATGCAATGGAGCTGGCGCA

GAAAAAGGGTATCAATATCACTGCCCTGGGTGGCTTTACCTCCATTATCTTTGAGAACTTCAACC

TGTTGCAGCACAAGCAAATCCGTAATACCAGCCTGGAGTGGGAGCGTTTCACCACGGGTAACACG

CACACGGCATGGGTGATTTGTCGTCAGCTGGAGATCAACGCACCGCGCATTGGCATCGACCTGAA

AACTGCAACGGTCGCTGTTATCGGCGCGACCGGCGATATTGGTAGCGCGGTGTGTCGCTGGCTGG

TCAATAAGACCGGCATTAGCGAACTGCTGATGGTCGCTCGCCAACAACAGCCACTGACCCTGCTG

CAAAAAGAACTGGACGGTGGCACCATCAAGAGCCTGGATGAAGCCCTGCCGCAGGCGGATATTGT

CGTGTGGGTTGCTTCGATGCCTAAGACGATCGAAATTGAGATTGAAAACCTGAAAAAGCCGTGCC

TGATGATCGACGGTGGCTACCCGAAGAATCTGGACGAGAAATTCAAAGGCAAAAACATTCACGTG

TTGAAGGGTGGTATCGTCGAGTTTTTCAACGACATTGGCTGGAACATGATGGAGTTGGCGGAGAT

GCAAAACCCGCAGCGTGAGATGTTTGCGTGCTTCGCCGAAGCTATGATTCTGGAGTTTGAGAAAT

GCCATACCAACTTTAGCTGGGGCCGTAACAATATCAGCTTGGAGAAGATGGAGTTCATCGGTGCT

GCATCTCTGAAGCACGGTTTCAGCGCGATCGGTCTGGATAAACAGCCGAAAGTCTTGACCGTTTG

A (SEQ ID NO: 9)
```

```
                                                        SEQ ID NO: 10
Prochlorococcus marinus MIT9312 PMT9312_0533 (AAR)
protein sequence
MFGLIGHSTSFEDAKRKASLLGFDHIADGDLDVWCTAPPQLVENVEVKSATGISIEGSYIDSCFV

PEMLSRFKTARRKVLNAMELAQKKGINITALGGFTSIIFENFNLLQHKQIRNTSLEWERFTTGNT

HTAWVICRQLEINAPRIGIDLKTATVAVIGATGDIGSAVCRWLVNKTGISELLMVARQQQPLTLL

QKELDGGTIKSLDEALPQADIVVWVASMPKTIEIEIENLKKPCLMIDGGYPKNLDEKFKGKNIHV

LKGGIVEFFNDIGWNMMELAEMQNPQREMFACFAEAMILEEKCHTNFSWGRNNISLEKMEFIGAA

SLKHGFSAIGLDKQPKVLTV (SEQ ID NO: 10)
```

```
                                                        SEQ ID NO: 11
Prochlorococcus marinus MIT9312 PMT9312_0532 (ADM)
optimized nucleic acid sequence
ATGCACAATGAATTGAAAATCACGGATATGCAAACGCTGGAAACCAACACCAAGACGACCGAAGA

GTCTATTGACACCAATAGCCTGAACCTGCCGGACTTTACTACCGACAGCTACAAGGATGCCATT

CTCGCATTAACGCCATCGTTATTGAGGGCGAACAGGAAGCTCATGACAATTACATCTCCATCGCA

ACGCTGATCCCGAATGAGCTGGAAGAGCTGACGAAGCTGGCACGTATGGAGCTGAAACACAAGAA
```

-continued

AGGTTTTACTGCGTGCGGTCGTAATCTGGGTGTGGACGCAGACATGGTTTTCGCGAAAAAGTTCT

TCAGCAAACTGCACGGCAATTTCCAAATCGCGCTGGAAAAAGGTAACCTGACCACCTGCTTGCTG

ATCCAAGCGATTCTGATCGAAGCATTTGCGATTTCCGCGTACAATGTTTACATCCGTGTGGCCGA

CCCATTTGCCAAAAAGATTACCGAGGGTGTTGTCAAAGACGAGTATCTGCATCTGAACTATGGTC

AGGAGTGGCTGAAAAAGAATCTGTCCACGTGTAAAGAAGAGCTGATGGAGGCCAACAAGGTCAAT

CTGCCGCTGATTAAGAAAATGCTGGACGAAGTGGCAGAAGATGCGAGCGTTTTGGCGATGGATCG

TGAAGAGTTGATGGAAGAGTTCATGATTGCGTACCAGGATACCCTGTTGGAGATTGGCCTGGATA

ATCGCGAAATTGCCCGTATGGCGATGGCGGCCATTGTTTAG (SEQ ID NO: 11)

SEQ ID NO: 12
Prochlorococcus marinus MIT9312 PMT9312_0532 (ADM)
protein sequence
MHNELKITDMQTLETNTKTTEESIDTNSLNLPDFTTDSYKDAYSRINAIVIEGEQEAHDNYISIA

TLIPNELEELTKLARMELKHKKGFTACGRNLGVDADMVFAKKFFSKLHGNFQIALEKGNLTTCLL

IQAILIEAFAISAYNVYIRVADPFAKKITEGVVKDEYLHLNYGQEWLKKNLSTCKEELMEANKVN

LPLIKKMLDEVAEDASVLAMDREELMEEFMIAYQDTLLEIGLDNREIARMAMAAIV (SEQ ID

NO: 12)

SEQ ID NO: 13
Prochlorococcus marinus MIT9312 PMT9312_0533 (AAR)
nucleic acid sequence
ATGTTTGGGTTAATAGGCCACTCAACTAGTTTTGAAGATGCAAAAAGAAAAGCTTCATTACTAGG

CTTTGATCATATTGCTGATGGTGATCTAGATGTTTGGTGTACAGCCCCTCCTCAATTGGTTGAAA

ATGTAGAAGTTAAGAGTGCTACTGGAATATCTATTGAAGGTTCTTATATAGATTCTTGCTTTGTT

CCTGAAATGCTTTCTAGGTTTAAAACCGCAAGAAGAAAAGTATTAAATGCTATGGAATTAGCTCA

GAAAAAAGGGATTAACATTACGGCTTTAGGAGGATTTACTTCTATTATTTTCGAAAATTTTAATC

TTCTTCAACATAAACAAATTAGAAATACTTCATTAGAGTGGGAAAGGTTTACTACAGGTAATACA

CACACTGCCTGGGTTATTTGTAGGCAACTAGAAATAAATGCTCCTCGCATAGGGATAGATCTTAA

AACTGCAACTGTTGCTGTTATTGGTGCTACAGGTGATATAGGAAGTGCTGTTTGTAGGTGGCTTG

TCAATAAAACTGGTATTTCAGAACTTCTTATGGTGGCTAGCAACAACAACCATTAACTCTATTA

CAGAAAGAATTAGATGGTGGCACTATAAAAAGTTTAGATGAAGCATTGCCTCAAGCGGATATTGT

TGTATGGGTTGCAAGTATGCCTAAAACGATTGAAATTGAAATTGAAAACTTAAAAAAACCATGTT

TAATGATTGATGGTGGATACCCTAAAAATCTTGATGAGAAATTTAAAGGTAAAAATATTCATGTT

TTAAAAGGAGGTATAGTAGAGTTTTTCAATGATATTGGCTGGAATATGATGGAACTTGCAGAAAT

GCAGAACCCTCAGAGAGAGATGTTTGCTTGCTTTGCAGAAGCTATGATTTTAGAATTTGAAAGT

GTCATACCAACTTTAGTTGGGGAAGGAATAACATTTCTCTTGAAAAAATGGAATTTATTGGAGCA

GCTTCTTTGAAACATGGTTTTTCTGCGATTGGACTTGATAAACAGCCTAAAGTATTGACTGTTTG

A (SEQ ID NO: 13)

SEQ ID NO: 14
Prochlorococcus marinus MIT9312 PMT9312_0532 (ADM)
nucleic acid sequence
ATGCATAATGAGCTAAAGATTACTGACATGCAAACTCTAGAAACAAATACAAAAACTACTGAAGA

ATCCATAGACACGAATTCTTTGAATCTTCCCGACTTTACAACAGATTCCTATAAGGATGCATATA

GCAGAATAAATGCAATTGTTATAGAGGGAGAGCAAGAGGCTCATGATAATTACATTTCAATAGCA

ACGTTAATACCAAATGAGTTAGAAGAATTAACTAAGTTGGCGAGAATGGAACTCAAGCATAAAAA

AGGATTTACTGCTTGTGGAAGAAATTTAGGAGTAGATGCTGATATGGTATTCGCAAAAAAATTCT

TTTCTAAATTGCATGGTAATTTTCAAATTGCTTTAGAAAAAGGAAATTTAACAACTTGTCTTCTG

-continued

ATACAAGCTATTTTAATTGAAGCTTTTGCTATATCTGCTTATAACGTTTACATAAGAGTTGCTGA

TCCTTTTGCAAAAAAATAACAGAGGGAGTGGTTAAAGATGAATATCTCCATCTAAATTACGGCC

AAGAGTGGCTTAAAAAGAATTTATCTACTTGTAAAGAAGAATTAATGGAAGCCAATAAGGTTAAC

CTTCCCTTAATTAAAAAGATGTTAGATGAAGTAGCAGAAGATGCATCAGTTTTGGCTATGGATAG

AGAAGAGTTAATGGAAGAATTTATGATTGCTTACCAAGACACTCTTCTAGAAATAGGTCTTGATA

ATAGAGAAATTGCAAGAATGGCTATGGCAGCGATTGTTTAA (SEQ ID NO: 14)

SEQ ID NO: 15 plasmid JB823
1st underlined sequence      Upstream homology region for pAQ1
1st double-underlined        NotI site for promoter swapping
lowercase sequence
1st italic sequence          aphII promoter
2nd double-underlined        NdeI site for promoter swapping
lowercase sequence
1st bold sequence            SYNPCC7942_1593 (adm) coding sequence
1st lower case sequence      Intergenic sequence
2nd bold sequence            SYNPCC7942_1594 (aar) coding sequence
2nd italic sequence          aadA coding sequence; spectinomycin
                             selection marker
2nd underlined sequence      Downstream homology region for pAQ1
2nd lowercase sequence       Vector backbone <u>GTCAGCAAGCTCTGGAATTTCCCGATTCTCTGATGGGAGATCCAAAAATTCTCGCAGTCCCTCA</u>

<u>ATCACGATATCGGTCTTGGATCGCCCTGTAGCTTCCGACAACTGCTCAATTTTTTCGAGCATCT</u>

<u>CTACCGGGCATCGGAATGAAATTAACGGTGTTTTAGCCATGTGTTATACAGTGTTTACAACTTG</u>

<u>ACTAACAAATACCTGCTAGTGTATACATATTGTATTGCAATGTATACGCTATTTTCACTGCTGT</u>

<u>CTTTAATGGGGATTATCGCAAGCAAGTAAAAAAGCCTGAAAACCCCAATAGGTAAGGGATTCCG</u>

<u>AGCTTACTCGATAATTATCACCTTTGAGCGCCCCTAGGAGGAGGCGAAAAGCTATGTCTGACAA</u>

<u>GGGGTTTGACCCCTGAAGTCGTTGCGCGAGCATTAAGGTCTGCGGATAGCCCATAACATACTTT</u>

<u>TGTTGAACTTGTGCGCTTTTATCAACCCCTTAAGGGCTTGGGAGCGTTTTAT</u><u>gcggccgc</u>*GGGG*

*GGGGGGGGAAAGCCACGTTGTGTCTCAAAATCTCTGATGTTACATTGCACAAGATAAAAATAT*

*ATCATCATGAACAATAAAACTGTCTGCTTACATAAACAGTAATACAAGGGGT*<u>catatg</u>CCGCAG

CTTGAAGCCAGCCTTGAACTGGACTTTCAAAGCGAGTCCTACAAAGACGCTTACAGCCGCATCA

ACGCGATCGTGATTGAAGGCGAACAAGAGGCGTTCGACAACTACAATCGCCTTGCTGAGATGCT

GCCCGACCAGCGGGATGAGCTTCACAAGCTAGCCAAGATGGAACAGCGCCACATGAAAGGCTTT

ATGGCCTGTGGCAAAAATCTCTCCGTCACTCCTGACATGGGTTTTGCCCAGAAATTTTTCGAGC

GCTTGCACGAGAACTTCAAAGCGGCGGCTGCGGAAGGCAAGGTCGTCACCTGCCTACTGATTCA

ATCGCTAATCATCGAGTGCTTTGCGATCGCGGCTTACAACATCTACATCCCAGTGGCGGATGCT

TTTGCCCGCAAAATCACGGAGGGGGTCGTGCGCGACGAATACCTGCACCGCAACTTCGGTGAAG

AGTGGCTGAAGGCGAATTTTGATGCTTCCAAAGCCGAACTGGAAGAAGCCAATCGTCAGAACCT

GCCCTTGGTTTGGCTAATGCTCAACGAAGTGGCCGATGATGCTCGCGAACTCGGGATGGAGCGT

GAGTCGCTCGTCGAGGACTTTATGATTGCCTACGGTGAAGCTCTGGAAAACATCGGCTTCACAA

CGCGCGAAATCATGCGTATGTCCGCCTATGGCCTTGCGGCCGTTTGAtccaggaaatctgaATG

TTCGGTCTTATCGGTCATCTCACCAGTTTGGAGCAGGCCCGCGACGTTTCTCGCAGGATGGGCT

ACGACGAATACGCCGATCAAGGATTGGAGTTTTGGAGTAGCGCTCCTCCTCAAATCGTTGATGA

AATCACAGTCACCAGTGCCACAGGCAAGGTGATTCACGGTCGCTACATCGAATCGTGTTTCTTG

CCGGAAATGCTGGCGGCGCGCCGCTTCAAAACAGCCACGCGCAAAGTTCTCAATGCCATGTCCC

ATGCCCAAAAACACGGCATCGACATCTCGGCCTTGGGGGGCTTTACCTCGATTATTTTCGAGAA

TTTCGATTTGGCCAGTTTGCGGCAAGTGCGCGACACTACCTTGGAGTTTGAACGGTTCACCACC

-continued

```
GGCAATACTCACACGGCCTACGTAATCTGTAGACAGGTGGAAGCCGCTGCTAAAACGCTGGGCA
TCGACATTACCCAAGCGACAGTAGCGGTTGTCGGCGCGACTGCCGATATCGGTAGCGCTGTCTG
CCGCTGGCTCGACCTCAAACTGGGTGTCGGTGATTTGATCCTGACGGCGCGCAATCAGGAGCGT
TTGGATAACCTGCAGGCTGAACTCGGCCGGGGCAAGATTCTGCCCTTGGAAGCCGCTCTGCCGG
AAGCTGACTTTATCGTGTGGGTCGCCAGTATGCCTCAGGGCGTAGTGATCGACCCAGCAACCCT
GAAGCAACCCTGCGTCCTAATCGACGGGGGCTACCCCAAAAACTTGGGCAGCAAAGTCCAAGGT
GAGGGCATCTATGTCCTCAATGGCGGGGTAGTTGAACATTGCTTCGACATCGACTGGCAGATCA
TGTCCGCTGCAGAGATGGCGCGGCCCGAGCGCCAGATGTTTGCCTGCTTTGCCGAGGCGATGCT
CTTGGAATTTGAAGGCTGGCATACTAACTTCTCCTGGGGCCGCAACCAAATCACGATCGAGAAG
ATGGAAGCGATCGGTGAGGCATCGGTGCGCCACGGCTTCCAACCCTTGGCATTGGCAATTTGAG
GTCTGTGAATTCGGTTTTCCGTCCTGTCTTGATTTTCAAGCAAACAATGCCTCCGATTTCTAAT
CGGAGGCATTTGTTTTTGTTTATTGCAAAAACAAAAAATATTGTTACAAATTTTTACAGGCTAT
TAAGCCTACCGTCATAAATAATTTGCCATTTACTAGTTTTTAATTAACCAGAACCTTGACCGAA
CGCAGCGGTGGTAACGGCGCAGTGGCGGTTTTCATGGCTTGTTATGACTGTTTTTTTGGGGTAC
AGTCTATGCCTCGGGCATCCAAGCAGCAAGCGCGTTACGCCGTGGGTCGATGTTTGATGTTATG
GAGCAGCAACGATGTTACGCAGCAGGGCAGTCGCCCTAAAACAAAGTTAAACATCATGAGGGAA
```

*GCGGTGATCGCCGAAGTATCGACTCAACTATCAGAGGTAGTTGGCGTCATCGAGCGCCATCTCG*
*AACCGACGTTGCTGGCCGTACATTTGTACGGCTCCGCAGTGGATGGCGGCCTGAAGCCACACAG*
*TGATATTGATTTGCTGGTTACGGTGACCGTAAGGCTTGATGAAACAACGCGGCGAGCTTTGATC*
*AACGACCTTTTGGAAACTTCGGCTTCCCCTGGAGAGAGCGAGATTCTCCGCGCTGTAGAAGTCA*
*CCATTGTTGTGCACGACGACATCATTCCGTGGCGTTATCCAGCTAAGCGCGAACTGCAATTTGG*
*AGAATGGCAGCGCAATGACATTCTTGCAGGTATCTTCGAGCCAGCCACGATCGACATTGATCTG*
*GCTATCTTGCTGACAAAAGCAAGAGAACATAGCGTTGCCTTGGTAGGTCCAGCGGCGGAGGAAC*
*TCTTTGATCCGGTTCCTGAACAGGATCTATTTGAGGCGCTAAATGAAACCTTAACGCTATGGAA*
*CTCGCCGCCCGACTGGGCTGGCGATGAGCGAAATGTAGTGCTTACGTTGTCCCGCATTTGGTAC*
*AGCGCAGTAACCGGCAAAATCGCGCCGAAGGATGTCGCTGCCGACTGGGCAATGGAGCGCCTGC*
*CGGCCCAGTATCAGCCCGTCATACTTGAAGCTAGACAGGCTTATCTTGGACAAGAAGAAGATCG*
*CTTGGCCTCGCGCGCAGATCAGTTGGAAGAATTTGTCCACTACGTGAAAGGCGAGATCACCAAG*
*GTAGTCGGCAAATAATGTCTAACAATTCGTTCAAGCCGACGCCGCTTCGCGGCGCGGCTTAACT*

CAAGCGTTAGATGCACTAAGCACATAATTGCTCACAGCCAAACTATCAGGTCAAGTCTGCTTTT
ATTATTTTTAAGCGTGCATAATAAGCCCTACACAAATTGGGAGATATATCATGAGGCGCGCCA<u>C</u>
<u>GAGTGCGGGAAATTTCGGGGCGATCGCCCCTATATCGCAAAAAGGAGTTACCCCATCAGAGC</u>
<u>TATAGTCGAGAAGAAAACCATCATTCACTCAACAAGGCTATGTCAGAAGAGAAACTAGACCGGA</u>
<u>TCGAAGCAGCCCTAGAGCAATTGGATAAGGATGTGCAAACGCTCCAAACAGAGCTTCAGCAATC</u>
<u>CCAAAAATGGCAGGACAGGACATGGGATGTTGTGAAGTGGGTAGGCGGAATCTCAGCGGGCCTA</u>
<u>GCGGTGAGCGCTTCCATTGCCCTGTTCGGGTTGGTCTTTAGATTTTCTGTTTCCCTGCCATAAA</u>
<u>AGCACATTCTTATAAGTCATACTTGTTTACATCAAGGAACAAAAACGGCATTGTGCCTTGCAAG</u>
<u>GCACAATGTCTTTCTCTTATGCACAGATGGGACTGGAAACCACACGCACAATTCCCTTAAAAA</u>
<u>GCAACCGCAAAAATAACCATCAAAATAAAACTGGACAAATTCTCATGTG</u>ggccggccaaaatg aagtgaagttcctatactttctagagaataggaacttctatagtgagtcgaataagggcgacac
aaaatttattctaaatgcataataaatactgataacatcttatagtttgtattatattttgtat

```
tatcgttgacatgtataattttgatatcaaaaactgattttcccttattattttcgagattta ttttcttaattctctttaacaaactagaaatattgtatatacaaaaaatcataaataatagatg aatagtttaattataggtgttcatcaatcgaaaaagcaacgtatcttatttaaagtgcgttgct tttttctctatttataaggttaaataattctcatatatcaagcaaagtgacaggcgcccttaaat attctgacaaatgctctttccctaaactcccccccataaaaaaacccgccgaagcgggtttttac gttatttgcggattaacgattactcgttatcagaaccgcccaggggcccgagcttaagactgg ccgtcgttttacaacacagaaagagtttgtagaaacgcaaaaaggccatccgtcaggggccttc tgcttagtttgatgcctggcagttccctactctcgccttccgcttcctcgctcactgactcgct gcgctcggtcgttcggctgcggcgagcggtatcagctcactcaaaggcggtaatacggttatcc acagaatcaggggataacgcaggaaagaacatgtgagcaaaaggccagcaaaaggccaggaacc gtaaaaaggccgcgttgctggcgtttttccataggctccgcccccctgacgagcatcacaaaaa tcgacgctcaagtcagaggtggcgaaacccgacaggactataaagataccaggcgtttccccct ggaagctccctcgtgcgctctcctgttccgaccctgccgcttaccggatacctgtccgcctttc tcccttcgggaagcgtggcgctttctcatagctcacgctgtaggtatctcagttcggtgtaggt cgttcgctccaagctgggctgtgtgcacgaaccccccgttcagcccgaccgctgcgccttatcc ggtaactatcgtcttgagtccaacccggtaagacacgacttatcgccactggcagcagccactg gtaacaggattagcagagcgaggtatgtaggcggtgctacagagttcttgaagtggtgggctaa ctacggctacactagaagaacagtatttggtatctgcgctctgctgaagccagttaccttcgga aaaagagttggtagctcttgatccggcaaacaaaccaccgctggtagcggtggtttttttgttt gcaagcagcagattacgcgcagaaaaaaaggatctcaagaagatcctttgatcttttctacggg gtctgacgctcagtggaacgacgcgcgcgtaactcacgttaagggattttggtcatgagcttgc gccgtcccgtcaagtcagcgtaatgctctgcttttaccaatgcttaatcagtgaggcacctatc tcagcgatctgtctatttcgttcatccatagttgcctgactccccgtcgtgtagataactacga tacgggagggcttaccatctggccccagcgctgcgatgataccgcgagaaccacgctcaccggc tccggatttatcagcaataaaccagccagccggaagggccgagcgcagaagtggtcctgcaact ttatccgcctccatccagtctattaattgttgccgggaagctagagtaagtagttcgccagtta atagtttgcgcaacgttgttgccatcgctacaggcatcgtggtgtcacgctcgtcgtttggtat ggcttcattcagctccggttcccaacgatcaaggcgagttacatgatcccccatgttgtgcaaa aaagcggttagctccttcggtcctccgatcgttgtcagaagtaagttggccgcagtgttatcac tcatggttatggcagcactgcataattctcttactgtcatgccatccgtaagatgcttttctgt gactggtgagtactcaaccaagtcattctgagaatagtgtatgcggcgaccgagttgctcttgc ccggcgtcaatacgggataataccgcgccacatagcagaactttaaaagtgctcatcattggaa aacgttcttcggggcgaaaactctcaaggatcttaccgctgttgagatccagttcgatgtaacc cactcgtgcacccaactgatcttcagcatcttttactttcaccagcgtttctgggtgagcaaaa acaggaaggcaaaatgccgcaaaaaagggaataagggcgacacggaaatgttgaatactcatat tcttcctttttcaatattattgaagcatttatcagggttattgtctcatgagcggatacatatt tgaatgtatttagaaaaataaacaaataggggtcagtgttacaaccaattaaccaattctgaac attatcgcgagcccatttatacctgaatatggctcataacacccccttgtttgcctggcggcagt agcgcggtggtcccacctgaccccatgccgaactcagaagtgaaacgccgtagcgccgatggta
```

-continued gtgtggggactccccatgcgagagtagggaactgccaggcatcaaataaaacgaaaggctcagt cgaaagactgggcctttcgcccgggctaattatggggtgtcgcccttattcgactctatagtga agttcctattctctagaaagtataggaacttctgaagtggggcctgcagg (SEQ ID NO: 15)

SEQ ID NO: 16
plasmid pJB855
1st bold sequence      SYNPCC7942_1593 coding sequence
2nd bold sequence      SYNPCC7942_1594 coding sequence
Italic sequence        aadA spectinomycin selection marker
                       (reverse complement)

GGGGAATTGTGAGCGGATAACAATTCCCCTGTAGAAATAATTTTGTTTAACTTTAATAAGGAGAT

ATACCATGGGCAGCAGCCATCACCATCATCACCACAGCCAGGATCCGAATTCGAGCTCGGCGCG

CTGCAGGTCGACAAGCTTGCGGCCGCATAATGCTTAAGTCGAACAGAAAGTAATCGTATTGTACA

CGGCCGCATAATCGAAATTAATACGACTCACTATAGGGGAATTGTGAGCGGATAACAATTCCCCA

TCTTAGTATATTAGTTAAGTATAAGAAGGAGATATACATATGCCGCAGCTTGAAGCCAGCCTTGA

ACTGGACTTTCAAAGCGAGTCCTACAAAGACGCTTACAGCCGCATCAACGCGATCGTGATTGAAG

GCGAACAAGAGGCGTTCGACAACTACAATCGCCTTGCTGAGATGCTGCCCGACCAGCGGGATGAG

CTTCACAAGCTAGCCAAGATGGAACAGCGCCACATGAAAGGCTTTATGGCCTGTGGCAAAAATCT

CTCCGTCACTCCTGACATGGGTTTTGCCCAGAAATTTTTCGAGCGCTTGCACGAGAACTTCAAAG

CGGCGGCTGCGGAAGGCAAGGTCGTCACCTGCCTACTGATTCAATCGCTAATCATCGAGTGCTTT

GCGATCGCGGCTTACAACATCTACATCCCAGTGGCGGATGCTTTTGCCCGCAAAATCACGGAGGG

GGTCGTGCGCGACGAATACCTGCACCGCAACTTCGGTGAAGAGTGGCTGAAGGCGAATTTTGATG

CTTCCAAAGCCGAACTGGAAGAAGCCAATCGTCAGAACCTGCCCTTGGTTTGGCTAATGCTCAAC

GAAGTGGCCGATGATGCTCGCGAACTCGGGATGGAGCGTGAGTCGCTCGTCGAGGACTTTATGAT

TGCCTACGGTGAAGCTCTGGAAAACATCGGCTTCACAACGCGCGAAATCATGCGTATGTCCGCCT

ATGGCCTTGCGGCCGTTTGATCCAGGAAATCTGAATGTTCGGTCTTATCGGTCATCTCACCAGTT

TGGAGCAGGCCCGCGACGTTTCTCGCAGGATGGGCTACGACGAATACGCCGATCAAGGATTGGAG

TTTTGGAGTAGCGCTCCTCCTCAAATCGTTGATGAAATCACAGTCACCAGTGCCACAGGCAAGGT

GATTCACGGTCGCTACATCGAATCGTGTTTCTTGCCGGAAATGCTGGCGGCGCGCCGCTTCAAAA

CAGCCACGCGCAAAGTTCTCAATGCCATGTCCCATGCCCAAAAACACGGCATCGACATCTCGGCC

TTGGGGGGCTTTACCTCGATTATTTTCGAGAATTTCGATTTGGCCAGTTTGCGGCAAGTGCGCGA

CACTACCTTGGAGTTTGAACGGTTCACCACCGGCAATACTCACACGGCCTACGTAATCTGTAGAC

AGGTGGAAGCCGCTGCTAAAACGCTGGGCATCGACATTACCCAAGCGACAGTAGCGGTTGTCGGC

GCGACTGGCGATATCGGTAGCGCTGTCTGCCGCTGGCTCGACCTCAAACTGGGTGTCGGTGATTT

GATCCTGACGGCGCGCAATCAGGAGCGTTTGGATAACCTGCAGGCTGAACTCGGCCGGGGCAAGA

TTCTGCCCTTGGAAGCCGCTCTGCCGGAAGCTGACTTTATCGTGTGGGTCGCCAGTATGCCTCAG

GGCGTAGTGATCGACCCAGCAACCCTGAAGCAACCCTGCGTCCTAATCGACGGGGGCTACCCCAA

AAACTTGGGCAGCAAAGTCCAAGGTGAGGGCATCTATGTCCTCAATGGCGGGGTAGTTGAACATT

GCTTCGACATCGACTGGCAGATCATGTCCGCTGCAGAGATGGCGCGGCCCGAGCGCCAGATGTTT

GCCTGCTTTGCCGAGGCGATGCTCTTGGAATTTGA**AGGTGGCATACTAACTTCTCCTGGGGCCG

CAACCAAATCACGATCGAGAAGATGGAAGCGATCGGTGAGGCATCGGTGCGCCACGGCTTCCAAC

CCTTGGCATTGGCAATTTGAGGTCTGTGAATTGGATATCGGCCGGCCACGCGATCGCTGACGTCG

GTACCCTCGAGTCTGGTAAAGAAACCGCTGCTGCGAAATTTGAACGCCAGCACATGGACTCGTCT

*ACTAGCGCAGCTTAATTAACCTAGGCTGCTGCCACCGCTGAGCAATAACTAGCATAACCCCTTGG*

-continued

```
GGCCTCTAAACGGGTCTTGAGGGGTTTTTTGCTGAAACCTCAGGCATTTGAGAAGCACACGGTCA
CACTGCTTCCGGTAGTCAATAAACCGGTAAACCAGCAATAGACATAAGCGGCTATTTAACGACCC
TGCCCTGAACCGACGACCGGGTCATCGTGGCCGGATCTTGCGGCCCCTCGGCTTGAACGAATTGT
TAGACATTATTTGCCGACTACCTTGGTGATCTCGCCTTTCACGTAGTGGACAAATTCTTCCAACT
GATCTGCGCGCGAGGCCAAGCGATCTTCTTCTTGTCCAAGATAAGCCTGTCTAGCTTCAAGTATG
ACGGGCTGATACTGGGCCGGCAGGCGCTCCATTGCCCAGTCGGCAGCGACATCCTTCGGCGCGAT
TTTGCCGGTTACTGCGCTGTACCAAATGCGGGACAACGTAAGCACTACATTTCGCTCATCGCCAG
CCCAGTCGGGCGGCGAGTTCCATAGCGTTAAGGTTTCATTTAGCGCCTCAAATAGATCCTGTTCA
GGAACCGGATCAAAGAGTTCCTCCGCCGCTGGACCTACCAAGGCAACGCTATGTTCTCTTGCTTT
TGTCAGCAAGATAGCCAGATCAATGTCGATCGTGGCTGGCTCGAAGATACCTGCAAGAATGTCAT
TGCGCTGCCATTCTCCAAATTGCAGTTCGCGCTTAGCTGGATAACGCCACGGAATGATGTCGTCG
TGCACAACAATGGTGACTTCTACAGCGCGGAGAATCTCGCTCTCTCCAGGGGAAGCCGAAGTTTC
CAAAAGGTCGTTGATCAAAGCTCGCCGCGTTGTTTCATCAAGCCTTACGGTCACCGTAACCAGCA
AATCAATATCACTGTGTGGCTTCAGGCCGCCATCCACTGCGGAGCCGTACAAATGTACGGCCAGC
AACGTCGGTTCGAGATGGCGCTCGATGACGCCAACTACCTCTGATAGTTGAGTCGATACTTCGGC
GATCACCGCTTCCCTCATACTCTTCCTTTTTCAATATTATTGAAGCATTTATCAGGGTTATTGTC
TCATGAGCGGATACATATTTGAATGTATTTAGAAAAATAAACAAATAGCTAGCTCACTCGGTCGC
TACGCTCCGGGCGTGAGACTGCGGCGGGCGCTGCGGACACATACAAAGTTACCCACAGATTCCGT
GGATAAGCAGGGGACTAACATGTGAGGCAAAACAGCAGGGCCGCGCCGGTGGCGTTTTTCCATAG
GCTCCGCCCTCCTGCCAGAGTTCACATAAACAGACGCTTTTCCGGTGCATCTGTGGGAGCCGTGA
GGCTCAACCATGAATCTGACAGTACGGGCGAAACCCGACAGGACTTAAAGATCCCCACCGTTTCC
GGCGGGTCGCTCCCTCTTGCGCTCTCCTGTTCCGACCCTGCCGTTTACCGGATACCTGTTCCGCC
TTTCTCCCTTACGGGAAGTGTGGCGCTTTCTCATAGCTCACACACTGGTATCTCGGCTCGGTGTA
GGTCGTTCGCTCCAAGCTGGGCTGTAAGCAAGAACTCCCCGTTCAGCCCGACTGCTGCGCCTTAT
CCGGTAACTGTTCACTTGAGTCCAACCCGGAAAAGCACGGTAAAACGCCACTGGCAGCAGCCATT
GGTAACTGGGAGTTCGCAGAGGATTTGTTTAGCTAAACACGCGGTTGCTCTTGAAGTGTGCGCCA
AAGTCCGGCTACACTGGAAGGACAGATTTGGTTGCTGTGCTCTGCGAAAGCCAGTTACCACGGTT
AAGCAGTTCCCCAACTGACTTAACCTTCGATCAAACCACCTCCCCAGGTGGTTTTTTCGTTTACA
GGGCAAAAGATTACGCGCAGAAAAAAAGGATCTCAAGAAGATCCTTTGATCTTTTCTACTGAACC
GCTCTAGATTTCAGTGCAATTTATCTCTTCAAATGTAGCACCTGAAGTCAGCCCCATACGATATA
AGTTGTAATTCTCATGTTAGTCATGCCCCGCGCCCACCGGAAGGAGCTGACTGGGTTGAAGGCTC
TCAAGGGCATCGGTCGAGATCCCGGTGCCTAATGAGTGAGCTAACTTACATTAATTGCGTTGCGC
TCACTGCCCGCTTTCCAGTCGGGAAACCTGTCGTGCCAGCTGCATTAATGAATCGGCCAACGCGC
GGGGAGAGGCGGTTTGCGTATTGGGCGCCAGGGTGGTTTTCTTTTCACCAGTGAGACGGGCAAC
AGCTGATTGCCCTTCACCGCCTGGCCCTGAGAGAGTTGCAGCAAGCGGTCCACGCTGGTTTGCCC
CAGCAGGCGAAAATCCTGTTTGATGGTGGTTAACGGCGGGATATAACATGAGCTGTCTTCGGTAT
CGTCGTATCCCACTACCGAGATGTCCGCACCAACGCGCAGCCCGGACTCGGTAATGGCGCGCATT
GCGCCCAGCGCCATCTGATCGTTGGCAACCAGCATCGCAGTGGGAACGATGCCCTCATTCAGCAT
TTGCATGGTTTGTTGAAAACCGGACATGGCACTCCAGTCGCCTTCCCGTTCCGCTATCGGCTGAA
TTTGATTGCGAGTGAGATATTTATGCCAGCCAGCCAGACGCAGACGCGCCGAGACAGAACTTAAT
```

-continued

GGGCCCGCTAACAGCGCGATTTGCTGGTGACCCAATGCGACCAGATGCTCCACGCCCAGTCGCGT

ACCGTCTTCATGGGAGAAAATAATACTGTTGATGGGTGTCTGGTCAGAGACATCAAGAAATAACG

CCGGAACATTAGTGCAGGCAGCTTCCACAGCAATGGCATCCTGGTCATCCAGCGGATAGTTAATG

ATCAGCCCACTGACGCGTTGCGCGAGAAGATTGTGCACCGCCGCTTTACAGGCTTCGACGCCGCT

TCGTTCTACCATCGACACCACCACGCTGGCACCCAGTTGATCGGCGCGAGATTTAATCGCCGCGA

CAATTTGCGACGGCGCGTGCAGGGCCAGACTGGAGGTGGCAACGCCAATCAGCAACGACTGTTTG

CCCGCCAGTTGTTGTGCCACGCGGTTGGGAATGTAATTCAGCTCCGCCATCGCCGCTTCCACTTT

TTCCCGCGTTTTCGCAGAAACGTGGCTGGCCTGGTTCACCACGCGGGAAACGGTCTGATAAGAGA

CACCGGCATACTCTGCGACATCGTATAACGTTACTGGTTTCACATTCACCACCCTGAATTGACTC

TCTTCCGGGCGCTATCATGCCATACCGCGAAAGGTTTTGCGCCATTCGATGGTGTCCGGGATCTC

GACGCTCTCCCTTATGCGACTCCTGCATTAGGAAATTAATACGACTCACTATA (SEQ ID

NO: 16)

SEQ ID NO: 17 plasmid pJB947
1st underlined sequence    Upstream homology region for pAQ1
1st italic sequence        aphII promoter
1st bold sequence          PMT9312_0532 (adm) coding sequence
1st lower case sequence    Intergenic sequence
2nd bold sequence          PMT9312_0533 (aar)
2nd italic sequence        aadA coding sequence; spectinomycin
                           selection marker
2nd underlined sequence    Downstream homology region for pAQ1
2nd lower case sequence    Vector backbone

GTCAGCAAGCTCTGGAATTTCCCGATTCTCTGATGGGAGATCCAAAAATTCTCGCAGTCCCTCAAT

CACGATATCGGTCTTGGATCGCCCTGTAGCTTCCGACAACTGCTCAATTTTTTCGAGCATCTCTAC

CGGGCATCGGAATGAAATTAACGGTGTTTTAGCCATGTGTTATACAGTGTTTACAACTTGACTAAC

AAATACCTGCTAGTGTATACATATTGTATTGCAATGTATACGCTATTTTCACTGCTGTCTTTAATG

GGGATTATCGCAAGCAAGTAAAAAAGCCTGAAAACCCCAATAGGTAAGGGATTCCGAGCTTACTCG

ATAATTATCACCTTTGAGCGCCCCTAGGAGGAGGCGAAAAGCTATGTCTGACAAGGGGTTTGACCC

CTGAAGTCGTTGCGCGAGCATTAAGGTCTGCGGATAGCCCATAACATACTTTTGTTGAACTTGTGC

GCTTTTATCAACCCCTTAAGGGCTTGGGAGCGTTTTATGCGGCCGCGGGGGGGGGGGGGAAAGCCA

CGTTGTGTCTCAAAATCTCTGATGTTACATTGCACAAGATAAAAATATATCATCATGAACAATAAA

ACTGTCTGCTTACATAAACAGTAATACAAGGGGTCATATGCACAATGAATTGAAAATCACGGATAT

GCAAACGCTGGAAACCAACACCAAGACGACCGAAGAGTCTATTGACACCAATAGCCTGAACCTGCC

GGACTTTACTACCGACAGCTACAAGGATGCCTATTCTCGCATTAACGCCATCGTTATTGAGGGCGA

ACAGGAAGCTCATGACAATTACATCTCCATCGCAACGCTGATCCCGAATGAGCTGGAAGAGCTGAC

GAAGCTGGCACGTATGGAGCTGAAACACAAGAAAGGTTTTACTGCGTGCGGTCGTAATCTGGGTGT

GGACGCAGACATGGTTTTCGCGAAAAAGTTCTTCAGCAAACTGCACGGCAATTTCCAAATCGCGCT

GGAAAAAGGTAACCTGACCACCTGCTTGCTGATCCAAGCGATTCTGATCGAAGCATTTGCGATTTC

CGCGTACAATGTTTACATCCGTGTGGCCGACCCATTTGCCAAAAAGATTACCGAGGGTGTTGTCAA

AGACGAGTATCTGCATCTGAACTATGGTCAGGAGTGGCTGAAAAAGAATCTGTCCACGTGTAAAGA

AGAGCTGATGGAGGCCAACAAGGTCAATCTGCCGCTGATTAAGAAAATGCTGGACGAAGTGGCAGA

AGATGCGAGCGTTTTGGCGATGGATCGTGAAGAGTTGATGGAAGAGTTCATGATTGCGTACCAGGA

TACCCTGTTGGAGATTGGCCTGGATAATCGCGAAATTGCCCGTATGGCGATGGCGGCCATTGTTTA

GtaatatttctaattaactaataaaggaagtctgaATGTTTGGTCTGATTGGTCATAGCACCAGCT

TTGAGGACGCAAAGCGCAAGGCGAGCCTGCTGGGTTTCGACCACATCGCGGATGGCGATCTGGATG

-continued

TGTGGTGTACCGCACCGCCGCAACTGGTTGAAAACGTGGAAGTCAAAAGCGCGACGGGTATCAGCA

TTGAAGGTAGCTATATCGATAGCTGCTTCGTGCCGGAGATGCTGAGCCGCTTCAAGACCGCGCGTC

GTAAAGTTCTGAATGCAATGGAGCTGGCGCAGAAAAAGGGTATCAATATCACTGCCCTGGGTGGCT

TTACCTCCATTATCTTTGAGAACTTCAACCTGTTGCAGCACAAGCAAATCCGTAATACCAGCCTGG

AGTGGGAGCGTTTCACCACGGGTAACACGCACACGGCATGGGTGATTTGTCGTCAGCTGGAGATCA

ACGCACCGCGCATTGGCATCGACCTGAAAACTGCAACGGTCGCTGTTATCGGCGCGACCGGCGATA

TTGGTAGCGCGGTGTGTCGCTGGCTGGTCAATAAGACCGGCATTAGCGAACTGCTGATGGTCGCTC

GCCAACAACAGCCACTGACCCTGCTGCAAAAAGAACTGGACGGTGGCACCATCAAGAGCCTGGATG

AAGCCCTGCCGCAGGCGGATATTGTCGTGTGGGTTGCTTCGATGCCTAAGACGATCGAAATTGAGA

TTGAAAACCTGAAAAAGCCGTGCCTGATGATCGACGGTGGCTACCCGAAGAATCTGGACGAGAAAT

TCAAAGGCAAAAACATTCACGTGTTGAAGGGTGGTATCGTCGAGTTTTTCAACGACATTGGCTGGA

ACATGATGGAGTTGGCGGAGATGCAAAACCCGCAGCGTGAGATGTTTGCGTGCTTCGCCGAAGCTA

TGATTCTGGAGTTTGAGAAATGCCATACCAACTTTAGCTGGGGCCGTAACAATATCAGCTTGGAGA

AGATGGAGTTCATCGGTGCTGCATCTCTGAAGCACGGTTTCAGCGCGATCGGTCTGGATAAACAGC

CGAAAGTCTTGACCGTTTGAaattGAATTCGGTTTTCCGTCCTGTCTTGATTTTCAAGCAAACAAT

GCCTCCGATTTCTAATCGGAGGCATTTGTTTTTGTTTATTGCAAAAACAAAAAATATTGTTACAAA

TTTTTACAGGCTATTAAGCCTACCGTCATAAATAATTTGCCATTTACTAGTTTTTAATTAACCAGA

ACCTTGACCGAACGCAGCGGTGGTAACGGCGCAGTGGCGGTTTTCATGGCTTGTTATGACTGTTTT

TTTGGGGTACAGTCTATGCCTCGGGCATCCAAGCAGCAAGCGCGTTACGCCGTGGGTCGATGTTTG

ATGTTATGGAGCAGCAACGATGTTACGCAGCAGGGCAGTCGCCCTAAAACAAAGTTAAACATCATG

*AGGGAAGCGGTGATCGCCGAAGTATCGACTCAACTATCAGAGGTAGTTGGCGTCATCGAGCGCCAT*

*CTCGAACCGACGTTGCTGGCCGTACATTTGTACGGCTCCGCAGTGGATGGCGGCCTGAAGCCACAC*

*AGTGATATTGATTTGCTGGTTACGGTGACCGTAAGGCTTGATGAAACAACGCGGCGAGCTTTGATC*

*AACGACCTTTTGGAAACTTCGGCTTCCCCTGGAGAGAGCGAGATTCTCCGCGCTGTAGAAGTCACC*

*ATTGTTGTGCACGACGACATCATTCCGTGGCGTTATCCAGCTAAGCGCGAACTGCAATTTGGAGAA*

*TGGCAGCGCAATGACATTCTTGCAGGTATCTTCGAGCCAGCCACGATCGACATTGATCTGGCTATC*

*TTGCTGACAAAAGCAAGAGAACATAGCGTTGCCTTGGTAGGTCCAGCGGCGGAGGAACTCTTTGAT*

*CCGGTTCCTGAACAGGATCTATTTGAGGCGCTAAATGAAACCTTAACGCTATGGAACTCGCCGCCC*

*GACTGGGCTGGCGATGAGCGAAATGTAGTGCTTACGTTGTCCCGCATTTGGTACAGCGCAGTAACC*

*GGCAAAATCGCGCCGAAGGATGTCGCTGCCGACTGGGCAATGGAGCGCCTGCCGGCCCAGTATCAG*

*CCCGTCATACTTGAAGCTAGACAGGCTTATCTTGGACAAGAAGAAGATCGCTTGGCCTCGCGCGCA*

*GATCAGTTGGAAGAATTTGTCCACTACGTGAAAGGCGAGATCACCAAGGTAGTCGGCAAATAATGT*

CTAACAATTCGTTCAAGCCGACGCCGCTTCGCGGCGCGGCTTAACTCAAGCGTTAGATGCACTAAG

CACATAATTGCTCACAGCCAAACTATCAGGTCAAGTCTGCTTTTATTATTTTTAAGCGTGCATAAT

AAGCCCTACACAAATTGGGAGATATATCATGAGGCGCGCC<u>ACGAGTGCGGGGAAATTTCGGGGGCG</u>

<u>ATCGCCCCTATATCGCAAAAAGGAGTTACCCCATCAGAGCTATAGTCGAGAAGAAAACCATCATTC</u>

<u>ACTCAACAAGGCTATGTCAGAAGAGAAACTAGACCGGATCGAAGCAGCCCTAGAGCAATTGGATAA</u>

<u>GGATGTGCAAACGCTCCAAACAGAGCTTCAGCAATCCCAAAAATGGCAGGACAGGACATGGGATGT</u>

<u>TGTGAAGTGGGTAGGCGGAATCTCAGCGGGCCTAGCGGTGAGCGCTTCCATTGCCCTGTTCGGGTT</u>

<u>GGTCTTTAGATTTTCTGTTTCCCTGCCATAAAAGCACATTCTTATAAGTCATACTTGTTTACATCA</u>

<u>AGGAACAAAAACGGCATTGTGCCTTGCAAGGCACAATGTCTTTCTCTTATGCACAGATGGGGACTG</u>

-continued

GAAACCACACGCACAATTCCCTTAAAAAGCAACCGCAAAAAATAACCATCAAAATAAAACTGGACA
AATTCTCATGTGggccggccaaaatgaagtgaagttcctatactttctagagaataggaacttcta
tagtgagtcgaataagggcgacacaaaatttattctaaatgcataataaatactgataacatctta
tagtttgtattatattttgtattatcgttgacatgtataattttgatatcaaaaactgattttccc
tttattattttcgagatttattttcttaattctcttaacaaactagaaatattgtatatacaaaa
aatcataaataatagatgaatagtttaattataggtgttcatcaatcgaaaagcaacgtatctta
tttaaagtgcgttgcttttttctcatttataaggttaaataattctcatatatcaagcaaagtgac
aggcgcccttaaatattctgacaaatgctctttccctaaactccccccataaaaaaacccgccgaa
gcgggttttacgttatttgcggattaacgattactcgttatcagaaccgcccagggggcccgagc
ttaagactggccgtcgttttacaacacagaaagagtttgtagaaacgcaaaaaggccatccgtcag
gggccttctgcttagtttgatgcctggcagttccctactctcgccttccgcttcctcgctcactga
ctcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaa
ccgtaaaaaggccgcgttgctggcgtttttccataggctccgcccccctgacgagcatcacaaaaa
tcgacgctcaagtcagaggtggcgaaacccgacaggactataaagataccaggcgtttccccctgg
aagctccctcgtgcgctctcctgttccgaccctgccgcttaccggatacctgtccgcctttctccc
ttcgggaagcgtggcgctttctcatagctcacgctgtaggtatctcagttcggtgtaggtcgttcg
ctccaagctgggctgtgtgcacgaaccccccgttcagcccgaccgctgcgccttatccggtaacta
tcgtcttgagtccaacccggtaagacacgacttatcgccactggcagcagccactggtaacaggat
tagcagagcgaggtatgtaggcggtgctacagagttcttgaagtggtgggctaactacggctacac
tagaagaacagtatttggtatctgcgctctgctgaagccagttaccttcggaaaaagagttggtag
ctcttgatccggcaaacaaaccaccgctggtagcggtggtttttttgtttgcaagcagcagattac
gcgcagaaaaaaaggatctcaagaagatcctttgatcttttctacggggtctgacgctcagtggaa
cgacgcgcgcgtaactcacgttaagggattttggtcatgagcttgcgccgtcccgtcaagtcagcg
taatgctctgcttttaccaatgcttaatcagtgaggcacctatctcagcgatctgtctatttcgtt
catccatagttgcctgactccccgtcgtgtagataactacgatacgggagggcttaccatctggcc
ccagcgctgcgatgataccgcgagaaccacgctcaccggctccggatttatcagcaataaaccagc
cagccggaagggccgagcgcagaagtggtcctgcaactttatccgcctccatccagtctattaatt
gttgccgggaagctagagtaagtagttcgccagttaatagtttgcgcaacgttgttgccatcgcta
caggcatcgtggtgtcacgctcgtcgtttggtatggcttcattcagctccggttcccaacgatcaa
ggcgagttacatgatcccccatgttgtgcaaaaaagcggttagctccttcggtcctccgatcgttg
tcagaagtaagttggccgcagtgttatcactcatggttatggcagcactgcataattctcttactg
tcatgccatccgtaagatgcttttctgtgactggtgagtactcaaccaagtcattctgagaatagt
gtatgcggcgaccgagttgctcttgcccggcgtcaatacgggataataccgcgccacatagcagaa
ctttaaaagtgctcatcattggaaaacgttcttcggggcgaaaactctcaaggatcttaccgctgt
tgagatccagttcgatgtaacccactcgtgcacccaactgatcttcagcatcttttactttcacca
gcgtttctgggtgagcaaaaacaggaaggcaaaatgccgcaaaaaagggaataagggcgacacgga
aatgttgaatactcatattcttccttttcaatattattgaagcatttatcagggttattgtctca
tgagcggatacatatttgaatgtatttagaaaaataaacaaataggggtcagtgttacaaccaatt
aaccaattctgaacattatcgcgagcccatttataccotgaatatggctcataacaccccttgtttg -continued cctggcggcagtagcgcggtggtcccacctgaccccatgccgaactcagaagtgaaacgccgtagc gccgatggtagtgtggggactccccatgcgagagtagggaactgccaggcatcaaataaaacgaaa ggctcagtcgaaagactgggcctttcgcccgggctaattatggggtgtcgcccttattcgactcta tagtgaagttcctattctctagaaagtataggaacttctgaagtggggcctgcagg (SEQ ID NO: 17)

SEQ ID NO: 18
plasmid pJB825t
| | |
|---|---|
| 1st underlined sequence | Upstream homology region for TS1 chromosomal integration site |
| 1st italic sequence | cI promoter with JCC138 rbcL ribosome-binding sequence |
| 1st bold sequence | Tll1313 (adm) coding sequence |
| 1st lower case sequence | Native intergenic sequence |
| 2nd bold sequence | Tll1312 (aar) coding sequence |
| 2nd italic sequence | kan$^{HTK}$ coding sequence; thermostable kanamycin selection marker |
| 2nd underlined sequence | Downstream homology region for TS1 chromosomal integration site |
| 2nd lower case sequence | Vector backbone |

TGGGAGTCAATAAACCCGATGTGCGTTGGATTTGCCACTACCAGCCGCCCCTGCAACTCAGTGAA

TATCTCCAAGAGGTGGGACGCGCTGGGCGAGATGGCGAAGCGGCACAGGCCCTGGTTTTGGTGAG

CGATCGCTGGGGCTTGGATCGCGAAGATCAACAGCGTTGGTCTTTTTTTCAGCACCAAAGTCAAG

ACACCTACAATCGCGCCATGGCACTTCAGACGCAGCTGCCCCTCCAGGGTAATCTGCAGCAACTG

CGGCAACACTTTCCTGAAGTGGAATTGACCCTGGCATTACTGCATCAACAGGGGGCCCTCCGCTG

GCAAGATCCCTTTCACTATTGCCGTCAACCCTTGGCACAGGTGCCACCCCCACCCAAAGACCCTC

AAGAACAGTTGATGCAAAAGTTCCTCTATCACCGGGGCTGCCGCTGGCAGTTTCTCCTCCAAGCC

TTTGGTTTTGCCACTGAGGCAAGGGGATTCCACTGTGGCCATTGCGATCGCTGTCGGCCGCCGCA

CCGCTCCCGCAAAATACCGTAAATTGCCAGCGCTGTATCACTGGAATATTGGGTACACTGGCACA

TAGAACGGTCGCTTTACCATTGGTAGGCAAAAGTTTCTCAGCAGTCATTCTGTTGCCGCAAGGTA

GGGGTTGCAGGCATGGGCTACTACAAGTTGAGGAAATTCGCGAAGCACTTCAAGATGTGCTTTC

AGAACACGCCCTTGTTGTGCAAGTTAATCAGTTTCGCAACCAATTAAACATTATTTTGAACAAGC

CCCCCGGCACCGTTGCCCATTATTCTGCCCTAGCGGATTTTCTCAAGTCGCGCTTGGGACAGTTT

CATCTCAATGATATTGACCGCATTAAAATAATTGGCCGCATACAGGGTTCGCCTAAACCCGATTG

GGAAGAGGTCATTGATCTACGTCCCCCCAACCCAGCCCTAGCTGCCCCTGTGTATGCTTCTTCTG

CCCCGTGGGTGGTGGCGATCGCTGCTGGCTTTGTCAGTTTACTGGTGATCTTTAGCTATCACCTT

GGTCAGTAGCAGCAACAGCAACGGCTGTAGCCGTTGATCGAAGGTTCCTTTGGTCAAAAGGGCGT

CGTGATGACGGACTTTAAGTGGCACATTGAGGGTGGTACAGGGTTTATTGTCGGGGTTCTTAAAA

ACTACAGTAAAGGGTATTTTCGCTTAGTTCAGGCGGACTTTGAACTCTTTGACCAAGGCGGTCAG

CAAGTTGGGACAGTGGCGGTACAGGTTTATGGTCTTGGCCCTGAGGAAACATGGCAATTCCGTGA

ACTGATAGCCAATCATCAGGCAGTGCGAGCACGGCTGGTAAAATTACAGTCATTCAATTAAGGTT

TTTCTAATGTTTAGGTTTCCCCAGCAGGGAGCGACACCGCTTGCTATGGCACACCTTAAAGCCCT

GATCTTTGATGTCGATGGCACCTTAGCAGATACGGAGCGGGATGGCCATCGTATCGCCTTCAACA

AGGCCTTTGCCGCCGCTGGTCTAGATTGGGAATGGGACATTCCCCTCTATGGTCAACTCCTGGCG

GTGGCTGGGGCAAGGAGCGGATCCGGTATTACCTTGAGTGCTTTCGTCCCGATTGGCCACGTCC

CCAAAATTTGGATGCTCTGATTGCCGATTTACACAAGGCCAAGACCCGCTATTATACCGAGCTAT

TGGCCGGCAGGGGCTATTCCCCTGCGGCCGGGGGTGAAACGGCTCCTCACTGAAGCCCGGGAAGCA

GGATTACGTTTGGCGATCGCCACCACGACCACCCCTGCCAATGTCACCGCACTCCTTGAAAATGC

CCTCGCTCCTGATGGCGTCAGTTGGTTTGAGATAATTGCTGCCGGGGATGTAGTTCCAGCCAAGA

AACCCGCGCCCGACATTTACTTCTACACGCTTGAAAAGATGCGCCTCTCACCCCAAGAGTGCCTT

GCCTTTGAGGATTCCGCCAATGGGATTCAGGCGGCCACTGCCAGTCACCTAGCGACCATTATCAC

GATTACCGACTACACCAAGGATCATGATTTTCGTGATGCAGCGCTGGTCTTGGATTGCTTAGGGG

AACCGGACTACCCCTTTCAGGTTCTGCGCGGTGAGGTGGGTTGGACAACCTATGTGGATGTCCCC

CTATTGCGATCGCTGCACCAGCAGTGGACAAGCACGTTGAGTCAGGGATAATTTTCTGGCCGCAG

CGTTTTACATTGAATATGACCCCCTTAGTCTGAGGATCAAGGAACATAATGTACACGATTGATTT

AATTCTGCGTCATGTCCCCATGCCCGTCAGCATTGAACGCAAGGAAAGTGCAGCAGCGATGGCAG

TCTATCAGCAAATTCAGCAGGCCATGGCCAGTGGTACTCCAACTTTCCTCGAACTGACGTGCGAT

CGCCAAGTGGGCAAGAAGTTAACGGTGCTCACCTCAGAAATTGTCGCCGTGCAAATGGCGGATAA

GGATGCCCCCTCCAGTACTATCAGTCGTGGGGGATTCTTTGCTCAATTAGTGCAGCAAACCAGCA

ACTGAGGGAAAATGCCTCAATAAAGTTGAGTTTTTCTTGGCAATGCTGATTCTTTGCCGTTAGGA

TACTAAGCAGACCGATCCGTAGGGGAACGTGAAGCAAATCCTCCCCGTCTGAAAGTCAGGTATCT

CTGGTGTGTCGTAATAGGGTTGTCTATGGTGCAGCGTTTCCTGCCGGTTCTGATTTTGTTGGGGT

GTAGTTTTGGTCTTGCGACCCCTGCCCTTGTGCGTGCCCAAGCCAATCAGGGCTTTACGTTTACT

TGGGGTGAGGGGCCGAGTGGCCGACAGCAGTTGCAATACCACTTAGATAACGGCACCCCCGGTTT

TATGGGCGATCGCTATTGGCTGCGGCTGGGTCAGCAGAAAGTGGCCATCAATCGCATTAACATTA

CCTATCCCGACTACTACAACGGTATTATTGATCCCAAAGGCATTGAGGTGCGCATCGGTGGCGAT

CGCGGCAATCGCTTCTTCCAATTTCGCCGTGACCCCGGCACCAAAATTCAATTGGCGGAAGTCTC

CGTTGATCGCGATAACCGCGTGATTGATATTGTGCCGGCTGAGGTGATTCCCGCCGGAACACCGG

TGCAAGTTATTCTCAATAATGTGCGCAACCCTAACAATGGCGGCATGTACTATTTCAATGCCCGC

ATTGGCTCCCCTGGAGATATTCCCCTCATGCGCTACGTTGGCACCTGGATTCTCAGCATTGCCAA

TAACTAAAACCCGTCAAACTCGAGCATTGGTGAGCGGGTTAGCCATTTCTAACTATTGCGGGCG

ATCGCCCTAGACTAGTTTTTTGTCTATTATTGCCGGTTCACTCTTTACACCAGATGCCAGATTCC

GTTAGGTCTTCATTCCCCTCCATTTCTCCTCTGCTCACGCCTCTGATGTACCGCCTCGTGGGGGA

CGTTGTCCTGCGGCGCTATTTTCGTACCCTTGAGGTGCAAGGGCAGGAGCGGGTGCCCCAAAGGG

GTCCAGTGATCTTGGCCCCCACCCACCGTTCCCGCTGGGATGCGCTGATTATTCCCTATGTCACT

GGGCGGCGGGTGAGTGGGCGCGACCTCTACTACATGGTGTCCCACGATGAGATGTTGGGACTACA

GGGCTGGGTGATTGCTCAGTGTGGCGGTTTTCCCGTCAATACCCAAGCGCCTTCGGTGAGTGCGT

TGCGTACGGGTGTGGAACTGCTCCGGCAGGGGCAAGCCTTGGTGGTGTTCCCTGAGGGGAATATC

TTTCGCGATCGCCAGATTCATCCCCTCAAGCCGGGGTTGGCTCGCTTAGCCCTTCAGGCGGCCCA

GCGCTGTGAACAAGCAATCCAGATTCTGCCAATTTTACTCGATTATGCCCAGCCCTACCCACAGT

GGGGAAGTGCGGTCAAGGTAATCATTGGGGCTCCCTTGAGTACCGACAATTACGATGCCAGCCGG

CCAAAAAGTGCTGCCCAACAACTGACCAGTGATCTCTTTAGAAGACTTCAGCAGCTCCAAGGGGG

GCGATCGCCCCTGTGTTTTGCTTAGACCTCAAACTTCCATCCCCGCGGCCGCTCTTGATAACCCA

AGAGGGCATTTTTTAGGCGCGCCTCGAGTAA*CACCGTGCGTGTTGACTATTTTACCTCTGGCGGT*

*GATAATGGTTGCAGGATCCTTTTGCTGGAGGAAGAATTC*ATGACAACGGCTACCGCTACACCTGT

TTTGGACTACCATAGCGATCGCTACAAGGATGCCTACAGCCGCATTAACGCCATTGTCATTGAAG

GTGAACAGGAAGCTCACGATAACTATATCGATTTAGCCAAGCTGCTGCCACAACACCAAGAGGAA

CTCACCCGCCTTGCCAAGATGGAAGCTCGCCACAAAAAGGGGTTTGAGGCCTGTGGTCGCAACCT

GAGCGTAACGCCAGATATGGAATTTGCCAAAGCCTTCTTTGAAAAACTGCGCGCTAACTTTCAGA

-continued

```
GGGCTCTGGCGGAGGGAAAAACTGCGACTTGTCTTCTGATTCAAGCTTTGATCATCGAATCCTTT
GCGATCGCGGCCTACAACATCTACATCCCAATGGCGGATCCTTTCGCCCGTAAAATTACTGAGAG
TGTTGTTAAGGACGAATACAGCCACCTCAACTTTGGCGAAATCTGGCTCAAGGAACACTTTGAAA
GCGTCAAAGGAGAGCTCGAAGAAGCCAATCGCGCCAATTTACCCTTGGTCTGGAAAATGCTCAAC
CAAGTGGAAGCAGATGCCAAAGTGCTCGGCATGGAAAAAGATGCCCTTGTGGAAGACTTCATGAT
TCAGTACAGTGGTGCCCTAGAAAATATCGGCTTTACCACCCGCGAAATTATGAAGATGTCAGTTT
ATGGCCTCACTGGGGCATAAtggtggcttaacgtatcgttacatttcagtcaccacacgcttgtA
TGTTTGGATTAATTGGTCATCTGACGAGTCTGGAGCACGCCAAGCCGTTGCCCATCAGTTGGGT
TACCCCGAATATGCCGATCAAGGCTTGGAATTTTGGTGTATGGCACCGCCGCAGATCGTCGATGA
GATTACGGTGACGAGCGTAACGGGCAAAACTATCTATGGCAAATACGTTGAGTCCTGCTTTTTAC
CAGAGATGCTGGCCAACCAGCGGGTGAAGGCAGCGACTCGCAAAGTTATTAACGCCATGGCCCAT
GCCCAAAAGCACAACATTGACATTACGGCCTTGGGGGGCTTCTCCTCGATCATCTTTGAGAACTT
TGATCTGGAGAAAATGTCCCACATTCGCAACATTGAACTGGACTTTCGCCGCTTTACAACGGGGA
ATACCCATACCGCCTATATCATCTGCCAACAAATTGAGCAGGCGGCGCCCCAAGTGGGGATTGAT
TTGCGGCAGGCAACCGTGGCTGTTTGTGGGGCTACGGGGGATATTGGTAGTGCCGTCTGCCGTTG
GTTGAATACCTGTTTAGATGTGCAAGATCTCTTACTCGTAGCACGGAATCGCGATCGCCTGCTGG
AGCTACAGGCGGAATTGGGACGGGGGAAAATCCTCGACTTGATGGAGGCGCTGCCCCTTGCCGAT
ATTGTGGTTTGGGTGGCCAGTATGCCCAAGGGAGTTGAGCTGAGCATTGAGCAGTTAAAACGCCC
CTCCCTGATGATTGATGGTGGTTATCCCAAAAATATGGCCACCAAAATTCAGCACCCCCAGATTC
ATGTTCTCAATGGTGGCATTGTCGAGCATGCCCTCGACATTGACTGGAAAATTATGGAAATTGTG
AATATGGATGTGCCCTCGCGGCAGATGTTTGCCTGTTTTGCAGAGGCTATGCTTTTAGAGTTCGA
GGGCTGGCACACCAATTTCTCTTGGGGACGCAATCAAATCACTGTGGAAAAGATGCAGCAAATTG
GTGAGGTCTCCCGTAAACATGGATTTCAGCCACTACTGTTGAATCCTCAGTAAGCGGCCGCAAAA
AAAACGGGCCGGCGTATTATCGCCGGCCCGAGTAACACCGTGCGTGTTGACTATTTTACCTCTGG
CGGTGATAATGGTTGCAGGATCCTTTTGCTGGAGGAAAACCATATGAAAGGACCAATAATAATGA
CTAGAGAAGAAAGAATGAAGATTGTTCATGAAATTAAGGAACGAATATTGGATAAATATGGGAT
GATGTTAAGGCAATTGGTGTTTATGGCTCTCTTGGTCGTCAGACTGATGGGCCCTATTCGGATAT
TGAGATGATGTGTGTTCTGTCAACAGAGGGAGTAGAGTTCAGCTATGAATGGACAACCGGTGAGT
GGAAGGCGGAAGTGAATTTTTATAGCGAAGAGATTCTACTAGATTATGCATCTCGGGTGGAACCG
GATTGGCCGCTTACACATGGTCGATTTTTCTCTATTTTGCCGATTTATGATCCAGGTGGATACTT
TGAGAAAGTGTACCAAACTGCTAAATCGGTAGAAGCCCAAAAGTTCCACGATGCGATCTGTGCCC
TTATCGTAGAAGAGCTGTTTGAATATGCAGGCAAATGGCGTAATATTCGTGTGCAAGGACCGACA
ACATTTCTACCATCCTTGACTGTACAGGTGGCAATGGCAGGTGCCATGTTGATTGGTCTGCATCA
TCGCATCTGTTATACGACGAGCGCTTCGGTCTTAACTGAAGCAGTTAAGCAACCAGATCTTCCTC
CAGGTTATGTCCAACTGTGCCAGCTCGTAATGTCTGGTCAACTTTCCGACCCTGAGAAACTTCTG
GAATCGCTAGAGAATTTCTGGAATGGGGTTCAGGAGTGGGCGGAACGACACGGATATATAGTGGA
TGTGTCAAAACGCATACCATTTTGATGTCTAACCCCCTTCCTTGCCCACAGCTTCGTCGATGGCG
CGAAATTTCGGGTAAATATAATGACCCTCTTGATAACCCAAGAGGGCATTTTTTAGGCGCGCCCT
AAGCGTCCGTAGGCACAATTAAGGCTTCAAATTGTTGGCGAAGCTGCTCAGTCACTTCCTTGACG
GCTTGCCGTGCCCCTTGGCGATCGCGCCGGTACGAGGCCAATAGCTCTCTAAATTGAGAGGGTC
GCCGACACTGAGGCGCACCTGCCGCAAACCCACCAAACGATTGAGATTCGAGCTTTTTCCCTCTA
```

```
GCCAATCAAATGTGCGCCAGAGAATCAGCGCGACATCTGCAAAGCGATGAATCGTGAATTTCTCA

CGGATATAGCTACCCGTAATTGAGGTAAATCGCTCCGCAAGACGCATATGACGCAATCGCACATT

GGCTTCCTCGGCCAACCAATCGGCTAGGCAGCGCTCTACGGCCGAAAGTTGTGCCAAATCACTGC

GAAACATCCGTTCCCAAGCAGCCTGTTCAATGCGTCGGCAGCGACTCACAAAATCGGCACTGGGC

TTCAGACCAAAGTAGGACTCTGCCACCACAAGGGCGCTGTTGAGGAGGCGCTGAATTCGCGCTGC

CAATTTAGCATTGGCAGAGTCAAAGGGGGGCAGTTCGGGAAAATCTTGACCATAGGAGGTGGCAT

AAAAAGCCTCCAGGCGATCCAAGAGGTGGATCGCTAAATTCAGCAGGCGGCGGTAGAGGTCGTCT

GGCTGGGTACTGTGAGAATCTGTAGGGCACCCAAGGCGGTTCTCCAGTTGTGCCATCAGCCTTGC

CATGCGCTCCCAAGAGGGCTGACTGAGGCTGTACTGAATGCCAATGGGAAGAATGACCACGGGGA

GCGATCGCCCCGCCTTGGCTAAATCTTCTAGACACCAAAATCCCAGTTGGGCCACCCCCGGCTCC

AAAGGTGCGACCAGTTCGTTGTGCTCATTCGTTGCTCCCTCCGGCGCTGCCGCTAGGGGAAATCG

TCCTCCGAGAAGTAGCTCCCGCGCTGAGCGCAGGGCTTGGCTATCGAGCTTACCGCGCATGATGG

AAATCCCCCCCAACCGTGAAAAGAGCCAACCAATCTGCGCCCCTGCCCAGAGGGGAATCCCGCGA

TCGTAGAGAAAATAGCCATTTGTCGGCGGACGCAAGGGAATGCCCAGCCGCCGTGCTGTTTGCGG

CAGTAAATGCCACATCAAATAGCCCATCACCAACGGATCATCCGTACAGGGATGGCGAAAGGCAA

TGAGGAGCCGGACCTGTCCCTGCTGAAACTGCTGGTAATAACGGGCAAGGGTCTCCACATTCACC

CCTTCAACCCGCTGTAGCCCAAGACCATAGCGAATGTAGAGGGGCAGGAGTCTTGCTACTGTCCA

CCAGACGGGTAGCTAAACCGCTGGGGGAGAAAATGCAACGGCGGTTGGGCAGTTGTCACTACAC

TGGACATTAGGCAAGCTCCTCAGGGCAATGGCTAAACTGAGGCAGTGGCCAACTCCGCAATTAAC

TGCTCTAACATCGGTTGATCGGCCCAATAGACAGCATTACAAAACTGACAGGTGGCTTCTGCCTT

TGCCTCTGTGGCTAGGATATCTCTTAATTCTGCCTCCCCTAGGAGCTTGAGTGCCGCTAACATCC

GTTCATGGGAACAGCCACAGTGGAAGCGCACCATTTGCCGTTGGGGCAAGATTTGTAAATCCATA

TCCCCTAAGAGTTCCTGAAAGATATCTGGCAGTGTCCGCCCTGCCTGTAGCAGTGGTGTAAAGCC

CTTAAGATTGGCCACCCGTTGTTCAAGGGTCGCGATCAGGTGTTCATCATTGGCCGCTTTGGGTA

GCACCTGTAACATCAACCCACCGGCGGCAGTCACCCCGGACTCTTCGACAAAAACACCCAACATC

AGGGCGGAGGGGGTTTGCTCTGAGGTGGCGAGGTAGTAGGTGATGTCTTCTGCAATTTCGCCGGA

GACTAGCTCCACCGTGCTGGAATAGGGGTAGCCGTAGCCAAGATCGTGGATGACGTAGAGATATC

CCTGATGGCCCACCGCTGCCCCCACATCGAGTTTGCCCTTGGCATTGGGGGGCAGTTCAACACTG

GGGTACTGCACATAGCCGCGAACTGTGCCATCGGCACCAGCATCGGCAAAATGGTTCCTAGGGG

ACCGTTGCCCTGAATGCGCACATTCACCCGTGCTTGGGGCTGTTTGAAACTGGAGGCAAGGATTA

AGCCTGCGGCCATGGTTCGTCCCAAGGCCGCTGTGGCCACGTAGGACAGTTGGTGACGTTTGCGG

GCTTCATCAGTGAGTTGAGTGGTAATCACACCTACGGCCCGGATGCCTTCGGCAGCGGCAGTTGC

TCGCAACAGAAAATCGGCCATGTTCAACCTACGAAATGTTTTGTTACATTTAGTGTGACATACTC

CCACCGCTGACCAGGGCACAATGGGGCAAAAAACCATCAATCCTGCCTTTGGTGACCGATCCAGT

ACAGCCAGCCAGGGCTTAAGACTGGGAAGACCCCTAGCACTGGGGCTAGAAAATTGGCGATGATA

GGCAAGCAATAGTCATTCAGCGTCCAGTCATTCCGCCTATGGCCATGCCCCTCACTGTCTTGCCT

GCCACAACTGTTTTGACAGAAGCGACTCAATTGCCCCAGGGCGGCTTGATTACGGAGATTCCGAC

GCTGGCGATCGCCCACCGTTTGGCCCAGCAGTTGCGCCGCCATTGGCCCCTAGAGACCCCCTTAA

CGCTGATTGATGCGCAATACCAGAGTATCCCCCTGACCCTTGGGGAATTGGCCGAGCTCACCGAT

GCCAACTGTCCTTTACAGCTCTATGTGCCGCCCCCCTTGCCAGAGGCCTTGACGCAATTTCAACG
```

-continued

CCTGATGGATGTGGTTCGAGAGCTGCGCCATCCGGAGCGTGGCTGTCCTTGGGATTTGCAGCAAA

CCCCAACCAGTCTCATTCCCTATGTCCTTGAGGAAGCCTATGAAGTGGTACATGCCCTGCAGGAG

GGAGATGCGGGGCGATCGCCGAAGAATTGGGAGACCTGTTGCTTCAAGTTGTTCTCCAGAGCCA

ACTTGCCCAAGAAGCCGGCCAATTTACCCTTGCTCAAGTCATTCAAAGGATTACCGATAAACTCA

TCCGCCGCCATCCCCACGTCTTTGGTGAAGTGGCACTCACCACTGCTCAAGAGGTGCGCGACCAA

TGGGAGCAAATCAAAGCGGCTGAAAAAGGCACCGAACTCCCCCTGAGTCAAACGCTGCAACGTTA

CGCACGCACCCTCCCACCCCTGATGGCCGGCATGAAAATTGGTGAGCGAGCCAGTCGCGCTGGCC

TCGATTGGCCGACGATTAGTGGTGCATGGGAGAAATTTTACGAGGAACTGGCGGAGTTTCAGGAG

GCCCTTCTGCAAGGGAATGCTGAGCAACAGGCAGCGGAATTAGGAGACCTGCTCTTCAGTGTGAT

TAACCTTGCCCGCTGGTGCCAACTGGATCCTGTTAATGCCCTGCAACAAACCTACCAACGCTTTA

TTCAACGCTTGGCCTGTATTGAGGCAGTCATCGATCGCCCCCTTGAGACGTACACCCTAGAAGAA

CTAGAAGCCCTCTGGCAACAGGCCAAAGTACAGTTAGCCACCGACAGCGAGGCAACCCCTATGGA

GACTGAGGAAGAGGCCTAGTCCGCTGCGGCCCTTGCCACCTTCAGTTCATCGAGATTCCACAGGG

GGCCCCCCAGCGCCGTGGGCTTGGCGCCAATGACATGATTGCGAAAAGCTGTAAGGGAGAGGGGA

TTCACGAGGTAAATAAAGGGGAGATATTCCTGAGCTAGTCGTTGGGCTTCCGCATAAATTTGCTG

CCGTCGTTCCAGATTGAGCTCCTGGGCACCTTGGACATACAGGTCACTGATGCGCTGCTCCCAGT

CAGCGACGACTCGACCCGTAATGGGTGGTTGATTCGGTGACGGTTGCTGATTGAATGTATGCAAA

AGGCCATCCACACGCCAGATATTGGCACCGCTATTGGGTTCATTGCCCCCCCCAGTAAAGCCGAG

GATATGGGCTTCCCACTCTAGGGAATTGGAGAGACGATCCACGAGGGTACCAAAGGCCAAAAATT

GCAGATCCACCTGCATGCCGATCGCCCCTAGGTCCTGCTGAACTTGCGTCGggccggccaaaatg aagtgaagttcctatactttctagagaataggaacttctatagtgagtcgaataagggcgacaca aaatttattctaaatgcataataaatactgataacatcttatagtttgtattatattttgtatta tcgttgacatgtataattttgatatcaaaaactgattttcccttattattttcgagatttattt tcttaattctctttaacaaactagaaatattgtatatacaaaaaatcataaataatagatgaata gtttaattataggtgttcatcaatcgaaaaagcaacgtatcttatttaaagtgcgttgctttttt ctcatttataaggttaaataattctcatatatcaagcaaagtgacaggcgcccttaaatattctg acaaatgctctttccctaaactcccccataaaaaaaccgccgaagcgggttttttacgttatt gcggattaacgattactcgttatcagaaccgcccaggggcccgagcttaagactggccgtcgtt ttacaacacagaaagagtttgtagaaacgcaaaaaggccatccgtcaggggccttctgcttagtt tgatgcctggcagttccctactctcgccttccgcttcctcgctcactgactcgctgcgctcggtc gttcggctgcggcgagcggtatcagctcactcaaaggcggtaatacggttatccacagaatcagg ggataacgcaggaaagaacatgtgagcaaaaggccagcaaaaggccaggaaccgtaaaaaggccg cgttgctggcgtttttccataggctccgcccccctgacgagcatcacaaaaatcgacgctcaagt cagaggtggcgaaacccgacaggactataaagataccaggcgtttccccctggaagctccctcgt gcgctctcctgttccgaccctgccgcttaccggatacctgtccgcctttctcccttcgggaagcg tggcgctttctcatagctcacgctgtaggtatctcagttcggtgtaggtcgttcgctccaagctg ggctgtgtgcacgaaccccccgttcagcccgaccgctgcgccttatccggtaactatcgtcttga gtccaacccggtaagacacgacttatcgccactggcagcagccactggtaacaggattagcagag cgaggtatgtaggcggtgctacagagttcttgaagtggtgggctaactacggctacactagaaga acagtatttggtatctgcgctctgctgaagccagttaccttcggaaaaagagttggtagctcttg atccggcaaacaaaccaccgctggtagcggtggtttttttgtttgcaagcagcagattacgcgca -continued gaaaaaaggatctcaagaagatcctttgatcttttctacggggtctgacgctcagtggaacgac gcgcgcgtaactcacgttaagggattttggtcatgagcttgcgccgtcccgtcaagtcagcgtaa tgctctgcttttaccaatgcttaatcagtgaggcacctatctcagcgatctgtctatttcgttca tccatagttgcctgactcccgtcgtgtagataactacgatacgggagggcttaccatctggccc cagcgctgcgatgataccgcgagaaccacgctcaccggctccggatttatcagcaataaaccagc cagccggaagggccgagcgcagaagtggtcctgcaactttatccgcctccatccagtctattaat tgttgccgggaagctagagtaagtagttcgccagttaatagtttgcgcaacgttgttgccatcgc tacaggcatcgtggtgtcacgctcgtcgtttggtatggcttcattcagctccggttcccaacgat caaggcgagttacatgatccccatgttgtgcaaaaaagcggttagctccttcggtcctccgatc gttgtcagaagtaagttggccgcagtgttatcactcatggttatggcagcactgcataattctct tactgtcatgccatccgtaagatgcttttctgtgactggtgagtactcaaccaagtcattctgag aatagtgtatgcggcgaccgagttgctcttgcccggcgtcaatacgggataataccgcgccacat agcagaactttaaaagtgctcatcattggaaaacgttcttcggggcgaaaactctcaaggatctt accgctgttgagatccagttcgatgtaacccactcgtgcacccaactgatcttcagcatctttta ctttcaccagcgtttctgggtgagcaaaaacaggaaggcaaatgccgcaaaaaagggaataagg gcgacacggaaatgttgaatactcatattcttccttttttcaatattattgaagcatttatcaggg ttattgtctcatgagcggatacatatttgaatgtatttagaaaaataaacaaatagggtcagtg ttacaaccaattaaccaattctgaacattatcgcgagcccatttatacctgaatatggctcataa caccccttgtttgcctggcggcagtagcgcggtggtcccacctgacccatgccgaactcagaag tgaaacgccgtagcgccgatggtagtgtggggactccccatgcgagagtagggaactgccaggca tcaaataaaacgaaaggctcagtcgaaagactgggcctttcgcccgggctaattatgggtgtcg cccttattcgactctatagtgaagttcctattctctagaaagtataggaacttctgaagtggggc ctgcagg (SEQ ID NO: 18)

SEQ ID NO: 19
PcI promoter used for transcription in pJB886. Terminal NotI
and NdeI sites used for promoter exchanges are capitalized.
GCGGCCGCtcgagtaacaccgtgcgtgttgactattttacctctggcggtgataatggttgcagg atccttttgctggaggaaaaacCATATG (SEQ ID NO: 19)

SEQ ID NO: 20
PcpcB promoter used for transcription in pJB887.
GCGGCCGCttcgttataaaataaacttaacaaatctatacccacctgtagagaagagtccctgaa tatcaaaatggtgggataaaaagctcaaaaaggaaagtaggctgtggttccctaggcaacagtct tccctaccccactggaaactaaaaaaacgagaaaagttcgcaccgaacatcaattgcataatttt agccctaaaacataagctgaacgaaactggttgtcttcccttcccaatccaggacaatctgagaa tcccctgcaacattacttaacaaaaaagcaggaataaaattaacaagatgtaacagacataagtc ccatcaccgttgtataaagttaactgtgggattgcaaaagcattcaagcctaggcgctgagctgt ttgagcatcccggtggcccttgtcgctgcctccgtgtttctccctggatttatttaggtaatatc tctcataaatcccgggtagttaacgaaagttaatggagatcagtaacaataactctagggtcat tactttggactccctcagtttatccgggggaattgtgtttaagaaaatcccaactcataaagtca agtaggagattaatCATATG (SEQ ID NO: 20)

-continued

SEQ ID NO: 21
PlacI-trc promoter used for transcription in pJB889. Terminal
NotI and NdeI sites used for promoter exchanges are capitalized.
GCGGCCGCgaaggcgaagcggcatgcatttacgttgacaccatcgaatggtgcaaaacctttcgc ggtatggcatgatagcgcccggaagagagtcaattcagggtggtgaatatgaaaccagtaacgtt atacgatgtcgcagagtatgccggtgtctcttatcagaccgtttcccgcgtggtgaaccaggcca gccacgtttctgcgaaaacgcgggaaaaagtggaagcggcgatggcggagctgaattacattccc aaccgcgtggcacaacaactggcgggcaaacagtcgttgctgattggcgttgccacctccagtct ggccctgcacgcgccgtcgcaaattgtcgcggcgattaaatctcgcgccgatcaactgggtgcca gcgtggtggtgtcgatggtagaacgaagcggcgtcgaagcctgtaaagcggcggtgcacaatctt ctcgcgcaacgcgtcagtgggctgatcattaactatccgctggatgaccaggatgccattgctgt ggaagctgcctgcactaatgttccggcgttatttcttgatgtctctgaccagacacccatcaaca gtattattttctcccatgaagacggtacgcgactgggcgtggagcatctggtcgcattgggtcac cagcaaatcgcgctgttagcgggcccattaagttctgtctcggcgcgtctgcgtctggctggctg gcataaatatctcactcgcaatcaaattcagccgatagcggaacggggaaggcgactggagtgcca tgtccggttttcaacaaaccatgcaaatgctgaatgagggcatcgttcccactgcgatgctggtt gccaacgatcagatggcgctgggcgcaatgcgcgccattaccgagtccgggctgcgcgttggtgc ggatatctcggtagtgggatacgacgataccgaagacagctcatgttatatcccgccgtcaacca ccatcaaacaggattttcgcctgctggggcaaaccagcgtggaccgcttgctgcaactctctcag ggccaggcggtgaagggcaatcagctgttgcccgtctcactggtgaaaagaaaaaccaccctggc gcccaatacgcaaaccgcctctccccgcgcgttggccgattcattaatgcagctggcacgacagg tttcccgactggaaagcgggcagtgagcgcaacgcaattaatgtgagttagcgcgaattgatctg gtttgacagcttatcatcgagctcgactgcacggtgcaccaatgcttctggcgtcaggcagccat cggaagctgtggtatggctgtgcaggtcgtaaatcactgcataattcgtgtcgctcaaggcgcac tcccgttctggataatgttttttgcgccgacatcataacggttctggcaaatattctgaaatgag ctgttgacaattaatcatccggctcgtataatgtgtggaattgtgagcggataacaatttcacac aggaaacagCATATG (SEQ ID NO: 21)

SEQ ID NO: 22
EM7 promoter used for transcription in pJB888. Terminal NotI and
NdeI sites used for promoter exchanges are capitalized.
GCGGCCGCtgttgacaattaatcatcggcatagtatatcggcatagtataatacgacaaggtgag gaactaaCATATG (SEQ ID NO: 22)

---

What is claimed is:

1. An engineered cyanobacterium, wherein said engineered cyanobacterium comprises a recombinant acyl-ACP reductase enzyme and a recombinant alkanal decarboxylative monooxygenase enzyme; and wherein said cyanobacterium, when cultured in the presence of light and carbon dioxide, produces n-alkanes, wherein at least one of said n-alkanes is selected from the group consisting of n-tridecane, n-tetradecane, n-pentadecane, n-hexadecane, and n-heptadecane, and wherein the amount of said n-alkanes produced is between 0.1% and 5% dry cell weight and at least two times the amount produced by an otherwise identical cyanobacterium, cultured under identical conditions, but lacking said recombinant acyl-ACP reductase and alkanal decarboxylative monooxygenase enzymes.

2. The engineered cyanobacterium of claim 1, wherein said enzymes are encoded by genes which are present in multiple copies in said engineered cyanobacterium.

3. The engineered cyanobacterium of claim 2, wherein said enzymes are encoded by a plasmid.

4. The engineered cyanobacterium of claim 1, wherein said enzymes are encoded by genes which are part of an operon, and wherein the expression of said genes is controlled by a single promoter.

5. The engineered cyanobacterium of claim 3, wherein said enzymes are encoded by genes which are part of an operon, and wherein the expression of said genes is controlled by a single promoter.

6. The engineered cyanobacterium of claim 1, wherein expression of the recombinant acyl-ACP reductase or alkanal decarboxylative monooxygenase enzymes in said engineered cyanobacterium is controlled by a promoter selected from the group consisting of a cI promoter, a cpcB promoter, a lacI-trc promoter, an EM7 promoter, and an aphII promoter.

7. The engineered cyanobacterium of claim 3, wherein expression of the recombinant acyl-ACP reductase or alkanal decarboxylative monooxygenase enzymes in said engineered cyanobacterium is controlled by a promoter selected from the group consisting of a cI promoter, a cpcB promoter, a lacI-trc promoter, an EM7 promoter, and a aphII promoter.

8. The engineered cyanobacterium of claim 1, wherein said engineered cyanobacterium is a thermophile.

* * * * *